(12) United States Patent
Bader et al.

(10) Patent No.: US 9,187,550 B2
(45) Date of Patent: *Nov. 17, 2015

(54) TETRANECTIN-APOLIPOPROTEIN A-I, LIPID PARTICLES CONTAINING IT AND ITS USE

(75) Inventors: Martin Bader, Penzberg (DE); Monika Baehner, Munich (DE); Juergen Fingerle, Kandern (DE); Ulrich Kohnert, Habach (DE); Jean-Luc Mary, Huningue (FR); Silke Mohl, Basel (CH)

(73) Assignee: Hoffman—La Roche Inc., Little Falls, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/217,534

(22) Filed: Aug. 25, 2011

(65) Prior Publication Data

US 2012/0190610 A1    Jul. 26, 2012

(30) Foreign Application Priority Data

Aug. 30, 2010   (EP) ................................... 10008993
Oct. 21, 2010   (EP) ................................... 10188392

(51) Int. Cl.
   *A61K 38/17*    (2006.01)
   *A61K 47/14*    (2006.01)
   *C07K 14/775*   (2006.01)
   (Continued)

(52) U.S. Cl.
   CPC .............. *C07K 14/775* (2013.01); *A61K 9/127* (2013.01); *A61K 38/1709* (2013.01); *A61K 47/186* (2013.01); *A61K 47/44* (2013.01); *C07K 2319/73* (2013.01)

(58) Field of Classification Search
   None
   See application file for complete search history.

(56) References Cited

U.S. PATENT DOCUMENTS

| 6,291,245 | B1 | 9/2001 | Kopetzki et al. |
| 6,897,039 | B2 * | 5/2005 | Graversen et al. ........... 435/69.1 |

(Continued)

FOREIGN PATENT DOCUMENTS

| EP | 0972838 | 1/2000 |
| EP | 1 486 571 | 12/2005 |

(Continued)

OTHER PUBLICATIONS

Sequence Comparison of Applicants' Seq ID Nos:1, 2, 6, 66, and 67 with Graverson et al (U.S. Pat. No. 6,897,039), compiled Jun. 4, 2013.*

(Continued)

*Primary Examiner* — Jeffrey E Russel
(74) *Attorney, Agent, or Firm* — Robert C. Hall

(57) ABSTRACT

A lipid particle comprising an apolipoprotein, a phosphatidylcholine and a lipid, such as a phospholipid, fatty acid or steroid lipid. In one embodiment the lipid particle comprises only one apolipoprotein. In one embodiment the lipid particle is consisting of one apolipoprotein, a phospholipid, a lipid, and a detergent. In one embodiment the lipid is a second phosphatidylcholine, wherein the first phosphatidylcholine and the second phosphatidylcholine differ in one or two fatty acid residues or fatty acid residue derivatives which are esterified to the glycerol backbone of the phosphatidylcholine. In one embodiment the apolipoprotein is selected from an apolipoprotein that has the amino acid sequence selected from SEQ ID NO: 01, 02, 06, 66, and 67, or is a variant thereof that has at least 70% sequence identity with the selected sequence.

19 Claims, 24 Drawing Sheets

(51) Int. Cl.
  *A61K 47/44* (2006.01)
  *A61K 47/18* (2006.01)
  *A61K 9/127* (2006.01)

(56) References Cited

U.S. PATENT DOCUMENTS

| | | | |
|---|---|---|---|
| 2002/0142953 | A1 | 10/2002 | Ballinger et al. |
| 2005/0176625 | A1* | 8/2005 | Curstedt et al. ............... 514/7 |
| 2005/0287636 | A1 | 12/2005 | Cho |
| 2006/0217312 | A1* | 9/2006 | Dasseux ..................... 514/12 |

FOREIGN PATENT DOCUMENTS

| | | |
|---|---|---|
| EP | 1 422 237 | 2/2007 |
| WO | 98/56906 | 12/1998 |
| WO | 99/16409 | 4/1999 |
| WO | 02/38609 | 5/2002 |
| WO | 03/096983 | 11/2003 |
| WO | 2005/084642 | 9/2005 |
| WO | 2006/100567 | 9/2006 |
| WO | 2006/125304 | 11/2006 |
| WO | 2007/098122 | 8/2007 |
| WO | 2007/137400 | 12/2007 |
| WO | 2008/017906 | 2/2008 |
| WO | 2008/106660 | 9/2008 |
| WO | 2008/156873 | 12/2008 |
| WO | 2009/036460 | 3/2009 |
| WO | 2009/097587 | 8/2009 |
| WO | 2009/131704 | 10/2009 |

OTHER PUBLICATIONS

Kuksis, "Animal Lecithins." in Lecithins, Eds. B.F. Szhuhaj and G.R. List, 1985, pp. 105-162, published by American Oil Chemists' Society.*

Matz et al. Micellar Complexes of Human Apolipoprotein A-I with Phosphatidylcholines . . . The Journal of Biological Chemistry. Apr. 25, 1982. vol. 257, No. 8, pp. 4535-4540.*

International Search Report and Written Opinion for International Patent Application PCT/EP2011/064601, mailed Aug. 27, 2012.*

Beck et al., "Nucleotide sequence and genome orgnanisation of filamentous bacteriophages fl and fd" Gene 16(1-3):35-58 (1981).

Bujard et al., "A T5 promoter-based transcription-translation system for the analysis of proteins in vitro and in vivo" Methods Enzymol. 155:416-33 (1987).

Chen et al., "Apolipoprotein AI tertiary structures determine stability and phospholipid-binding activity of discoidal high-density lipoprotein particles of different sizes" Protein Sci. 18(5):921-35 (2009).

Farabaugh et al., "Sequence of the lacI gene" Nature 274:765-9 (1978).

International Search Peport and Written Opinion for International Patent Application No. PCT/EP2011/064600, mailed Sep. 4, 2002.

Jonas et al., "Reconstitution of high-density lipoproteins" Methods Enzymol. 128:553-82 (1986).

Jonas, "A review of plasma apolipoprotein A-I interactions with phosphatidylcholines" Exp Lung Res. 6(3-4):255-70 (1984).

Matz et al., "Micellar complexes of human apolipoprotein A-I with phosphatidylcholines and cholesterol prepared from cholate-lipid dispersions" J Biol Chem. 257(8):4535-40 (1982).

Nissen et al., "Effect of recombinant ApoA-I Milano on coronary atherosclerosis in patients with acute coronary syndromes: a randomized controlled trial" JAMA 290(17):2292-300 (2003).

Queen et al., "A humanized antibody that binds to the interleukin 2 receptor" P Natl Acad Sci USA 86(24):10029-10033 (Dec. 1989).

Reichmann et al., "Reshaping human antibodies for therapy" Nature 332:323-327 (Mar. 24, 1988).

Riesenberg et al., "High cell density cultivation of *Escherichia coli* at controlled specific growth rate" J Biotechnol. 20(1):17-27 (Aug. 1991).

Rose et al., "Structure and function of the yeast URA3 gene: expression in *Escherichia coli*" Gene 29(1-2):113-24 (1984).

Schwarz et al., "Nucleotide sequence of cro, cII and part of the O gene in phage λDNA 410" Nature 272:410-14 (1978).

Shay et al., "High-productivity fermentation process for cultivating industrial microorganisms" Journal of Industrial Microbiology & Biotechnology 2:79-85 (1987).

Stuber et al., "System for high level production in *E. coli* and rapid purification of recombinant proteins: application to eptiope mapping, preparation of antibodies and structure-function analysis" Immunological methods, IV:121-152 (1990).

Sutcliffe et al., "Complete nucleotide sequence of the *Escherichia coli* plasmid pBR322" Cold Spring Harb Symp Quant Biol. 43(Pt 1):77-90 (1979).

* cited by examiner

Fig. 1
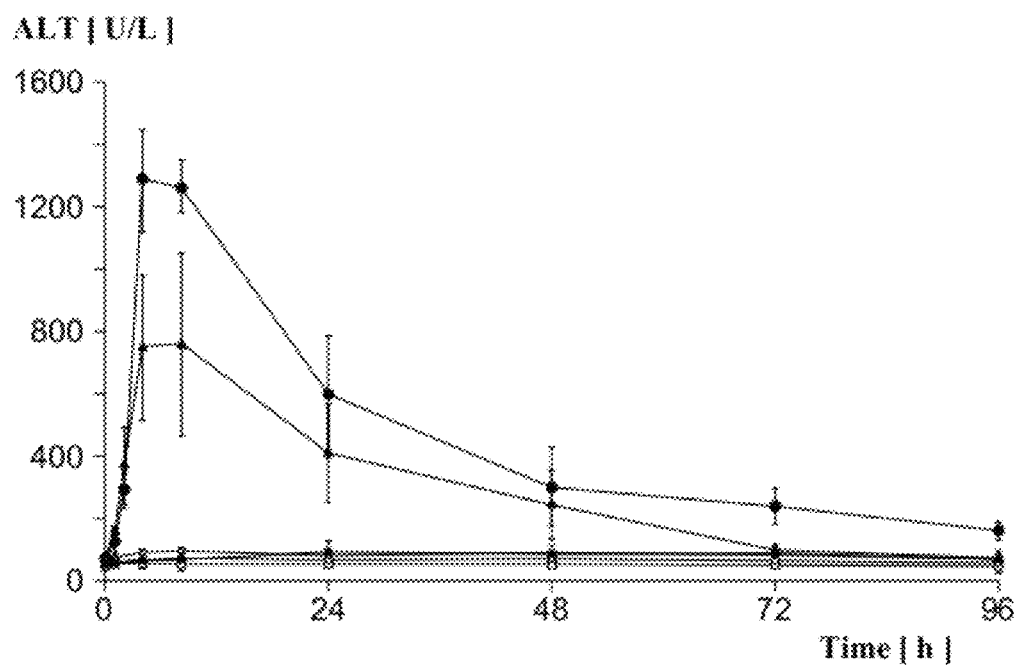
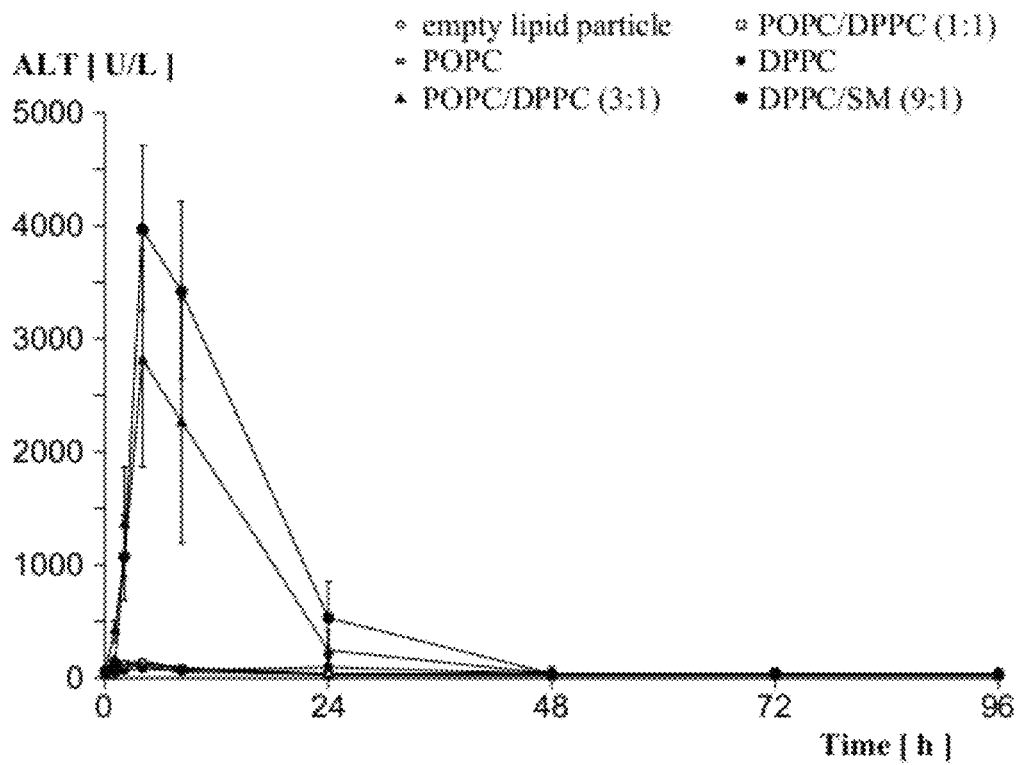

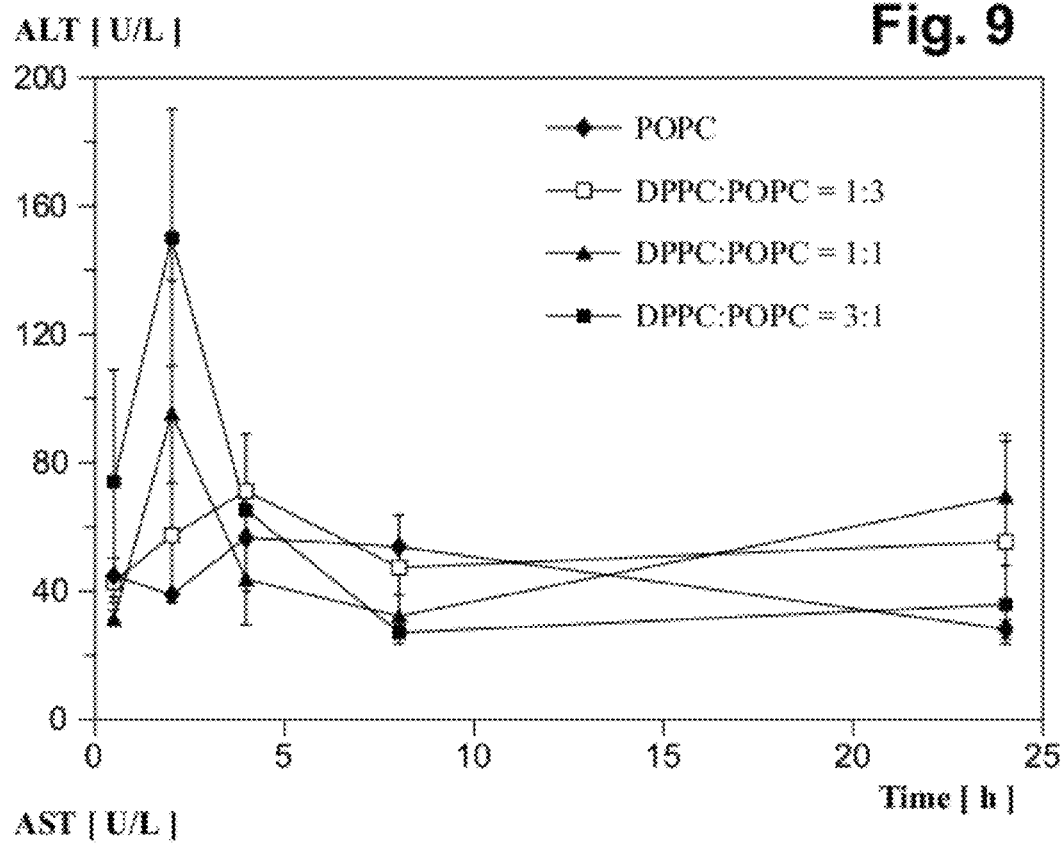
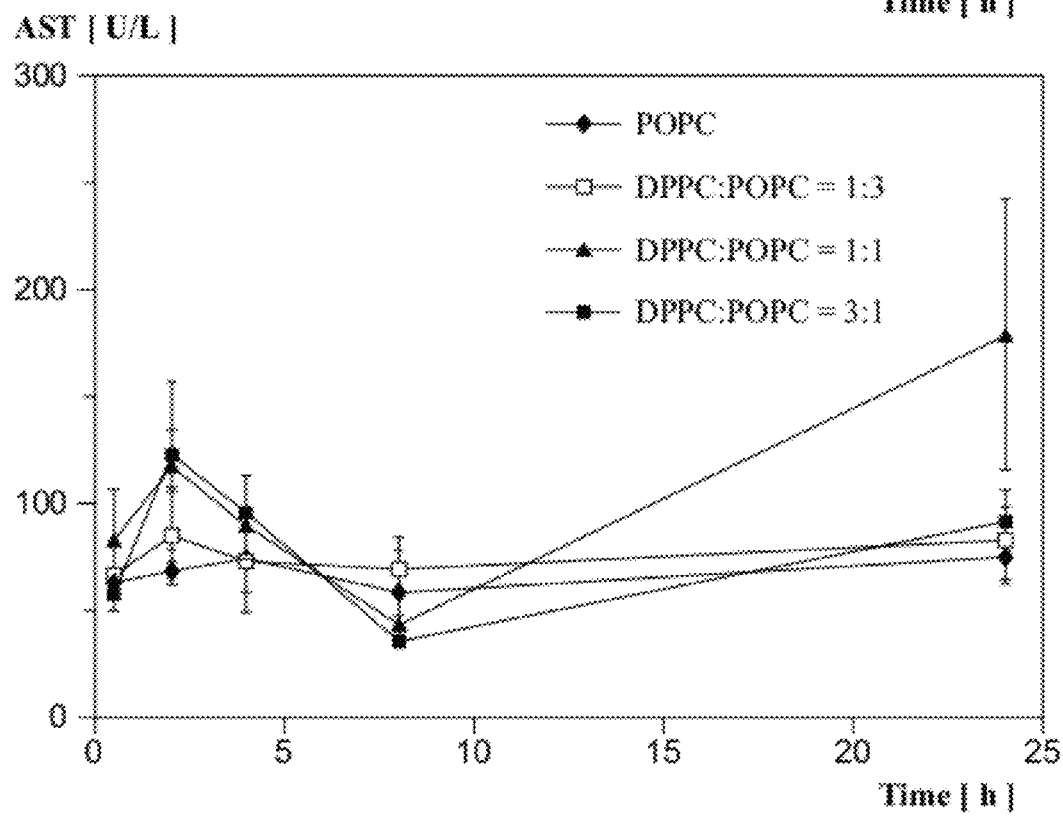
Fig. 9

Fig. 22
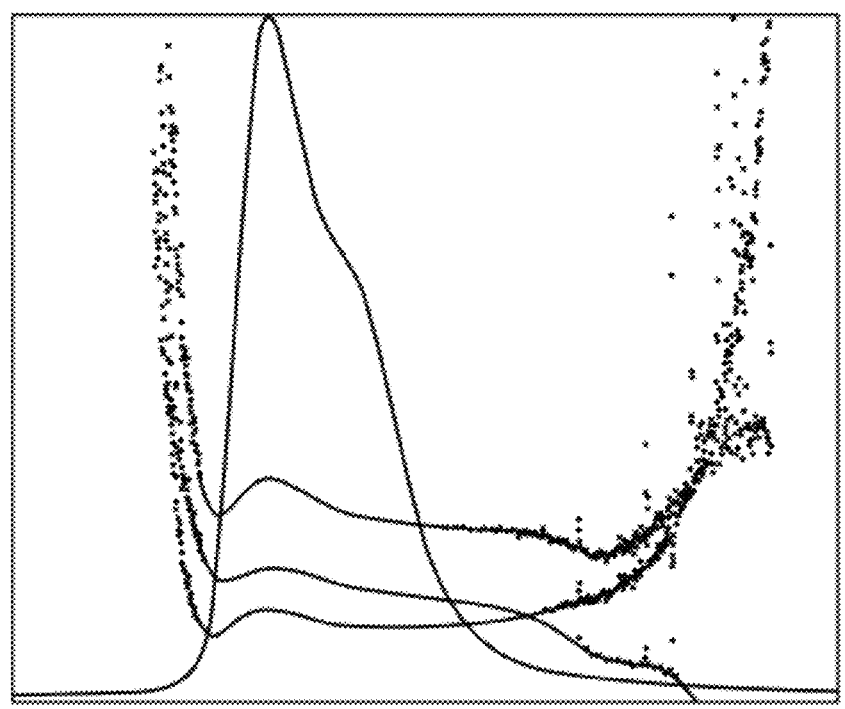
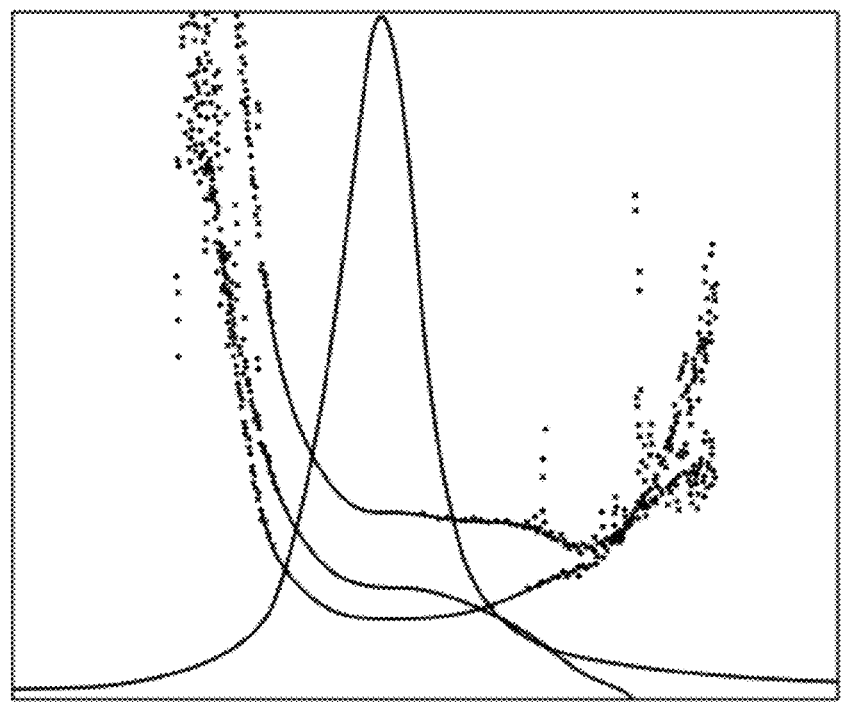

Fig. 23
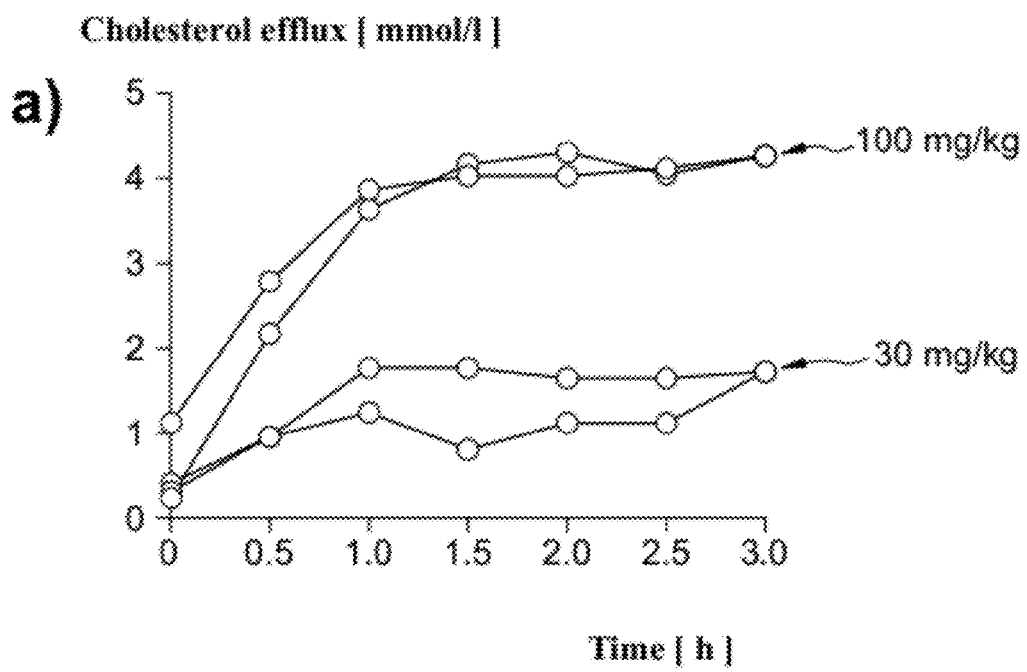
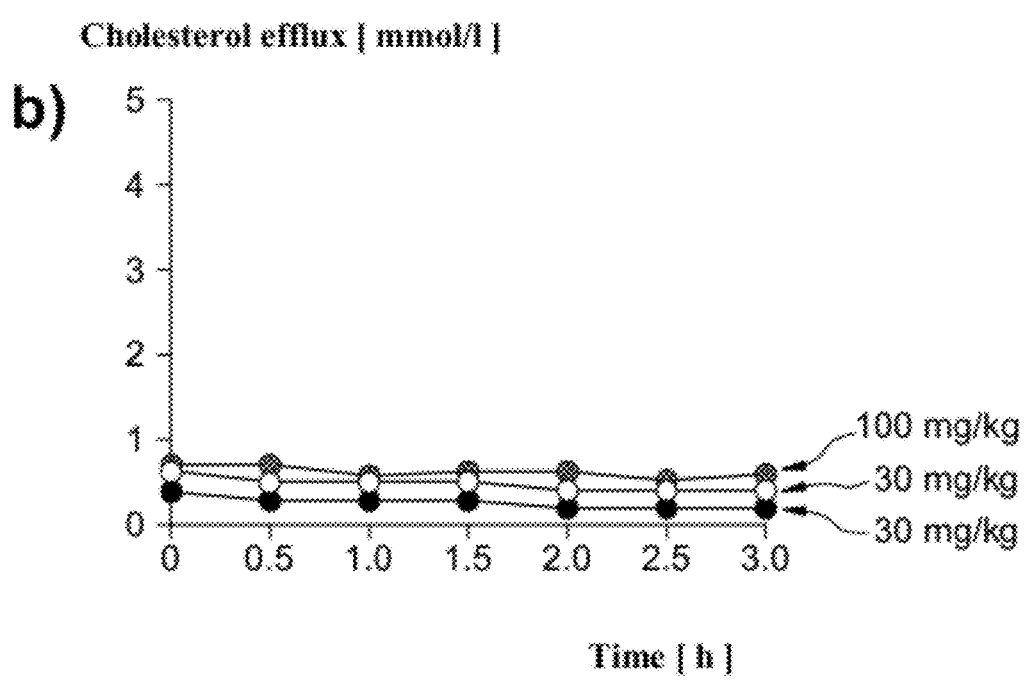

TETRANECTIN-APOLIPOPROTEIN A-I, LIPID PARTICLES CONTAINING IT AND ITS USE

CROSS-REFERENCE TO RELATED APPLICATIONS

This Application claims priority under 35 U.S.C. §119 to European Application No. EP 10008993.7 filed Aug. 30, 2010, and European Application No. EP 10188392.4 filed Oct. 21, 2010, the disclosures of which are incorporated herein by reference.

SEQUENCE LISTING

The instant application contains a Sequence Listing which has been submitted in ASCII format via EFS-Web and is hereby incorporated by reference in its entirety. Said ASCII copy, created on Feb. 15, 2012, is named P4515.txt and is 144,359 bytes in size.

FIELD OF THE INVENTION

The current invention is in the field of lipoproteins and lipid particles. It is reported herein a lipid particle comprising an apolipoprotein, a phosphatidylcholine and a lipid, as well as a tetranectin-apolipoprotein A-I, and the use thereof.

BACKGROUND OF THE INVENTION

Plasma lipoproteins are soluble protein-lipid complexes that carry out lipid transport and metabolism in blood. Several major classes of lipoproteins are distinguished on the basis of their density, size, chemical compositions, and functions. Among them high-density-lipoprotein (HDL) particles alternatively denoted as high-density-lipid particles, are made up of several subclasses that vary in their average molecular weight of from 180 kDa to 360 kDa. Their average lipid and protein content is 50% by weight of each. Phosphatidylcholine (PC) accounts for 38% of the total lipid followed by cholesteryl esters and small amounts of other polar and non-polar lipids, including free cholesterol. The main protein component is apolipoprotein A-I (Apo A-I), representing about 60% of total protein weight in human HDL.

HDL particles and its major polypeptide apolipoprotein A-I participate in the reverse cholesterol transport (RCT). Therein the apolipoprotein A-I increases the efflux of cholesterol from cells, e.g. from cells of the wall of blood vessels, the binding of the lipid and the activation of the lecithin-cholesterol-acetyl-transferase and thereby the elimination of cholesterol via plasmatic flow by the liver. This is an active transport process involving the cell membrane protein ATP-binding-cassette-transporter-A-I (ABCA-I).

Apolipoprotein A-I and apolipoprotein-based therapeutics, e.g. reconstituted HDL particles, were already identified in the late 70ties and early 80ties of the last century. For apolipoprotein A-I-Milano containing lipid particles the clinical proof (meaning significant plaque reduction in arteriosclerotic patients) could be shown. Apolipoprotein A-I-Milano, a dimeric form of wild-type apolipoprotein A-I, was designed according to a naturally occurring mutant of the apolipoprotein A-I molecule. The dimer formation is enabled by the exchange of amino acid residue 173 (arginine) by cysteine allowing the formation of a disulfide bond.

In WO 2009/131704 nanostructures are reported, which are suitable for sequestering cholesterol and other molecules, comprising a core comprising an inorganic material. In WO 2006/125304 pharmaceutical compositions for treating or preventing coronary artery disease are reported. Compositions encoding apolipoproteins that are related to lipid metabolism and cardiovascular disease are reported in US 2002/0142953. In WO 2005/084642 an apoprotein-cochelate composition is reported. In WO 2009/036460 modified human apolipoprotein A-I polypeptides and their uses are reported. Plant production of dimeric and/or oligomeric forms of human apolipoprotein A-I protein muteins is reported in WO 2008/017906. In WO 2007/137400 a method and compound for the treatment of valvular stenosis is reported. In WO 2006/100567 charged lipoprotein complexes and their uses are reported.

In US 2002/0156007 apolipoprotein analogues are reported. Tetranectin trimerising polypeptides are reported in US 2010/0028995. In J. Cardiovascular Pharmacol. (51 (2008) 170-177) report Graversen, J. H., et al., that the trimerization of apolipoprotein A-I retards plasma clearance and preserves anti-atherosclerotic properties. High density lipoprotein administration—a new therapeutic modality for the treatment of cardiovascular disease is reported by Sirtori, C. R., et al. (Curr. Med. Chem. Immunol. Endocrine Metabol. Agents 5 (2005) 321-333.

In WO 03/097696 methods and compositions for the treatment of ischemic reperfusion are reported. Nanoscale bound bilayers, methods of use and production are reported in WO 2009/097587. In WO 2007/098122 methods for the treatment of macular degeneration and related eye conditions are reported. Apolipoprotein Analogues are reported in WO 02/38609. In WO 2005/041866 pharmaceutical formulations are reported. Methods and dosing regimens for the treatment and prevention of coronary syndromes are reported. Gene therapy, approaches to supply apolipoprotein A-I agonists and their use to treat dislipidemic disorders are reported in WO 99/16409. In WO 2008/106660 isolated phospholipid-protein particles are reported. Method for the prevention and treatment of diastolic dysfunction employing an apolipoprotein (APO A-I) mimetic peptide/phospholipid complex are reported in WO 2010/083611. In WO 2008/156873 APO A-I peptide mimetics are reported. Encapsulated HDL mimetic peptides are reported in WO 2008/094905. In WO 98/56906 a trimerising module is reported.

SUMMARY OF THE INVENTION

Herein is reported as one aspect a tetranectin-apolipoprotein A-I with improved production properties, especially less side-product formation during cultivation and improved downstream processing properties.

Also herein is reported as one aspect a lipid particle comprising an apolipoprotein, a phosphatidylcholine and a further lipid, such as a phospholipid, lysophospholipid, galactocerebrosides, gangliosides, cerebrosides, glycerides, fatty acid, triglyceride, or steroid lipid, cholesterol, cholesterol esters or an analog or derivative thereof.

In one embodiment the lipid particle comprises only one type of apolipoprotein.

In one embodiment the lipid particle is consisting of one apolipoprotein, a phosphatidylcholine, a further lipid, and a detergent.

In one embodiment the further lipid is a phosphatidylcholine, wherein both of the phosphatidylcholines differ in one or two carboxylic acid moieties or carboxylic acid moiety derivatives which are esterified to the phosphoglycerol backbone of the phosphatidylcholine.

In a further embodiment the apolipoprotein is a human apolipoprotein A, in another embodiment a human apolipoprotein conjugated to a multimerization domain, and in still a further embodiment a tetranectin-apolipoprotein A-I. In one embodiment the apolipoprotein is selected from an apolipoprotein that has the amino acid sequence selected from SEQ ID NO: 01, 02, 06, 66, and 67, or is a variant thereof that has at least 70% sequence identity with the selected sequence.

In one embodiment the lipid particle comprises
a) an apolipoprotein,
b) a phosphatidylcholine, and
c) a further lipid,
wherein the apolipoprotein is a tetranectin-apolipoprotein A-I when the lipid is phosphatidylethanolamine, phosphatidylinositol, 1-palmitoyl-2-oleoyl-phosphatidyl serine, sphingosine I-phosphate, cholate, or dimyristoyl phosphatidylglycerol, and/or
wherein the apolipoprotein is not apolipoprotein A-I Milano when the lipid is a small alkyl chain phospholipid, phosphatidylglycerol, phosphatidylserine, phosphatidic acid, sphingomyelin, sphingolipid, ganglioside, cerebroside, lysolecithin, cephaline, cardiolipine, dicetylphosphate, or cholesterol.

In another embodiment the lipid particle comprises
a) an apolipoprotein,
b) a phosphatidylcholine, and
c) a further lipid,
wherein the apolipoprotein is a tetranectin-apolipoprotein A-I when the lipid is phosphatidylethanolamine, sphingosine I-phosphate, or cholate, and/or
wherein the apolipoprotein is not apolipoprotein A-I Milano when the lipid is a small alkyl chain phospholipid, sphingomyelin, sphingolipid, ganglioside, cerebroside, lysolecithin, cephaline, cardiolipine, dicetylphosphate, or cholesterol.

In one embodiment the further lipid is any lipid except phosphatidylglycerol, phosphatidylinositol, phosphatidylserine, phosphatidylglycerol and phosphatidic acid.

In one embodiment the further lipid is a second phosphatidylcholine. In one embodiment the phosphatidylcholine is POPC and the second phosphatidylcholine is DPPC.

In one embodiment the molar ratio of the phosphatidylcholine to the lipid is of from 99:1 to 1:99. In another embodiment the molar ratio of the phosphatidylcholine to the lipid is of from 99:1 to 10:90. In a further embodiment the molar ratio of the phosphatidylcholine to the lipid is of from 99:1 to 25:75. In another embodiment the apolipoprotein is non-covalently associated with the phosphatidylcholine and the lipid.

In one embodiment the molar ratio of POPC to DPPC is of from 99:1 to 1:99. In another embodiment the molar ratio of POPC to DPPC is of from 99:1 to 10:90. In a further embodiment the molar ratio of POPC to DPPC is of from 99:1 to 25:75.

In another embodiment the apolipoprotein is non-covalently associated with the POPC and DPPC.

In one embodiment the apolipoprotein is a multimer comprising three apolipoprotein monomers. In another embodiment the multimer comprises three tetranectin-apolipoprotein A-I monomers.

In one embodiment the lipid particle comprises less than 0.75% by weight detergent. In one embodiment the detergent is selected from sugar-based detergents, polyoxyalkylene-based detergents, bile-salt based detergents, synthetic detergents, and a combination thereof. In another embodiment the detergent is cholic acid.

In one embodiment the combined number of phosphatidylcholine molecules and lipid molecules per apolipoprotein monomer in the lipid particle is of from 40 to 120, in one embodiment of from 50 to 110, in one embodiment of from 54 to 102, in one embodiment of from 60 to 90, in one embodiment of from 65 to 70.

In one embodiment the combined number of phosphatidylcholine molecules and lipid molecules per apolipoprotein monomer in the lipid particle is of from 60 to 90. In one embodiment the combined number of phosphatidylcholine molecules and lipid molecules per apolipoprotein monomer in the lipid particle is of from 60 to 88. In one embodiment the combined number of phosphatidylcholine molecules and lipid molecules per apolipoprotein monomer in the lipid particle is of from 62 to 80. In one embodiment the combined number of phosphatidylcholine molecules and lipid molecules per apolipoprotein monomer in the lipid particle is of from 64 to 70. In one embodiment the combined number of phosphatidylcholine molecules and lipid molecules per apolipoprotein monomer in the lipid particle is about 66.

In one embodiment the combined number of POPC and DPPC molecules per apolipoprotein monomer in the lipid particle is of from 40 to 115, in a further embodiment of from 50 to 110, and in another embodiment of from 54 to 102.

In one embodiment the combined number of POPC and DPPC molecules per apolipoprotein monomer in the lipid particle is of from 60 to 90. In one embodiment the combined number of POPC and DPPC molecules per apolipoprotein monomer in the lipid particle is of from 60 to 88. In one embodiment the combined number of POPC and DPPC molecules per apolipoprotein monomer in the lipid particle is of from 62 to 80. In one embodiment the combined number of POPC and DPPC molecules per apolipoprotein monomer in the lipid particle is of from 64 to 70. In one embodiment the combined number of POPC and DPPC molecules per apolipoprotein monomer in the lipid particle is about 66.

In one embodiment the lipid particle is capable of binding to a receptor selected from the group consisting of cubilin, Scavenger receptor class B, type 1 (SR-BI), ATP-binding cassette 1 (ABCA-1), Lecithin-cholesterol acyltransferase (LCAT), Cholesteryl-ester transfer protein (CETP), or Phospholipid transfer protein (PLTP).

A further aspect as reported herein is a pharmaceutical composition comprising a lipid particle as reported herein, or a apolipoprotein A-I multimer as reported herein, or a tetranectin-apolipoprotein A-I as reported herein, or a fusion protein as reported herein.

One aspect as reported herein is a lipid particle as reported herein, or an apolipoprotein A-I multimer as reported herein, or a tetranectin-apolipoprotein A-I as reported herein, or a fusion protein as reported herein for use as a medicament.

One aspect as reported herein is the use of a lipid particle as reported herein, or a apolipoprotein A-I multimer as reported herein, or a tetranectin-apolipoprotein A-I as reported herein, or a fusion protein as reported herein for the manufacture of a medicament.

One aspect as reported herein is the use of a lipid particle as reported herein, or a apolipoprotein A-I multimer as reported herein, or a tetranectin-apolipoprotein A-I as reported herein, or a fusion protein as reported herein for the manufacture of a medicament
for secondary prevention in patients with an acute coronary syndrome, or
for the prevention or treatment of atherosclerosis wherein a lipid particle as reported herein, or a apolipoprotein A-I multimer as reported herein, or a tetranectin-apolipoprotein A-I as reported herein, or a fusion protein as reported herein is comprised in an amount sufficient to induce reverse cholesterol transport and/or plaques pacification in a subject, or
for inducing reverse cholesterol transport and/or plaques pacification, or for cleaning/dissolution/stabilization of atherosclerotic plaques in blood vessels of a subject or for redistributing cholesterol from the wall of arteries to the liver of a subject, or for preventing or treating a valvular stenosis in a subject, or
for increasing the number of HDL particles in a subject, or
for initiation of reverse cholesterol transport in a subject, or
for the removal of endotoxins, or
for the prevention of septic shock
for the treatment of angina pectoris, or
for the treatment of myocardial infarction, or
for the treatment of unstable angina pectoris, or
for the treatment of arterial stenoses such as peripheral artery diseases (PAD), carotis stenosis, cerebral arterial stenosis or coronary arterial stenosis, or
for the treatment of vascular demencia, or
for the treatment of amaurosis fugax.

One aspect as reported herein is the use of a lipid particle as reported herein, or a apolipoprotein A-I multimer as reported herein, or a tetranectin-apolipoprotein A-I as reported herein, or a fusion protein as reported herein in the manufacture of a medicament.

One aspect as reported herein is a method for the manufacture of a medicament
for secondary prevention in patients with an acute coronary syndrome, or
for the prevention or treatment of atherosclerosis wherein a lipid particle as reported herein, or a apolipoprotein A-I multimer as reported herein, or a tetranectin-apolipoprotein A-I as reported herein, or a fusion protein as reported herein is comprised in an amount sufficient to induce reverse cholesterol transport and/or plaques pacification in a subject, or
for inducing reverse cholesterol transport and/or plaques pacification, or
for cleaning/dissolution/stabilization of atherosclerotic plaques in blood vessels of a subject or for redistributing cholesterol from the wall of arteries to the liver of a subject, or
for preventing or treating a valvular stenosis in a subject, or
for increasing the number of HDL particles in a subject, or
for initiation of reverse cholesterol transport in a subject, or
for the removal of endotoxins, or
for the prevention of septic shock
for the treatment of angina pectoris, or
for the treatment of myocardial infarction, or
for the treatment of unstable angina pectoris, or
for the treatment of arterial stenoses such as peripheral artery diseases (PAD), carotis stenosis, cerebral arterial stenosis or coronary arterial stenosis, or
for the treatment of vascular demencia, or
for the treatment of amaurosis fugax.

One aspect as reported herein is a method for
secondary prevention in patients with an acute coronary syndrome, or
the prevention or treatment of atherosclerosis wherein a lipid particle as reported herein, or a apolipoprotein A-I multimer as reported herein, or a tetranectin-apolipoprotein A-I as reported herein, or a fusion protein as reported herein is comprised in an amount sufficient to induce reverse cholesterol transport and/or plaques pacification in a subject, or
for inducing reverse cholesterol transport and/or plaques pacification, or
for cleaning/dissolution/stabilization of atherosclerotic plaques in blood vessels of a subject or for redistributing cholesterol from the wall of arteries to the liver of a subject, or
for preventing or treating a valvular stenosis in a subject, or
for increasing the number of HDL particles in a subject, or
for initiation of reverse cholesterol transport in a subject, or
for the removal of endotoxins, or
for the prevention of septic shock
for the treatment of angina pectoris, or
for the treatment of myocardial infarction, or
for the treatment of unstable angina pectoris, or
for the treatment of arterial stenoses such as peripheral artery diseases (PAD), carotis stenosis, cerebral arterial stenosis or coronary arterial stenosis, or
for the treatment of vascular demencia, or
for the treatment of amaurosis fugax.

One aspect as reported herein is a lipid particle as reported herein, or a apolipoprotein A-I multimer as reported herein, or a tetranectin-apolipoprotein A-I as reported herein, or a fusion protein as reported herein for use in treating
acute coronary syndrome, or
atherosclerosis, or
atherosclerotic plaques in blood vessels of a subject, or
valvular stenosis in a subject, or
septic shock, or
angina pectoris, or
myocardial infarction, or
unstable angina pectoris, or
arterial stenoses, or
peripheral artery diseases (PAD), or
carotis stenosis, or
cerebral arterial stenosis, or
coronary arterial stenosis, or
vascular demencia, or
amaurosis fugax.

One aspects as reported herein is a lipid particle as reported herein, or a apolipoprotein A-I multimer as reported herein, or a tetranectin-apolipoprotein A-I as reported herein, or a fusion protein as reported herein for use in
inducing reverse cholesterol transport, or
inducing plaques pacification, or
cleaning or dissoluting or stabilizing atherosclerotic plaques, or
redistributing cholesterol from the wall of arteries to the liver, or
increasing the number of HDL particles, or
removal of endotoxins.

One aspect as reported herein is a method of treating an individual having acute coronary syndrome, or atherosclerosis, or atherosclerotic plaques in blood vessels, or valvular stenosis, or septic shock, or angina pectoris, or myocardial infarction, or unstable angina pectoris, or arterial stenoses, or peripheral artery diseases (PAD), or carotis stenosis, or cerebral arterial stenosis, or coronary arterial stenosis, or vascular demencia, or amaurosis fugax comprising administering to the individual an effective amount of a lipid particle as reported herein, or a apolipoprotein A-I multimer as reported herein, or a tetranectin-apolipoprotein A-I as reported herein, or a fusion protein as reported herein.

One aspect as reported herein is a method of inducing reverse cholesterol transport, or inducing plaques pacification, or cleaning or dissoluting or stabilizing atherosclerotic plaques, or redistributing cholesterol from the wall of arteries to the liver, or increasing the number of HDL particles, or removing endotoxins in an individual comprising administering to the individual an effective amount of a lipid particle as reported herein, or a apolipoprotein A-I multimer as reported herein, or a tetranectin-apolipoprotein A-I as reported herein, or a fusion protein as reported herein to induce reverse cholesterol transport, or to induce plaques pacification, or to clean or dissolute or stabilize atherosclerotic plaques, or to redistribute cholesterol from the wall of arteries to the liver, or to increase the number of HDL particles, or to remove endotoxins.

In one embodiment the non-normal lipid level is in a body fluid. In another embodiment the body fluid is whole blood or blood serum.

In one embodiment the non-normal lipid level is an increased cholesterol level.

In one embodiment the lipid containing deposition is a plaque in a blood vessel.

In one embodiment the disease is a cardiovascular disease.

One aspect as reported herein is a method of treating a disease or condition characterized by non-normal lipid levels or a lipid containing deposition within body components comprising
  i) administering a therapeutically effective amount of a lipid particle as reported herein to a subject in need of a treatment or an artificial system, and
  ii) optionally monitoring the lipid level or the lipid containing deposition of a subject for a change.

One aspect as reported herein is a method for secondary prevention in patients with an acute coronary syndrome comprising administering to a subject in need thereof a lipid particle as reported herein, or a apolipoprotein A-I multimer as reported herein, or a tetranectin-apolipoprotein A-I as reported herein, or a fusion protein as reported herein.

One aspect as reported herein is a diagnostic composition comprising a lipid particle as reported herein, or a apolipoprotein A-I multimer as reported herein, or a tetranectin-apolipoprotein A-I as reported herein, or a fusion protein as reported herein wherein the apolipoprotein is labeled allowing for the detection of the labeled apolipoprotein or lipid particle within a sample or subject.

One aspect as reported herein is the use of a lipid particle as reported herein, or an apolipoprotein A-I multimer as reported herein, or a tetranectin-apolipoprotein A-I as reported herein, or a fusion protein as reported herein for diagnosis.

One aspect as reported herein is the use of a lipid particle as reported herein for the prevention or treatment of a subject suffering from a disease or condition characterized by the presence of a non-normal lipid level or a lipid containing deposition.

One aspect as reported herein is a nucleic acid encoding a tetranectin-apolipoprotein A-I as reported herein, or a fusion protein as reported herein as well as a cell comprising a nucleic acid as reported herein.

One aspect as reported herein is a tetranectin-apolipoprotein A-I that has the amino acid sequence of SEQ ID NO: 01, or SEQ ID NO: 02, or SEQ ID NO: 66, or SEQ ID NO: 67, or a pharmaceutically acceptable salt thereof, or a prodrug thereof. In one embodiment the tetranectin-apolipoprotein A-I has the amino acid sequence of SEQ ID NO: 01, or SEQ ID NO: 02, or SEQ ID NO: 66, or SEQ ID NO: 67 with one or more conservative amino acid modifications. In one embodiment the tetranectin-apolipoprotein A-I has the amino acid sequence of SEQ ID NO: 01, or SEQ ID NO: 02, or SEQ ID NO: 66, or SEQ ID NO: 67 wherein one or more amino acids are substituted, added or deleted.

One aspect as reported herein is a tetranectin-apolipoprotein A-I that has an amino acid sequence of SEQ ID NO: 01, or SEQ ID NO: 02, or SEQ ID NO: 66, or SEQ ID NO: 67. In one embodiment the amino acid sequence has at least 70% sequence identity with an amino acid sequence of SEQ ID NO: 01, or SEQ ID NO: 02, or SEQ ID NO: 66, or SEQ ID NO: 67.

In one embodiment the tetranectin-apolipoprotein A-I monomer, or the tetranectin-apolipoprotein A-I trimer is capable of binding to a receptor selected from the group consisting of cubilin, Scavenger receptor class B, type 1 (SR-BI), ATP-binding cassette 1 (ABCA-1), Lecithin-cholesterol acyltransferase (LCAT), Cholesteryl-ester transfer protein (CETP), or Phospholipid transfer protein (PLTP).

One aspect as reported herein is a multimer comprising three tetranectin-apolipoprotein A-I monomers, wherein the tetranectin-apolipoprotein A-I monomers are not covalently bound to each other.

One aspect as reported herein is a fusion protein comprising the amino acid sequence of SEQ ID NO: 01, SEQ ID NO: 02, or SEQ ID NO: 66, a nucleic acid encoding the fusion protein, and a plasmid comprising the nucleic acid encoding the fusion protein.

In one embodiment the fusion protein comprises in N- to C-terminal direction
  the amino acid methionine (M),
  a fragment of an interferon sequence that has the amino acid sequence of CDLPQTHSL (SEQ ID NO: 55),
  a GS linker,
  a hexa-histidine tag that has the amino acid sequence of HHHHHH (SEQ ID NO: 56),
  a GS linker,
  an IgA protease cleavage site that has the amino acid sequence of VVAPPAP (SEQ ID NO: 60), and
  a tetranectin-apolipoprotein A-I that has the amino acid sequence of SEQ ID NO: 02.

In one embodiment the fusion protein has the amino acid sequence of SEQ ID NO: 57.

One aspect as reported herein is a cell comprising a nucleic acid encoding the fusion protein as reported herein. In one embodiment the cell is selected from the $E.\ coli$ strains such as CSPZ-2, K12 strain 294 (ATCC 31446), B, X 1776 (ATCC 31537), W3110 (ATCC 273325), BL21, RM_82, SCS_110, G, XL-1_F-, SE_13009, LA_5709, C 600, CSH_1, TG_1, UT400, and UT5600.

One aspect as reported herein is a lipid particle comprising
  a) a tetranectin-apolipoprotein A-I that has an amino acid sequence selected from the amino acid sequences of SEQ ID NO: 01, SEQ ID NO: 02, SEQ ID NO: 66, and SEQ ID NO: 67,
  b) a phosphatidylcholine, and
  c) a lipid.

In one embodiment the lipid is selected from phosphatidylethanolamine, phosphatidylinositol, 1-palmitoyl-2-oleoyl-phosphatidyl serine, sphingosine I-phosphate, cholate, or dimyristoyl phosphatidylglycerol.

In one embodiment the lipid is any lipid except phosphatidylglycerol, phosphatidylinositol, phosphatidylserine, phosphatidylglycerol and phosphatidic acid.

In one embodiment the lipid particle comprises
  a) a tetranectin-apolipoprotein A-I that has an amino acid sequence selected from the amino acid sequences of SEQ ID NO: 01, SEQ ID NO: 02, SEQ ID NO: 66, and SEQ ID NO: 67,
  b) a first phosphatidylcholine, and
  c) a second phosphatidylcholine.

In one embodiment the first phosphatidylcholine is POPC and the second phosphatidylcholine is DPPC. In one embodiment the molar ratio of the first phosphatidylcholine to the second phosphatidylcholine for producing the lipid particle is of from 99:1 to 1:99. In one embodiment the molar ratio of the first phosphatidylcholine to the second phosphatidylcholine for producing the lipid particle is of from 99:1 to 10:90. In one embodiment the molar ratio of the first phosphatidylcholine to the second phosphatidylcholine for producing the lipid particle is of from 99:1 to 25:75. In one embodiment the molar ratio of the first phosphatidylcholine to the second phosphatidylcholine for producing the lipid particle is of from 99:1 to 50:50. In one embodiment the molar ratio of the first phosphatidylcholine to the second phosphatidylcholine for producing the lipid particle is about 75:25.

In one embodiment the first phosphatidylcholine is POPC and the second phosphatidylcholine is DPPC. In one embodiment the molar ratio of the first phosphatidylcholine to the second phosphatidylcholine in the lipid particle is of from 99:1 to 1:99. In one embodiment the molar ratio of the first phosphatidylcholine to the second phosphatidylcholine in the lipid particle is of from 99:1 to 10:90. In one embodiment the molar ratio of the first phosphatidylcholine to the second phosphatidylcholine in the lipid particle is of from 99:1 to 25:75. In one embodiment the molar ratio of the first phosphatidylcholine to the second phosphatidylcholine in the lipid particle is of from 99:1 to 50:50. In one embodiment the molar ratio of the first phosphatidylcholine to the second phosphatidylcholine in the lipid particle is about 75:25.

In one embodiment the apolipoprotein is non-covalently associated with the first phosphatidylcholine and the lipid. In one embodiment the tetranectin-apolipoprotein A-I is non-covalently associated with the first phosphatidylcholine and the second phosphatidylcholine.

In one embodiment the tetranectin-apolipoprotein A-I is a multimer comprising three tetranectin-apolipoprotein A-I monomers.

In one embodiment the lipid particle comprises less than 0.75% by weight detergent. In one embodiment the detergent is selected from sugar-based detergents, polyoxyalkylene-based detergents, bile-salt based detergents, synthetic detergents and a combination thereof. In one embodiment the detergent is cholic acid or a Zwittergent.

In one embodiment the combined number of phospholipid molecules per apolipoprotein monomer in the lipid particle is of from 40 to 120, in a further embodiment of from 50 to 110, and in another embodiment of from 54 to 102. In one embodiment the phospholipid is a phosphatidylcholine.

One aspect as reported herein is a pharmaceutical composition comprising a lipid particle as reported herein, or a apolipoprotein A-I multimer as reported herein, or a tetranectin-apolipoprotein A-I as reported herein, or a fusion protein as reported herein.

One aspect as reported herein is a lipid particle as reported herein, or an apolipoprotein A-I multimer as reported herein, or a tetranectin-apolipoprotein A-I as reported herein, or a fusion protein as reported herein for use as a medicament.

One aspect as reported herein is the use of a lipid particle as reported herein, or a apolipoprotein A-I multimer as reported herein, or a tetranectin-apolipoprotein A-I as reported herein, or a fusion protein as reported herein for the manufacture of a medicament
- for prevention of secondary Major Adverse CV Events (MACE),
- for secondary prevention in patients with an acute coronary syndrome, or
- for the prevention or treatment of atherosclerosis wherein a lipid particle as reported herein, or a apolipoprotein A-I multimer as reported herein, or a tetranectin-apolipoprotein A-I as reported herein, or a fusion protein as reported herein is comprised in an amount sufficient to induce reverse cholesterol transport and/or plaques pacification in a subject, or
- for inducing reverse cholesterol transport and/or plaques pacification, or
- for cleaning/dissolution/stabilization of atherosclerotic plaques in blood vessels of a subject or for redistributing cholesterol from the wall of arteries to the liver of a subject, or
- for preventing or treating a valvular stenosis in a subject, or
- for increasing the number of HDL particles in a subject, or
- for initiation of reverse cholesterol transport in a subject, or
- for the removal of endotoxins, or
- for the prevention of septic shock
- for the treatment of angina pectoris, or
- for the treatment of myocardial infarction, or
- for the treatment of unstable angina pectoris, or
- for the treatment of arterial stenoses such as peripheral artery diseases (PAD), carotis stenosis, cerebral arterial stenosis or coronary arterial stenosis, or
- for the treatment of vascular demencia, or
- for the treatment of amaurosis fugax.

One aspect as reported herein is the use of a lipid particle as reported herein, or a apolipoprotein A-I multimer as reported herein, or a tetranectin-apolipoprotein A-I as reported herein, or a fusion protein as reported herein in the manufacture of a medicament.

One aspect as reported herein is a method for the manufacture of a medicament
- for secondary prevention in patients with an acute coronary syndrome, or
- for prevention of secondary Major Adverse CV Events (MACE), or
- for the prevention or treatment of atherosclerosis wherein a lipid particle as reported herein, or a apolipoprotein A-I multimer as reported herein, or a tetranectin-apolipoprotein A-I as reported herein, or a fusion protein as reported herein is comprised in an amount sufficient to induce reverse cholesterol transport and/or plaques pacification in a subject, or
- for inducing reverse cholesterol transport and/or plaques pacification, or
- for cleaning/dissolution/stabilization of atherosclerotic plaques in blood vessels of a subject or for redistributing cholesterol from the wall of arteries to the liver of a subject, or
- for preventing or treating a valvular stenosis in a subject, or
- for increasing the number of HDL particles in a subject, or
- for initiation of reverse cholesterol transport in a subject, or
- for the removal of endotoxins, or
- for the prevention of septic shock
- for the treatment of angina pectoris, or
- for the treatment of myocardial infarction, or
- for the treatment of unstable angina pectoris, or
- for the treatment of arterial stenoses such as peripheral artery diseases (PAD), carotis stenosis, cerebral arterial stenosis or coronary arterial stenosis, or
- for the treatment of vascular demencia, or
- for the treatment of amaurosis fugax.

One aspect as reported herein is a method for
- secondary prevention in patients with an acute coronary syndrome, or
- for prevention of secondary Major Adverse CV Events (MACE), or
- the prevention or treatment of atherosclerosis wherein a lipid particle as reported herein, or a apolipoprotein A-I multimer as reported herein, or a tetranectin-apolipoprotein A-I as reported herein, or a fusion protein as reported herein is comprised in an amount sufficient to induce reverse cholesterol transport and/or plaques pacification in a subject, or for inducing reverse cholesterol transport and/or plaques pacification, or for cleaning/dissolution/stabilization of atherosclerotic plaques in blood vessels of a subject or for redistributing cholesterol from the wall of arteries to the liver of a subject, or for preventing or treating a valvular stenosis in a subject, or for increasing the number of HDL particles in a subject, or for initiation of reverse cholesterol transport in a subject, or for the removal of endotoxins, or for the prevention of septic shock for the treatment of angina pectoris, or for the treatment of myocardial infarction, or for the treatment of unstable angina pectoris, or for the treatment of arterial stenoses such as peripheral artery diseases (PAD), carotis stenosis, cerebral arterial stenosis or coronary arterial stenosis, or for the treatment of vascular demencia, or for the treatment of amaurosis fugax.

One aspect as reported herein is a lipid particle as reported herein, or a apolipoprotein A-I multimer as reported herein, or a tetranectin-apolipoprotein A-I as reported herein, or a fusion protein as reported herein for use in treating or preventing acute coronary syndrome, or secondary Major Adverse CV Events (MACE), or atherosclerosis, or atherosclerotic plaques in blood vessels of a subject, or valvular stenosis in a subject, or septic shock, or angina pectoris, or myocardial infarction, or unstable angina pectoris, or arterial stenoses, or peripheral artery diseases (PAD), or carotis stenosis, or cerebral arterial stenosis, or coronary arterial stenosis, or vascular demencia, or amaurosis fugax.

One aspect as reported herein is a lipid particle as reported herein, or a apolipoprotein A-I multimer as reported herein, or a tetranectin-apolipoprotein A-I as reported herein, or a fusion protein as reported herein for use in inducing reverse cholesterol transport, or inducing plaques pacification, or cleaning or dissolving or stabilizing atherosclerotic plaques, or redistributing cholesterol from the wall of arteries to the liver, or increasing the number of HDL particles, or removal of endotoxins.

One aspect as reported herein is a method for prevention of secondary Major Adverse CV Events (MACE) when applied post-intervention in patients presenting at the ER with an acute CV event, or a method for treating an individual having acute coronary syndrome, or having atherosclerosis, or having atherosclerotic plaques in blood vessels, or having valvular stenosis, or having septic shock, or having angina pectoris, or having myocardial infarction, or having unstable angina pectoris, or having arterial stenoses, or having peripheral artery diseases (PAD), or having carotis stenosis, or having cerebral arterial stenosis, or having coronary arterial stenosis, or having vascular demencia, or having amaurosis fugax comprising administering to the individual an effective amount of a lipid particle as reported herein, or a multimer as reported herein, or a fusion protein as reported herein, or a tetranectin-apolipoprotein A-I as reported herein.

One aspect as reported herein is a method of inducing reverse cholesterol transport, or inducing plaques pacification, or cleaning or dissoluting or stabilizing atherosclerotic plaques, or redistributing cholesterol from the wall of arteries to the liver, or increasing the number of HDL particles, or removing endotoxins in an individual comprising administering to the individual an effective amount of a lipid particle as reported herein, or a multimer as reported herein, or a fusion protein as reported herein, or a tetranectin-apolipoprotein A-I as reported herein to induce reverse cholesterol transport, or to induce plaques pacification, or to clean or dissolute or stabilize atherosclerotic plaques, or to redistribute cholesterol from the wall of arteries to the liver, or to increase the number of HDL particles, or to remove endotoxins.

In one embodiment the non-normal lipid level is in a body fluid. In another embodiment the body fluid is whole blood or blood serum.

In one embodiment the non-normal lipid level is an increased cholesterol level.

In one embodiment the lipid containing deposition is a plaque in a blood vessel.

In one embodiment the disease is a cardiovascular disease.

One aspect as reported herein is a method of treating a disease or condition characterized by non-normal lipid levels or a lipid containing deposition within body components comprising i) administering a therapeutically effective amount of a lipid particle as reported herein to a subject in need of a treatment or an artificial system, and ii) optionally monitoring the lipid level or the lipid containing deposition of a subject for a change.

One aspect as reported herein is a method for secondary prevention in patients with an acute coronary syndrome comprising administering to a subject in need thereof a lipid particle as reported herein, or a multimer as reported herein, or a fusion protein as reported herein, or a tetranectin-apolipoprotein A-I as reported herein.

One aspect as reported herein is a method for prevention of secondary Major Adverse CV Events (MACE) comprising administering post-intervention to a subject in need thereof a lipid particle as reported herein, or a multimer as reported herein, or a fusion protein as reported herein, or a tetranectin-apolipoprotein A-I as reported herein wherein the subject presents at the ER with an acute CV event, One aspect as reported herein is a diagnostic composition comprising a lipid particle as reported herein, or a multimer as reported herein, or a fusion protein as reported herein, or a tetranectin-apolipoprotein A-I as reported herein, wherein the apolipoprotein is labeled allowing for the detection of the labeled apolipoprotein or lipid particle within a sample or subject.

One aspect as reported herein is the use of a lipid particle as reported herein for diagnosis.

One aspect as reported herein is the use of a lipid particle as reported herein for the prevention or treatment of a subject suffering from a disease or condition characterized by the presence of a non-normal lipid level or a lipid containing deposition.

One aspect as reported herein is a nucleic acid encoding a tetranectin-apolipoprotein A-I as reported herein, or a fusion protein as reported herein as well as a cell comprising a nucleic acid as reported herein.

One aspect as reported herein is a polypeptide that has an amino acid sequence selected from: SEQ ID NO: 01; SEQ ID NO: 02; SEQ ID NO: 06; SEQ ID NO: 66; and SEQ ID NO: 67; or is a variant thereof that has at least 70% sequence identity with the amino acid sequence of SEQ ID NO: 01; SEQ ID NO: 02; SEQ ID NO: 06; SEQ ID NO: 66; or SEQ ID NO: 67.

One aspect as reported herein is a polypeptide that has the amino acid sequence of SEQ ID NO: 01 or is a variant thereof that has at least 70% sequence identity with the amino acid sequence of SEQ ID NO: 01.

One aspect as reported herein is a polypeptide that has the amino acid sequence of SEQ ID NO: 02 or is a variant thereof that has at least 70% sequence identity with the amino acid sequence of SEQ ID NO: 02.

One aspect as reported herein is a polypeptide that has the amino acid sequence of SEQ ID NO: 06 or is a variant thereof that has at least 70% sequence identity with the amino acid sequence of SEQ ID NO: 06.

One aspect as reported herein is a polypeptide that has the amino acid sequence of SEQ ID NO: 66 or is a variant thereof that has at least 70% sequence identity with the amino acid sequence of SEQ ID NO: 66.

One aspect as reported herein is a polypeptide that has the amino acid sequence of SEQ ID NO: 67 or is a variant thereof that has at least 70% sequence identity with the amino acid sequence of SEQ ID NO: 67.

One aspect as reported herein is a lipid particle comprising an apolipoprotein A-I or a variant thereof, and
1-palmitoyl-2-oleoyl-phosphatidyl choline and 1,2-dipalmitoyl-phosphatidyl choline,
wherein the number of phospholipid molecules per apolipoprotein monomer in the lipid particle is of from 50 to 105, and wherein the apolipoprotein A-I has an amino acid sequence selected from SEQ ID NO: 01; SEQ ID NO: 02; SEQ ID NO: 06; SEQ ID NO: 66; and SEQ ID NO: 67.

In one embodiment the number phospholipid molecules per apolipoprotein monomer in the lipid particle is of from 60 to 88. In one embodiment the number phospholipid molecules per apolipoprotein monomer in the lipid particle is of from 62 to 80. In one embodiment the number phospholipid molecules per apolipoprotein monomer in the lipid particle is of from 64 to 70. In one embodiment the number phospholipid molecules per apolipoprotein monomer in the lipid particle is about 66.

One aspect as reported herein is a lipid particle comprising an apolipoprotein A-I or a variant thereof, and
1-palmitoyl-2-oleoyl-phosphatidyl choline and 1,2-dipalmitoyl-phosphatidyl choline,
wherein the number of phospholipid molecules per apolipoprotein monomer in the lipid particle is of from 50 to 90, and wherein the apolipoprotein A-I has the amino acid sequence of SEQ ID NO: 01.

In one embodiment the number phospholipid molecules per apolipoprotein monomer in the lipid particle is of from 60 to 88. In one embodiment the number phospholipid molecules per apolipoprotein monomer in the lipid particle is of from 62 to 80. In one embodiment the number phospholipid molecules per apolipoprotein monomer in the lipid particle is of from 64 to 70. In one embodiment the number phospholipid molecules per apolipoprotein monomer in the lipid particle is about 66.

One aspect as reported herein is a lipid particle comprising an apolipoprotein A-I or a variant thereof, and
1-palmitoyl-2-oleoyl-phosphatidyl choline and 1,2-dipalmitoyl-phosphatidyl choline,
wherein the number of phospholipid molecules per apolipoprotein monomer in the lipid particle is of from 60 to 90, and wherein the apolipoprotein A-I has the amino acid sequence of SEQ ID NO: 02.

In one embodiment the number phospholipid molecules per apolipoprotein monomer in the lipid particle is of from 60 to 88. In one embodiment the number phospholipid molecules per apolipoprotein monomer in the lipid particle is of from 62 to 80. In one embodiment the number phospholipid molecules per apolipoprotein monomer in the lipid particle is of from 64 to 70. In one embodiment the number phospholipid molecules per apolipoprotein monomer in the lipid particle is about 66.

One aspect as reported herein is a lipid particle comprising an apolipoprotein A-I or a variant thereof, and
1-palmitoyl-2-oleoyl-phosphatidyl choline and 1,2-dipalmitoyl-phosphatidyl choline,
wherein the number of phospholipid molecules per apolipoprotein monomer in the lipid particle is of from 60 to 90, and wherein the apolipoprotein A-I has the amino acid sequence of SEQ ID NO: 06.

In one embodiment the number phospholipid molecules per apolipoprotein monomer in the lipid particle is of from 60 to 88. In one embodiment the number phospholipid molecules per apolipoprotein monomer in the lipid particle is of from 62 to 80. In one embodiment the number phospholipid molecules per apolipoprotein monomer in the lipid particle is of from 64 to 70. In one embodiment the number phospholipid molecules per apolipoprotein monomer in the lipid particle is about 66.

One aspect as reported herein is a lipid particle comprising an apolipoprotein A-I or a variant thereof, and
1-palmitoyl-2-oleoyl-phosphatidyl choline and 1,2-dipalmitoyl-phosphatidyl choline,
wherein the number of phospholipid molecules per apolipoprotein monomer in the lipid particle is of from 60 to 90, and wherein the apolipoprotein A-I has the amino acid sequence of SEQ ID NO: 66.

In one embodiment the number phospholipid molecules per apolipoprotein monomer in the lipid particle is of from 60 to 88. In one embodiment the number phospholipid molecules per apolipoprotein monomer in the lipid particle is of from 62 to 80. In one embodiment the number phospholipid molecules per apolipoprotein monomer in the lipid particle is of from 64 to 70. In one embodiment the number phospholipid molecules per apolipoprotein monomer in the lipid particle is about 66.

One aspect as reported herein is a lipid particle comprising an apolipoprotein A-I or a variant thereof, and
1-palmitoyl-2-oleoyl-phosphatidyl choline and 1,2-dipalmitoyl-phosphatidyl choline,
wherein the number of phospholipid molecules per apolipoprotein monomer in the lipid particle is of from 60 to 90, and wherein the apolipoprotein A-I has the amino acid sequence of SEQ ID NO: 67.

In one embodiment the number phospholipid molecules per apolipoprotein monomer in the lipid particle is of from 60 to 88. In one embodiment the number phospholipid molecules per apolipoprotein monomer in the lipid particle is of from 62 to 80. In one embodiment the number phospholipid molecules per apolipoprotein monomer in the lipid particle is of from 64 to 70. In one embodiment the number phospholipid molecules per apolipoprotein monomer in the lipid particle is about 66.

DESCRIPTION OF THE SEQUENCE LISTINGS

SEQ ID NO: 01 Tetranectin-apolipoprotein A-I (1).
SEQ ID NO: 02 Tetranectin-apolipoprotein A-I (2).

SEQ ID NO: 03 Excised peptide.
SEQ ID NO: 04 Apolipoprotein A-I mimetic (1).
SEQ ID NO: 05 Apolipoprotein A-I mimetic (2).
SEQ ID NO: 06 Human apolipoprotein A-I.
SEQ ID NO: 07 Human apolipoprotein A-II.
SEQ ID NO: 08 Human apolipoprotein A-IV.
SEQ ID NO: 09 Human apolipoprotein A-V.
SEQ ID NO: 10 Human apolipoprotein C-I.
SEQ ID NO: 11 Human apolipoprotein C-II.
SEQ ID NO: 12 Human apolipoprotein C-III.
SEQ ID NO: 13 Human apolipoprotein C-IV.
SEQ ID NO: 14 Human apolipoprotein D.
SEQ ID NO: 15 Human apolipoprotein E.
SEQ ID NO: 16 Human apolipoprotein F.
SEQ ID NO: 17 Human apolipoprotein H.
SEQ ID NO: 18 Human apolipoprotein L-I.
SEQ ID NO: 19 Human apolipoprotein L-II.
SEQ ID NO: 20 Human apolipoprotein L-III.
SEQ ID NO: 21 Human apolipoprotein L-IV.
SEQ ID NO: 22 Human apolipoprotein L-V.
SEQ ID NO: 23 Human apolipoprotein L-VI.
SEQ ID NO: 24 Human apolipoprotein M.
SEQ ID NO: 25 Human apolipoprotein O.
SEQ ID NO: 26 Human apolipoprotein OL.
SEQ ID NO: 27 Human apolipoprotein clus.
SEQ ID NO: 28 to 52 Apolipoprotein.
SEQ ID NO: 53 Human tetranectin trimerization domain.
SEQ ID NO: 54 Shortened human tetranectin trimerization domain.
SEQ ID NO: 55 Human interferon fragment.
SEQ ID NO: 56 Hexahistidine tag.
SEQ ID NO: 57 Fusion protein.
SEQ ID NO: 58 Primer N1.
SEQ ID NO: 59 Primer N2.
SEQ ID NO: 60 to 65 IgA protease cleavage site.
SEQ ID NO: 66 Tetranectin-apolipoprotein A-I.
SEQ ID NO: 67 Tetranectin-apolipoprotein A-I with his-tag.
SEQ ID NO: 68 to 105 Linker.

DESCRIPTION OF THE FIGURES

FIG. 1 Results of in vivo rabbit studies conducted with five lipid particles differing in their lipid composition. Top: cholesterol mobilization and, thus, efficacy could be shown for all prepared batches. Bottom: Increase of liver enzyme was noticed for lipid particles generated by the use of DPPC as single phospholipid.

FIG. 9 Comparison of liver enzyme release by different compositions comprising apolipoprotein according to the invention in mice after a single i.v. injection of 100 mg/kg.

FIG. 22 SEC-MALLS protein conjugate analysis of lipid particle of tetranectin-apolipoprotein A-I using POPC. Upper: lipid particle formed from native tetranectin-apolipoprotein A-I; lower: lipid particle formed from denatured tetranectin-apolipoprotein A-I.

FIG. 23 Results of in vivo rabbit studies performed with tetranectin-apolipoprotein A-I lipidated with DMPC (1:100) (di myristoyl phosphatidylcholine) (a) and not lipidated in PBS (b).

DETAILED DESCRIPTION OF THE INVENTION

Definitions

Figure 2:
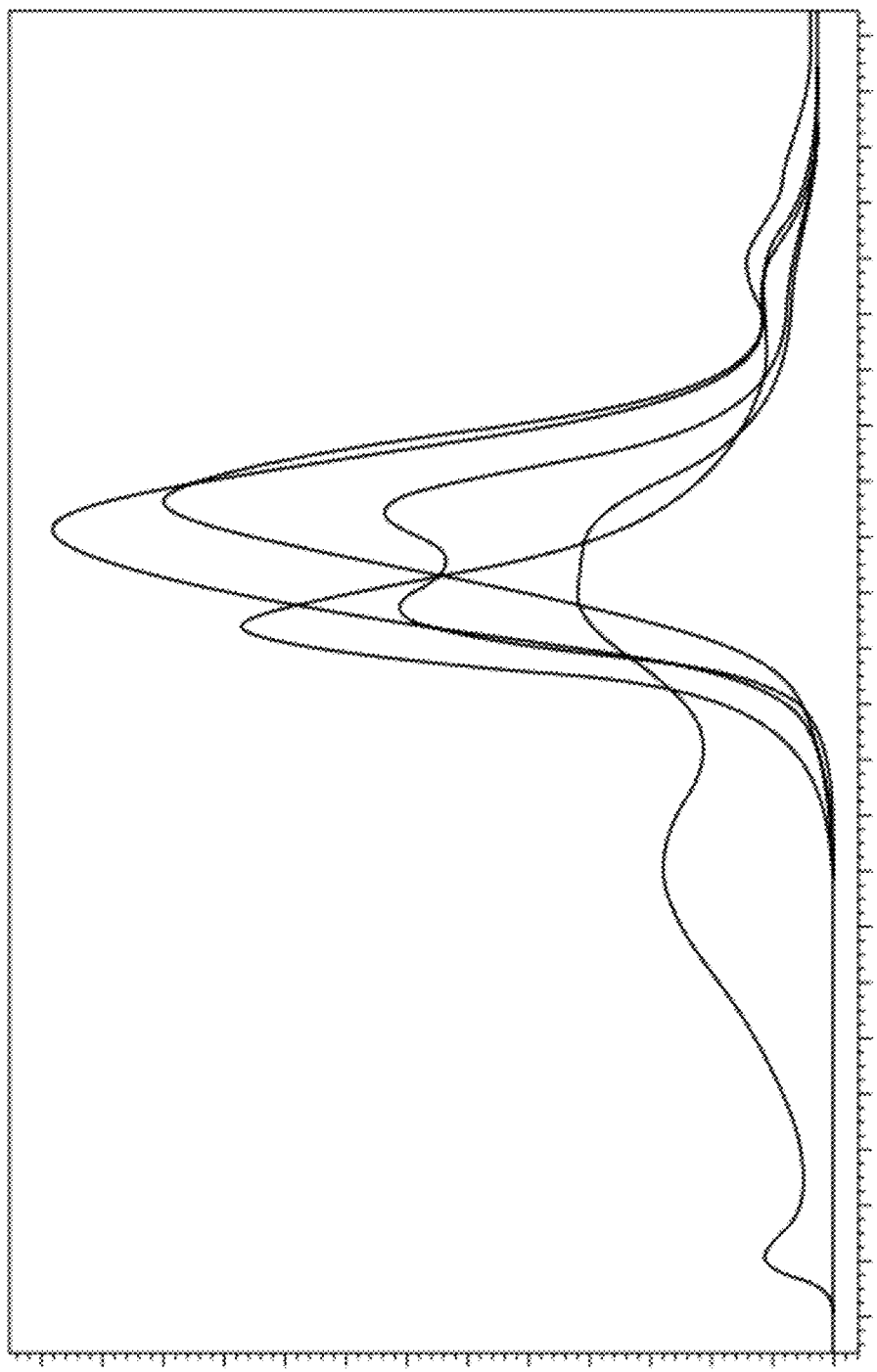
FIG. 2 SEC-MALLS analysis of lipid particles of POPC and apolipoprotein according to the current invention; molar ratios 1:20 to 1:160.

The term "apolipoprotein" denotes a protein that is comprised in a lipid or lipoprotein particle, respectively.

The term "apolipoprotein A-I" denotes an amphiphilic, helical polypeptide with protein-lipid and protein-protein interaction properties. Apolipoprotein A-I is synthesized by the liver and small intestine as prepro-apolipoprotein of 267 amino acid residues which is secreted as a pro-apolipoprotein that is cleaved to the mature polypeptide having 243 amino acid residues. Apolipoprotein A-I is consisting of 6 to 8 different amino acid repeats consisting each of 22 amino acid residues separated by a linker moiety which is often proline, and in some cases consists of a stretch made up of several residues. An exemplary human apolipoprotein A-I amino acid sequence is reported in GenPept database entry NM-000039 or database entry X00566; GenBank NP-000030.1 (gi 4557321). Of human apolipoprotein A-I (SEQ ID NO: 06) naturally occurring variants exist, such as P27H, P27R, P28R, R34L, G50R, L84R, D113E, A-A119D, D127N, deletion of K131, K131M, W132R, E133K, R151C (amino acid residue 151 is changed from Arg to Cys, apolipoprotein A-I-Paris), E160K, E163G, P167R, L168R, E171V, P189R, R197C (amino acid residue 173 is change from Arg to Cys, apolipoprotein A-I-Milano) and E222K. Also included are variants that have conservative amino acid modifications.

In one embodiment the tetranectin-apolipoprotein A-I comprises a fragment of the cleavage site of Immunoglobulin A protease (IgA protease). The recognition sites known from IgA proteases comprise the following sequences with "↓" denoting the position of the cleaved bond:

Pro-Ala-Pro ↓ Ser-Pro  (SEQ ID NO: 61)

Pro-Pro ↓ Ser-Pro  (SEQ ID NO: 62)

Pro-Pro ↓ Ala-Pro  (SEQ ID NO: 63)

Pro-Pro ↓ Thr-Pro  (SEQ ID NO: 64)

Pro-Pro ↓ Gly-Pro,  (SEQ ID NO: 65)

wherein the first three are more frequently chosen and cleaved.

The term "apolipoprotein mimic" denotes a synthetic polypeptide that mimics the function of the respective apolipoprotein. For example an "apolipoprotein A-I mimic" is a synthetic polypeptide that shows comparable biological function with respect to removal of cholesterol, i.e. reverse cholesterol efflux, as the natural apolipoprotein A-I. In one embodiment the apolipoprotein A-I mimic comprises at least one amphiphilic alpha-helix with positively charged amino acid residues clustered at a hydrophobic-hydrophilic interface and negatively-charged amino acid residues clustered at a center of a hydrophilic face. In order to mimic the function of apolipoprotein A-I the apolipoprotein mimic comprise a repeat polypeptide of from 15 to 29 amino acid residues, in one embodiment of 22 amino acid residues (PVLDEFREK-LNEELEALKQKLK (SEQ ID NO: 04); PVLDLFRELL-NELLEAL KQKLK (SEQ ID NO: 05)).

The term "cardiovascular disease" in general denotes a disease or condition with respect to heart or blood vessels, such as arteriosclerosis, coronary heart disease, cerebrovascular disease, aortoiliac disease, ischemic heart disease or peripheral vascular disease. Such a disease may not be discovered prior to an adverse event as a result of the disease, such as myocardial infarct, stroke, angina pectoris, transient ischemic attacks, congestive heart failure, aortic aneurysm, mostly resulting in death of the subject.

The term "cholate" denotes 3α,7α,12α-trihydroxy-5β-cholan-24-oic acid or a salt thereof, especially the sodium salt.

The term "critical micelle concentration" and its abbreviation "CMC", which can be used interchangeably, denote the concentration of surfactants or detergents above which individual detergent molecules (monomers) aggregate spontaneously to micelles (micelles, round rods, lamellar structures etc.). The term "conservative amino acid modification" denotes modifications of the amino acid sequence which do not affect or alter the characteristics of the lipid particle or the apolipoprotein according to the invention. Modifications can be introduced by standard techniques known in the art, such as site-directed mutagenesis and PCR-mediated mutagenesis. Conservative amino acid modifications include ones in which the amino acid residue is replaced with an amino acid residue having a similar side chain. Families of amino acid residues having similar side chains have been defined in the art. These families include amino acids with basic side chains (e.g. lysine, arginine, histidine), acidic side chains (e.g. aspartic acid, glutamic acid), uncharged polar side chains (e.g. glycine, asparagine, glutamine, serine, threonine, tyrosine, cysteine, tryptophan), non-polar side chains (e.g. alanine, valine, leucine, isoleucine, proline, phenylalanine, methionine), beta-branched side chains (e.g. threonine, valine, isoleucine), and aromatic side chains (e.g. tyrosine, phenylalanine, tryptophan, histidine). A "variant" protein, refers therefore herein to a molecule which differs in amino acid sequence from a "parent" protein's amino acid sequence by up to ten, in one embodiment from about two to about five, additions, deletions, and/or substitutions Amino acid sequence modifications can be performed by mutagenesis based on molecular modeling as described by Riechmann, L., et al., Nature 332 (1988) 323-327, and Queen, C., et al., Proc. Natl. Acad. Sci. USA 86 (1989) 10029-10033.

The homology and identity of different amino acid sequences may be calculated using well known algorithms such as BLOSUM 30, BLOSUM 40, BLOSUM 45, BLOSUM 50, BLOSUM 55, BLOSUM 60, BLOSUM 62, BLOSUM 65, BLOSUM 70, BLOSUM 75, BLOSUM 80, BLOSUM 85, or BLOSUM 90. In one embodiment the algorithm is BLOSUM 30.

The formation of lipid particles may be performed by incubating the apolipoprotein with detergent solubilized lipids at their respective transition temperature. The term "detergent" denotes a surface active chemical substance. A "detergent" is generally an amphiphatic molecule with a non-polar, hydrophobic part and a polar, hydrophilic part. The term "zwitterionic detergent" denotes a surface active chemical compound that has overall zero charge and at the same time comprises at least one positively charged moiety and at least one negatively charged moiety. In one embodiment the detergent is selected from sugar-based detergents, polyoxyalkylene-based detergents, bile-salt based detergents, synthetic detergents or a combination thereof. The term "sugar-based detergent" denotes a detergent selected from n-octyl-beta-D-glucopyranoside, n-nonyl-beta-D-glucopyranoside, n-dodecyl-beta-D-maltopyranoside, or 5-cyclohexylpentyl-beta-D-maltopyranoside, and derivatives thereof. The term "bile-salt based detergent" denotes a detergent selected from sodium cholate, potassium cholate, lithium cholate, 3-[(3-chloramidopropyl)dimethylammonio]-yl-propane sulfonate (CHAPS), 3-[(3-chloramidopropyl)dimethylammonio]-2-hydroxyl propane sulfonate (CHAPSO), and derivatives thereof. The term "polyoxyalkylene-based detergent" denotes a detergent selected from Tween 20, Triton X-100, Pluronic F68, and a derivatives thereof. The term "synthetic detergents" denotes a detergent selected from Zwittergent 3-6, Zwittergent 3-8, Zwittergent 3-10, Zwittergent 3-12, and derivatives thereof.

An "effective amount" of an agent, e.g., a pharmaceutical formulation, refers to an amount effective, at dosages and for periods of time necessary, to achieve the desired therapeutic or prophylactic result.

The term "high density lipoprotein particle" or its abbreviation "HDL particle", which can be used interchangeably, denotes a lipid-protein-complex comprising as main proteinaceous compound apolipoprotein A-I.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

The term "increase lipid efflux" and grammatical equivalents thereof denotes an increased level and/or rate of lipid efflux, promoting lipid efflux, enhancing lipid efflux, facilitating lipid efflux, upregulating lipid efflux, improving lipid efflux, and/or augmenting lipid efflux from cells or plaques. In one embodiment, the lipid efflux comprises efflux of phospholipid, triglyceride, cholesterol, and/or cholesterol ester.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

The term "DPPC" denotes the phospholipid 1,2-di-palmitoyl-sn-glycero-3-phosphatidyl choline also referred to as 1,2-dipalmitoyl-phosphatidyl choline.

The term "multimer" denotes a complex consisting of two or more monomers. A multimer is formed by non-covalent interactions between the monomers. Each monomer comprises a multimerization domain. In one embodiment the multimer comprises 2 or 3 monomers. In another embodiment the multimerization domains interact via non-covalent interactions between the individual multimerization domains comprised in each monomer. The term "multimerization domain" denotes amino acid sequences capable of covalently or non-covalently associating two or more monomeric molecules. A multimerization domain is capable of interacting with multimerization domains of different, similar, or identical amino acid sequence. In one embodiment the multimerization domain is the tetranectin trimerising structural element or a derivative thereof that has an amino acid sequence that is at least 68% identical with the consensus amino acid sequence of SEQ ID NO: 53. In one embodiment the cysteine residue at position 50 of SEQ ID NO: 53 is substituted by a different amino acid residue, in another embodiment by a serine residue, or a threonine residue, or a methionine residue. Polypeptides comprising a multimerization domain can associate with one or more other polypeptides also comprising a multimerization domain. The multimer formation can be initiated simply by mixing the polypeptides under suitable conditions. In another embodiment the multimerization domain has the amino acid sequence of SEQ ID NO: 53 wherein of from 1 to 10 residues have been deleted from or added to the N- or C-terminus of the amino acid sequence. In a further embodiment the multimerization domain has an amino acid sequence of SEQ ID NO: 53 wherein six or nine amino acid residues have been deleted from the N-terminus of the amino acid sequence. In still another embodiment the multimerization domain has an amino acid sequence of SEQ ID NO: 53 wherein the N-terminal amino acid residue L or the N-terminal amino acid residues C and L have been deleted. In one embodiment the multimerization domain is the tetranectin trimerising structural element and has the amino acid sequence of SEQ ID NO: 54. The multimer is in one embodiment a homomer.

The multimers may be homomers or heteromers, since different apolipoproteins comprising a multimerization domain can be combined to be incorporated into the multimer. In one embodiment the multimer is a trimeric homomer.

According to one embodiment the multimerization domain is obtained from tetranectin. In one embodiment the multimerization domain comprises the tetranectin trimerising structural element that has an amino acid sequence of SEQ ID NO: 54. The trimerising effect of the tetranectin trimerising structural element is caused by a coiled coil structure which interacts with the coiled coil structure of two other tetranectin trimerising structural elements to form a trimer. The tetranectin trimerising structural element may be obtained from human tetranectin, from rabbit tetranectin, from murine tetranectin, or from C-type lectin of shark cartilage. In one embodiment the tetranectin trimerising structural element comprises a sequence having at least 68%, or at least 75%, or at least 81%, or at least 87%, or at least 92% identity with the consensus sequence of SEQ ID NO: 53.

The term "non-covalent interactions" denotes non-covalent binding forces such as ionic interaction forces (e.g. salt bridges), non-ionic interaction forces (e.g. hydrogen-bonds), or hydrophobic interaction forces (e.g. van-der-Waals forces or π-stacking interactions).

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The term "phosphatidylcholine" denotes a molecule consisting of one glycerol moiety, two carboxylic acid moieties and one phosphocholine moiety, wherein the glycerol moiety is covalently bound to the other moieties each by a ester bond, i.e. two carboxylic ester bonds and one phosphoric ester bond, whereby the phosphoric ester bond is either to the 1-hydroxyl group or the 3-hydroxyl group of the glycerol moiety. The term "carboxylic acid moiety" denotes an organic moiety comprising at least one acyl group (R—C(O)O). The phosphatidylcholine may be of any kind or source. In one embodiment the phosphatidylcholine is selected from egg phosphatidylcholine, soybean phosphatidylcholine, dipalmitoyl phosphatidylcholine, dimyristoyl phosphatidylcholine, distearoyl phosphatidylcholine, dilauryl phosphatidylcholine, dipalmitoyl phosphatidylcholine, 1-myristoyl-2-palmitoyl phosphatidylcholine, 1-palmitoyl-2-myristoyl phosphatidylcholine, 1-palmitoyl-2-stearoyl phosphatidylcholine, 1-stearoyl-2-palmitoyl phosphatidylcholine, dioleoyl phosphatidylcholine, 1-palmitoyl-2-oleoyl phosphatidylcholine, 1-oleoyl-2-palmitoyl phosphatidylcholine, and an analogues and derivatives thereof.

All phospholipids as used herein may be derived from any source, i.e. (where appropriate) from soybean, milk, egg or even inner organs of animals excluding humans, they may be derived from natural origin, or semi-synthetic or even fully synthetic.

The term "POPC" denotes the phospholipid 1-palmitoyl-2-oleoyl-sn-glycero-3-phosphatidyl choline also referred to as 1-palmitoyl-2-oleoyl-phosphatidyl choline.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "variant" includes also variants of an apolipoprotein or an apolipoprotein mimic as reported herein wherein in the variants the amino acid sequence of the respective apolipoprotein or apolipoprotein mimic comprises one or more amino acid substitution, addition or deletion. The modification may increase or decrease the affinity of the apolipoprotein for an apolipoprotein receptor or an apolipoprotein converting enzyme, or may increase the stability of the apolipoprotein variant compared to the respective apolipoprotein, or may increase the solubility of the apolipoprotein variant compared to the respective apolipoprotein in aqueous solutions, or may increase the recombinant production of the apolipoprotein variant compared to the respective apolipoprotein in/by host cells.

Lipid Particle

Herein is reported a lipid particle comprising
a) a tetranectin-apolipoprotein A-I,
b) a phosphatidylcholine, and
c) a further lipid.

In one embodiment the lipid particle comprises a tetranectin-apolipoprotein A-I, a first phosphatidylcholine and a second phosphatidylcholine. In one embodiment the first phosphatidylcholine and the second phosphatidylcholine differ in one or two carboxylic acid moieties or carboxylic acid moiety derivatives esterified to the phospho-glycerol backbone of the phosphatidylcholine. In one embodiment the first phosphatidylcholine is POPC and the second phosphatidylcholine is DPPC. In one embodiment the tetranectin-apolipoprotein A-I, the phosphatidylcholine, and the in the lipid particle are non-covalently associated. In one embodiment the tetranectin-apolipoprotein A-I is a recombinantly produced tetranectin-apolipoprotein A-I.

The choice of the combination of lipids determines the efficacy and liver safety of lipid particles comprising apolipoprotein. In in vivo studies of DMPC containing lipid particles using rabbits it has been found that rabbits treated with 30 mg/kg showed severe side effects but survived whereas rabbits treated with 100 mg/kg died.

In vitro functional tests confirmed that a lipid particle containing a single phosphatidylcholine such as DPPC or POPC activate LCAT.

It was also shown that cholesterol efflux was higher when the lipid particle comprised a combination of different phospholipids.

TABLE 1

Phospholipid combinations differing in their lipid composition prepared for in vivo rabbit studies.

| phospholipid molar ratio used for producing the lipid particle | LCAT substrate | cholesterol efflux |
| --- | --- | --- |
| POPC | yes | yes |
| POPC:DPPC 3:1 | yes | yes |
| POPC:DPPC 1:1 | yes | yes |
| POPC:DPPC 1:3 | no | yes |
| DPPC | no | yes |

These results were also confirmed by in vivo data demonstrating cholesterol mobilization for all combinations. However, for lipid particles containing only the single phosphatidylcholine DPPC, or the combination of DPPC and sphingomyelin (SM) an increase in liver enzymes can be determined (FIG. 1).

From the technical point of view the formation of lipid particles with pure DPPC is more convenient compared to the formation with pure POPC. The risk of precipitate formation is reduced by using a combination of different phospholipids. Also the phase transition temperature of 41° C. for pure DPPC makes it easier to prepare the lipid particle compared to pure POPC that has a phase transition temperature of 4° C. Also the obtained product is more homogeneous. This can be confirmed by lipid particle analysis via SEC-MALLS, an analytical tool which also allows the determination of the protein-lipid composition (protein-conjugate analysis). In FIG. 2 a chromatogram of samples resolved in a size-exclusion chromatography (UV280 detection) is shown. An inhomogeniety of a sample can be seen by the occurrence of multiple separated or semi-detached peaks.

The number of POPC molecules per apolipoprotein monomer in the lipid particle when pure POPC is used for producing the lipid particle is in one embodiment of from 40 to 85, in one embodiment of from 50 to 80, in one embodiment of from 54 to 75.

The number of DPPC molecules per apolipoprotein monomer in the lipid particle when pure DPPC is used for producing the lipid particle is in one embodiment of from 50 to 150, in one embodiment of from 65 to 135, in one embodiment of from 76 to 123, and in one embodiment of from 86 to 102.

The number of phospholipid molecules per apolipoprotein monomer in the lipid particle when a mixture of POPC and DPPC at a molar ratio of 1:3 is used for producing the lipid particle is in one embodiment of from about 50 to about 120, in one embodiment of from about 65 to about 105, and in one embodiment of from about 72 to about 96.

The number of lipid molecules per apolipoprotein monomer in the lipid particle when a mixture of POPC and DPPC at a molar ratio of 1:1 is used for producing the lipid particle is in one embodiment of from 50 to 120, in one embodiment of from 60 to 100, in one embodiment of from 71 to 92, and in one embodiment of from 71 to 85.

The number of lipid molecules per apolipoprotein monomer in the lipid particle when a mixture of POPC and DPPC at a molar ratio of 3:1 is used for producing the lipid particle is in one embodiment of from 50 to 105.

The number of lipid molecules per apolipoprotein monomer in the lipid particle when a mixture of POPC and DPPC at a molar ratio of 3:1 is used for producing the lipid particle is in one embodiment of from 60 to 95.

The number of lipid molecules per apolipoprotein monomer in the lipid particle when a mixture of POPC and DPPC at a molar ratio of 3:1 is used for producing the lipid particle is in one embodiment of from 60 to 90.

The number of lipid molecules per apolipoprotein monomer in the lipid particle when a mixture of POPC and DPPC at a molar ratio of 3:1 is used for producing the lipid particle is in one embodiment of from 60 to 88.

The number of lipid molecules per apolipoprotein monomer in the lipid particle when a mixture of POPC and DPPC at a molar ratio of 3:1 is used for producing the lipid particle is in one embodiment of from 62 to 80.

The number of lipid molecules per apolipoprotein monomer in the lipid particle when a mixture of POPC and DPPC at a molar ratio of 3:1 is used for producing the lipid particle is in one embodiment of from 66 to 86.

The number of lipid molecules per apolipoprotein monomer in the lipid particle when a mixture of POPC and DPPC at a molar ratio of 3:1 is used for producing the lipid particle is in one embodiment of from 64 to 70.

The number of lipid molecules per apolipoprotein monomer in the lipid particle when a mixture of POPC and DPPC at a molar ratio of 3:1 is used for producing the lipid particle is in one embodiment about 66.

For the production of a lipid particle comprising apolipoprotein and POPC a molar ratio of apolipoprotein to POPC in one embodiment of from 1:40 to 1:100 is employed, in one embodiment a molar ratio of from 1:40 to 1:80 is employed, and in one embodiment a molar ratio of about 1:60 is employed.

For the production of a lipid particle comprising apolipoprotein and DPPC a molar ratio of apolipoprotein to DPPC in one embodiment of from 1:70 to 1:100 is employed, in one embodiment a molar ratio of from 1:80 to 1:90 is employed, and in one embodiment a molar ratio of about 1:80 is employed.

For the production of a lipid particle comprising apolipoprotein, POPC and DPPC a molar ratio of apolipoprotein to POPC and DPPC with POPC and DPPC at a 1:3 molar ratio in one embodiment of from 1:60 to 1:100 is employed, in one embodiment a molar ratio of from 1:70 to 1:90 is employed, and in one embodiment a molar ratio of about 1:80 is employed.

For the production of a lipid particle comprising apolipoprotein, DPPC and POPC a molar ratio of apolipoprotein to POPC and DPPC with POPC and DPPC at a 1:1 molar ratio in one embodiment of from 1:60 to 1:100 is employed, in one embodiment a molar ratio of from 1:60 to 1:80 is employed, and in one embodiment a molar ratio of about 1:70 is employed.

For the production of a lipid particle comprising apolipoprotein, DPPC and POPC a molar ratio of apolipoprotein to POPC and DPPC with POPC and DPPC at a 3:1 molar ratio in one embodiment of from 1:60 to 1:100 is employed, in one embodiment a molar ratio of from 1:50 to 1:70 is employed, and in one embodiment a molar ratio of about 1:60 is employed.

In one embodiment if a mixture of lipids is used for producing the lipid particle the mixture has a phase transition temperature of from 4° C. to 45° C., in one embodiment of from 10° C. to 38° C., and in one embodiment of from 15° C. to 35° C.

The lipid particle comprises in one embodiment an average number of from 1 to 10 apolipoprotein molecules per lipid particle, in one embodiment of from 1 to 8 apolipoprotein molecules per lipid particle, and in one embodiment of from 1 to 4 apolipoprotein molecules per lipid particle.

In one embodiment the lipid particle comprises an average number of at least 1, or 2, or 3, or 4, or 5, or 6, or 7, or 8, or 9, or 10 apolipoprotein molecules per lipid particle. In one embodiment the average number is 1.

In one embodiment the lipid particle comprises one or more further polypeptides beside the apolipoprotein.

Without limitation the lipid particle may serve as an enzymatic co-factor and/or a carrier for taking up lipids, especially cholesterol.

One or more detergents can be present in the lipid particle as reported herein. Such a detergent can be any detergent, i.e. a pharmaceutically acceptable detergent or other detergents at non-toxic concentrations, such as a non-ionic or ionic detergent. The non-ionic detergent can be an alkylene oxide derivative of an organic compound which contains one or more hydroxyl groups. In one embodiment the non-ionic detergent is selected from ethoxylated and/or propoxylated alcohol or ester compounds or mixtures thereof. In another embodiment the ester is selected from esters of sorbitol and fatty acids, such as sorbitan monooleate or sorbitan monopalmitate, oily sucrose esters, polyoxyethylene sorbitane fatty acid esters, polyoxyethylene sorbitol fatty acid esters, polyoxyethylene fatty acid esters, polyoxyethylene alkyl ethers, polyoxyethylene sterol ethers, polyoxyethylenepolypropoxy alkyl ethers, block polymers and cethyl ether, polyoxyethylene castor oil or hydrogenated castor oil derivatives and polyglycerine fatty acid esters. In one embodiment the non-ionic detergent is selected from Pluronic®, Poloxamer®, Span®, Tween®, Polysorbate®, Tyloxapol®, Emulphor® or Cremophor®.

The ionic detergent can be a bile duct agent. In one embodiment the ionic detergent is selected from cholic acid or deoxycholic acid, or their salts and derivatives, or from free fatty acids, such as oleic acid, linoleic acid and others.

In one embodiment the ionic detergent is selected from cationic lipids like $C_{10}$-$C_{24}$ alkylamine or alkanolamine and cationic cholesterol esters.

In one embodiment the lipid particle comprises less than 0.75% by weight detergent.

In one embodiment the lipid particle comprises less than 0.3% by weight detergent.

In one embodiment the detergent is selected from sugar-based detergents, polyoxyalkylene-based detergents, bile-salt based detergents, synthetic detergents, or a combination thereof. In one embodiment the detergent is cholic acid.

The efficiency at which cholesterol is mobilized into the blood can be determined by comparing the respective excursion of total cholesterol with apolipoprotein concentrations after administration of apolipoprotein in vivo. For a quantitative assessment, the quotient of the baseline corrected area under the concentration-time curve (AUC) of total cholesterol and the area under the concentration-time curve of apolipoprotein was calculated.

The lipid particle as reported herein, especially a lipid particle comprising a tetranectin-apolipoprotein of SEQ ID NO: 01 and POPC and DPPC at a molar ratio of 3:1, shows enhanced cholesterol mobilization in vivo.

Tetranectin-Apolipoprotein A-I

Beside the lipid particle as outlined above is herein reported also a tetranectin-apolipoprotein A-I.

Tetranectin-apolipoprotein A-I is a fusion protein of the human tetranectin trimerising structural element and the wild-type human apolipoprotein A-I. The amino acid sequence of the human tetranectin part can be shortened by the first 9 amino acids starting with the isoleucine residue of position 10, a naturally occurring truncation site. As a consequence of this truncation the O-glycosylation site at threonine residue of position 4 has been deleted. Between the tetranectin trimerising structural element and the human apolipoprotein A-I the five amino acid residues "SLKGS" (SEQ ID NO: 03) were removed.

For improved expression and purification a construct can be generated comprising an N-terminal purification tag, e.g. a hexahistidine-tag (SEQ ID NO: 56), and an IgA protease cleavage site. As a result of the specific cleavage two amino acids—as first alanine or glycine or serine or proline and as second proline—are maintained at the N-terminus of the tetranectin-apolipoprotein A-I. The tetranectin-apolipoprotein A-I can have the amino acid sequence of SEQ ID NO: 01.

The tetranectin trimerising structural element provides for a domain that allows for the formation of a trimeric tetranectin-apolipoprotein A-I multimer that is constituted by non-covalent interactions between each of the individual tetranectin-apolipoprotein A-I monomers.

By using an alternative purification method, the purification-tag and the IgA protease cleavage site can be omitted resulting in a tetranectin-apolipoprotein A-I of the amino acid sequence of SEQ ID NO: 02.

In one embodiment the apolipoprotein can be a variant comprising conservative amino acid substitutions.

Apolipoprotein A-I can be determined enzymatically, via NMR spectroscopy, or by using monoclonal or polyclonal anti-apolipoprotein-A-I antibodies. Other aspects as reported herein are therefore polyclonal and monoclonal antibodies specifically binding the tetranectin-apolipoprotein A-I as reported herein. Such antibodies can be obtained with methods known to a person skilled in the art. Also the labeling of the antibodies for use in immunoassays can be performed with methods known to a person of skill in the art.

In one embodiment the apolipoprotein can be a variant comprising conservative amino acid substitutions, or an apolipoprotein A-I mimic. In one embodiment the tetranectin-apolipoprotein A-I has the amino acid sequence of SEQ ID NO: 02, or SEQ ID NO: 66, or SEQ ID NO: 67, wherein X is selected from SEQ ID NO: 68 to SEQ ID NO: 105.

Thus, in one embodiment the tetranectin-apolipoprotein A-I has the amino acid sequence of

```
                                           (SEQ ID NO: 02)
IVNAKKDVVNTKMFEELKSRLDTLAQEVALLKEQQALQTVDEPPQSPWDR

VKDLATVYVDVLKDSGRDYVSQFEGSALGKQLNLKLLDNWDSVTSTFSK

LREQLGPVTQEFWDNLEKETEGLRQEMSKDLEEVKAKVQPYLDDFQKKW

QEEMELYRQKVEPLRAELQEGARQKLHELQEKLSPLGEEMRDRARAHVD

ALRTHLAPYSDELRQRLAARLEALKENGGARLAEYHAKATEHLSTLSEKA

KPALEDLRQGLLPVLESFKVSFLSALEEYTKKLNTQ.
```

In one embodiment the tetranectin-apolipoprotein A-I has the amino acid sequence of

```
                                           (SEQ ID NO: 66)
(A, G, S, T)PIVNAKKDVVNTKMFEELKSRLDTLAQEVALLKEQQA

LQTVDEPPQSPWDRVKDLATVYVDVLKDSGRDYVSQFEGSALGKQLNLK

LLDNWDSVTSTFSKLREQLGPVTQEFWDNLEKETEGLRQEMSKDLEEVK

AKVQPYLDDFQKKWQEEMELYRQKVEPLRAELQEGARQKLHELQEKLSP

LGEEMRDRARAHVDALRTHLAPYSDELRQRLAARLEALKENGGARLAEY

HAKATEHLSTLSEKAKPALEDLRQGLLPVLESFKVSFLSALEEYTKKLN

TQ.
```

In one embodiment the tetranectin-apolipoprotein A-I has the amino acid sequence of

```
                                           (SEQ ID NO: 67)
(M)HHHHHHXIVNAKKDVVNTKMFEELKSRLDTLAQEVALLKEQQALQTV

DEPPQSPWDRVKDLATVYVDVLKDSGRDYVSQFEGSALGKQLNLKLLDN

WDSVTSTFSKLREQLGPVTQEFWDNLEKETEGLRQEMSKDLEEVKAKVQP

YLDDFQKKWQEEMELYRQKVEPLRAELQEGARQKLHELQEKLSPLGEEM

RDRARAHVDALRTHLAPYSDELRQRLAARLEALKENGGARLAEYHAKAT

EHLSTLSEKAKPALEDLRQGLLPVLESFKVSFLSALEEYTKKLNTQ,
``` wherein X can be any of the following amino acid sequences A, G, S, P, AP, GP, SP, PP, GSAP (SEQ ID NO: 68), GSGP (SEQ ID NO: 69), GSSP (SEQ ID NO: 70), GSPP (SEQ ID NO: 71), GGGS (SEQ ID NO: 72), GGGGS (SEQ ID NO: 73), GGGSGGGS (SEQ ID NO: 74), GGGGSGGGGS (SEQ ID NO: 75), GGGSGGGSGGGS (SEQ ID NO: 76), GGGGSGGGGSGGGGS (SEQ ID NO: 77), GGGSAP (SEQ ID NO: 78), GGGSGP (SEQ ID NO: 79), GGGSSP (SEQ ID NO: 80), GGGSPP (SEQ ID NO: 81), GGGGSAP (SEQ ID NO: 82), GGGGSGP (SEQ ID NO: 83), GGGGSSP (SEQ ID NO: 84), GGGGSPP (SEQ ID NO: 85), GGGSGGGSAP (SEQ ID NO: 86), GGGSGGGSGP (SEQ ID NO: 87), GGGSGGGSSP (SEQ ID NO: 88), GGGSGGGSPP (SEQ ID NO: 89), GGGSGGGSGGGSAP (SEQ ID NO: 90), GGGSGGGSGGGSGP (SEQ ID NO: 91), GGGSGGGSGGGSSP (SEQ ID NO: 92), GGGSGGGSGGGSPP (SEQ ID NO: 93), GGGGSAP (SEQ ID NO: 94), GGGGSGP (SEQ ID NO: 95), GGGGSSP (SEQ ID NO: 96), GGGGSPP (SEQ ID NO: 97), GGGGSGGGSAP (SEQ ID NO: 98), GGGGSGGGSGP (SEQ ID NO: 99), GGGGSGGGSSP (SEQ ID NO: 100), GGGGSGGGSPP (SEQ ID NO: 101), GGGGSGGGSGGGSAP (SEQ ID NO: 102), GGGGSGGGSGGGSGP (SEQ ID NO: 103), GGGGSGGGSGGGSSP (SEQ ID NO: 104), and GGGGSGGGSGGGSPP (SEQ ID NO: 105).

It has to be noted that if a polypeptide is recombinantly produced in *E. coli* strains the N-terminal methionine residue is usually not efficiently cleaved off by *E. coli* proteases. Thus, the N-terminal methionine residue is partially present in the produced polypeptide.

Properties:

The tetranectin-apolipoprotein A-I as reported herein or the lipid particle as reported herein can be used for the treatment and/or diagnosis of a disease or condition characterized by non-normal lipid levels or a deposition of lipids within body components, such as plaques in blood vessels.

Figure 3:
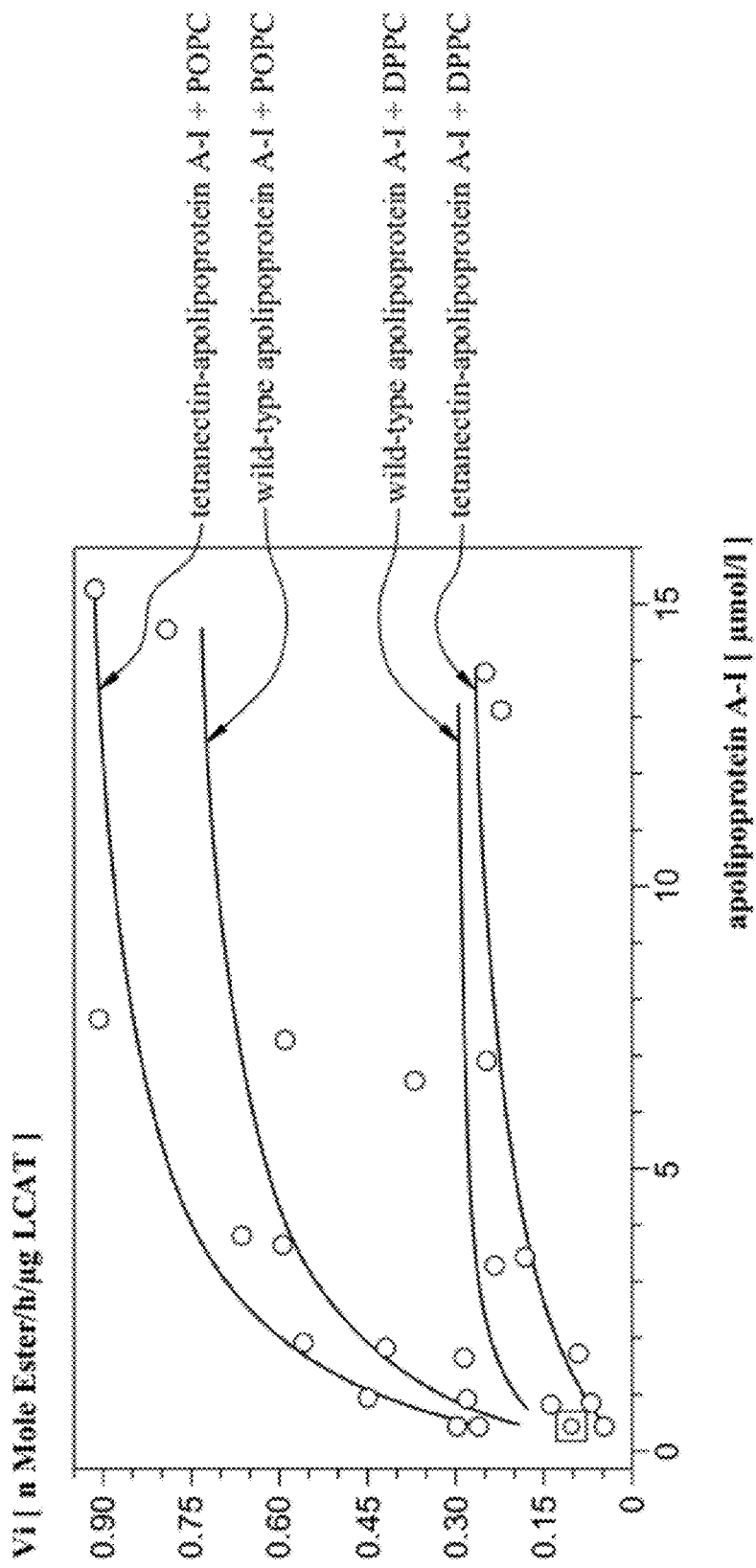
FIG. 3 Impact of DPPC and POPC on LCAT activity.

In order to determine the capacity of the lipid particle as reported herein to support LCAT catalyzed cholesterol esterification cholesterol can be incorporated in the lipid particle by addition of an ethanolic cholesterol solution. Lipid particles containing pure POPC are better LCAT substrates than complexes containing DPPC independent of their apolipoprotein constituent, such as wild-type apolipoprotein A-I or tetranectin-apolipoprotein A-I (FIG. 3).

Initial velocity of cholesterol esterification in lipid particles comprising different mixtures of POPC and DPPC show that mixtures are better LCAT substrates than a single pure phosphatidylcholine. This can be seen from the initial velocities of cholesterol esterification (see Table 2 and FIG. 4).

TABLE 2

Initial velocities of cholesterol esterification in lipid particles comprising different mixtures of phospholipids.

| phospholipid molar ratio used for producing the lipid particle | $K_m$ [μM] | $V_{max}$ [nmol ester/h/μg LCAT] |
|---|---|---|
| POPC | 4.6 | 1.6 |
| POPC:DPPC 3:1 | 0.4 | 1.9 |
| POPC:DPPC 1:1 | 0.5 | 1.8 |
| POPC:DPPC 1:3 | 1.0 | 1.7 |
| DPPC | 0.9 | 1.8 |

Macrophage like human THP1 cells obtained by exposing THP-1 monocytic leukemia cells to phorbol myristate acetate and loaded with a radioactive labeled cholesterol tracer can be exposed to cholesterol acceptor test compounds.

Efflux velocity induced by acceptor test compounds can be calculated as the ratio of cholesterol radioactivity in the supernatant to the sum of the radioactivity in the cells plus their supernatant and compared to cells exposed to medium containing no acceptors and analyzed by linear fit. Parallel experiments can be performed using cells exposed and not exposed to a RX-LXR agonist which is known to upregulate mainly ABCA-1 and bias efflux toward ABCA-1 mediated transport.

Figure 5:
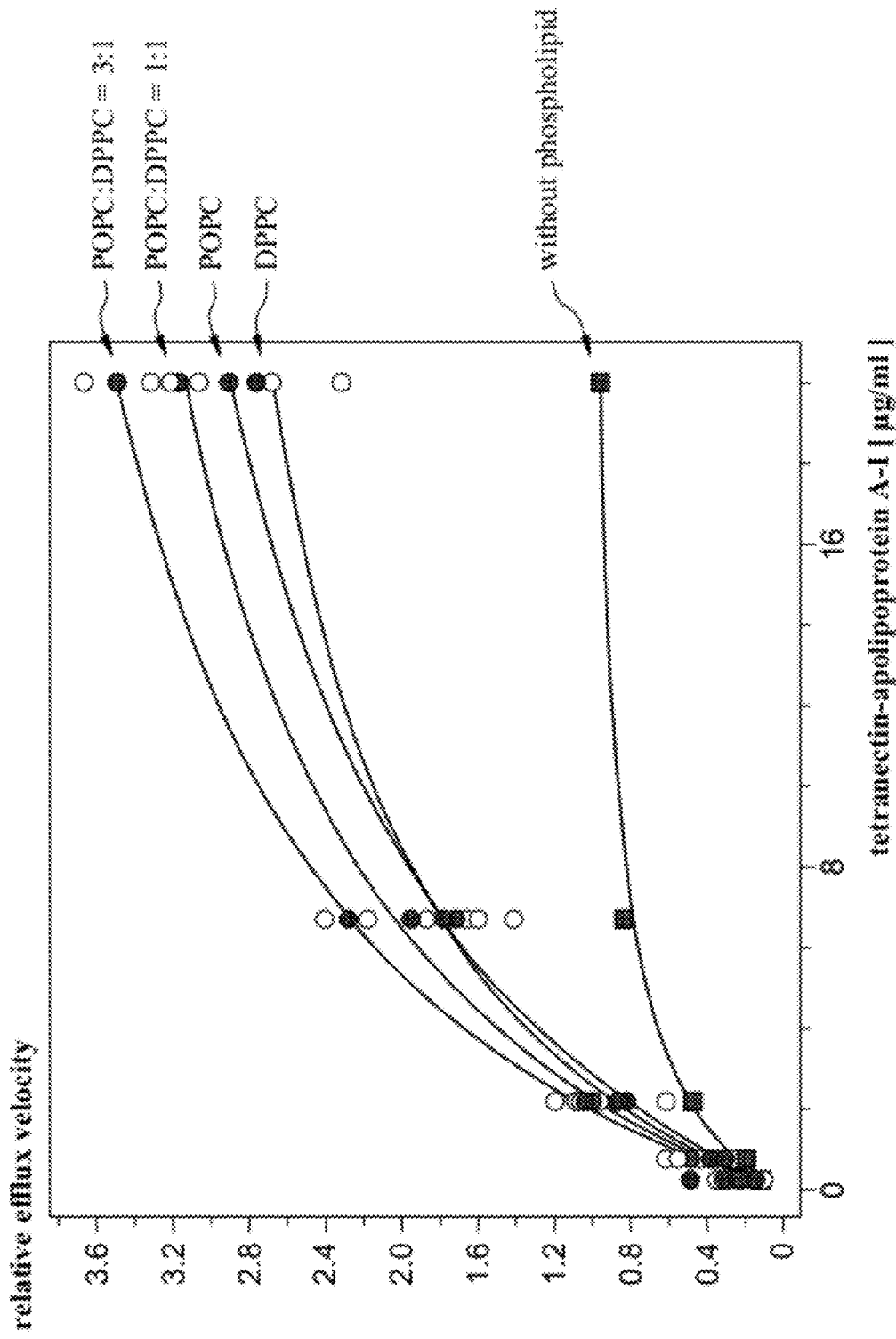
FIG. 5 Cholesterol efflux to THP-1 derived foam cells in cells not primed with a RXR-LXR agonist.
Figure 6:
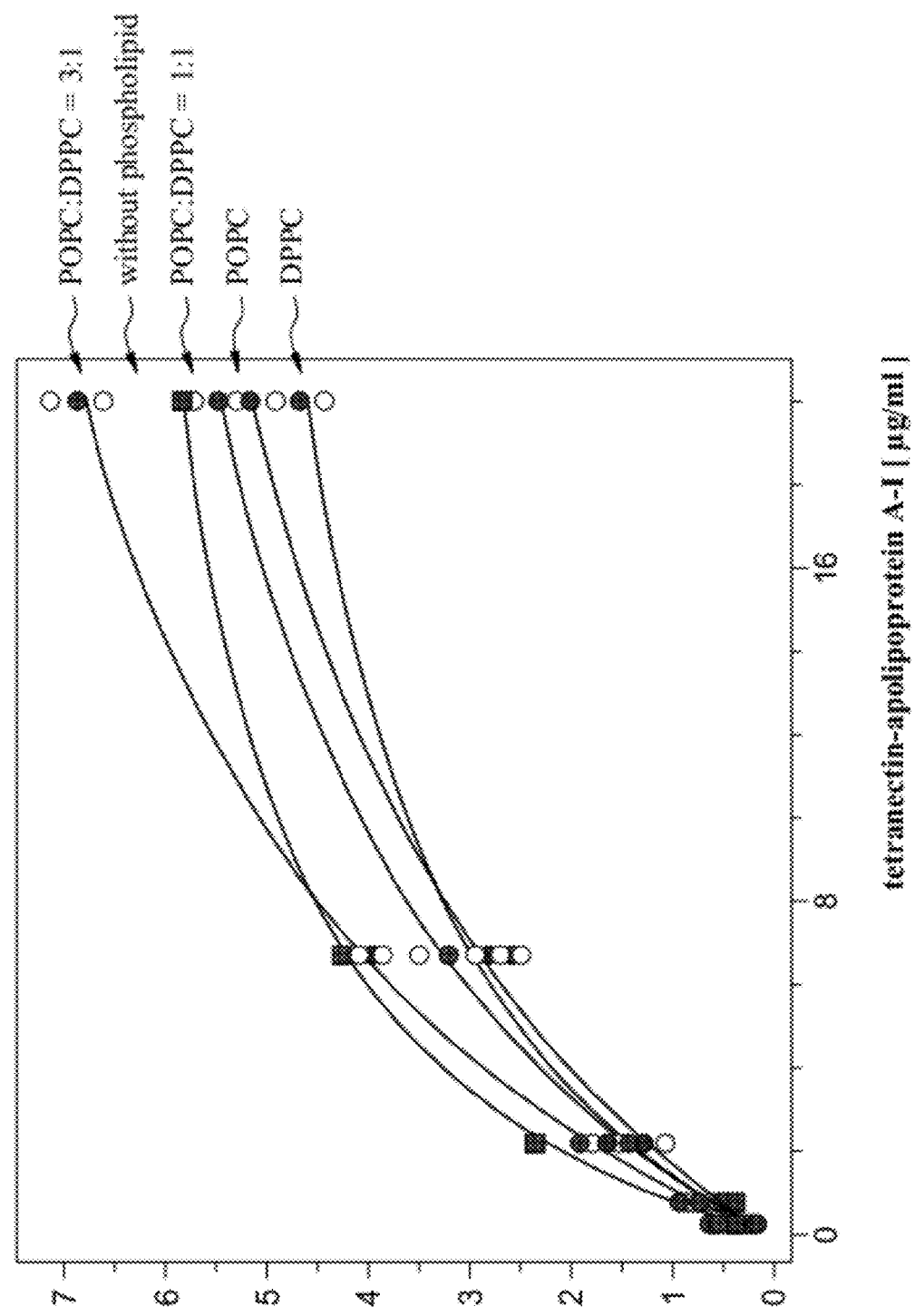
FIG. 6 Cholesterol efflux to THP-1 derived foam cells after ABCA-I pathway activation using an RXR-LXR agonist.

In cells not pre-treated with RX-LXR lipid particles a higher increase in cholesterol efflux compared to the efflux obtained with non lipidated tetranectin-apolipoprotein A-I can be seen. Only a small influence of the lipid mixture on efflux can be observed in the tested series (FIG. 5). In cells pre-treated with RX R-LXR a comparable increase in cholesterol efflux can be seen using a non-lipidated tetranectin-apolipoprotein A-I. The overall increase was higher as compared to that observed with not pre-treated cells. Only a small influence of the lipid mixture on efflux can be observed in the tested series (FIG. 6).

Figure 7:
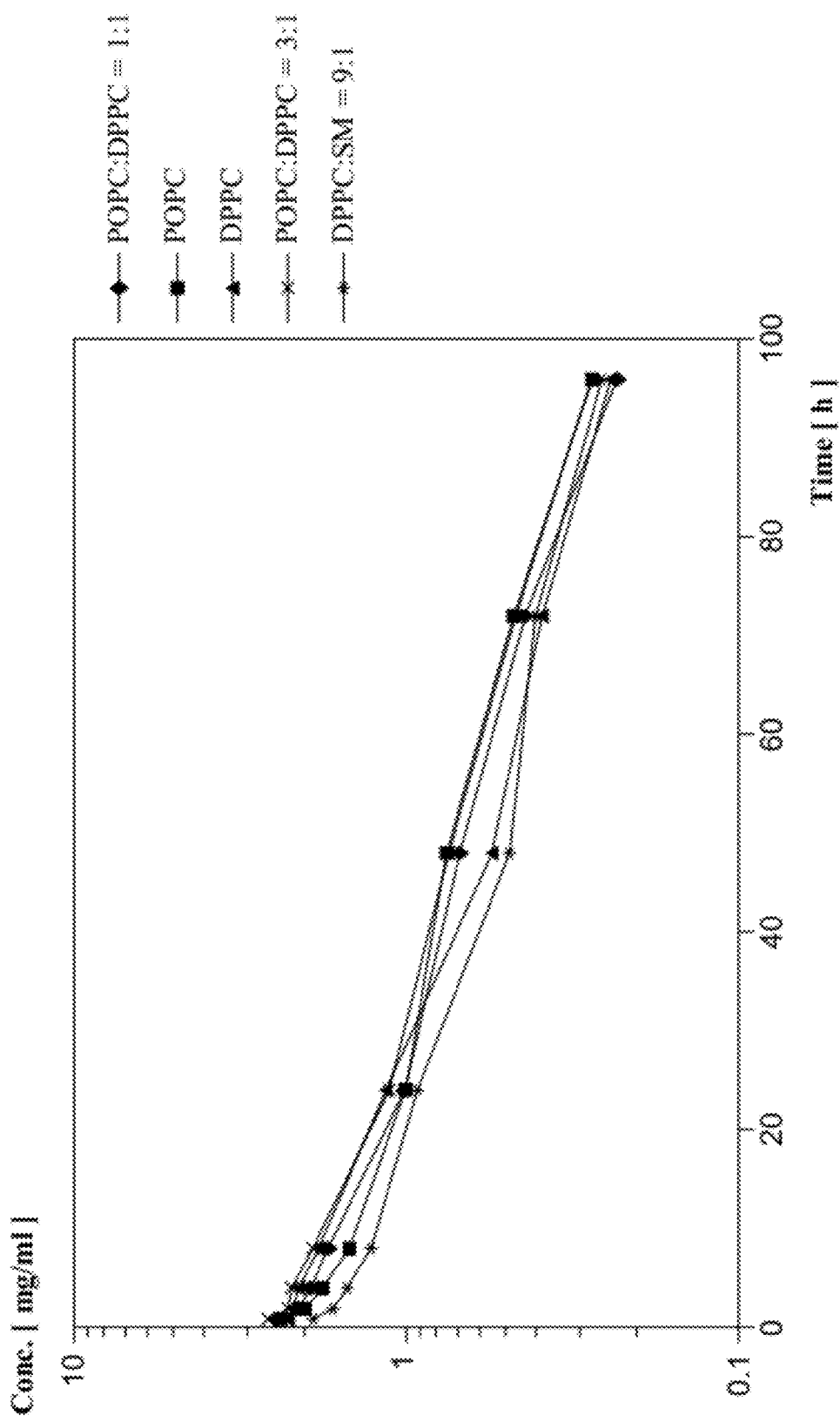
FIG. 7 Time dependent plasma concentration of different apolipoprotein compositions.

Different lipid particles were tested in vivo in rabbits. The lipid particle was applied as intravenous infusion and serial blood sampling was performed over 96 h after application. Values of liver enzymes, cholesterol, and cholesterol ester were determined. Plasma concentrations are comparable for all tested lipid particles comprising an initial distribution phase followed by log-linear decline of plasma concentrations (FIG. 7). As can be seen from Table 3 pharmacokinetic parameters are similar for all tested compounds. The observed half-lives are close to 1.5 days.

TABLE 3

Determined pharmacokinetic parameters.

| phospholipid molar ratio used for producing the lipid particle | $C_L$ [ml/h/kg] | $V_{ss}$ [ml/kg] | $T_{1/2}$ [h] | $C_{max}$ [mg/ml] |
|---|---|---|---|---|
| POPC | 0.89 ± 0.22 | 45.0 ± 2.5 | 36.9 ± 8.2 | 2.40 ± 0.19 |
| POPC:DPPC 3:1 | 0.82 ± 0.06 | 37.8 ± 5.6 | 34.2 ± 4.5 | 2.65 ± 0.28 |
| POPC:DPPC 1:1 | 0.85 ± 0.14 | 43.1 ± 5.9 | 38.6 ± 10.6 | 2.34 ± 0.31 |
| DPPC | 0.96 ± 0.10 | 37.8 ± 4.9 | 30.2 ± 7.7 | 2.29 ± 0.19 |
| DPPC:SM 9:1 | 1.28 ± 0.62 | 50.7 ± 8.7 | 31.3 ± 8.2 | 1.91 ± 0.33 |

Figure 8:
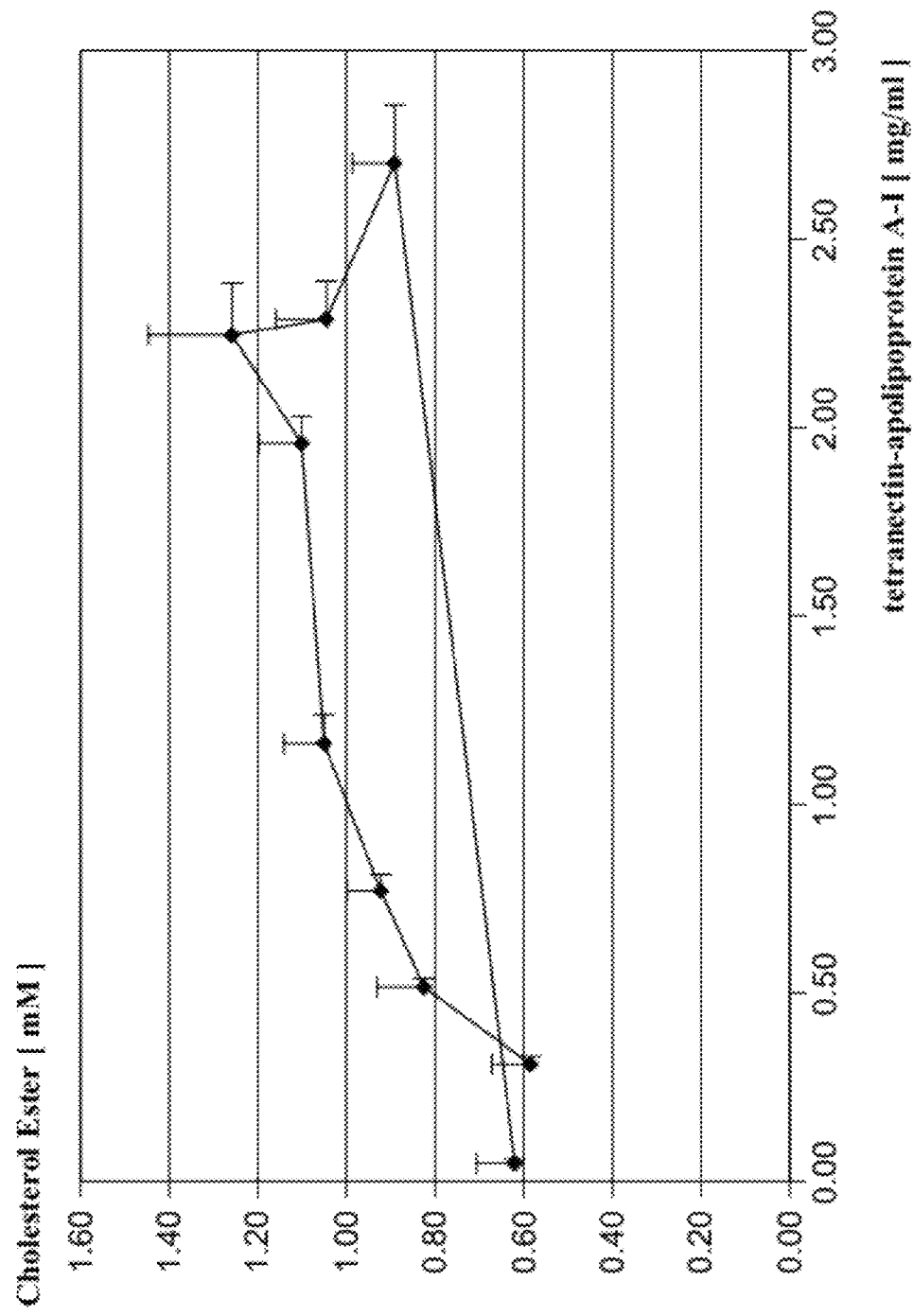
FIG. 8 Time and concentration course of cholesterol mobilization and esterification in plasma.

As can be seen from FIG. 8 cholesterol is mobilized and esterified in plasma. Plasma cholesterol ester levels do continue to increase even after the concentration of tetranectin-apolipoprotein A-I is already decreasing. When plasma tetranectin-apolipoprotein A-I levels have decreased to about 0.5 mg/ml (about 50% of normal wild-type apolipoprotein A-I) increased cholesterol ester levels can still be detected.

Figure 10:
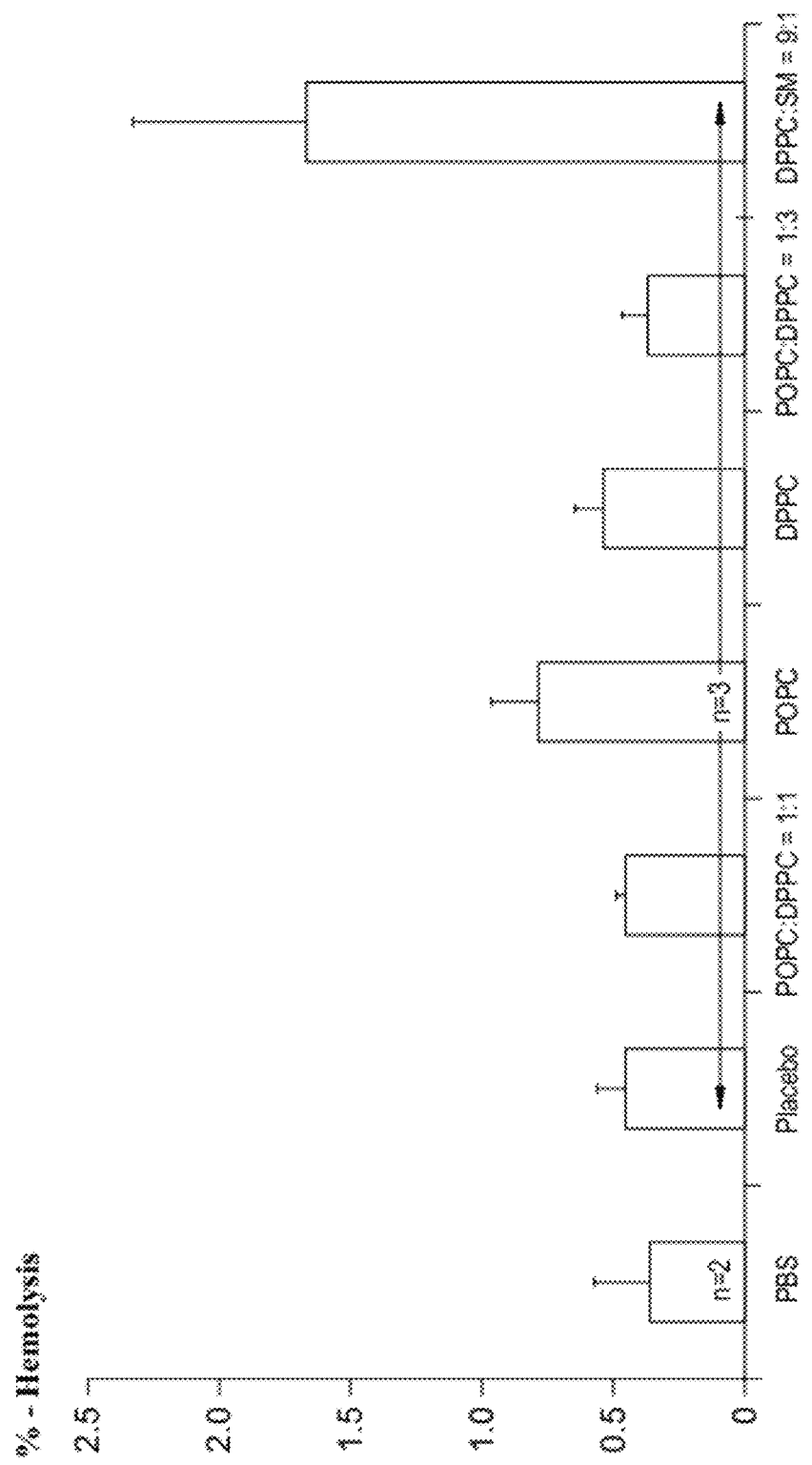
FIG. 10 In vivo rabbit study—spontaneous hemolysis in plasma.

Lipid particles comprising tetranectin-apolipoprotein A-I do not induced liver enzymes in rabbits as well as in mice as can be seen from FIGS. 1 and 9. Also no hemolysis can be determined in plasma samples obtained two hours after intravenous application (FIG. 10).

Therefore aspects as reported herein are a pharmaceutical composition and a diagnostic composition comprising a lipid particle as reported herein, or a tetranectin-apolipoprotein A-I as reported herein.

The lipid particle as reported herein has improved in vivo properties compared to non-lipidated apolipoprotein and other lipid particles as shown in the following Table 4.

TABLE 4

In vivo properties of different apolipoproteins and lipid particles.

| protein | lipid particle comprising | applied to | highest applied dose | acute liver toxicological effect | reference |
|---|---|---|---|---|---|
| apolipoprotein A-I mutants | no particle | rat | orally, 1 g/kg | no toxic effect up to 500 mg/kg | US 2005/0287636 |
| A-I, tetranectin-apolipoprotein A-I | DMPC | mouse | i.v. 1 to 1.2 mg/mouse | not described | WO 2002/38609; Graversen, (2008) |
| pro apolipoprotein A-I | SM | not reported | not reported | injection, toxic at dose of 200 mg/kg | WO 2003/096983 |
| apolipoprotein A-I | PG/SM | rabbit | i.v. 15 mg/kg | not described | WO 2006/100567 |
| apolipoprotein A-I | PC (soybean) | human | 80 mg/kg | treatment group was discontinued early because of liver function test abnormalities (10-fold increase in alanine aminotransferase) | WO 2007/137400 |
| apolipoprotein A-I Milano variant | POPC | human | 45 mg/kg | one patient withdrawn due to development of an elevated aspartate aminotransferase level (3× upper limit of normal) | Nissen, S. E., et al., JAMA 290 (2003) 2292-2300 |
| tetranectin-apolipoprotein A-I | DMPC | rabbit | 100 mg/kg | lethal after 3-4 hours in all animals tested | |
| tetranectin-apolipoprotein A-I | POPC/DPPC | rabbit | 100 mg/kg | increase not observed | |
| tetranectin-apolipoprotein A-I | POPC/DPPC | rat | i.v. 500 mg/kg | increase not observed | |
| tetranectin-apolipoprotein A-I | POPC/DPPC | cynomolgus monkey | i.v. 200 mg/kg | increase not observed | |

Formation of Lipid Particles

For the formation of lipid particles as reported herein different methods are known, such as freeze-drying, freeze-thawing, detergent solubilization followed by dialysis, microfluidization, sonification, and homogenization.

For example aqueous mixtures of phospholipids with detergents can be incubated with purified apolipoprotein. The apolipoprotein can be added in native form. The detergent is afterwards removed by dialysis or diafiltration. The formation of lipid particles comprising tetranectin-apolipoprotein A-I can be achieved by incubating tetranectin-apolipoprotein A-I in monomeric or multimeric form with detergent solubilized lipids at their respective transition temperature. Removal of the detergent by dialysis results in the formation of lipid particles. A common method for the formation of lipid particles containing an apolipoprotein is based on the cholate method as described e.g. in Jonas, A., Methods Enzymol. 128 (1986) 553-582 or Experimental Lung Res. 6 (1984) 255-270. Removal of the detergent by dialysis results in the formation of lipid particles.

The main points which have to be considered for the lipid particle formation are i) the requirements for biological activity, and ii) technical requirements directed to the manufacturability of the lipid particle. For the formation of lipid particles comprising an apolipoprotein these requirements point in opposite directions.

From a technical point of view saturated phospholipids containing carboxylic acid moieties with a chain of 16 carbon atoms and shorter would be chosen (e.g. dipalmitoyl-sn-glycero-3-phosphocholine, DPPC; dimyristoyl-sn-glycero-3-phosphocholine, DMPC etc.). In contrast thereto from biological data it can be assumed that non-saturated phospholipids containing carboxylic acid moieties with a chain of at least 16 carbon-atoms (e.g. palmitoyl-2-oleoyl-sn-glycero-3-phosphocholine, POPC; stearoyl-2-oleoyl-sn-glycero-3-phosphocholine, SOPC) are more effective and non-liver toxic.

The phosphatidylcholines DPPC and POPC and mixtures thereof can be used for the formation of lipid particles containing an apolipoprotein. These exemplary phosphatidylcholines differ in one carboxylic acid moiety and have one identical carboxylic acid moiety esterified to the phosphoglycerol backbone. The manufacture of lipid particles was easier when DPPC was used. In contrast POPC was more effective in in vitro functional assays, particularly as substrate for the activation of the lecithin cholesterol acetyl transferase (LCAT) enzyme which is necessary for the conversion of the mobilized cholesterol into cholesterol ester. It has been found that lipid particles comprising mixtures of two phosphatidylcholines, as e.g. POPC and DPPC, in different molar ratios have improved properties compared to lipid particles comprising only one phosphatidylcholine (see e.g. FIG. 4).

Different methods to reconstitute lipid particles from recombinant apolipoprotein or delipidated apolipoprotein derived from human HDL particles have been reported (HDL=high density lipoprotein). For example aqueous mixtures of phospholipids with detergents are incubated with purified apolipoprotein. The apolipoprotein is added in native form. The detergent is afterwards removed by dialysis or diafiltration. The formation of lipid particles comprising tetranectin-apolipoprotein A-I can be achieved by incubating tetranectin-apolipoprotein A-I or a multimer thereof with detergent solubilized lipids at their respective transition temperature. Removal of the detergent by dialysis results in the formation of lipid particles.

The lipid particle can be purified by a combination of precipitation and/or chromatography steps. For example excess detergent, i.e. detergent not part of the lipid particle, can be removed in a hydrophobic adsorption chromatography step. The lipid particle can be recovered from the hydrophobic adsorption material with a detergent-free solution.

The following examples are provided to aid the understanding of the present invention, the true scope of which is set forth in the appended claims. It is understood that modifications can be made in the procedures set forth without departing from the spirit of the invention.

Materials and Methods

Size-Exclusion-HPLC:

The chromatography was conducted with a Tosoh Haas TSK 3000 SWXL column on an ASI-100 HPLC system (Dionex, Idstein, Germany). The elution peaks were monitored at 280 nm by a UV diode array detector (Dionex). After dissolution of the concentrated samples to 1 mg/ml the column was washed with a buffer consisting of 200 mM potassium dihydrogen phosphate and 250 mM potassium chloride pH 7.0 until a stable baseline was achieved. The analyzing runs were performed under isocratic conditions using a flow rate of 0.5 ml/min. over 30 minutes at room temperature. The chromatograms were integrated manually with Chromeleon (Dionex, Idstein, Germany). Aggregation in % was determined by comparing the area under the curve (AUC) of high molecular weight forms with the AUC of the monomer peak.

Dynamic Light Scattering (DLS):

DLS is a non-invasive technique for measuring particle size, typically in the sub-micron size range. In the current invention the Zetasizer Nano S apparatus (Malvern Instruments, Worcestershire, UK) with a temperature controlled quartz cuvette (25° C.) was used for monitoring a size range between 1 nm and 6 µm. The intensity of the back scattered laser light was detected at an angle of 173°. The intensity fluctuates at a rate that is dependent upon the particle diffusion speed, which in turn is governed by particle size. Particle size data can therefore be generated from an analysis of the fluctuation in scattered light intensity (Dahneke, B. E. (ed.), Measurement of Suspended Particles by Quasielectric Light Scattering, Wiley Inc. (1983); Pecora, R., Dynamic Light Scattering: Application of Photon Correlation Spectroscopy, Plenum Press (1985)). The size distribution by intensity was calculated using the multiple narrow mode of the DTS software (Malvern). Experiments were conducted with undiluted samples.

SEC-MALLS:

SEC-MALLS is a combination of size exclusion chromatography with a three detector system: i) UV detection, ii) refraction index detection and iii) light scattering detection. For the separation by size a Superose 6 column 10/300 GL column from GE Healthcare is used. The method is run isocratically with a PBS buffer pH 7.4 applying a flow rate of 0.4 ml/min. Three detector systems are connected in series. The complete lipid particle (protein-lipid particle) signal is monitored by the refraction index detector whereas the UV absorbance determined at 280 nm determines the signal induced by the protein part. The proportion of the lipid fraction is obtained by a simple subtraction of the protein UV signal from the complete signal. Applying light scattering allows for the detection of the molecular mass of the respective species and, thus, a complete and detailed description of the lipid particle.

Detergent Determination:

The determination of residual detergent was conducted by reversed-phase chromatography coupled with an evaporative light scattering detector (RP-ELSD). As column a Luna C18 4.6×150 mm, 5 µm, 100 Å from Phenomenex (Aschaffenburg, Germany) was used. After centrifugation through a 10 kDa membrane 90 µl of the flow-through were used for HPLC separation. Elution was performed under isocratic conditions with 74% (v/v) methanol solution containing 0.1% (v/v) trifluoro acetic acid. Column temperature was set to 30° C. Detection was performed by an evaporative light scattering detector applying a nebulization temperature of 30° C., an evaporating temperature of 80° C. and a gas flow of 1.0 l/min. Quantification of the residual detergent was conducted by the establishment of a calibration curve, in case of cholate in the range of 0.22 µg to 7.5 Ξg cholate.

Protein Determination:

The protein concentration was determined by determining the optical density (OD) at 280 nm, using the molar extinction coefficient calculated on the basis of the amino acid sequence.

Recombinant DNA Technique:

Standard methods were used to manipulate DNA as described in Sambrook, J., et al., Molecular cloning: A laboratory manual; Cold Spring Harbor Laboratory Press, Cold Spring Harbor, N.Y., 1989. The molecular biological reagents were used according to the manufacturer's instructions.

Example 1

Making and Description of the *E. coli* Expression Plasmids

The tetranectin-apolipoprotein A-I fusion polypeptide was prepared by recombinant means. The amino acid sequence of the expressed fusion polypeptide in N- to C-terminal direction is as follows:

the amino acid methionine (M),
a fragment of an interferon sequence that has the amino acid sequence of CDLPQTHSL (SEQ ID NO: 55),
a GS linker,
a hexa-histidine tag that has the amino acid sequence of HHHHHH (SEQ ID NO: 56),
a GS linker,
an IgA protease cleavage site that has the amino acid sequence of VVAPPAP (SEQ ID NO: 60), and
a tetranectin-apolipoprotein A-I that has the amino acid sequence of SEQ ID NO: 02.

The tetranectin-apolipoprotein A-I fusion polypeptides as described above are precursor polypeptides from which the tetranectin-apolipoprotein A-I fusion polypeptides was released by enzymatic cleavage in vitro using IgA protease.

The precursor polypeptide encoding fusion gene was assembled with known recombinant methods and techniques by connection of appropriate nucleic acid segments. Nucleic acid sequences made by chemical synthesis were verified by DNA sequencing. The expression plasmid for the production of tetranectin-apolipoprotein A-I of SEQ ID NO: 01 encoding a fusion protein of SEQ ID NO: 31 was prepared as follows.

Making of the E. coli Expression Plasmid

Plasmid 4980 (4980-pBRori-URA3-LACI-SAC) is an expression plasmid for the expression of core-streptavidin in E. coli. It was generated by ligation of the 3142 bp long EcoRI/CelII-vector fragment derived from plasmid 1966 (1966-pBRori-URA3-LACI-T-repeat; reported in EP-B1 422 237) with a 435 bp long core-streptavidin encoding EcoRI/CelII-fragment.

The core-streptavidin E. coli expression plasmid comprises the following elements:
- the origin of replication from the vector pBR322 for replication in E. coli (corresponding to by position 2517-3160 according to Sutcliffe, G., et al., Quant. Biol. 43 (1979) 77-90),
- the URA3 gene of Saccharomyces cerevisiae coding for orotidine 5'-phosphate decarboxylase (Rose, M. et al. Gene 29 (1984) 113-124) which allows plasmid selection by complementation of E. coli pyrF mutant strains (uracil auxotrophy),
- the core-streptavidin expression cassette comprising
  - the T5 hybrid promoter (T5-PN25/03/04 hybrid promoter according to Bujard, H., et al. Methods. Enzymol. 155 (1987) 416-433 and Stueber, D., et al., Immunol. Methods IV (1990) 121-152) including a synthetic ribosomal binding site according to Stueber, D., et al. (see before),
  - the core-streptavidin gene,
  - two bacteriophage-derived transcription terminators, the λ-T0 terminator (Schwarz, E., et al., Nature 272 (1978) 410-414) and the fd-terminator (Beck E. and Zink, B. Gene 1-3 (1981) 35-58),
- the lacI repressor gene from E. coli (Farabaugh, P. J., Nature 274 (1978) 765-769).

The final expression plasmid for the expression of the tetranectin-apolipoprotein A-I precursor polypeptide was prepared by excising the core-streptavidin structural gene from vector 4980 using the singular flanking EcoRI and CelII restriction endonuclease cleavage site and inserting the EcoRII/CelII restriction site flanked nucleic acid encoding the precursor polypeptide into the 3142 bp long EcoRI/CelII-4980 vector fragment.

Example 2

Expression of Tetranectin-Apolipoprotein A-I

For the expression of the fusion protein as described in example 1 there was employed an E. coli host/vector system which enables an antibiotic-free plasmid selection by complementation of an E. coli auxotrophy (PyrF) (EP 0 972 838 and U.S. Pat. No. 6,291,245).

The E. coli K12 strain CSPZ-2 (leuB, proC, trpE, th-1, pyrF) was transformed by electroporation with the expression plasmid p(IFN-His6-IgA-tetranectin-apolipoprotein A-I) ("His6" disclosed as SEQ ID NO: 56). The transformed E. coli cells were first grown at 37° C. on agar plates.

Fermentation Protocol 1:

For pre-fermentation a M9 medium according to Sambrook et al (Molecular Cloning: A laboratory manual. Cold Spring Harbor Laboratory Press; 2nd edition (December 1989) supplemented with about 1 g/l L-leucine, about 1 g/l L-proline and about 1 mg/l thiamine-HCl has been used.

For pre-fermentation 300 ml of M9-medium in a 1000 ml Erlenmeyer-flask with baffles was inoculated with 2 ml out of a primary seed bank ampoule. The cultivation was performed on a rotary shaker for 13 hours at 37° C. until an optical density (578 nm) of 1-3 was obtained.

For fermentation a batch medium according to Riesenberg et al. was used (Riesenberg, D., et al., J. Biotechnol. 20 (1991) 17-27): 27.6 g/l glucose*$H_2O$, 13.3 g/l $KH_2PO_4$, 4.0 g/l $(NH_4)_2HPO_4$, 1.7 g/l citrate, 1.2 g/l $MgSO_4$*7 $H_2O$, 60 mg/l iron(III)citrate, 2.5 mg/l $CoCl_2$*6 $H_2O$, 15 mg/l $MnCl_2$*4 $H_2O$, 1.5 mg/l $CuCl_2$*2 $H_2O$, 3 mg/l $H_3BO_3$, 2.5 mg/l $Na_2MoO_4$*2 $H_2O$, 8 mg/l $Zn(CH_3COO)_2$*2 $H_2O$, 8.4 mg/l Titriplex III, 1.3 ml/l Synperonic 10% anti foam agent. The batch medium was supplemented with 5.4 mg/l Thiamin-HCl and 1.2 g/l L-leucine and L-proline respectively. The feed 1 solution contained 700 g/l glucose supplemented with 19.7 g/l $MgSO_4$*7 $H_2O$. The alkaline solution for pH regulation was an aqueous 12.5% (w/v) $NH_3$ solution supplemented with 50 g/l L-leucine and 50 g/l L-proline respectively. All components were dissolved in deionized water.

The fermentation was carried out in a 10 l Biostat C DCU3 fermenter (Sartorius, Melsungen, Germany). Starting with 6.4 l sterile fermentation batch medium plus 300 ml inoculum from the pre-fermentation the batch fermentation was performed at 37° C., pH 6.9±0.2, 500 mbar and an aeration rate of 10 l/min. After the initially supplemented glucose was depleted the temperature was shifted to 28° C. and the fermentation entered the fed-batch mode. Here the relative value of dissolved oxygen (pO2) was kept at 50% (DO-stat, see e.g. Shay, L. K., et al., J. Indus. Microbiol. Biotechnol. 2 (1987) 79-85) by adding feed 1 in combination with constantly increasing stirrer speed (550 rpm to 1000 rpm within 10 hours and from 1000 rpm to 1400 rpm within 16 hours) and aeration rate (from 10 l/min to 16 l/min in 10 hours and from 16 l/min to 20 l/min in 5 hours). The supply with additional amino acids resulted from the addition of the alkaline solution, when the pH reached the lower regulation limit (6.70) after approximately 8 hours of cultivation. The expression of recombinant therapeutic protein was induced by the addition of 1 mM IPTG at an optical density of 70.

At the end of fermentation the cytoplasmatic and soluble expressed tetranectin-apolipoprotein A-I is transferred to insoluble protein aggregates, the so called inclusion bodies, with a heat step where the whole culture broth in the fermenter is heated to 50° C. for 1 or 2 hours before harvest (see e.g. EP-B 1 486 571). Thereafter, the content of the fermenter was centrifuged with a flow-through centrifuge (13,000 rpm, 13 l/h) and the harvested biomass was stored at −20° C. until further processing. The synthesized tetranectin-apolipoprotein A-I precursor proteins were found exclusively in the insoluble cell debris fraction in the form of insoluble protein aggregates, so-called inclusion bodies (IBs).

The synthesized fusion protein was found exclusively in the insoluble cell debris fraction in the form of insoluble protein aggregates, so-called inclusion bodies (IBs).

Samples drawn from the fermenter, one prior to induction and the others at dedicated time points after induction of protein expression are analyzed with SDS-Polyacrylamide gel electrophoresis. From every sample the same amount of cells ($OD_{Target}$=5) are resuspended in 5 mL PBS buffer and disrupted via sonication on ice. Then 100 μL of each suspension are centrifuged (15,000 rpm, 5 minutes) and each supernatant is withdrawn and transferred to a separate vial. This is to discriminate between soluble and insoluble expressed target protein. To each supernatant (=soluble) fraction 300 μL and to each pellet (=insoluble) fraction 400 μL of SDS sample buffer (Laemmli, U.K., Nature 227 (1970) 680-685) are added. Samples are heated for 15 minutes at 95° C. under shaking to solubilize and reduce all proteins in the samples. After cooling to room temperature 5 μL of each sample are transferred to a 4-20% TGX Criterion Stain Free polyacrylamide gel (Bio-Rad). Additionally 5 μl molecular weight standard (Precision Plus Protein Standard, Bio-Rad) and 3 amounts (0.3 μl, 0.6 μl and 0.9 μl) quantification standard with known product protein concentration (0.1 μg/μl) are positioned on the gel.

The electrophoresis was run for 60 Minutes at 200 V and thereafter the gel was transferred the GelDOC EZ Imager (Bio-Rad) and processed for 5 minutes with UV radiation. Gel images were analyzed using Image Lab analysis software (Bio-Rad). With the three standards a linear regression curve was calculated with a coefficient of >0.99 and thereof the concentrations of target protein in the original sample was calculated.

Fermentation Protocol 2:

For pre-fermentation a M9 medium according to Sambrook et al. (Molecular Cloning: A laboratory manual. Cold Spring Harbor Laboratory Press; 2nd edition (December 1989)) supplemented with about 1 g/l L-leucine, about 1 g/l L-proline and about 1 mg/l thiamine-HCl has been used.

For pre-fermentation 300 ml of modified M9-medium in a 1000 ml Erlenmeyer-flask with baffles was inoculated from agar plate or with 1-2 ml out of a primary seed bank ampoule. The cultivation was performed on a rotary shaker for 13 hours at 37° C. until an optical density (578 nm) of 1-3 was obtained.

For fermentation and high yield expression of tetranectin-apolipoprotein A-I the following batch medium and feeds were used:

8.85 g/l glucose, 63.5 g/l yeast extract, 2.2 g/l $NH_4Cl$, 1.94 g/l L-leucine, 2.91 g/l L-proline, 0.74 g/l L-methionine, 17.3 g/l $KH_2PO_4*H2_O$, 2.02 g/l $MgSO_4*7\ H_2O$, 25.8 mg/l Thiamin-HCl, 1.0 ml Synperonic 10% anti foam agent. The feed 1 solution contained 333 g/l yeast extract and 333 g/l 85%-glycerol supplemented with 1.67 g/l L-methionine and 5 g/l L-leucine and L-proline each. The feed 2 was a solution of 600 g/l L-Proline. The alkaline solution for pH regulation was a 10% (w/v) KOH solution and as acid a 75% glucose solution was used. All components were dissolved in deionized water.

The fermentation was carried out in a 10 l Biostat C DCU3 fermenter (Sartorius, Melsungen, Germany). Starting with 5.15 l sterile fermentation batch medium plus 300 ml inoculum from the pre-fermentation the fed-batch fermentation was performed at 25° C., pH 6.7±0.2, 300 mbar and an aeration rate of 10 l/min. Before the initially supplemented glucose was depleted the culture reached an optical density of 15 (578 nm) and the fermentation entered the fed-batch mode when feed 1 was started with 70 g/h. Monitoring the glucose concentration in the culture the feed 1 was increased to a maximum of 150 g/h while avoiding glucose accumulation and keeping the pH near the upper regulation limit of 6.9. At an optical density of 50 (578 nm) feed 2 was started with a constant feed rate of 10 ml/h. The relative value of dissolved oxygen ($pO_2$) was kept above 50% by increasing stirrer speed (500 rpm to 1500 rpm), aeration rate (from 10 l/min to 20 l/min) and pressure (from 300 mbar to 500 mbar) in parallel. The expression of recombinant therapeutic protein was induced by the addition of 1 mM IPTG at an optical density of 90.

Seven samples drawn from the fermenter, one prior to induction and the others at dedicated time points after induction of protein expression are analyzed with SDS-Polyacrylamide gel electrophoresis. From every sample the same amount of cells ($OD_{Target}=5$) are resuspended in 5 mL PBS buffer and disrupted via sonication on ice. Then 100 µL of each suspension are centrifuged (15,000 rpm, 5 minutes) and each supernatant is withdrawn and transferred to a separate vial. This is to discriminate between soluble and insoluble expressed target protein. To each supernatant (=soluble) fraction 300 µL and to each pellet (=insoluble) fraction 200 µL of SDS sample buffer (Laemmli, U.K., Nature 227 (1970) 680-685) are added. Samples are heated for 15 minutes at 95° C. under shaking to solubilize and reduce all proteins in the samples. After cooling to room temperature 5 µL of each sample are transferred to a 10% Bis-Tris polyacrylamide gel (Novagen). Additionally 5 µL molecular weight standard (Precision Plus Protein Standard, Bio-Rad) and 3 amounts (0.3 µL, 0.6 µL and 0.9 µL) quantification standard with known product protein concentration (0.1 µg/µl) are positioned on the gel.

The electrophoresis was run for 35 minutes at 200 V and then the gel was stained with Coomassie Brilliant Blue R dye, destained with heated water and transferred to an optical densitometer for digitalization (GS710, Bio-Rad). Gel images were analyzed using Quantity One 1-D analysis software (Bio-Rad). With the three standards a linear regression curve is calculated with a coefficient of >0.98 and thereof the concentrations of target protein in the original sample was calculated.

At the end of fermentation the cytoplasmatic and soluble expressed tetranectin-apolipoprotein A-I is transferred to insoluble protein aggregates, the so called inclusion bodies (IBs), with a heat step where the whole culture broth in the fermenter is heated to 50° C. for 1 or 2 hours before harvest (see e.g. EP-B 1 486 571). After the heat step the synthesized tetranectin-apolipoprotein A-I precursor proteins were found exclusively in the insoluble cell debris fraction in the form of IBs.

The contents of the fermenter are cooled to 4-8° C., centrifuged with a flow-through centrifuge (13,000 rpm, 13 l/h) and the harvested biomass is stored at −20° C. until further processing. The total harvested biomass yield ranged between 39 g/l and 90 g/l dry matter depending on the expressed construct.

Example 3

Preparation of Tetranectin-Apolipoprotein A-I

Inclusion body preparation was carried out by resuspension of harvested bacteria cells of example 2 in a potassium phosphate buffer solution or Tris buffer solution (0.1 M, supplemented with 1 mM $MgSO_4$, pH 6.5). After the addition of DNAse the cell were disrupted by homogenization at a pressure of 900 bar. A buffer solution comprising 1.5 M NaCl and 60 mM EDTA was added to the homogenized cell suspension. After the adjustment of the pH value to 5.0 with 25% (w/v) HCl the final inclusion body slurry was obtained after a further centrifugation step. The slurry was stored at −20° C. in single use, sterile plastic bags until further processing.

The inclusion body slurry (about 15 kg) was solubilized in a guanidinium hydrochloride solution (150 l, 6.7 M). After clarification of the solubilisate by depth filtration, the solution was applied to a Zn-chelate affinity chromatography material. The fusion polypeptide was purified by Zn-chelate chromatography material and cleaved by IgA protease. Thereafter the polypeptide was further purified with an anion exchange chromatography and a cation exchange chromatography step. These steps were performed in a urea containing solution (7 M), i.e. under denaturing conditions. These steps were used for the removal of polypeptide fragments, endotoxins, and further impurities. A diafiltration into 6.7 M guanidinium hydrochloride containing solution was carried out. The obtained final solution contains denatured tetranectin-apolipoprotein A-I.

Example 4

Refolding and Lipidation of Tetranectin-Apolipoprotein A-I

In the following the tetranectin-apolipoprotein A-I as produced in the previous examples 1 to 3 of SEQ ID NO: 01 was used.

a) General Method

Pure crystalline POPC or DPPC (Lipoid, Switzerland) have been dissolved in an aqueous buffer (lipidation buffer)

containing cholate in a molar ratio phospholipid:cholate of 1:1.35. The mixtures have been incubated under nitrogen atmosphere and protected from light at room temperature (POPC) or at 55° C. (DPPC) until a clear solution has been obtained. The clear lipid-cholate solution is cooled to 4° C. (POPC) or stored at 41° C. (DPPC). Purified tetranectin-apolipoprotein A-I has been added at 4° C. (POPC) or 41° C. (DPPC) at a defined apolipoprotein:phospholipid ratio. For lipid particle formation the reaction mixture was incubated over night at 4° C. (POPC) or 41° C. (DPPC) under nitrogen atmosphere and protected from light. Finally, cholate was removed by extensive dialysis (4° C./41° C.) against lipidation buffer. Finally samples were centrifuged to remove precipitated material.

Cholate solubilized lipid solutions containing pure POPC or pure DPPC have been prepared as described above. Lipid mixtures were prepared by combining the lipid solutions at the desired ratio followed by storage at the respective $T_m$ ($T_m$=phase transition temperature). Lipid particle formation of tetranectin-apolipoprotein A-I was performed as described for pure lipid solutions but at the respective $T_m$ of the lipid mixture chosen.

The following lipidation buffers have been tested:
1. 50 mM potassium phosphate buffer supplemented with 250 mM arginine hydrochloride, 7.5% sucrose at pH 7.5
2. 50 mM dipotassium hydrogen phosphate buffer supplemented with 250 mM arginine hydrochloride, 7.5% sucrose, 10 mM methionine at pH 7.5
3. 250 mM tris-hydroxylamino methane (TRIS) supplemented with 140 mM NaCl, 10 mM methionine at pH 7.5
4. 50 mM dipotassium hydrogen phosphate buffer supplemented with 250 mM arginine hydrochloride, 7% trehalose, 10 mM methionine at pH 7.5.

Figure 11:
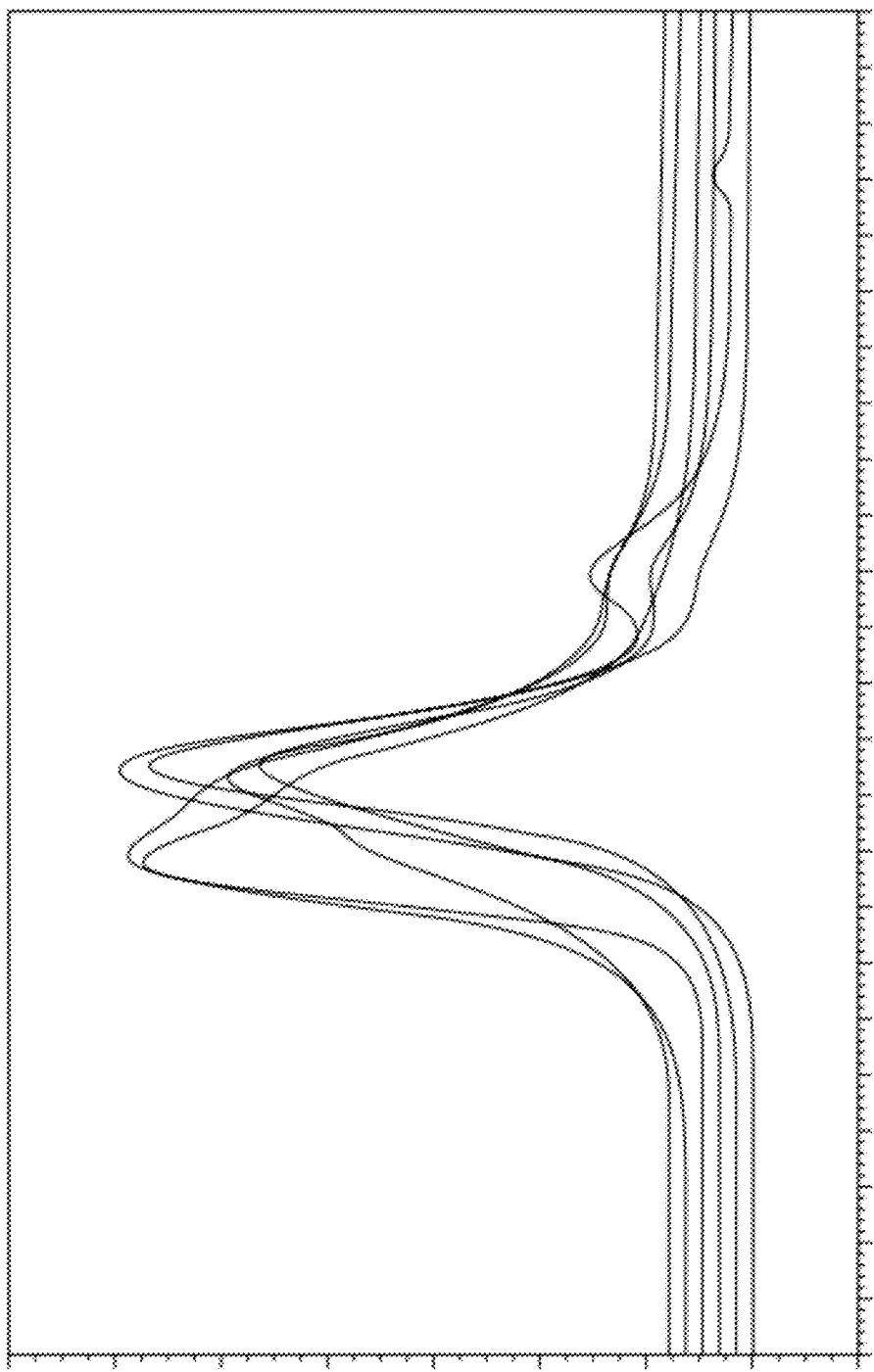
FIG. 11 Analytical SEC of lipid particles using 250 mM Tris-HCl, 140 mM NaCl, pH 7.5.
Figure 12:
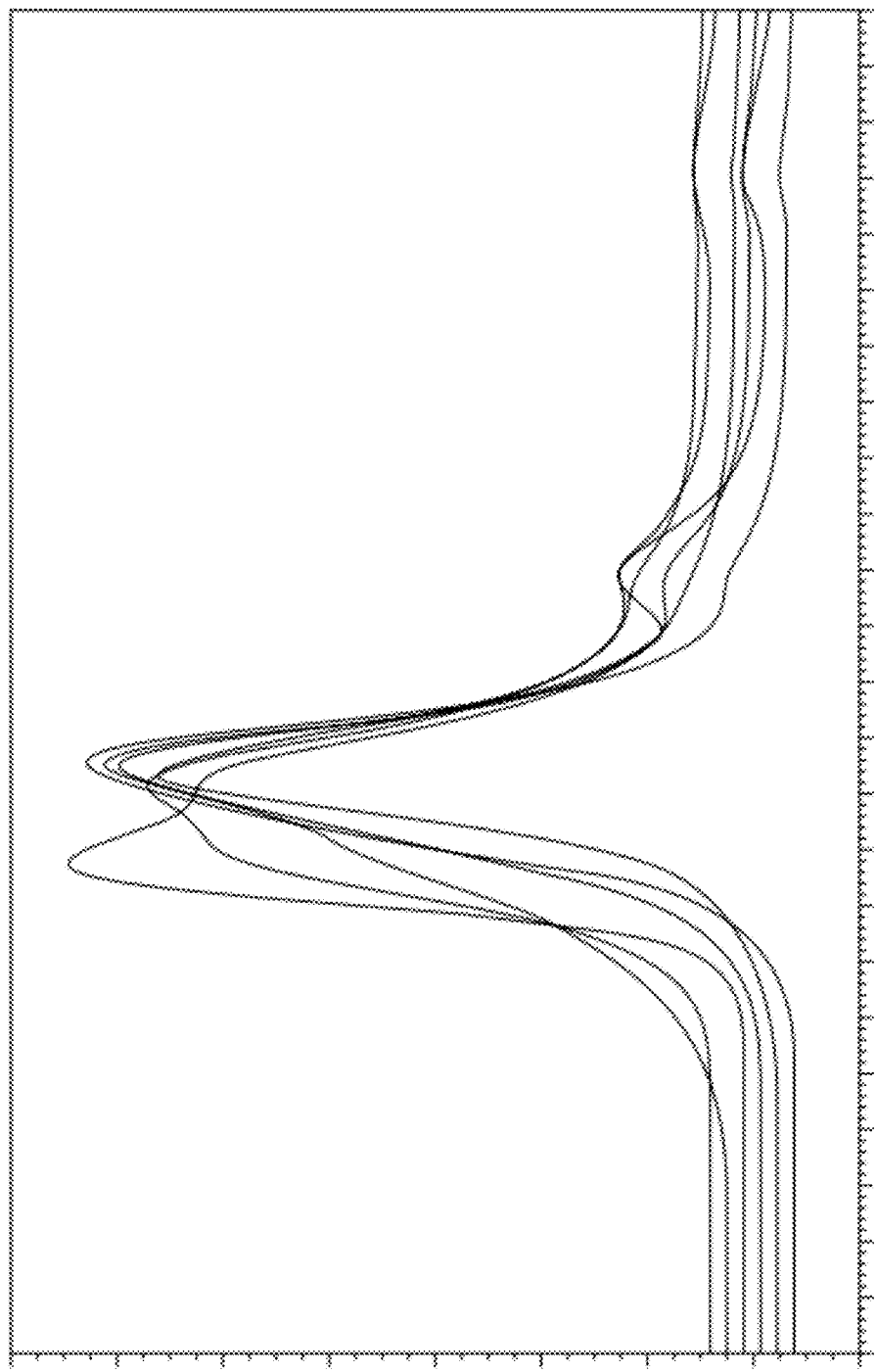
FIG. 12 Analytical SEC of lipid particles using 50 mM $K_2HPO_4$, 250 mM arginine hydrochloride, 7.5% trehalose at pH 7.5.

The homogeneity of the lipid particles formed from tetranectin-apolipoprotein A-I samples has been assessed by analytical SEC (FIGS. 11 and 12). Overall, the choice of the lipidation buffer has only a minor effect compared to the choice of phospholipid. DPPC-lipid particles elute as one main peak, whereas POPC-lipid particles shows a two peak pattern. The choice of lipidation buffer was influenced by the purification process of the apolipoprotein and the supply of stabilized lipid-free apolipoprotein. Lipid particle formation was shown to be feasible irrespective of the lipidation buffer. Among various buffers tested the most appropriate lipidation buffer was identified to be 250 mM Tris, 140 mM NaCl, 10 mM methionine, pH 7.5.

Lipidation mixtures contained a defined amount of apolipoprotein each and the amount of phospholipid, e.g. POPC, was calculated accordingly. All calculations of the molar amount of lipid were based on the tetranectin-apolipoprotein A-I monomer.

b) POPC and Cholate

TABLE 5

Lipid particle formation with tetranectin-apolipoprotein A-I as example using pure POPC. Molar ratios apolipoprotein:phospholipid are calculated for the protein monomer. Controls: apolipoprotein incubated without addition of lipid (pure Apo) and lipid without apolipoprotein (no Apo).

| molar ratio apolipo-protein:phos-pholipid | observation after overnight incubation | protein conc. before dialysis [mg/ml] | protein conc. after dialysis [mg/ml] | observation after dialysis |
|---|---|---|---|---|
| 1:320 | clear | 0.67 | n.d. | turbid |
| 1:160 | clear | 1.34 | 1.47 | clear |
| 1:80 | clear | 2.68 | 2.6 | clear |
| 1:40 | clear | 5.36 | 4.87 | clear |
| 1:20 | turbid | 10.73 | 5.02 | turbid* |
| only Apo | turbid | 2.68 | 0.51 | turbid* |
| no Apo | clear | — | — | clear |

*clear after centrifugation

The molar ratios from 1:40 to 1:160 remain clear during the whole process. Neither turbidity through excess phospholipid nor protein precipitation was observed.

Figure 13:
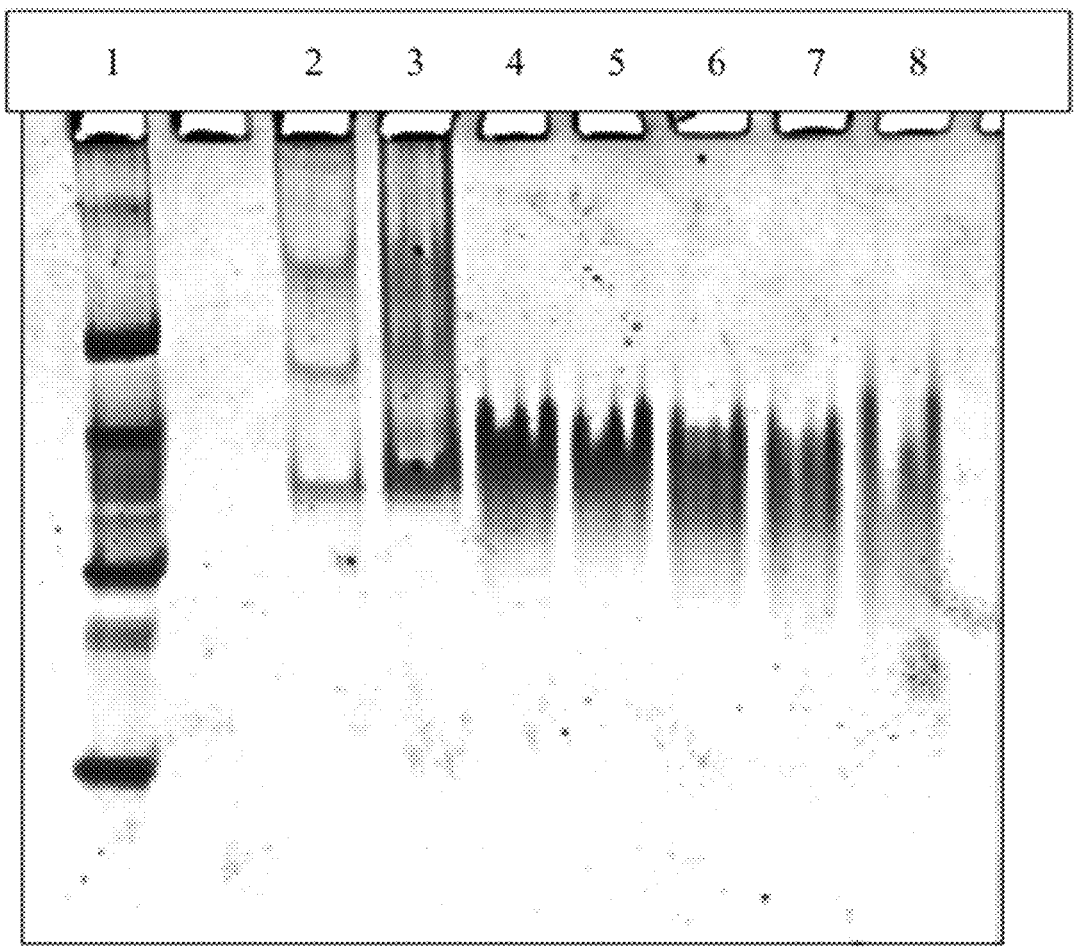
FIG. 13 Native PAGE of lipid particles of POPC and tetranectin-apolipoprotein A-I in molar ratios of from 1:20 to 1:320 (lane 1: native Marker; lane 2: molar ratio 1:320; lane 3: molar ratio 1:160; lane 4: molar ratio 1:80; lane 5: molar ratio 1:80 (f/t); lane 6: molar ratio 1:40; lane 7: molar ratio 1:20; lane 8: apolipoprotein (forming hexamers)).

Lipid particle samples have been analyzed by native PAGE (see FIG. 13). The most homogeneous band pattern was found with the sample 1:80 (lane 4). In addition 1× freeze/thaw (−80° C.) did not alter appearance of the sample (lane 5). The band patterns of samples 1:320 and 1:160 indicate an inhomogeneous product resulting in multiple bands (lane 2 and 3). Samples 1:40 and also 1:20 have additional bands below the main product band (lane 6 and 7). The migration pattern of pure tetranectin-apolipoprotein A-I is shown in lane 8 of FIG. 13.

Figure 14:
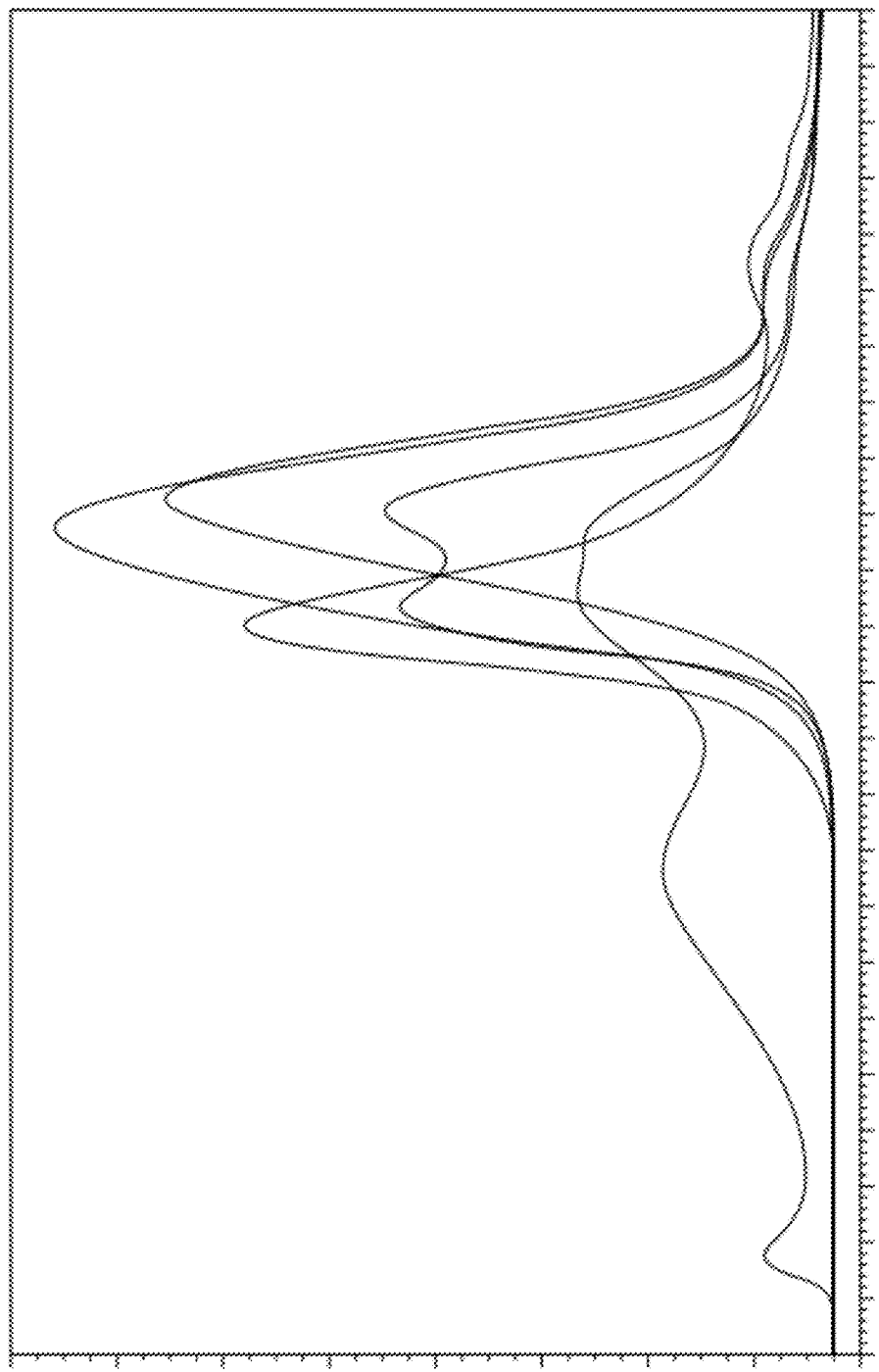
FIG. 14 SEC-MALLS analysis of lipid particles of POPC and tetranectin-apolipoprotein A-I in molar ratios of from 1:20 to 1:160.

SEC-MALLS analysis was used to gain more detailed information on the homogeneity of the lipid particles and their apolipoprotein-phospholipid composition (protein-conjugate analysis). FIG. 14 shows the chromatogram of SEC resolved samples (UV280 detection). Here the 1:160 sample is divided into three separated peaks. The 1:80 sample appeared to contain at least two species of different size as displayed as double peak. The peak obtained from sample 1:20 shows the most homogeneous product.

The experiment was carried out using tetranectin-apolipoprotein A-I (3.84 mg/ml; 10 mg per sample) and the molar ratio apolipoprotein:phospholipid was increased from 1:40 to 1:80 in steps of 5. At molar ratios below 1:40 the lipid particle formation is incomplete. Molar ratios above 1:80 are excluded experimentally: after removal of cholate by dialysis the samples became turbid. Moreover the lipid particles became more inhomogeneous at higher lipid ratios.

TABLE 6

Lipid particle formation of tetranectin-apolipoprotein A-I using pure POPC. Molar ratio apolipoprotein:phospholipid has been calculated based on the tetranectin-apolipoprotein A-I monomer.

| molar ratio apolipo-protein:phos-pholipid | protein conc. before dialysis [mg/ml]* | protein conc. after dialysis [mg/ml]* | yield [%] | observation after dialysis |
|---|---|---|---|---|
| 1:40 | 3.5 | 2.67 | 76 | precipitation |
| 1:45 | 3.5 | 2.74 | 78 | precipitation |
| 1:50 | 3.5 | 2.94 | 84 | precipitation |
| 1:55 | 3.5 | 3.05 | 87 | precipitation |
| 1:60 | 3.5 | 3.19 | 91 | precipitation |
| 1:65 | 3.5 | 3.34 | 95 | precipitation |
| 1:70 | 3.5 | 3.52 | 100** | |
| 1:75 | 3.5 | 3.56 | 100** | |
| 1:80 | 3.5 | 3.57 | 100** | |

*volume before and after dialysis 2.6 ml
**within SD of the method

During incubation at the transition temperature of −3° C. all samples remained optically clear. After removal of cholate by dialysis increasing turbidity of the samples 1:40 to 1:65 was observed. Precipitate could be removed by centrifugation and the samples remained clear afterwards.

Figure 15:
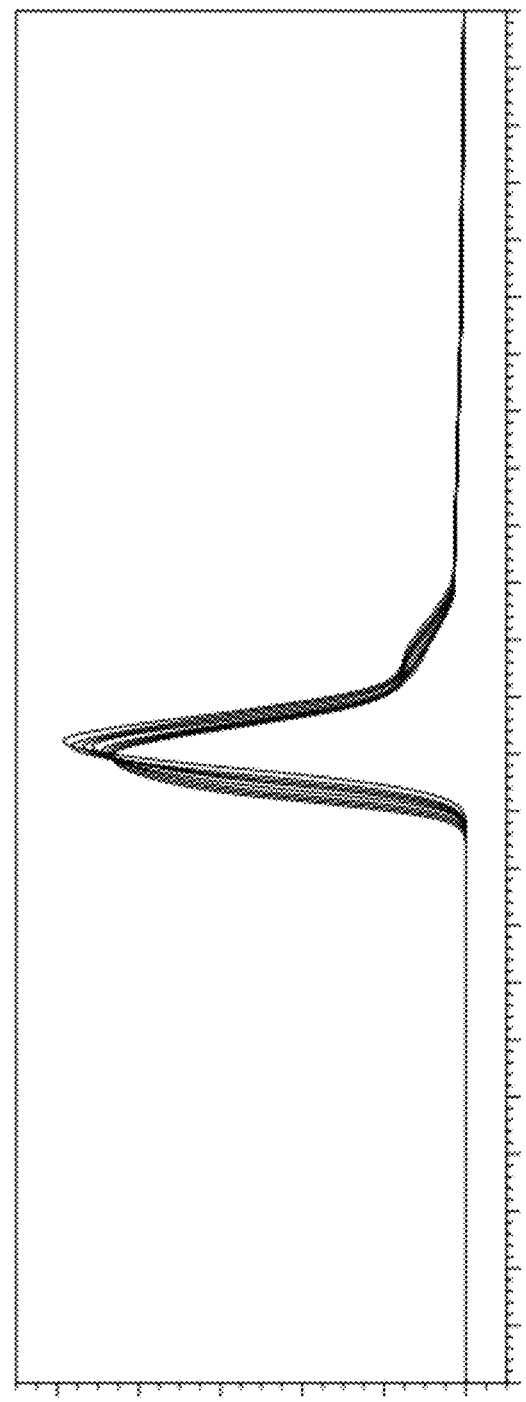
FIG. 15 Superposition of SEC chromatograms (UV280 signal) of lipid particle of POPC and tetranectin-apolipoprotein A-I.

SEC-MALLS analysis was used to gain detailed information on the homogeneity of the formed lipid particles and their apolipoprotein-phospholipid composition (protein-conjugate analysis). All lipid particles were comparably homogeneous on analytical size exclusion chromatography (SEC; FIG. 15) displaying a minor post peak which is more pronounced at lower molar ratios. In addition, there is a noticeable shift in the peak pattern at higher molar ratios towards higher molecular weights. The respective retention times are given in Table 7.

A-I monomer varies between 54 and 75 though molar ratios from 1:40 up to 1:80 have been applied. The value % protein is a parameter for the degree of lipidation. The lower the percentage of the protein in the lipid particle, the higher the degree of lipidation.

TABLE 8

Figure 16:
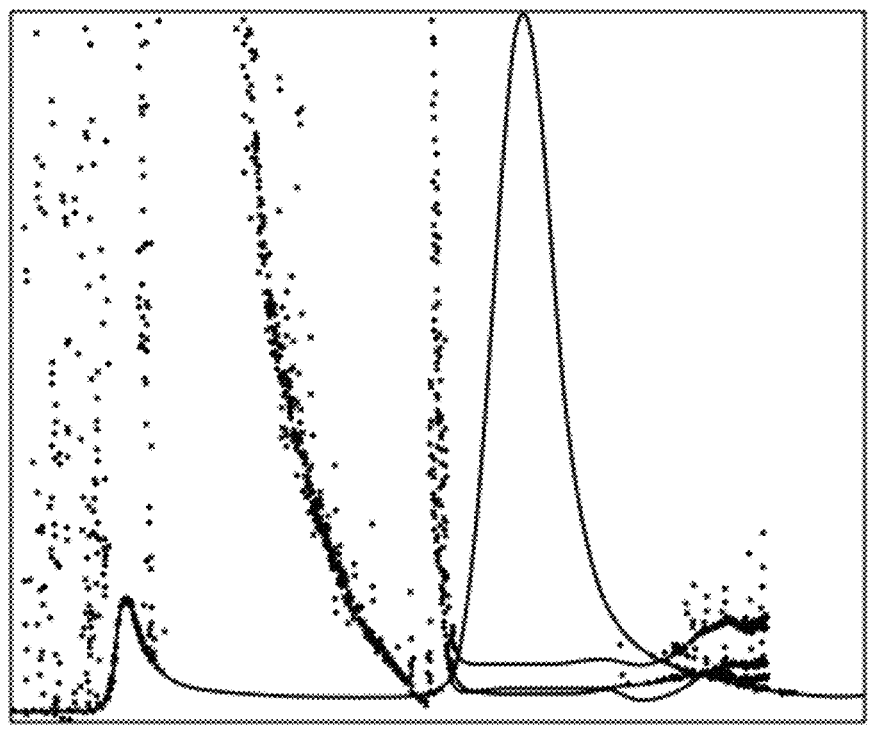
FIG. 16 SEC-MALLS analysis of a lipid particle of POPC and tetranectin-apolipoprotein A-I obtained at a molar ratio of 1:40.

Summary of protein conjugate analysis of lipid particles of POPC and tetranectin-apolipoprotein A-I as shown in FIG. 16.

| | | MW total [kDa] | MW Protein [kDa] | n (monomer) | MW lipid [kDa] | n (POPC) | n(POPC)/ n(monomer) | % protein |
|---|---|---|---|---|---|---|---|---|
| 1:40 | Main peak | 238 | 104 | 3.3 | 135 | 178 | 54 | 44 |
| | Post peak | 230 | 148 | 4.6 | 81 | 107 | 23 | 65 |
| 1:45 | Main peak | 238 | 101 | 3.2 | 138 | 182 | 57 | 42 |
| | Post peak | 184 | 118 | 3.7 | 66 | 87 | 24 | 64 |
| 1:50 | Main peak | 244 | 100 | 3.1 | 143 | 188 | 61 | 41 |
| | Post peak | 187 | 118 | 3.7 | 70 | 92 | 25 | 63 |
| 1:55 | Main peak | 247 | 99 | 3.1 | 148 | 195 | 63 | 40 |
| | Post peak | 182 | 107 | 3.3 | 75 | 99 | 30 | 59 |
| 1:60 | Main peak | 248 | 98 | 3.1 | 150 | 197 | 64 | 40 |
| | Post peak | 183 | 106 | 3.3 | 76 | 100 | 30 | 58 |
| 1:65 | Main peak | 255 | 97 | 3.0 | 158 | 208 | 69 | 38 |
| | Post peak | 191 | 103 | 3.2 | 88 | 116 | 36 | 54 |
| 1:70 | Main peak | 260 | 97 | 3.0 | 163 | 214 | 71 | 37 |
| | Post peak | 196 | 100 | 3.1 | 95 | 125 | 40 | 51 |
| 1:75 | Main peak | 266 | 99 | 3.1 | 168 | 221 | 71 | 37 |
| | Post peak | 208 | 118 | 3.7 | 91 | 120 | 32 | 56 |
| 1:80 | Main peak | 275 | 99 | 3.1 | 176 | 232 | 75 | 36 |
| | Post peak | 215 | 112 | 3.5 | 103 | 136 | 39 | 52 |

TABLE 7

Summary of size exclusion chromatography results; percentages were calculated by integration of the area under the curve (AUC).

| UV280 | retention time main peak [min.] | main peak [%] | post peak [%] | total area [mAU * min] |
|---|---|---|---|---|
| POPC 1:40 | 56.2 | 89.3 | 10.7 | 322.3 |
| POPC 1:45 | 55.9 | 89.7 | 10.4 | 331.3 |
| POPC 1:50 | 55.8 | 90.0 | 10.0 | 333.2 |
| POPC 1:55 | 55.7 | 91.0 | 9.1 | 342.5 |
| POPC 1:60 | 55.6 | 90.8 | 9.2 | 331.7 |
| POPC 1:65 | 55.3 | 90.9 | 9.2 | 337.2 |
| POPC 1:70 | 55.2 | 91.1 | 8.9 | 326.5 |
| POPC 1:75 | 55.1 | 91.3 | 8.7 | 347.1 |
| POPC 1:80 | 54.8 | 92.0 | 8.0 | 347.8 |

The protein-conjugate analysis (summarized in Table 8) enables the calculation of the total molecular weight of the protein (MW protein) and the lipid component (MW lipid) for each lipid particle eluted from the SEC column. Based on the molecular weights of tetranectin-apolipoprotein A-I monomer (32.7 kDa) and POPC (760 Da) the composition of the lipid particle can be calculated (n protein and n POPC). The molecular weight of the apolipoprotein component found in the lipid particle main peak at all molar ratios was approximately 100 kDa corresponding to a tetranectin-apolipoprotein A-I trimer per lipid particle. The ratio n(POPC)/n(protein monomer) gives the number of POPC molecules per tetranectin-apolipoprotein A-I monomer in the lipid particle. The number of POPC molecules per tetranectin-apolipoprotein c) DPPC and Cholate Prior to lipidation the tetranectin-apolipoprotein A-I was dialyzed against 50 mM $KH_2PO_4$, 250 mM arginine hydrochloride, 7% trehalose, 10 mM methionine at pH 7.5. Tetranectin-apolipoprotein A-I (3.84 mg/ml, 3 mg per sample) has been lipidated using molar ratios from 1:60 to 1:100 increasing lipid concentrations in steps of 5. The lipidation buffer was 250 mM Tris-HCl, 140 mM NaCl, 10 mM methionine, pH 7.5.

TABLE 9

Sample overview of lipid particles of apolipoprotein with DPPC.

| molar ratio apolipoprotein:phospholipid* | observation after o/n incubation | yield based on protein [%] |
|---|---|---|
| 1:20 | clear | 85 |
| 1:40 | clear | 88 |
| 1:60 | clear | 89 |
| 1:80 | clear | 91 |
| 1:100 | clear | 94 |
| only Apo | clear | 86 |
| no Apo | clear | DPPC precipitated |

*calculated for protein monomer

During lipid particle formation neither precipitation of protein nor turbidity through excess lipid was observed. The yield of tetranectin-apolipoprotein A-I in the final product was higher the more DPPC was used for lipidation.

Figure 17:
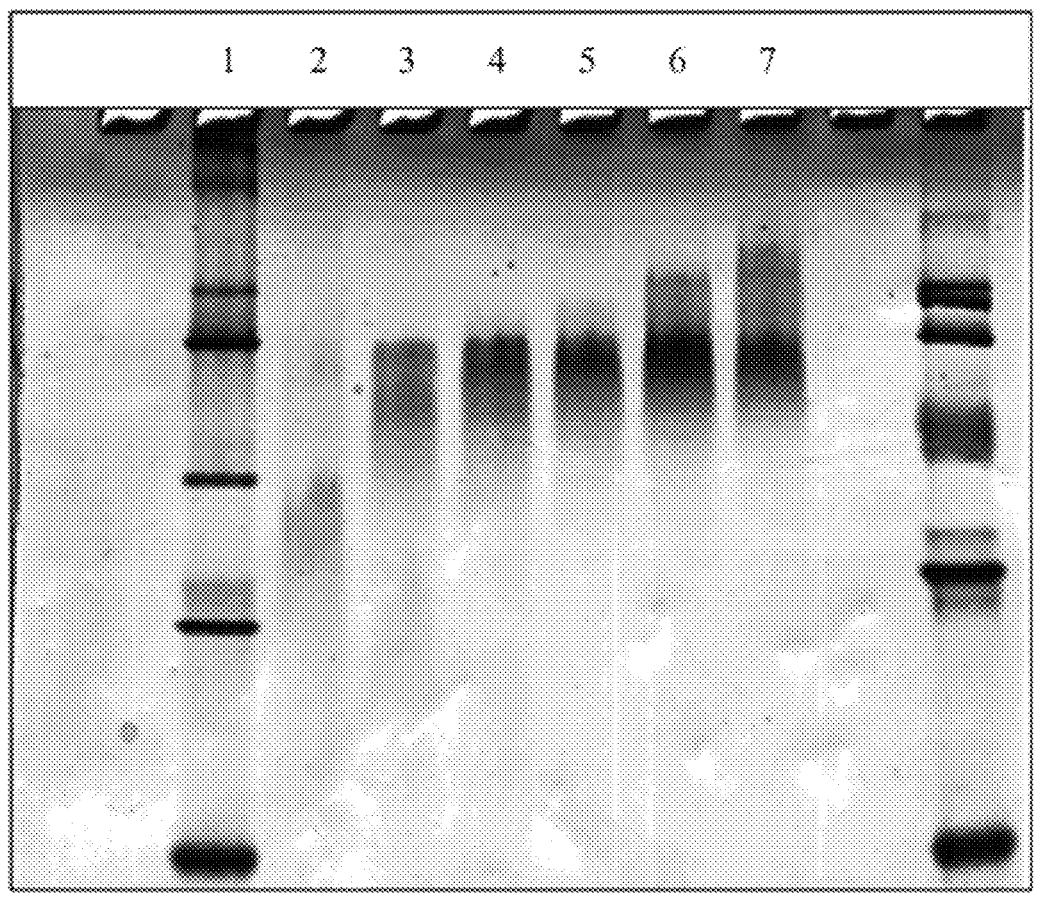
FIG. 17 Native PAGE of lipid particles of DPPC and tetranectin-apolipoprotein A-I obtained with molar ratios of from 1:20 to 1:100 (1: molecular weight marker; 2: tetranectin-apolipoprotein A-I without lipid; 3:1:20; 4:1:40; 5:1:60; 6:1:80; 7:1:100).

Residual lipid-free apolipoprotein was found in the 1:20 sample on native PAGE (lane 3, FIG. 17). The 1:40 and 1:60 sample look most homogeneous (lanes 4 and 5) on native PAGE whereas the 1:80 and 1:100 samples contain additional higher molecular bands above the main lipid particle band (lanes 6 and 7).

SEC-MALLS protein conjugate analysis was used to characterize the composition of the lipid particles obtained after DPPC lipid particle formation (MW DPPC: 734 Da). Homogeneous SEC peaks were obtained at molar ratios of 1:80 and below. At higher lipid ratios a pre-peak emerged (see e.g. 1:90 sample in Table 10).

TABLE 10

Summary SEC-MALLS protein conjugate analysis of lipid particles of DPPC and tetranectin-apolipoprotein A-I.

| molar ratio apolipoprotein:phospholipid | peak | MW total [kDa] | MW protein [kDa] | n (protein) | MW lipid [kDa] | n (DPPC)/ n (protein) | % protein |
|---|---|---|---|---|---|---|---|
| 1:60 | 1 | 724 | 298 | 9.0 | 425 | 193 | 41.2 |
| 1:65 | 1 | 281 | 109 | 3.3 | 171 | 77 | 38.9 |
| 1:70 | 1 | 273 | 103 | 3.1 | 169 | 76 | 37.9 |
| 1:75 | 1 | 286 | 103 | 3.1 | 183 | 83 | 36.0 |
| 1:80 | 1 | 295 | 100 | 3.0 | 194 | 88 | 34.1 |
| 1:85 | 1 | 307 | 99 | 3.0 | 207 | 94 | 32.6 |
| 1:90 | 1 | 361 | 117 | 3.5 | 244 | 110 | 32.6 |
|  | 2 | 319 | 101 | 3.0 | 217 | 98 | 31.8 |
| 1:95 | 1 | 397 | 134 | 4.0 | 262 | 118 | 33.8 |
|  | 2 | 327 | 100 | 3.0 | 226 | 102 | 30.8 |
| 1:100 | 1 | 405 | 132 | 4.0 | 273 | 123 | 32.6 |
|  | 2 | 344 | 101 | 3.0 | 243 | 110 | 29.3 |

The highest degree of lipidation (lowest percentage of protein) is found with the 1:80 to 1:90 molar ratios. In addition DLS revealed most homogeneous particle formation at ratios 1:80 to 1:90 (>98%) at a particle size of 14-17 nm.

d) 75% DPPC/25% POPC

The lipid particle formation was carried out accordingly as reported in items a) to c) of this example with the following parameters:

Protein: tetranectin-apolipoprotein A-I at 3.84 mg/ml, 3 mg per sample
Lipidation buffer: 250 mM Tris-HCl, 140 mM NaCl, 10 mM methionine pH 7.5
Lipidation: at 34° C.
Dialysis: at 4° C.
Molar ratios tested: 1:60 to 1:100 with increasing the lipid in steps of 5

Figure 18:
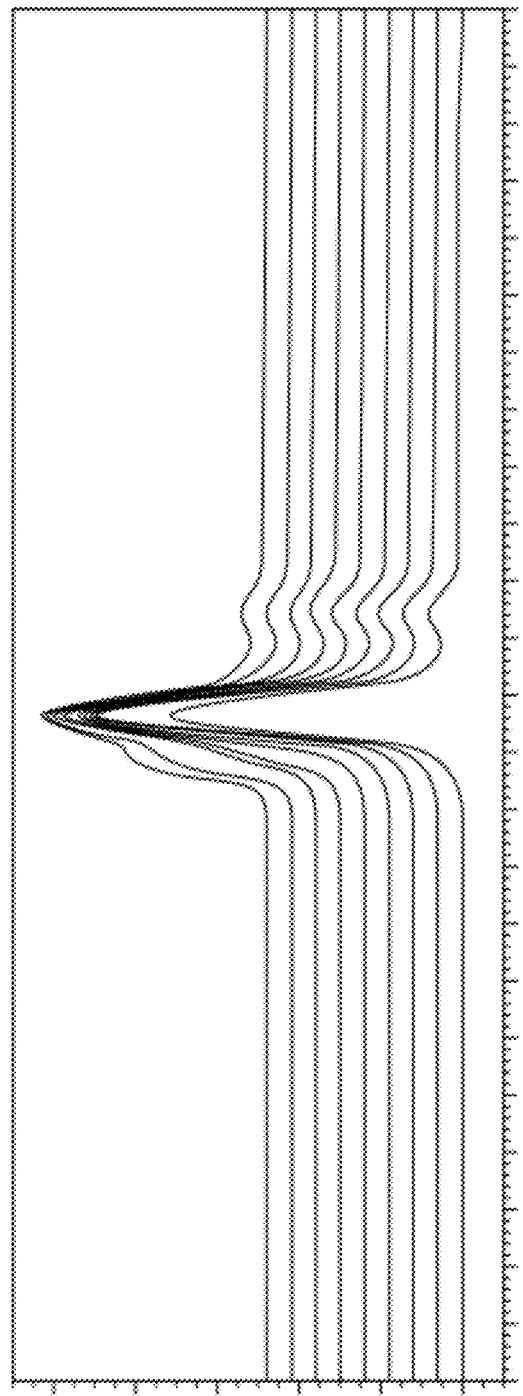
FIG. 18 SEC-MALLS analysis (UV280 signal) of a lipid particle of a mixture of POPC:DPPC=3:1 and tetranectin-apolipoprotein A-I obtained at molar ratios of from 1:60 (uppermost curve) to 1:100 (lowest curve).

Lipid particle formation was straight forward and comparable to the process using pure lipids. All samples remained clear during the process and dialysis. The yield of lipid particles was similar for all ratios tested (~85%). SEC-MALLS analysis showed that the molar ratio of 1:80 resulted in the most homogeneous lipid particles with 90.9% main peak, no pre-peak and 9.1% post-peak. Protein conjugate analysis revealed the presence of one tetranectin-apolipoprotein A-I trimer per lipid particle in the main species of all samples (see FIG. 18 and Tables 11 and 12).

TABLE 11

Summary of SEC results; percentages were calculated by integration of the AUC.

| UV280 | Retention time Main peak | Pre peak [%] | Main peak [%] | Post peak [%] | total [mAU * min] |
|---|---|---|---|---|---|
| 75/25 DPPC/POPC 1:60 | 58.3 | — | 89.7 | 10.3 | 360.5 |
| 75/25 DPPC/POPC 1:65 | 58.3 | — | 89.2 | 10.8 | 383.7 |
| 75/25 DPPC/POPC 1:70 | 58.3 | — | 89.5 | 10.5 | 376.8 |
| 75/25 DPPC/POPC 1:75 | 58.4 | — | 90.3 | 9.7 | 367.0 |
| 75/25 DPPC/POPC 1:80 | 58.3 | — | 90.9 | 9.1 | 383.5 |
| 75/25 DPPC/POPC 1:85 | 58.2 | 10.4 | 79.5 | 10.1 | 356.4 |
| 75/25 DPPC/POPC 1:90 | 58.3 | 10.2 | 81.5 | 8.3 | 344.6 |
| 75/25 DPPC/POPC 1:95 | 58.0 | 16.9 | 74.9 | 8.2 | 377.4 |
| 75/25 DPPC/POPC 1:100 | 58.0 | 21.0 | 70.4 | 7.7 | 365.0 |

TABLE 12

Summary protein-conjugate analysis of 75% DPPC/25% POPC and tetranectin-apolipoprotein A-I lipid particles.

|  |  | MW total | MW protein [kDa] | n (protein monomer) | MW lipid [kDa] | n (lipid) | n(lipid)/ n(monomer) | % protein |
|---|---|---|---|---|---|---|---|---|
| 1:60 | Main peak | 257 | 96 | 3.0 | 161 | 217 | 72 | 37 |
|  | Post peak | 92 | 75 | 2.3 | 17 | 23 | 10 | 82 |
| 1:65 | Main peak | 263 | 95 | 3.0 | 167 | 226 | 76 | 36 |
|  | Post peak | 116 | 102 | 3.2 | 14 | 19 | 6 | 88 |
| 1:70 | Main peak | 268 | 95 | 3.0 | 173 | 234 | 79 | 35 |
|  | Post peak | 93 | 83 | 2.6 | 10 | 14 | 5 | 89 |
| 1:75 | Main peak | 275 | 95 | 3.0 | 180 | 243 | 82 | 34 |
|  | Post peak | 98 | 82 | 2.6 | 16 | 22 | 8 | 84 |
| 1:80 | Main peak | 279 | 95 | 3.0 | 184 | 248 | 84 | 34 |
|  | Post peak | 97 | 86 | 2.7 | 11 | 15 | 6 | 89 |
| 1:85 | Pre peak | 329 | 104 | 3.3 | 224 | 302 | 93 | 32 |
|  | Main peak | 291 | 96 | 3.0 | 195 | 263 | 88 | 33 |
|  | Post peak | 129 | 107 | 3.3 | 22 | 30 | 9 | 83 |
| 1:90 | Pre peak | 443 | 107 | 3.3 | 237 | 320 | 96 | 31 |
|  | Main peak | 293 | 95 | 3.0 | 197 | 266 | 90 | 33 |
|  | Post peak | 126 | 102 | 3.2 | 25 | 34 | 11 | 81 |
| 1:95 | Pre peak | 384 | 110 | 3.4 | 274 | 370 | 108 | 29 |
|  | Main peak | 303 | 96 | 3.0 | 207 | 280 | 93 | 32 |
|  | Post peak | 130 | 103 | 3.2 | 27 | 36 | 11 | 79 |
| 1:100 | Pre peak | 398 | 111 | 3.5 | 287 | 388 | 112 | 28 |
|  | Main peak | 310 | 96 | 3.0 | 213 | 288 | 96 | 31 |
|  | Post peak | 122 | 86 | 2.7 | 36 | 49 | 18 | 71 | e) 50% DPPC/50% POPC

The lipid particle formation was carried out accordingly as reported in items a) to c) of this example with the following parameters:

Protein: tetranectin-lipoprotein A-I at 3.84 mg/ml, 3 mg per sample
Lipidation buffer: 250 mM Tris-HCl, 140 mM NaCl, 10 mM methionine, pH 7.5
Lipidation: at 27° C.
Dialysis: at room temperature
Molar ratios tested: 1:60 to 1:100 with increasing lipid in steps of 5

All samples remained clear during the process and dialysis. The yield of lipid particles was similar for all ratios tested.

TABLE 13

Summary of SEC results; percentages were calculated by integration of the AUC.

| UV280 | Retention time Main peak [min] | Pre peak [%] | Main peak [%] | Post peak [%] | total [mAU * min] |
|---|---|---|---|---|---|
| 50/50 DPPC/POPC 1:60 | 58.2 | — | 88.9 | 11.1 | 341.3 |
| 50/50 DPPC/POPC 1:65 | 58.3 | — | 89.3 | 10.7 | 349.6 |
| 50/50 DPPC/POPC 1:70 | 58.3 | — | 89.9 | 10.1 | 336.9 |
| 50/50 DPPC/POPC 1:75 | 58.2 | 6.1 | 84.3 | 9.6 | 347.4 |
| 50/50 DPPC/POPC 1:80 | 58.1 | 8.5 | 82.2 | 9.3 | 356.9 |
| 50/50 DPPC/POPC 1:85 | 58.0 | 11.3 | 79.8 | 8.9 | 352.7 |
| 50/50 DPPC/POPC 1:90 | 58.0 | 14.4 | 77.1 | 8.5 | 356.5 |
| 50/50 DPPC/POPC 1:95 | 58.0 | 19.3 | 72.6 | 8.1 | 367.0 |
| 50/50 DPPC/POPC 1:100 | 57.9 | 36.6 | 65.8 | 7.6 | 365.3 |

Using a lipid mixture of 50% DPPC and 50% POPC for lipid particle formation of tetranectin-apolipoprotein A-I the most homogeneous product was obtained at a molar ratio of 1:70 (see Table 14). The product was 89.9% pure with respect to the main peak and contained one single tetranectin-apolipoprotein A-I trimer (see Table 14).

f) 25% DPPC/75% POPC

The lipid particle formation was carried out accordingly as reported in items a) to c) of this example with the following parameters:

Protein: tetranectin-apolipoprotein A-I at 3.84 mg/ml, 3 mg per sample
Lipidation buffer: 250 mM Tris-HCl, 140 mM NaCl, 10 mM methionine, pH 7.5
Lipidation: at 18° C.
Dialysis: at room temperature
Molar ratios tested: 1:60 to 1:100 with increasing lipid in steps of 5

Lipid particle formation was straight forward and comparable to the process using pure lipids. All samples remained clear during the process and dialysis.

TABLE 15

Summary of SEC results; percentages were calculated by integration of the AUC.

| UV280 | Retention time Main peak [min] | Pre peak % | Main peak % | Post peak % | total [mAU * min] |
|---|---|---|---|---|---|
| 25/75 DPPC/POPC 1:60 | 58.2 | — | 90.2 | 9.8 | 342.6 |
| 25/75 DPPC/POPC 1:65 | 58.2 | 4.6 | 85.9 | 9.4 | 345.6 |
| 25/75 DPPC/POPC 1:70 | 58.1 | 8.8 | 82.3 | 8.9 | 353.2 |
| 25/75 DPPC/POPC 1:75 | 58.0 | 9.0 | 82.4 | 8.6 | 357.5 |
| 25/75 DPPC/POPC 1:80 | 57.9 | 10.8 | 81.2 | 8.0 | 356.7 |
| 25/75 DPPC/POPC 1:85 | 57.9 | 21.2 | 71.0 | 7.8 | 366.3 |
| 25/75 DPPC/POPC 1:90 | 57.8 | 26.1 | 66.4 | 7.5 | 357.8 |
| 25/75 DPPC/POPC 1:95 | 57.7 | 32.7 | 60.5 | 6.8 | 365.9 |
| 25/75 DPPC/POPC 1:100 | 57.6 | 36.1 | 57.5 | 6.4 | 373.4 |

Using a lipid mixture of 25% DPPC and 75% POPC for lipid particle formation of tetranectin-apolipoprotein A-I the most homogeneous product was obtained at a molar ratio of 1:60 (see Table 16). The product was 90.2% pure with respect to the main peak and contained one single tetranectin-apolipoprotein A-I trimer (see Table 15).

TABLE 14

Summary protein conjugate analysis of lipid particles with 50% DPPC/50% POPC and tetranectin-apolipoprotein A-I.

| | | MW total | MW protein | n (protein monomer) | MW lipid | n(lipid) | n(lipid)/ n (monomer) | % protein |
|---|---|---|---|---|---|---|---|---|
| 1:60 | Main peak | 331 | 124 | 3.9 | 207 | 277 | 71 | 38 |
| | Post peak | 131 | 106 | 3.3 | 24 | 32 | 10 | 81 |
| 1:65 | Main peak | 264 | 95 | 2.9 | 169 | 226 | 78 | 36 |
| | Post peak | 127 | 112 | 3.5 | 16 | 21 | 6 | 88 |
| 1:70 | Main peak | 273 | 96 | 3.0 | 178 | 238 | 79 | 35 |
| | Post peak | 258 | 213 | 6.7 | 45 | 60 | 9 | 82 |
| 1:75 | Pre peak | 319 | 108 | 3.4 | 211 | 282 | 83 | 34 |
| | Main peak | 271 | 93 | 2.9 | 178 | 238 | 82 | 34 |
| | Post peak | 126 | 106 | 3.3 | 20 | 27 | 8 | 84 |
| 1:80 | Pre peak | 333 | 108 | 3.4 | 225 | 301 | 89 | 32 |
| | Main peak | 278 | 95 | 2.9 | 184 | 246 | 85 | 34 |
| | Post peak | 122 | 100 | 3.1 | 21 | 28 | 9 | 83 |
| 1:85 | Pre peak | 359 | 109 | 3.4 | 250 | 335 | 98 | 30 |
| | Main peak | 284 | 94 | 2.9 | 189 | 253 | 87 | 33 |
| | Post peak | 132 | 118 | 3.7 | 14 | 19 | 5 | 89 |
| 1:90 | Pre peak | 373 | 109 | 3.4 | 264 | 353 | 104 | 29 |
| | Main peak | 286 | 94 | 2.9 | 192 | 257 | 89 | 33 |
| | Post peak | 133 | 110 | 3.4 | 23 | 31 | 9 | 83 |
| 1:95 | Pre peak | 390 | 111 | 3.5 | 278 | 372 | 106 | 29 |
| | Main peak | 290 | 94 | 2.9 | 195 | 261 | 90 | 33 |
| | Post peak | 162 | 136 | 4.3 | 26 | 35 | 8 | 84 |
| 1:100 | Pre peak | 404 | 113 | 3.5 | 291 | 390 | 111 | 28 |
| | Main peak | 293 | 94 | 2.9 | 199 | 266 | 92 | 32 |
| | Post peak | 142 | 107 | 3.3 | 35 | 47 | 14 | 75 |

TABLE 16

Summary protein conjugate analysis of lipid particles of 25% DPPC/75% POPC and tetranectin-apolipoprotein A-I.

|   |   | MW total | MW protein | n (protein monomer) | MW lipid | n(lipid) | n(lipid)/ n (monomer) | % protein |
|---|---|---|---|---|---|---|---|---|
| 1:60 | Main peak | 254 | 100 | 3.1 | 153 | 203 | 66 | 40 |
|  | Post peak | 127 | 110 | 3.4 | 17 | 23 | 7 | 86 |
| 1:65 | Pre peak | 272 | 132 | 4.1 | 141 | 187 | 46 | 48 |
|  | Main peak | 259 | 100 | 3.1 | 159 | 211 | 68 | 39 |
|  | Post peak | 183 | 131 | 4.1 | 7 | 9 | 2 | 95 |
| 1:70 | Pre peak | 280 | 121 | 3.8 | 159 | 211 | 56 | 43 |
|  | Main peak | 264 | 99 | 3.1 | 165 | 219 | 71 | 38 |
|  | Post peak | 119 | 105 | 3.3 | 14 | 19 | 6 | 88 |
| 1:75 | Pre peak | 291 | 109 | 3.4 | 183 | 243 | 71 | 37 |
|  | Main peak | 268 | 98 | 3.1 | 170 | 226 | 73 | 37 |
|  | Post peak | 120 | 101 | 3.2 | 19 | 25 | 8 | 84 |
| 1:80 | Pre peak | 311 | 114 | 3.6 | 197 | 261 | 73 | 37 |
|  | Main peak | 276 | 96 | 3.0 | 176 | 234 | 78 | 36 |
|  | Post peak | 137 | 127 | 4.0 | 10 | 13 | 3 | 93 |
| 1:85 | Pre peak | 331 | 115 | 3.6 | 216 | 287 | 80 | 35 |
|  | Main peak | 278 | 98 | 3.1 | 180 | 239 | 77 | 35 |
|  | Post peak | 139 | 117 | 3.7 | 22 | 29 | 8 | 85 |
| 1:90 | Pre peak | 345 | 113 | 3.5 | 232 | 308 | 88 | 33 |
|  | Main peak | 285 | 98 | 3.1 | 187 | 248 | 80 | 34 |
|  | Post peak | 143 | 110 | 3.4 | 33 | 44 | 13 | 77 |
| 1:95 | Pre peak | 363 | 115 | 3.6 | 248 | 329 | 91 | 32 |
|  | Main peak | 292 | 97 | 3.0 | 194 | 257 | 86 | 33 |
|  | Post peak | 155 | 122 | 3.8 | 33 | 44 | 12 | 79 |
| 1:100 | Pre peak | 377 | 117 | 3.7 | 260 | 345 | 93 | 31 |
|  | Main peak | 298 | 98 | 3.1 | 200 | 265 | 86 | 33 |
|  | Post peak | 160 | 114 | 3.6 | 46 | 61 | 17 | 71 | g) Lipid Particle Formation Using Zwittergent

The lipid particle formation was carried out accordingly as reported in items a) to c) of this example with the following parameters and the exception that cholate was replaced by the synthetic detergent Zwittergent:

Protein: tetranectin-apolipoprotein A-I at 23.5 mg/ml

Buffer: 50 mM Tris-HCl, 7.2 M guanidinium hydrochloride, 10 mM Methionine, pH 8

Lipidation buffer: 250 mM Tris-HCl, 140 mM NaCl, pH 7.5

100% POPC, molar ratio apolipoprotein:phospholipid=1:60

TABLE 17

Sample overview of various approaches and observations/parameters of lipid particle formation.

| sample | detergent [%] | dissolved lipid | turbidity after lipidation | turbidity after dialysis | volume after dialysis [ml] | c after dialysis [µg/ml] | [mg] TN-Apo A-I | yield [%] |
|---|---|---|---|---|---|---|---|---|
| Zwittergent 3-8 | | | | | | | | |
| 0.1 × CMC | 0.8 | +++ | +++ | +++ | 2.1 | 2230.18 | 4.68 | 99.6 |
| 0.5 × CMC | 4.2 | ++ | ++ | + | 2.9 | 1536.81 | 4.46 | 94.8 |
| 1 × CMC | 8.4 | + | + | + | 3 | 1475.07 | 4.43 | 94.2 |
| 2 × CMC | 16.7 | − | − | − | 4.3 | 1081.27 | 4.65 | 98.9 |
| 3 × CMC | 25.1 | − | − | − | 5.5 | 839.85 | 4.62 | 98.3 |
| Zwittergent 3-10 | | | | | | | | |
| 0.1 × CMC | 0.1 | +++ | +++ | +++ | 2 | 2361.56 | 4.72 | 100.5 |
| 0.5 × CMC | 0.6 | +++ | ++ | ++ | 2 | 2221.38 | 4.44 | 94.5 |
| 1 × CMC | 1.2 | ++ | + | + | 2.1 | 2267.16 | 4.76 | 101.3 |
| 2 × CMC | 2.5 | + | + | (+) | 2.3 | 2082.18 | 4.79 | 101.9 |
| 5 × CMC | 6.2 | − | − | − | 2.5 | 1941.61 | 4.85 | 103.3 |
| 10 × CMC | 12.3 | − | − | − | 4 | 1073.92 | 4.30 | 91.4 |
| Zwittergent 3-12 | | | | | | | | |
| 0.1 × CMC | 0.01 | +++ | +++ | +++ | 2 | 2722.85 | 5.45 | 115.9 |
| 1 × CMC | 0.1 | +++ | +++ | +++ | 2 | 2158.81 | 4.32 | 91.9 |
| 2 × CMC | 0.2 | +++ | +++ | ++ | 2 | 2636 | 5.27 | 112.2 |
| 20 × CMC | 1.9 | + | + | + | 2.1 | 2525.69 | 5.30 | 112.8 |
| 100 × CMC | 9.4 | − | − | − | 3.5 | 1567.85 | 5.49 | 116.8 |
| 300 × CMC | 28.1 | − | − | − | 5.6 | 1069.04 | 5.99 | 127.4 |
| Cholate | | | | | | | | |
| 0.1 × CMC | 0.06 | +++ | +++ | +++ | 2 | 2323.09 | 4.65 | 98.9 |
| 0.5 × CMC | 0.3 | + | − | − | 2 | 2301.15 | 4.60 | 97.9 |

TABLE 17-continued

Sample overview of various approaches and observations/parameters of lipid particle formation.

| sample | detergent [%] | dissolved lipid | turbidity after lipidation | turbidity after dialysis | volume after dialysis [ml] | c after dialysis [µg/ml] | [mg] TN-Apo A-I | yield [%] |
|---|---|---|---|---|---|---|---|---|
| 1 × CMC | 0.6 | – | – | – | 2 | 2316.86 | 4.63 | 98.6 |
| 2 × CMC | 1.2 | – | – | – | 2.5 | 1178.72 | 2.95 | 62.7 |
| 5 × CMC | 3 | – | – | – | 2.5 | 2435.34 | 6.09 | 129.5 |
| 10 × CMC | 6 | – | – | – | 3.5 | 1814.69 | 6.35 | 135.1 |

Lipid particles comprising tetranectin-apolipoprotein A-I have been analyzed on native PAGE. Lipid-free tetranectin-apolipoprotein A-I migrates at 140 kDa (lanes 1 in FIG. 19), whereas lipid particles show a characteristic shift to a higher molecular weight between 232 kDa and 440 kDa.

Figure 19:
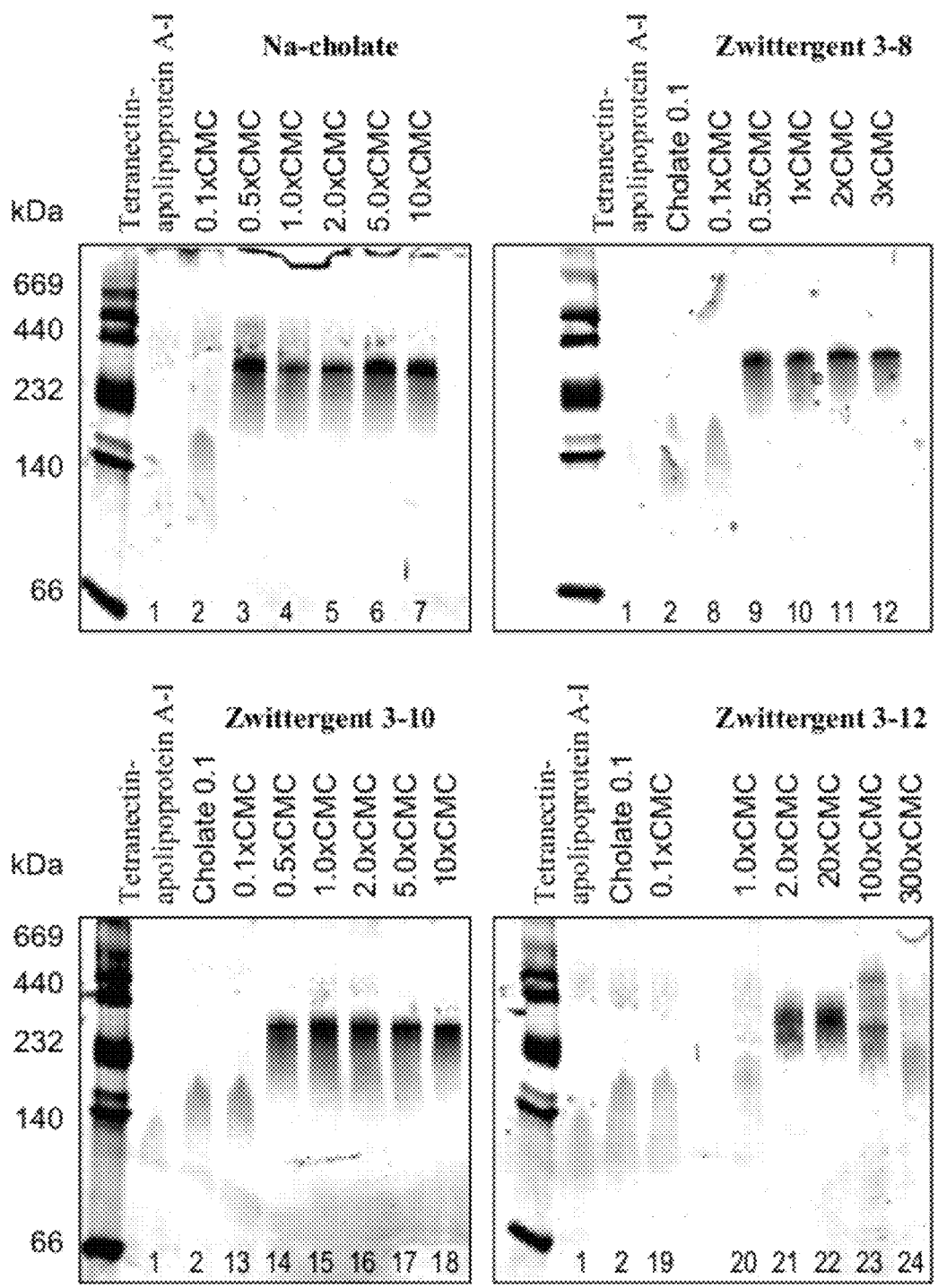
FIG. 19 Native PAGE SDS of a lipid particle of tetranectin-apolipoprotein A-I using cholate, Zwittergent 3-8, 3-10 and 3-12. Lane 1 on each gel: pure apolipoprotein; lane 2 on each gel: 0.1×CMC cholate lipidated sample as references.

Lipid-free tetranectin-apolipoprotein A-I but no lipid particles were detected in all samples prepared with only 0.1× CMC of the respective detergent (FIG. 19, lanes 2, 8, 13, and 19). However, a detergent concentration of 0.5×CMC was sufficient for Zwittergent 3-8 and 3-10 to enable the lipid particle formation with tetranectin-apolipoprotein A-I (lanes 3, 9, and 14). With Zwittergent 3-12 lipid particle formation did not occur until a concentration of 2.0×CMC was reached (lane 21).

Figure 20:
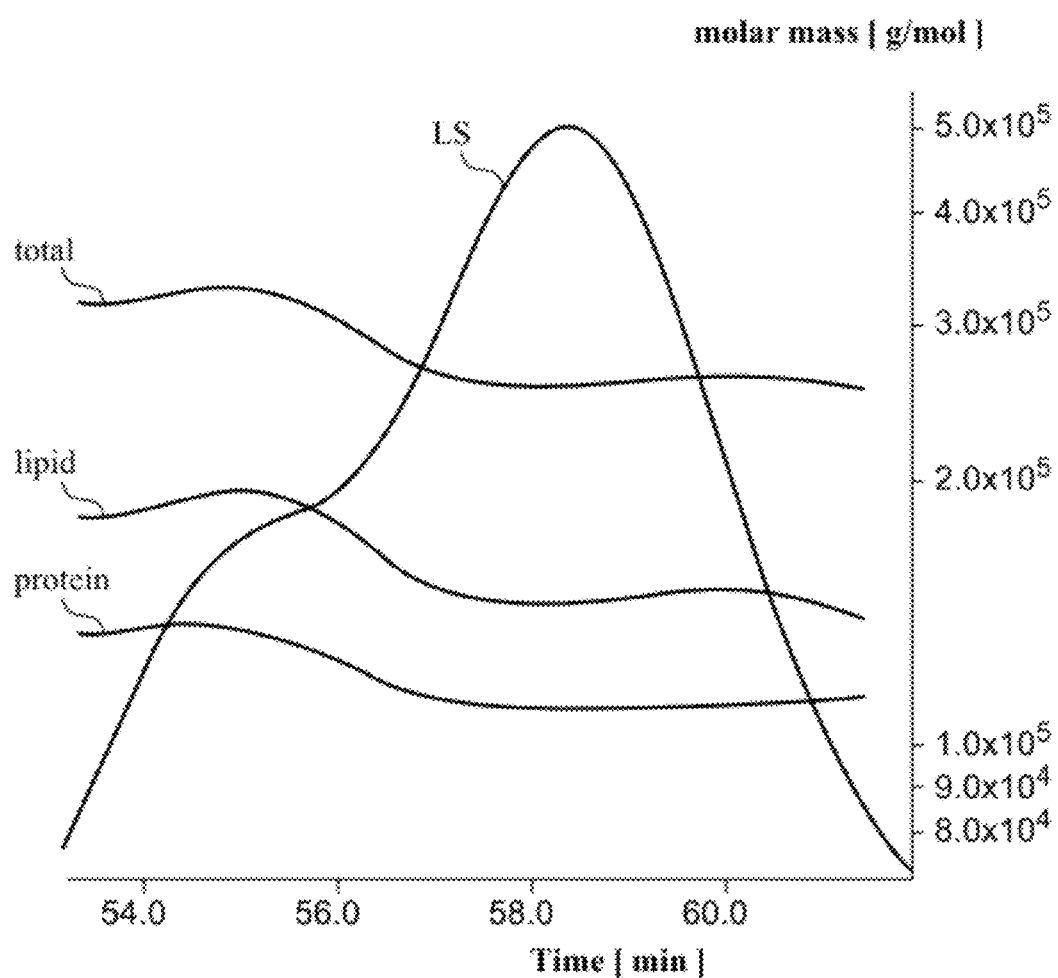
FIG. 20 SEC-MALLS protein conjugate analysis of lipid particle of tetranectin-apolipoprotein A-I using 3×CMC Zwittergent 3-8 and POPC (molar ratio apolipoprotein:phospholipid=1:60).

FIG. 20 shows the SEC-MALLS chromatogram of lipid particles comprising tetranectin-apolipoprotein A-I using 3×CMC Zwittergent 3-8 and POPC (molar ratio apolipoprotein:phospholipid=1:60). Results of the protein conjugate analysis are summarized in Table 18. The lipid particle fraction consists of two different species as displayed in two overlapping peaks in the SEC chromatogram. However, these two species are very similar, differentiating mainly in the number of tetranectin-apolipoprotein A-I molecules per particle (4.2 for peak 1 and 3.5 for peak 2).

TABLE 18

Summary of protein-conjugate analysis of lipid particles formed in the presence of Zwittergent 3-8.

| ×CMC | | MW total | MW protein | n (protein monomer) | MW lipid | n(lipid) | n(lipid)/ n (monomer) | % protein | Rh (w) (QELS) [nm] |
|---|---|---|---|---|---|---|---|---|---|
| 2 | Pre peak | 345 | 147 | 4.6 | 198 | 261.5 | 57 | 42.5 | 7.7 |
|   | Main peak | 268 | 113 | 3.6 | 154 | 203.2 | 56 | 42.4 | 6.5 |
| 3 | Pre peak | 323 | 134 | 4.2 | 188 | 249.9 | 60 | 41.6 | 7.4 |
|   | Main peak | 257 | 110 | 3.5 | 146 | 192.9 | 55 | 43.0 | 6.5 |

Figure 21:
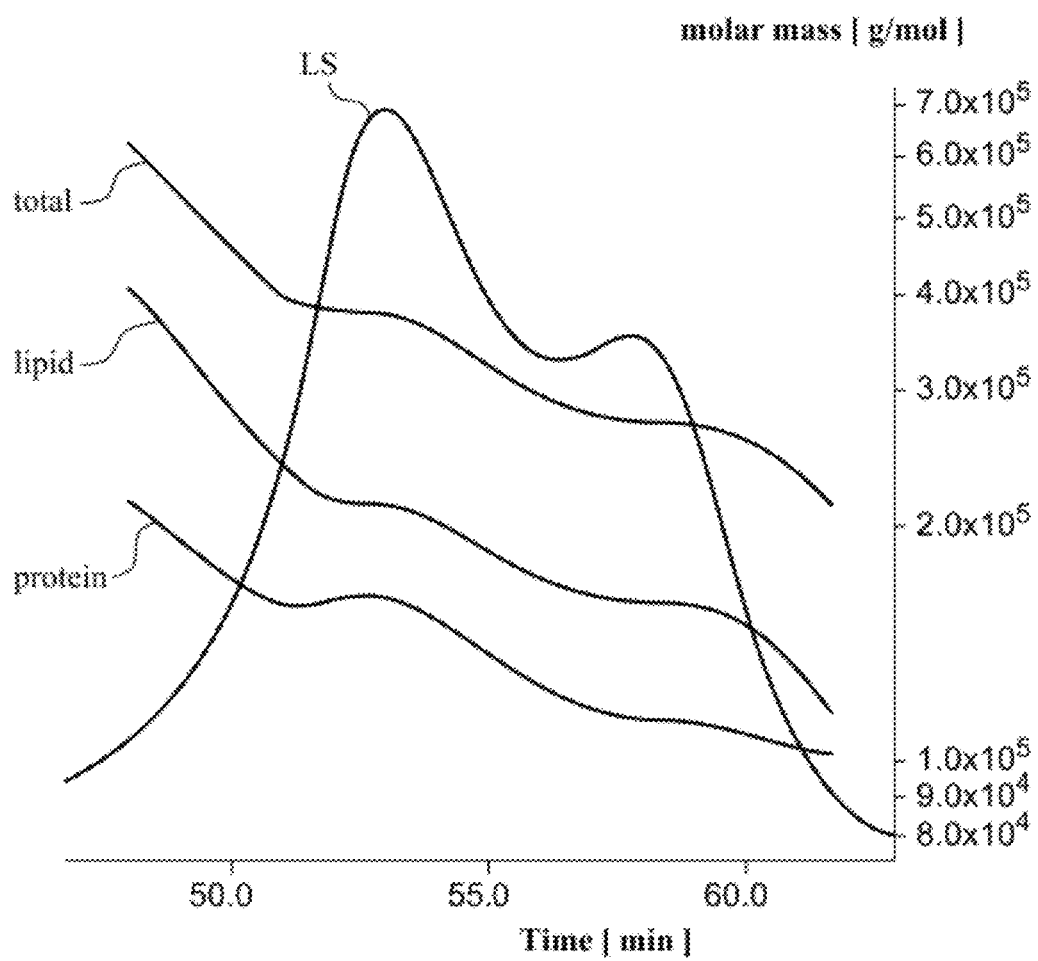
FIG. 21 SEC-MALLS protein conjugate analysis of lipid particle of tetranectin-apolipoprotein A-I using 2×CMC Zwittergent 3-10 and POPC (molar ratio apolipoprotein:phospholipid=1:60).
Figure 24:
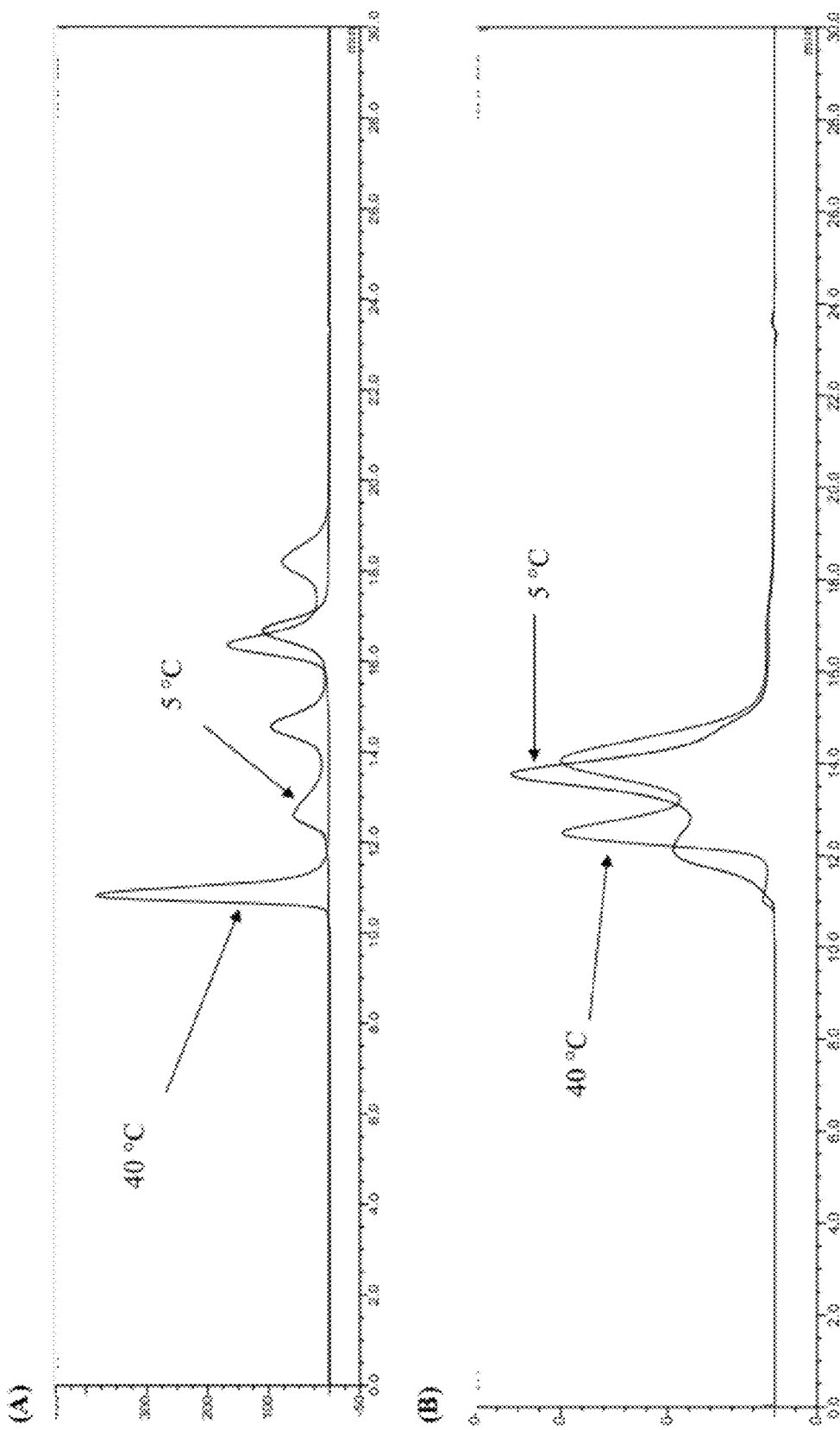
FIG. 24 SE-HPLC chromatogram of lipid particles containing wild-type apolipoprotein A-I (A) and tetranectin-apolipoprotein A-I as reported herein (B) stored at 5° C. and 40° C.

FIG. 21 shows the chromatogram of SEC-MALLS analysis and Table 19 the summary of the protein conjugate analysis for lipid particles comprising tetranectin-apolipoprotein A-I using 2×CMC Zwittergent 3-10 and POPC (molar ratio apolipoprotein:phospholipid=1:60). Both peaks contain lipid particles comprising 3.5 and 5 tetranectin-apolipoprotein A-I molecules, respectively.

TABLE 19

Summary of protein-conjugate analysis of lipid particles formed in the presence of Zwittergent 3-10.

| ×CMC | | MW total | MW protein | n (protein monomer) | MW lipid | n(lipid) | n(lipid)/ n (monomer) | % protein | Rh (w) (QELS) [nm] |
|---|---|---|---|---|---|---|---|---|---|
| 2 | Pre peak | 373 | 161 | 5.0 | 211 | 278.7 | 56 | 43.2 | 7.8 |
|   | Main peak | 272 | 112 | 3.5 | 159 | 210.3 | 60 | 41.4 | 6.6 |
| 5 | Pre peak | 345 | 150 | 4.7 | 195 | 256.6 | 55 | 43.6 | 7.5 |
|   | Main peak | 263 | 112 | 3.5 | 151 | 199.1 | 57 | 42.6 | 6.6 |
| 10 | Pre peak | 405 | 151 | 4.7 | 253 | 334.1 | 71 | 37.4 | 7.9 |
|   | Main peak | 265 | 110 | 3.3 | 154 | 203.2 | 58 | 41.8 | 6.5 |

The results of lipid particle formation comprising tetranectin-apolipoprotein A-I using Zwittergent 3-12 and POPC (molar ratio apolipoprotein:phospholipid=1:60) are summarized in Table 20. The lipid particle fraction consists of two different species as displayed in two overlapping peaks in the SEC chromatogram. However, these two species are very similar, differentiating mainly in the number of tetranectin-apolipoprotein A-I molecules per particle.

TABLE 20

Summary of protein-conjugate analysis of lipid particles formed in the presence of Zwittergent 3-12.

| xCMC | | MW total | MW protein | n (protein monomer) | MW lipid | n(lipid) | n(lipid)/ n (monomer) | % protein | Rh (w) (QELS) [nm] |
|---|---|---|---|---|---|---|---|---|---|
| 100 | Main peak | 487 | 342 | 10.7 | 145 | 191.3 | 18 | 70.2 | 11.9 |
| 300 | Main peak | 241 | 208 | 6.5 | 32 | 43.3 | 7 | 86.4 | 8.5 |

The results of lipid particle formation comprising tetranectin-apolipoprotein A-I using cholate and POPC (molar ratio apolipoprotein:phospholipid=1:60) are summarized in Table 21. The lipid particle fraction consists of two different species as displayed in two overlapping peaks in the SEC chromatogram. However, these two species are very similar, differentiating mainly in the number of tetranectin-apolipoprotein A-I molecules per particle.

TABLE 21

Summary of protein-conjugate analysis of lipid particles formed in the presence of cholate.

| CMC | | MW total | MW protein | n (protein monomer) | MW lipid | n(lipid) | n(lipid)/ n (monomer) | % protein | Rh (w) (QELS) [nm] |
|---|---|---|---|---|---|---|---|---|---|
| 0.5 | Pre peak | 1295 | 461 | 14.5 | 829 | 1091 | 75 | 35.9 | 12.7 |
| | Main peak | 361 | 153 | 4.8 | 207 | 273 | 57 | 42.5 | 7.7 |
| | Post peak | 283 | 115 | 3.6 | 168 | 221 | 62 | 40.6 | 6.8 |
| 1 | Pre peak | 1050 | 414 | 12.9 | 623 | 836 | 65 | 39.5 | 11.8 |
| | Main peak | 337 | 154 | 4.8 | 182 | 240 | 50 | 45.9 | 7.6 |
| | Post peak | 284 | 121 | 3.8 | 162 | 214 | 56 | 42.7 | 6.9 |
| 2 | Pre peak | 332 | 143 | 4.5 | 188 | 248 | 55 | 43.2 | 7.3 |
| | Main peak | 269 | 111 | 3.5 | 158 | 209 | 60 | 41.2 | 6.5 |
| 5 | Pre peak | 314 | 143 | 4.5 | 171 | 225 | 50 | 45.6 | 7.5 |
| | Main peak | 278 | 118 | 3.7 | 158 | 208 | 56 | 42.7 | 6.8 |
| 10 | Pre peak | 292 | 135 | 4.2 | 156 | 206 | 50 | 46.3 | 7.3 |
| | Main peak | 271 | 115 | 3.6 | 155 | 204 | 57 | 42.6 | 6.6 |

Example 5

Rapid Dilution Method for Refolding and Lipid Particle Formation

In the following the tetranectin-apolipoprotein A-I as produced in the previous examples 1 to 3 of SEQ ID NO: 01 was used.

a) POPC and Sodium Cholate

Tetranectin-apolipoprotein A-I was expressed in *E. coli* and purified according to Examples 1 to 3 (protocol 1). After purification, the buffer was exchanged by diafiltration to a solution containing 250 mM Tris, 140 mM NaCl, 6.7 M guanidinium hydrochloride, pH 7.4. The protein concentration was adjusted to 28 mg/ml.

A lipid stock solution was prepared by dissolving 100 moles/l of POPC in a buffer containing 250 mM Tris-HCl, 140 mM NaCl, 135 mM sodium cholate, pH 7.4 at room temperature. The lipid stock solution was incubated for 2 hours at room temperature. Refolding buffer was prepared by diluting 77 ml of the lipid stock mixture into 1478 ml of 250 mM Tris-HCl, 140 mM NaCl, pH 7.4. This buffer was stirred for an additional 7 hours at room temperature.

Refolding and lipid particle formation was initiated by the addition of 162 ml tetranectin-apolipoprotein A-I in 250 mM Tris, 140 mM NaCl, 6.7 M guanidinium hydrochloride, pH 7.4 to refolding buffer. This results in a 1:10 dilution of the guanidinium hydrochloride. The solution was incubated at room temperature for 16 hours while constantly stirring. The removal of the detergent was carried out by diafiltration.

TABLE 22

Summary protein conjugate analysis of lipid particle obtained by rapid dilution with POPC.

| Peak | MW total [kDa] | MW protein [kDa] | n (protein) monomer) | MW lipid [kDa] | n (lipid) | n (lipid)/ n (protein) | % protein |
|---|---|---|---|---|---|---|---|
| Pre Peak | 347 | 141 | 4.4 | 207 | 272 | 62 | 41 |
| Main Peak | 269 | 111 | 3.5 | 159 | 209 | 60 | 41 |

Tetranectin-apolipoprotein A-I was expressed in *E. coli* and purified according to Examples 1 to 3 (protocol 2). After purification, the buffer was exchanged by diafiltration to a solution containing 50 mM Tris, 10 mM L-methionine, 6.7 M guanidinium hydrochloride, pH 7.4. The protein concentration was adjusted to 20.4 mg/ml.

A lipid stock solution was prepared by dissolving 100 moles/l of phospholipid (POPC:DPPC in a ratio 3:1) in a buffer containing 250 mM Tris-HCl, 140 mM NaCl, 10 mM L-methionine, 135 mM sodium cholate, pH 7.4 at room temperature. Refolding buffer was prepared by diluting 3.7 ml of the lipid stock solution into 35.6 ml of 250 mM Tris-HCl, 140 mM NaCl, pH 7.4. This buffer was stirred for an additional 2 hours at room temperature.

Refolding and lipid particle formation was initiated by the addition of 9.8 ml tetranectin-apolipoprotein A-I in 50 mM Tris, 10 mM L-methionine, 6.7 M guanidinium hydrochloride, pH 8.0 to refolding buffer. This results in a 1:5 dilution of the guanidinium hydrochloride. The solution was incubated at room temperature over night while constantly stirring. The removal of the detergent was carried out by diafiltration.

TABLE 23

Summary protein conjugate analysis of lipid particle obtained by rapid dilution with a POPC/DPPC/cholate mixture.

| Peak | MW total [kDa] | MW Protein [kDa] | n Protein (APO-Monomer) | MW Lipid [kDa] | n Lipid | n Lipid/ n Protein | % Protein |
|---|---|---|---|---|---|---|---|
| Pre Peak | 419 | 167 | 5.2 | 251 | 333 | 64 | 41 |
| Main Peak | 252 | 101 | 3.2 | 151 | 200 | 63 | 41 | b) POPC and DPPC and Sodium Cholate

Tetranectin-apolipoprotein A-I was expressed in *E. coli* and purified according to Examples 1 to 3. After purification, the buffer was exchanged by diafiltration into a solution containing 250 mM Tris, 140 mM NaCl, 6.7 M guanidinium hydrochloride, pH 7.4. The protein concentration was adjusted to 30 mg/ml.

Two separate lipid stock solutions were prepared. Solution A was prepared by dissolving 100 moles/l of POPC in a buffer containing 250 mM Tris-HCl, 140 mM NaCl, 135 mM sodium cholate, pH 7.4 at room temperature. Solution B was prepared by dissolving 100 moles/l of DPPC in 250 mM Tris-HCl, 140 mM NaCl, 135 mM sodium cholate, pH 7.4 at 41° C. Lipid stock solutions A and B were mixed in a ratio of 3:1 and incubated for 2 hours at room temperature. Refolding buffer was prepared by diluting 384 ml of the lipid stock mixture into 6365 ml of 250 mM Tris-HCl, 140 mM NaCl, pH 7.4. This buffer was stirred for an additional 24 hours at room temperature.

Refolding and lipid particle formation was initiated by the addition of 750 ml tetranectin-apolipoprotein A-I solution in 250 mM Tris, 140 mM NaCl, 6.7 M guanidinium hydrochloride, pH 7.4 to the refolding buffer. This results in a 1:10 dilution of the guanidinium hydrochloride. The solution was incubated at room temperature for at least 12 hours while constantly stirring. Detergent removal was carried out by diafiltration.

TABLE 24

Summary protein conjugate analysis of lipid particle obtained by rapid dilution with POPC:DPPC = 1:1.

| Peak | MW total [kDa] | MW protein [kDa] | n (protein monomer) | MW lipid [kDa] | n (lipid) | n (lipid)/ n (protein) | % protein |
|---|---|---|---|---|---|---|---|
| Main peak | 263 | 102 | 3.2 | 161 | 214 | 67 | 39 |
| Post peak | 182 | 85 | 2.7 | 97 | 129 | 48 | 47 | c) Different Guanidinium Hydrochloride Concentrations

Tetranectin-apolipoprotein A-I according to the invention was expressed in *E. coli* and purified over a metal chelate affinity chromatographic process from inclusion bodies (see Examples 1 to 3). After purification, the buffer was exchanged by diafiltration into a solution containing 250 mM Tris, 140 mM NaCl, 6.7 M guanidinium hydrochloride, pH 7.4. The protein concentration was adjusted to 28 mg/ml.

A lipid stock solution was prepared by dissolving 100 moles/l of POPC in a buffer containing 250 mM Tris-HCl, 140 mM NaCl, 135 mM sodium cholate, pH 7.4 at room temperature. The lipid stock solution was incubated for 2 hours at room temperature. Refolding buffer was prepared by diluting lipid stock solution into 250 mM Tris-HCl, 140 mM NaCl, pH 7.4. This buffer was stirred for an additional 12 hours at room temperature. Varying amounts of tetranectin-apolipoprotein A-I were diluted into refolding buffer: 1:5, 1:7.5, 1:10, 1:12.5. This results in different residual concentrations of guanidinium hydrochloride in the refolding buffer. The solution was allowed to stir at room temperature o/n to initiate refolding and lipid particle formation. Detergent removal was carried out by dialysis.

TABLE 25

Summary protein conjugate analysis of lipid particle obtained by rapid dilution with different dilution ratios.

| dilution | Peak | MW total [kDa] | MW protein [kDa] | n (protein monomer) | MW lipid [kDa] | n (lipid) | n (lipid)/ n (protein) | % protein |
|---|---|---|---|---|---|---|---|---|
| 1:5 | Main | 273 | 103 | 3.2 | 170 | 226 | 70 | 38 |
| 1:7.5 | Main | 272 | 100 | 3.1 | 173 | 230 | 73 | 37 |
| 1:10 | Main | 266 | 106 | 3.3 | 160 | 212 | 64 | 40 |
| 1:12.5 | Main | 281 | 101 | 3.2 | 180 | 239 | 76 | 36 | d) POPC and Sodium Cholate in the Presence of Urea

Tetranectin-apolipoprotein A-I is expressed in *E. coli* and purified according to Examples 1 to 3. After purification, the buffer is exchanged by diafiltration to a solution containing 250 mM Tris, 140 mM NaCl, 6.7 M urea, pH 7.4. The protein concentration is adjusted to 28 mg/ml.

A lipid stock solution is prepared by dissolving 100 moles/l of POPC in a buffer containing 250 mM Tris-HCl, 140 mM NaCl, 135 mM sodium cholate, pH 7.4 at room temperature. The lipid stock solution is incubated for 2 hours at room temperature. Refolding buffer is prepared by diluting 77 ml of the lipid stock mixture into 1478 ml of 250 mM Tris-HCl, 140 mM NaCl, pH 7.4. This buffer is stirred for an additional 7 hours at room temperature.

Refolding and lipid particle formation is initiated by the addition of 162 ml tetranectin-apolipoprotein A-I solution in 250 mM Tris, 140 mM NaCl, 6.7 M urea, pH 7.4 to refolding buffer. This results in a 1:10 dilution of the urea. The solution is incubated at room temperature for 16 hours while constantly stirring. The removal of the detergent is carried out by diafiltration.

e) POPC and Sodium Cholate and Wild-Type Apolipoprotein A-I

In another exemplary second method human apolipoprotein A-I (wild-type apolipoprotein A-I) in 6.7 M guanidinium hydrochloride, 50 mM Tris, 10 mM methionine, at pH 8.0 was diluted 1:5 (v/v) into lipidation buffer resulting in a protein concentration of 0.6 mg/ml. The lipidation buffer was consisting of 7 mM cholate, 4 mM POPC and 1.3 mM DPPC corresponding to a lipid to protein ratio of 240:1. SEC-MALLS was employed to analyze complex formation. Approximately two apolipoprotein molecules were found in a complex consisting of around 200 lipid molecules.

The method as reported in Example 4 (first method) requires native apolipoprotein for lipid particle formation whereas the method reported in Example 5 (second method) starts with fully denatured apolipoprotein for lipid particle formation.

In an exemplary first method denatured tetranectin-apolipoprotein A-I in 6.7 M guanidinium hydrochloride, 50 mM Tris, 10 mM methionine, at pH 8.0 was extensively dialyzed against a buffer consisting of 250 mM Tris, 140 mM NaCl, 10 mM methionine, at pH 7.5 at a protein concentration of 3.46 mg/ml. A mixture of POPC and cholate was then added to yield a final concentration of 6 mM POPC and 8 mM cholate in the solution. This corresponds to a ratio of 60 molecules of POPC per molecule of tetranectin-apolipoprotein A-I monomer (60:1). The detergent was subsequently removed by diafiltration. Analysis of formed protein-lipid complexes was by SEC-MALLS. Using this method a heterogeneous product was formed wherein approximately 60% of the formed species comprised more than three tetranectin-apolipoprotein A-I monomers.

In an exemplary second method denatured tetranectin-apolipoprotein A-I in 6.7 M guanidinium hydrochloride, 50 mM Tris, 10 mM methionine, at pH 8.0 was directly diluted 1:10 (v/v) into lipidation buffer resulting in a protein concentration of 2.5 mg/ml. The lipidation buffer was consisting of 6 mM cholate and 4.5 mM POPC corresponding to a lipid to protein ratio of 60:1. Using this method a homogenous product was formed comprising more than 90% of a single formed species wherein 60 molecules of lipid where bound per molecule of tetranectin-apolipoprotein A-I (see FIG. 22).

TABLE 26

Summary of protein conjugate analysis.

| Starting material | | MW total | MW protein | n (protein monomer) | MW lipids | Number of lipids | Ratio lipid:protein |
|---|---|---|---|---|---|---|---|
| denatured | Mainpeak | 235 | 71 | 2.2 | 163 | 216 | 1:97 |

Example 6

Lipid Particle Formation Starting from Denatured or Native Protein

In the following the tetranectin-apolipoprotein A-I as produced in the previous examples 1 to 3 of SEQ ID NO: 01 was used.

TABLE 27

Summary of protein conjugate analysis.

| Starting material | | MW total | MW protein | n (protein monomer) | MW lipids | Number of lipids | Ratio lipid:protein |
|---|---|---|---|---|---|---|---|
| native | Prepeak (60%) | 321 | 131 | 4.1 | 190 | 250 | 61 |
| | Mainpeak (40%) | 269 | 107 | 3.3 | 162 | 213 | 65 |
| denatured | Mainpeak (>90%) | 269 | 111 | 3.5 | 159 | 209 | 60 |

Example 7

Lipidation of Insulin-F with Cholate- and Zwittergent-Solubilized POPC/DPPC

The protein chosen for lipid particle formation is commercially available Insulin (Humalog®, Insulin Lispro, Lilly). The molecular weight of the protein is 5808 Da. To increase the detection limit for insulin in the lipid particle the protein has been labeled with NHS-fluorescein (6-[fluorescein-5(6)-carboxamido]hexanoic acid N-hydroxysuccinimide ester, Sigma Aldrich #46940-5MG-F).

Zwittergent- and cholate-mediated lipidation of NHS-Fluorescein-labeled Insulin (Insulin-F) were carried out as reported in Example 4 using a 1:1 mixture of POPC and DPPC. A 0.5 mM lipid mixture was dissolved in either 1×CMC cholate, 2×CMC Zwittergent 3-8 or 5×CMC Zwittergent 3-10 in PBS pH 7.4. Solubilization of the lipids was achieved at 45° C. for 1 h in an ultrasonic bath. Insulin-F was added to the solubilized lipid at a molar ratio protein:lipid of 1:2 (Zwittergent 3-8) or 1:1.2 (Zwittergent 3-10 and cholate). The lipidation mixtures were incubated for one hour at room temperature followed by extensive dialysis against PBS pH 7.4 to remove the detergent.

The formed lipid particles and control samples were analyzed on SE-HPLC using fluorescence detection (494 nm ext., 521 nm em.) and UV280 absorption. Three different samples per lipidation approach were analyzed on SE-HPLC: Insulin-F dissolved in PBS, liposomes without Insulin F in PBS and lipid particles comprising Insulin-F. Non-lipidated Insulin-F elutes from the column at about 40 min. elution time and the peak is detected by fluorescence and UV280 detection. Lipidated Insulin-F samples elute from the column as two separate peaks detected by fluorescence and UV280. The late peak (peak maximum at approx. 40 min.) co-migrates with the Insulin-F control sample. The early peak at 15 min. elution time has a higher molecular weight then pure Insulin-F and consists of lipidated Insulin-F. Protein free lipid particles elute at 15 min. elution time.

Example 8

Application of Apolipoprotein a) Impact of DPPC and POPC on LCAT Activity

Lipid particles comprising either palmitoyl oleoyl phosphatidylcholine (POPC) or dipalmitoyl phosphatidylcholine (DPPC) and either recombinant wild-type apolipoprotein A-I or tetranectin-apolipoprotein A-I were examined for their ability to support cholesterol esterification by LCAT.

Tritiated cholesterol (4%; relative to the phosphatidylcholine content on a molar basis) was incorporated in the lipid particle by addition of an ethanolic cholesterol solution. The capacity of the resulting protein-lipid complex to support LCAT catalyzed cholesterol esterification was tested in presence of 0.2 µg/ml recombinant LCAT enzyme (ROAR biochemical) in 125 µl (10 mM Tris, 150 mM NaCl, 1 mM EDTA, 1 mM NaN$_3$; pH 7.4; 2 mg/ml HuFAF Albumin; 4 mM Beta mercapto ethanol) for 1 hour at 37° C. The reaction was stopped by addition of chloroform:methanol (2:1) and lipids were extracted. "Percent" esterification was calculated after cholesterol—cholesteryl ester separation by TLC and scintillation counting. As less than 20% of the tracer was incorporated into the formed ester, the reaction rate could be considered constant under the experimental conditions. Data were fitted to the Michaelis Menten equation using XLfit software (IDBS). For a visualization of the results see FIG. 3.

b) Impact of DPPC/POPC Mixtures on LCAT Activity

Lipid particles were prepared using cholate as detergent by mixing recombinant wild-type apolipoprotein A-I with $^3$H cholesterol, a DPPC/POPC mixture, and cholate in 1:4:80:113 molar ratios. DPPC/POPC mixtures contained either 100% POPC; 75% POPC; 50% POPC; 25% POPC.

Figure 4:
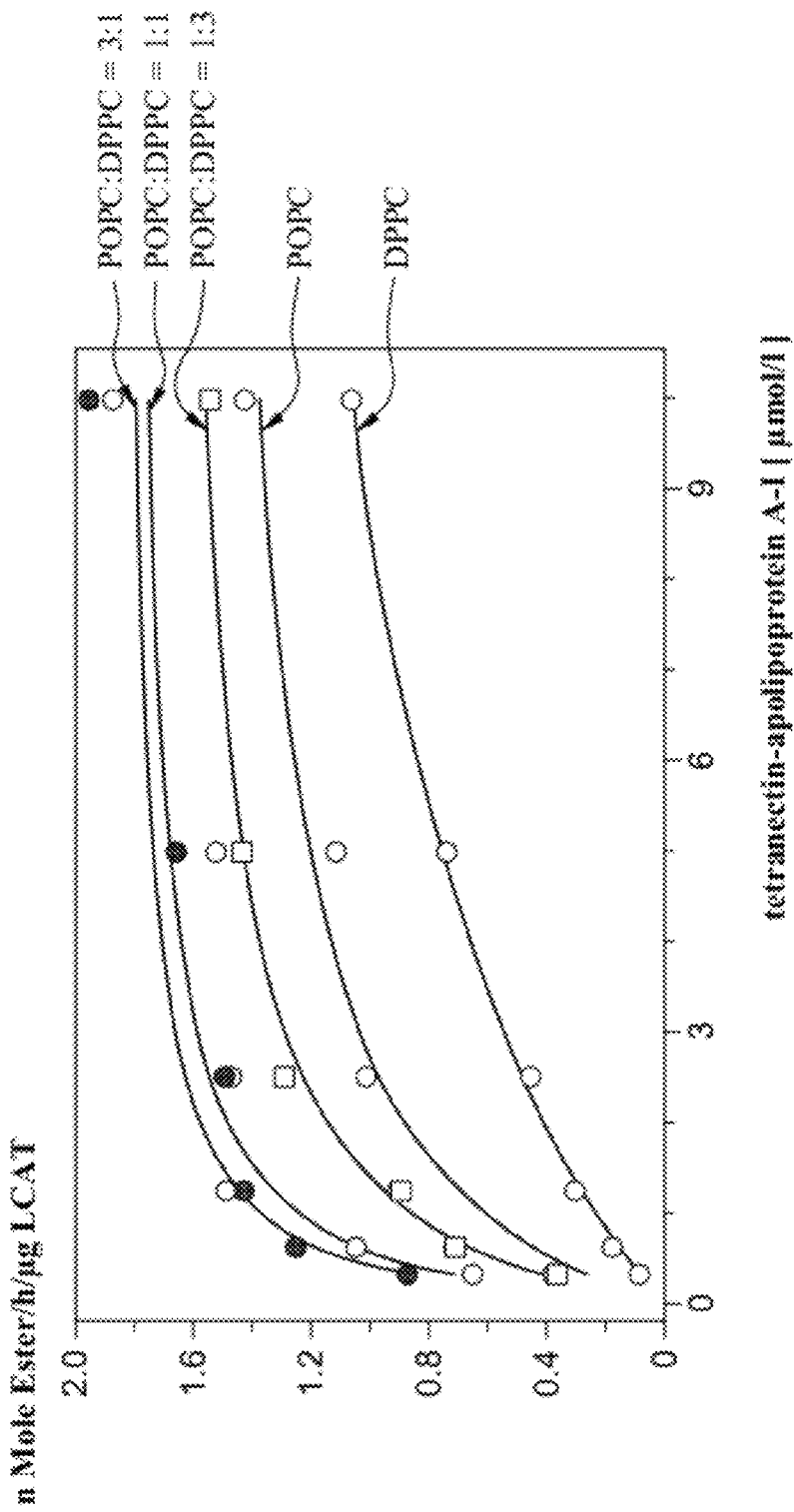
FIG. 4 Initial velocity of cholesterol esterification in lipid particles containing POPC and/or DPPC.

After cholate removal by dialysis, the capacity of the resulting protein-lipid complex to support LCAT catalyzed cholesterol esterification was tested. $^3$H cholesterol (4%; relative to the phosphatidylcholine content on a molar basis) was incorporated in the lipid particle by addition of an ethanolic cholesterol solution. The capacity of the resulting protein-lipid complex to support LCAT catalyzed cholesterol esterification was tested in presence of 0.2 µg/ml recombinant LCAT enzyme (ROAR biochemical) in 125 µL (10 mM Tris, 150 mM NaCl, 1 mM EDTA, 1 mM NaN$_3$; pH 7.4; 2 mg/ml HuFAF Albumin; 4 mM beta mercaptoethanol) for 1 hour at 37° C. The reaction was stopped by addition of chloroform:methanol (2:1) and lipids were extracted. "Percent" esterification was calculated after cholesterol—cholesteryl ester separation by TLC and scintillation counting. As less than 20% of the tracer was incorporated into esters, the reaction rate could be considered as constant in the experimental conditions. Data were fitted to the Michaelis Menten equation using XLfit software (IDBS) and are shown in FIG. 4.

TABLE 2a

Apparent kinetic parameters.

| substrate [% POPC] | $K_m$ [nM] | $V_{max}$ [n mole ester/h/U LCAT] |
|---|---|---|
| 100 | 4.6 | 1.6 |
| 75 | 0.4 | 1.9 |
| 50 | 0.5 | 1.8 |
| 25 | 1.0 | 1.7 |
| 0 | 6.9 | 1.8 |

C) Cholesterol Efflux to THP-1 Derived Foam Cells

Macrophage like human THP-1 cells, were obtained by exposing THP-1 monocytic leukemia cells to phorbol myristate acetate. Subsequently cells were loaded by further culture in the presence of acetylated LDL containing $^3$H Cholesterol tracer. These model foam cells were then exposed for 4 h-8 h to cholesterol acceptor test compounds (see below).

Cell culture supernatants were harvested and cells lysed in 5% NP40. Fractional efflux was calculated as the ratio of cholesterol radioactivity in the supernatant relative to the sum of the radioactivity in the cells plus supernatant. Efflux from cell exposed to medium containing no acceptors was subtracted and efflux velocity calculated by linear fit. Efflux velocity was standardized using efflux from cells to 10 µg/ml wild-type apolipoprotein A-I as reference (relative efflux velocity). Relative efflux velocities obtained in two separate experiments were plotted as function of cholesterol acceptor concentration and data fitted to the Michaelis Menten equation.

Parallel experiments were performed using cells exposed to a RX R-LXR agonist that is known to upregulate ABCA-1 transporters, and bias cholesterol transport toward ABCA-1 mediated efflux.

Only a modest influence of the lipid mixture was observed in the tested series (FIG. 5 and Table 27).

TABLE 28

Different samples.

| tetranectin-apolipoprotein A-I with | molar ratio apolipoprotein:phospholipid | preparation method |
|---|---|---|
| 100% POPC/0% DPPC | 1:60 | cholate |
| 75% POPC/25% DPPC | 1:60 | cholate |
| 50% POPC/50% DPPC | 1:70 | cholate |
| 0% POPC/100% DPPC | 1:80 | cholate |
| — | | not |

RX R-LXR pretreatment of the foam cells strongly increased efflux to the non-lipidated material with a six-fold increase of the maximal velocity over non treated cells. Impact on lipid particles was much less, with a two-fold increase, reflecting lower contribution of the ABCA-1 transporter to the cholesterol efflux (FIG. 6).

d) In vivo study

Five lipid particle variants were studied:
i) only POPC
ii) only DPPC
iii) POPC:DPPC 3:1
iv) POPC:DPPC 1:1
v) DPPC:SM 9:1

Rabbits were intravenous infused over 0.5 h at 80 mg/kg (n=3 rabbits/test compound) followed by serial blood sampling over 96 h post infusion.

Analysis of apolipoprotein levels with an ELISA:
drug levels
data on plasma values of liver enzymes, cholesterol, cholesterol ester.

Plasma concentrations are very similar for all tested compositions showing little pronounced initial "distribution" phase followed by log-linear decline of concentrations (FIG. 7, Table 3).

TABLE 3

Pharmacokinetic data.

| tetranectin-apolipoprotein A-I with | $C_L$ [ml/h/kg] | $V_{ss}$ [ml/kg] | $T_{1/2}$ [h] | $C_{max}$ [mg/m] |
|---|---|---|---|---|
| 100% POPC/0% DPPC | 0.897 ± 0.216 | 45.0 ± 2.5 | 36.9 ± 8.2 | 2.40 ± 0.19 |
| 0% POPC/100% DPPC | 0.922 ± 0.098 | 37.8 ± 4.9 | 30.2 ± 7.7 | 2.29 ± 0.19 |
| 75% POPC/25% DPPC | 0.815 ± 0.064 | 37.8 ± 5.6 | 34.2 ± 4.5 | 2.65 ± 0.28 |
| 50% POPC/50% DPPC | 0.850 ± 0.135 | 43.1 ± 5.9 | 38.6 ± 10.6 | 2.34 ± 0.31 |
| 90% DPPC/10% SM | 1.28 ± 0.62 | 50.7 ± 8.7 | 31.3 ± 8.2 | 1.91 ± 0.33 |

The determined pharmacokinetic (PK) parameters were similar for all tested compounds. Also a low inter-individual variability has been found. The determined half-lives are close to 1.5 days, i.e. increased compared to wild-type apolipoprotein A-I. The volume of distribution is similar to plasma volume (ca. 40 ml/kg in rabbits).

f) Cholesterol Mobilization

Cholesterol is mobilized and esterified in plasma. Plasma cholesteryl ester levels do continue to increase even after tetranectin-apolipoprotein A-I is already decreasing. When plasma tetranectin-apolipoprotein A-I levels have decreased to 0.5 mg/ml (about 50% of normal wild-type apolipoprotein A-I) increased cholesterol ester levels are still detectable (FIG. 8).

g) Liver Enzyme Release

Lipid particles comprising tetranectin-apolipoprotein A-I containing POPC do not induce liver enzyme release (FIG. 1). Similar to the rabbit, a single i.v. injection of the tetranectin-apolipoprotein A-I according to the current invention containing POPC or POPC/DPPC mixtures are safe in mice. The apolipoprotein composition containing DPPC:POPC at a molar ratio of 1:3 was comparable to POPC alone (FIG. 9).

No significant hemolysis was observed until two hours post infusion in any of the five preparations. Hemolysis was determined photometrically as red color in plasma samples obtained at two hours after i.v. application of tetranectin-apolipoprotein A-I. 100% hemolysis of whole blood (generated by 0.44% Triton X-100-final concentration) was used for calibration (FIG. 10).

h) Anti-Inflammatory Effects of Tetranectin-Apolipoprotein A-I on Human Umbilical Vein Endothelial Cells Passage 5-10 HUVECs (human umbilical vein endothelial cells) were incubated in the respective tetranectin-apolipoprotein A-I preparations for 16 h and stimulated with TNFα for the final 4 hours. VCAM1 surface expression was detected with specific antibodies by FACS.

Example 9

Lipid Particle Stability

Wild-type Apolipoprotein A-I containing an N-terminal histidine-tag and an IgA protease cleavage site was expressed in *E. coli* and purified by column chromatography as reported in the examples above. The histidine-tag was removed by IgA protease cleavage. Lipid particles (HDL particles) were assembled using a 1:150 ratio of protein to Lipoid 5100 soybean phospholipid mixture. The particles were stored in a buffer containing 5 mM sodium phosphate and 1% sucrose at pH value of 7.3. SE-HPLC revealed three distinct peaks upon incubation after lipidation and incubation for 10 days. After incubation at 40° C., a predominant peak at retention time 10.8 minutes can be detected (47% of total protein), which is absent in the sample stored at 5° C. The 10.8 minutes peak indicates the formation of soluble large molecular weight assemblies due to protein destabilization.

HDL particles containing tetranectin-apolipoprotein A-I as reported herein which were obtained starting from a POPC:DPPC mixture (ratio POPC to DPPC of 3:1) were also incubated at 5° C. and 40° C. Incubation at elevated temperature lead to a slight degree of pre-peak formation, but no significant shift to high molecular weight assemblies at 10.8 minutes (<2% increase at 11 minutes). This indicates improved HDL particle stability compared to the particle containing wild-type apolipoprotein A-I.

Example 10

Cholesterol Mobilization

The efficiency at which cholesterol is mobilized into the blood can be determined by comparing the respective excursion of total cholesterol with apolipoprotein concentrations after administration of apolipoprotein in vivo. For a quantitative assessment, the quotient of the baseline corrected area under the concentration-time curve (AUC) of total cholesterol and the area under the concentration-time curve of apolipoprotein was calculated.

In this experiment the following substances were analyzed:
wild-type apolipoprotein A-I containing an N-terminal histidine-tag and an IgA protease cleavage site expressed in *E. coli* and purified by column chromatography as reported in the examples above; the histidine-tag was removed by IgA protease cleavage; lipid particles (HDL particles) were assembled using a 1:150 ratio of protein to Lipoid 5100 soybean phospholipid mixture, apolipoprotein A-I Milano variant; lipid particles (HDL particles) were assembled using a 1:40 ratio of protein to POPC, tetranectin-apolipoprotein A-I as reported herein; lipid particles (HDL particles) were assembled using a 1:60 ratio of protein to POPC and DPPC (POPC and DPPC at a ratio of 3:1).

The three HDL particles were applied to rats. The values obtained for the respective AUC ratios are shown in Table 29.

TABLE 29

Cholesterol mobilization.

| | lipids | AUC (time dependent concentration cholesterol in blood)/ AUC (time dependent apolipoprotein A-I concentration in blood) |
|---|---|---|
| wt-apolipoprotein A-I | soybean phospholipid mixture | 0.0002 (mmol/l)/(μg/ml)). |
| apolipoprotein A-I Milano variant | POPC | 0.0004 (mmol/l)/(μg/ml)). |
| tetranectin-apolipoprotein A-I as reported herein | POPC:DPPC 3:1 | 0.0013 (mmol/l)/(μg/ml) |

The invention claimed is:

1. A lipid particle comprising
   an apolipoprotein A-I or a variant thereof, and
   1-palmitoyl-2-oleoyl-phosphatidyl choline and 1,2-dipalmitoyl-phosphatidyl choline, wherein the molar ratio of the 1-palmitoyl-2-oleoyl-phosphatidyl choline to the 1,2-dipalmitoyl-phosphatidyl choline is 3:1.

2. The lipid particle according to claim 1, characterized in that the apolipoprotein A-I or variant thereof is a multimer comprising three monomers.

3. The lipid particle according to claim 1, characterized in that the amino acid sequence of the apolipoprotein A-I or variant thereof is at least 70% homologous to the amino acid sequence of SEQ ID NO: 01, or SEQ ID NO: 02, or SEQ ID NO: 06, or SEQ ID NO: 66, or SEQ ID NO: 67.

4. The lipid particle according to claim 1, characterized in binding to a receptor selected from the group consisting of cubilin, Scavenger receptor class B, type 1 (SR-BI), ATP-binding cassette 1 (ABCA-1), Lecithin-cholesterol acyltransferase (LCAT), Cholesteryl-ester transfer protein (CETP), and Phospholipid transfer protein (PLTP).

5. The lipid particle according to claim 1, characterized in that the number of phospholipid molecules per apolipoprotein monomer in the lipid particle is from 40 to 120.

6. The lipid particle according to claim 1, characterized in that the number of phospholipid molecules per apolipoprotein monomer is from 50 to 110.

7. The lipid particle according to claim 1, characterized in that the number of phospholipid molecules per apolipoprotein monomer is from 54 to 102.

8. The lipid particle according to claim 1, characterized in that the number of phospholipid molecules per apolipoprotein monomer in the lipid particle is from 60 to 90.

9. The lipid particle according to claim 1, characterized in that the number of phospholipid molecules per apolipoprotein monomer in the lipid particle is from 60 to 88.

10. The lipid particle according to claim 1, characterized in that the number of phospholipid molecules per apolipoprotein monomer in the lipid particle is from 62 to 80.

11. The lipid particle according to claim 1, characterized in that the number of phospholipid molecules per apolipoprotein monomer in the lipid particle is from 64 to 70.

12. The lipid particle according to claim 1, characterized in that the number of phospholipid molecules per apolipoprotein monomer in the lipid particle is from 66 to 86.

13. The lipid particle according to claim 1, characterized in that the number of phospholipid molecules per apolipoprotein monomer in the lipid particle is about 66.

14. A pharmaceutical composition comprising a lipid particle according to claim 1.

15. A method of treating a disease or condition characterized by non-normal lipid levels or a lipid containing deposition within body components comprising
   i) administering to a subject in need of said treating a therapeutically effective amount of a lipid particle according to claim 1, and
   ii) optionally monitoring the lipid level or the lipid containing deposition of the subject.

16. A method of treating an individual having acute coronary syndrome, or atherosclerosis, or atherosclerotic plaques in blood vessels, or valvular stenosis, or septic shock, or angina pectoris, or myocardial infarction, or unstable angina pectoris, or arterial stenoses, or peripheral artery diseases (PAD), or carotis stenosis, or cerebral arterial stenosis, or coronary arterial stenosis, or vascular demencia, or amaurosis *fugax* comprising administering to the individual an effective amount of a lipid particle according to claim 1.

17. A method of inducing reverse cholesterol transport, or inducing plaques pacification, or cleaning or dissolving or stabilizing atherosclerotic plaques, or redistributing cholesterol from the wall of arteries to the liver, or increasing the number of HDL particles, or removing endotoxins in an individual, comprising administering to an individual an effective amount of a lipid particle according to claim 1 to induce reverse cholesterol transport, or to induce plaques pacification, or to clean or dissolve or stabilize atherosclerotic plaques, or to redistribute cholesterol from the wall of arteries to the liver, or to increase the number of HDL particles, or to remove endotoxins.

18. A lipid particle comprising
   a tectranectin apolipoprotein A-I or a variant thereof, and
   1-palmitoyl-2-oleoyl-phosphatidyl choline and 1,2-dipalmitoyl-phosphatidyl choline, wherein the molar ratio of the 1-palmitoyl-2-oleoyl-phosphatidyl choline to the 1,2-dipalmitoyl-phosphatidyl choline is 3:1;
   wherein the tetranectin-apolipoprotein A-I has the amino acid sequence of SEQ ID NO: 01, or SEQ ID NO: 02, or SEQ ID NO: 06, or SEQ ID NO: 66, or SEQ ID NO: 67.

19. A lipid particle comprising
   a tectranectin apolipoprotein A-I or a variant thereof, and
   1-palmitoyl-2-oleoyl-phosphatidyl choline and 1,2-dipalmitoyl-phosphatidyl choline, wherein the molar ratio of the 1-palmitoyl-2-oleoyl-phosphatidyl choline to the 1,2-dipalmitoyl-phosphatidyl choline is 3:1;
wherein the tetranectin-apolipoprotein A-I has a detectable label.

* * * * *

SEQUENCE LISTING

```
<160> NUMBER OF SEQ ID NOS: 105

<210> SEQ ID NO 1
<211> LENGTH: 285
<212> TYPE: PRT
<213> ORGANISM: Artificial Sequence
<220> FEATURE:
<223> OTHER INFORMATION: Description of Artificial Sequence: Synthetic
      Tetranectin-apolipoprotein A-I (1) polypeptide

<400> SEQUENCE: 1

Ala Pro Ile Val Asn Ala Lys Lys Asp Val Val Asn Thr Lys Met Phe
1               5                   10                  15

Glu Glu Leu Lys Ser Arg Leu Asp Thr Leu Ala Gln Glu Val Ala Leu
            20                  25                  30

Leu Lys Glu Gln Gln Ala Leu Gln Thr Val Asp Glu Pro Pro Gln Ser
        35                  40                  45

Pro Trp Asp Arg Val Lys Asp Leu Ala Thr Val Tyr Val Asp Val Leu
    50                  55                  60

Lys Asp Ser Gly Arg Asp Tyr Val Ser Gln Phe Glu Gly Ser Ala Leu
65                  70                  75                  80

Gly Lys Gln Leu Asn Leu Lys Leu Leu Asp Asn Trp Asp Ser Val Thr
                85                  90                  95

Ser Thr Phe Ser Lys Leu Arg Glu Gln Leu Gly Pro Val Thr Gln Glu
            100                 105                 110

Phe Trp Asp Asn Leu Glu Lys Glu Thr Glu Gly Leu Arg Gln Glu Met
        115                 120                 125

Ser Lys Asp Leu Glu Glu Val Lys Ala Lys Val Gln Pro Tyr Leu Asp
    130                 135                 140

Asp Phe Gln Lys Lys Trp Gln Glu Met Glu Leu Tyr Arg Gln Lys
145                 150                 155                 160

Val Glu Pro Leu Arg Ala Glu Leu Gln Glu Gly Ala Arg Gln Lys Leu
                165                 170                 175

His Glu Leu Gln Glu Lys Leu Ser Pro Leu Gly Glu Glu Met Arg Asp
            180                 185                 190

Arg Ala Arg Ala His Val Asp Ala Leu Arg Thr His Leu Ala Pro Tyr
        195                 200                 205

Ser Asp Glu Leu Arg Gln Arg Leu Ala Ala Arg Leu Glu Ala Leu Lys
    210                 215                 220
```

```
Glu Asn Gly Gly Ala Arg Leu Ala Glu Tyr His Ala Lys Ala Thr Glu
225                 230                 235                 240

His Leu Ser Thr Leu Ser Glu Lys Ala Lys Pro Ala Leu Glu Asp Leu
            245                 250                 255

Arg Gln Gly Leu Leu Pro Val Leu Glu Ser Phe Lys Val Ser Phe Leu
        260                 265                 270

Ser Ala Leu Glu Glu Tyr Thr Lys Lys Leu Asn Thr Gln
    275                 280                 285

<210> SEQ ID NO 2
<211> LENGTH: 283
<212> TYPE: PRT
<213> ORGANISM: Artificial Sequence
<220> FEATURE:
<223> OTHER INFORMATION: Description of Artificial Sequence: Synthetic
      Tetranectin-apolipoprotein A-I (2) polypeptide

<400> SEQUENCE: 2

Ile Val Asn Ala Lys Lys Asp Val Val Asn Thr Lys Met Phe Glu Glu
1               5                   10                  15

Leu Lys Ser Arg Leu Asp Thr Leu Ala Gln Glu Val Ala Leu Leu Lys
            20                  25                  30

Glu Gln Gln Ala Leu Gln Thr Val Asp Glu Pro Gln Ser Pro Trp
        35                  40                  45

Asp Arg Val Lys Asp Leu Ala Thr Val Tyr Val Asp Val Leu Lys Asp
50                  55                  60

Ser Gly Arg Asp Tyr Val Ser Gln Phe Glu Gly Ser Ala Leu Gly Lys
65                  70                  75                  80

Gln Leu Asn Leu Lys Leu Leu Asp Asn Trp Asp Ser Val Thr Ser Thr
                85                  90                  95

Phe Ser Lys Leu Arg Glu Gln Leu Gly Pro Val Thr Gln Glu Phe Trp
            100                 105                 110

Asp Asn Leu Glu Lys Glu Thr Glu Gly Leu Arg Gln Glu Met Ser Lys
        115                 120                 125

Asp Leu Glu Glu Val Lys Ala Lys Val Gln Pro Tyr Leu Asp Asp Phe
130                 135                 140

Gln Lys Lys Trp Gln Glu Glu Met Glu Leu Tyr Arg Gln Lys Val Glu
145                 150                 155                 160

Pro Leu Arg Ala Glu Leu Gln Glu Gly Ala Arg Gln Lys Leu His Glu
                165                 170                 175

Leu Gln Glu Lys Leu Ser Pro Leu Gly Glu Glu Met Arg Asp Arg Ala
            180                 185                 190

Arg Ala His Val Asp Ala Leu Arg Thr His Leu Ala Pro Tyr Ser Asp
        195                 200                 205

Glu Leu Arg Gln Arg Leu Ala Ala Arg Leu Glu Ala Leu Lys Glu Asn
210                 215                 220

Gly Gly Ala Arg Leu Ala Glu Tyr His Ala Lys Ala Thr Glu His Leu
225                 230                 235                 240

Ser Thr Leu Ser Glu Lys Ala Lys Pro Ala Leu Glu Asp Leu Arg Gln
                245                 250                 255

Gly Leu Leu Pro Val Leu Glu Ser Phe Lys Val Ser Phe Leu Ser Ala
            260                 265                 270

Leu Glu Glu Tyr Thr Lys Lys Leu Asn Thr Gln
        275                 280

<210> SEQ ID NO 3
```

```
<211> LENGTH: 5
<212> TYPE: PRT
<213> ORGANISM: Homo sapiens

<400> SEQUENCE: 3

Ser Leu Lys Gly Ser
1               5

<210> SEQ ID NO 4
<211> LENGTH: 22
<212> TYPE: PRT
<213> ORGANISM: Artificial Sequence
<220> FEATURE:
<223> OTHER INFORMATION: Description of Artificial Sequence: Synthetic
      Apolipoprotein A-I mimetic (1) peptide

<400> SEQUENCE: 4

Pro Val Leu Asp Glu Phe Arg Glu Lys Leu Asn Glu Glu Leu Glu Ala
1               5                   10                  15

Leu Lys Gln Lys Leu Lys
            20

<210> SEQ ID NO 5
<211> LENGTH: 22
<212> TYPE: PRT
<213> ORGANISM: Artificial Sequence
<220> FEATURE:
<223> OTHER INFORMATION: Description of Artificial Sequence: Synthetic
      Apolipoprotein A-I mimetic (2) peptide

<400> SEQUENCE: 5

Pro Val Leu Asp Leu Phe Arg Glu Leu Leu Asn Glu Leu Leu Glu Ala
1               5                   10                  15

Leu Lys Gln Lys Leu Lys
            20

<210> SEQ ID NO 6
<211> LENGTH: 267
<212> TYPE: PRT
<213> ORGANISM: Homo sapiens

<400> SEQUENCE: 6

Met Lys Ala Ala Val Leu Thr Leu Ala Val Leu Phe Leu Thr Gly Ser
1               5                   10                  15

Gln Ala Arg His Phe Trp Gln Gln Asp Glu Pro Pro Gln Ser Pro Trp
            20                  25                  30

Asp Arg Val Lys Asp Leu Ala Thr Val Tyr Val Asp Val Leu Lys Asp
        35                  40                  45

Ser Gly Arg Asp Tyr Val Ser Gln Phe Glu Gly Ser Ala Leu Gly Lys
    50                  55                  60

Gln Leu Asn Leu Lys Leu Leu Asp Asn Trp Asp Ser Val Thr Ser Thr
65                  70                  75                  80

Phe Ser Lys Leu Arg Glu Gln Leu Gly Pro Val Thr Gln Glu Phe Trp
                85                  90                  95

Asp Asn Leu Glu Lys Glu Thr Glu Gly Leu Arg Gln Glu Met Ser Lys
            100                 105                 110

Asp Leu Glu Glu Val Lys Ala Lys Val Gln Pro Tyr Leu Asp Asp Phe
        115                 120                 125

Gln Lys Lys Trp Gln Glu Glu Met Glu Leu Tyr Arg Gln Lys Val Glu
    130                 135                 140

Pro Leu Arg Ala Glu Leu Gln Glu Gly Ala Arg Gln Lys Leu His Glu
```

```
            145                 150                 155                 160
Leu Gln Glu Lys Leu Ser Pro Leu Gly Glu Glu Met Arg Asp Arg Ala
                    165                 170                 175

Arg Ala His Val Asp Ala Leu Arg Thr His Leu Ala Pro Tyr Ser Asp
                180                 185                 190

Glu Leu Arg Gln Arg Leu Ala Ala Arg Leu Glu Ala Leu Lys Glu Asn
            195                 200                 205

Gly Gly Ala Arg Leu Ala Glu Tyr His Ala Lys Ala Thr Glu His Leu
        210                 215                 220

Ser Thr Leu Ser Glu Lys Ala Lys Pro Ala Leu Glu Asp Leu Arg Gln
225                 230                 235                 240

Gly Leu Leu Pro Val Leu Glu Ser Phe Lys Val Ser Phe Leu Ser Ala
                    245                 250                 255

Leu Glu Glu Tyr Thr Lys Lys Leu Asn Thr Gln
                260                 265

<210> SEQ ID NO 7
<211> LENGTH: 100
<212> TYPE: PRT
<213> ORGANISM: Homo sapiens

<400> SEQUENCE: 7

Met Lys Leu Leu Ala Ala Thr Val Leu Leu Thr Ile Cys Ser Leu
1               5                   10                  15

Glu Gly Ala Leu Val Arg Arg Gln Ala Lys Glu Pro Cys Val Glu Ser
                20                  25                  30

Leu Val Ser Gln Tyr Phe Gln Thr Val Thr Asp Tyr Gly Lys Asp Leu
            35                  40                  45

Met Glu Lys Val Lys Ser Pro Glu Leu Gln Ala Glu Ala Lys Ser Tyr
        50                  55                  60

Phe Glu Lys Ser Lys Glu Gln Leu Thr Pro Leu Ile Lys Lys Ala Gly
65                  70                  75                  80

Thr Glu Leu Val Asn Phe Leu Ser Tyr Phe Val Glu Leu Gly Thr Gln
                    85                  90                  95

Pro Ala Thr Gln
            100

<210> SEQ ID NO 8
<211> LENGTH: 396
<212> TYPE: PRT
<213> ORGANISM: Homo sapiens

<400> SEQUENCE: 8

Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
                20                  25                  30

Asp Tyr Phe Ser Gln Leu Ser Asn Asn Ala Lys Glu Ala Val Glu His
            35                  40                  45

Leu Gln Lys Ser Glu Leu Thr Gln Gln Leu Asn Ala Leu Phe Gln Asp
        50                  55                  60

Lys Leu Gly Glu Val Asn Thr Tyr Ala Gly Asp Leu Gln Lys Lys Leu
65                  70                  75                  80

Val Pro Phe Ala Thr Glu Leu His Glu Arg Leu Ala Lys Asp Ser Glu
                    85                  90                  95

Lys Leu Lys Glu Glu Ile Gly Lys Glu Leu Glu Glu Leu Arg Ala Arg
```

```
            100                 105                 110
Leu Leu Pro His Ala Asn Glu Val Ser Gln Lys Ile Gly Asp Asn Leu
        115                 120                 125

Arg Glu Leu Gln Gln Arg Leu Glu Pro Tyr Ala Asp Gln Leu Arg Thr
130                 135                 140

Gln Val Asn Thr Gln Ala Glu Gln Leu Arg Arg Gln Leu Thr Pro Tyr
145                 150                 155                 160

Ala Gln Arg Met Glu Arg Val Leu Arg Glu Asn Ala Asp Ser Leu Gln
                165                 170                 175

Ala Ser Leu Arg Pro His Ala Asp Glu Leu Lys Ala Lys Ile Asp Gln
            180                 185                 190

Asn Val Glu Glu Leu Lys Gly Arg Leu Thr Pro Tyr Ala Asp Glu Phe
        195                 200                 205

Lys Val Lys Ile Asp Gln Thr Val Glu Glu Leu Arg Arg Ser Leu Ala
210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
                245                 250                 255

Ser Ala Ser Ala Glu Glu Leu Arg Gln Arg Leu Ala Pro Leu Ala Glu
            260                 265                 270

Asp Val Arg Gly Asn Leu Arg Gly Asn Thr Glu Gly Leu Gln Lys Ser
        275                 280                 285

Leu Ala Glu Leu Gly Gly His Leu Asp Gln Gln Val Glu Glu Phe Arg
290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
                325                 330                 335

Glu Gly His Leu Ser Phe Leu Glu Lys Asp Leu Arg Asp Lys Val Asn
            340                 345                 350

Ser Phe Phe Ser Thr Phe Lys Glu Lys Glu Ser Gln Asp Lys Thr Leu
        355                 360                 365

Ser Leu Pro Glu Leu Glu Gln Gln Gln Gln Gln Gln Gln Glu Gln Gln
370                 375                 380

Gln Glu Gln Val Gln Met Leu Ala Pro Leu Glu Ser
385                 390                 395

<210> SEQ ID NO 9
<211> LENGTH: 366
<212> TYPE: PRT
<213> ORGANISM: Homo sapiens

<400> SEQUENCE: 9

Met Ala Ser Met Ala Ala Val Leu Thr Trp Ala Leu Ala Leu Leu Ser
1               5                   10                  15

Ala Phe Ser Ala Thr Gln Ala Arg Lys Gly Phe Trp Asp Tyr Phe Ser
                20                  25                  30

Gln Thr Ser Gly Asp Lys Gly Arg Val Glu Gln Ile His Gln Gln Lys
            35                  40                  45

Met Ala Arg Glu Pro Ala Thr Leu Lys Asp Ser Leu Glu Gln Asp Leu
        50                  55                  60

Asn Asn Met Asn Lys Phe Leu Glu Lys Leu Arg Pro Leu Ser Gly Ser
65                  70                  75                  80
```

```
Glu Ala Pro Arg Leu Pro Gln Asp Pro Val Gly Met Arg Arg Gln Leu
                85                  90                  95

Gln Glu Glu Leu Glu Glu Val Lys Ala Arg Leu Gln Pro Tyr Met Ala
            100                 105                 110

Glu Ala His Glu Leu Val Gly Trp Asn Leu Glu Gly Leu Arg Gln Gln
        115                 120                 125

Leu Lys Pro Tyr Thr Met Asp Leu Met Glu Gln Val Ala Leu Arg Val
    130                 135                 140

Gln Glu Leu Gln Glu Gln Leu Arg Val Val Gly Glu Asp Thr Lys Ala
145                 150                 155                 160

Gln Leu Leu Gly Gly Val Asp Glu Ala Trp Ala Leu Leu Gln Gly Leu
                165                 170                 175

Gln Ser Arg Val Val His His Thr Gly Arg Phe Lys Glu Leu Phe His
            180                 185                 190

Pro Tyr Ala Glu Ser Leu Val Ser Gly Ile Gly Arg His Val Gln Glu
        195                 200                 205

Leu His Arg Ser Val Ala Pro His Ala Pro Ala Ser Pro Ala Arg Leu
    210                 215                 220

Ser Arg Cys Val Gln Val Leu Ser Arg Lys Leu Thr Leu Lys Ala Lys
225                 230                 235                 240

Ala Leu His Ala Arg Ile Gln Gln Asn Leu Asp Gln Leu Arg Glu Glu
                245                 250                 255

Leu Ser Arg Ala Phe Ala Gly Thr Gly Thr Glu Glu Gly Ala Gly Pro
            260                 265                 270

Asp Pro Gln Met Leu Ser Glu Glu Val Arg Gln Arg Leu Gln Ala Phe
        275                 280                 285

Arg Gln Asp Thr Tyr Leu Gln Ile Ala Ala Phe Thr Arg Ala Ile Asp
    290                 295                 300

Gln Glu Thr Glu Glu Val Gln Gln Leu Ala Pro Pro Pro Pro Pro Gly
305                 310                 315                 320

His Ser Ala Phe Ala Pro Glu Phe Gln Gln Thr Asp Ser Gly Lys Val
                325                 330                 335

Leu Ser Lys Leu Gln Ala Arg Leu Asp Asp Leu Trp Glu Asp Ile Thr
            340                 345                 350

His Ser Leu His Asp Gln Gly His Ser His Leu Gly Asp Pro
        355                 360                 365

<210> SEQ ID NO 10
<211> LENGTH: 83
<212> TYPE: PRT
<213> ORGANISM: Homo sapiens

<400> SEQUENCE: 10

Met Arg Leu Phe Leu Ser Leu Pro Val Leu Val Val Val Leu Ser Ile
1               5                   10                  15

Val Leu Glu Gly Pro Ala Pro Ala Gln Gly Thr Pro Asp Val Ser Ser
            20                  25                  30

Ala Leu Asp Lys Leu Lys Glu Phe Gly Asn Thr Leu Glu Asp Lys Ala
        35                  40                  45

Arg Glu Leu Ile Ser Arg Ile Lys Gln Ser Glu Leu Ser Ala Lys Met
    50                  55                  60

Arg Glu Trp Phe Ser Glu Thr Phe Gln Lys Val Lys Glu Lys Leu Lys
65                  70                  75                  80

Ile Asp Ser
```

-continued

```
<210> SEQ ID NO 11
<211> LENGTH: 101
<212> TYPE: PRT
<213> ORGANISM: Homo sapiens

<400> SEQUENCE: 11

Met Gly Thr Arg Leu Leu Pro Ala Leu Phe Leu Val Leu Leu Val Leu
1               5                   10                  15

Gly Phe Glu Val Gln Gly Thr Gln Gln Pro Gln Gln Asp Glu Met Pro
            20                  25                  30

Ser Pro Thr Phe Leu Thr Gln Val Lys Glu Ser Leu Ser Ser Tyr Trp
        35                  40                  45

Glu Ser Ala Lys Thr Ala Ala Gln Asn Leu Tyr Glu Lys Thr Tyr Leu
    50                  55                  60

Pro Ala Val Asp Glu Lys Leu Arg Asp Leu Tyr Ser Lys Ser Thr Ala
65                  70                  75                  80

Ala Met Ser Thr Tyr Thr Gly Ile Phe Thr Asp Gln Val Leu Ser Val
                85                  90                  95

Leu Lys Gly Glu Glu
            100

<210> SEQ ID NO 12
<211> LENGTH: 99
<212> TYPE: PRT
<213> ORGANISM: Homo sapiens

<400> SEQUENCE: 12

Met Gln Pro Arg Val Leu Leu Val Val Ala Leu Leu Ala Leu Leu Ala
1               5                   10                  15

Ser Ala Arg Ala Ser Glu Ala Glu Asp Ala Ser Leu Leu Ser Phe Met
            20                  25                  30

Gln Gly Tyr Met Lys His Ala Thr Lys Thr Ala Lys Asp Ala Leu Ser
        35                  40                  45

Ser Val Gln Glu Ser Gln Val Ala Gln Gln Ala Arg Gly Trp Val Thr
    50                  55                  60

Asp Gly Phe Ser Ser Leu Lys Asp Tyr Trp Ser Thr Val Lys Asp Lys
65                  70                  75                  80

Phe Ser Glu Phe Trp Asp Leu Asp Pro Glu Val Arg Pro Thr Ser Ala
                85                  90                  95

Val Ala Ala

<210> SEQ ID NO 13
<211> LENGTH: 127
<212> TYPE: PRT
<213> ORGANISM: Homo sapiens

<400> SEQUENCE: 13

Met Ser Leu Leu Arg Asn Arg Leu Gln Ala Leu Pro Ala Leu Cys Leu
1               5                   10                  15

Cys Val Leu Val Leu Ala Cys Ile Gly Ala Cys Gln Pro Glu Ala Gln
            20                  25                  30

Glu Gly Thr Leu Ser Pro Pro Lys Leu Lys Met Ser Arg Trp Ser
        35                  40                  45

Leu Val Arg Gly Arg Met Lys Glu Leu Leu Glu Thr Val Val Asn Arg
    50                  55                  60

Thr Arg Asp Gly Trp Gln Trp Phe Trp Ser Pro Ser Thr Phe Arg Gly
65                  70                  75                  80
```

-continued

```
Phe Met Gln Thr Tyr Tyr Asp Asp His Leu Arg Asp Leu Gly Pro Leu
                85                  90                  95

Thr Lys Ala Trp Phe Leu Glu Ser Lys Asp Ser Leu Leu Lys Lys Thr
            100                 105                 110

His Ser Leu Cys Pro Arg Leu Val Cys Gly Asp Lys Asp Gln Gly
        115                 120                 125
```

<210> SEQ ID NO 14
<211> LENGTH: 189
<212> TYPE: PRT
<213> ORGANISM: Homo sapiens

<400> SEQUENCE: 14

```
Met Val Met Leu Leu Leu Leu Ser Ala Leu Ala Gly Leu Phe Gly
1               5                   10                  15

Ala Ala Glu Gly Gln Ala Phe His Leu Gly Lys Cys Pro Asn Pro Pro
            20                  25                  30

Val Gln Glu Asn Phe Asp Val Asn Lys Tyr Leu Gly Arg Trp Tyr Glu
        35                  40                  45

Ile Glu Lys Ile Pro Thr Thr Phe Glu Asn Gly Arg Cys Ile Gln Ala
50                  55                  60

Asn Tyr Ser Leu Met Glu Asn Gly Lys Ile Lys Val Leu Asn Gln Glu
65                  70                  75                  80

Leu Arg Ala Asp Gly Thr Val Asn Gln Ile Gly Glu Ala Thr Pro
            85                  90                  95

Val Asn Leu Thr Glu Pro Ala Lys Leu Glu Val Lys Phe Ser Trp Phe
        100                 105                 110

Met Pro Ser Ala Pro Tyr Trp Ile Leu Ala Thr Asp Tyr Glu Asn Tyr
        115                 120                 125

Ala Leu Val Tyr Ser Cys Thr Cys Ile Ile Gln Leu Phe His Val Asp
        130                 135                 140

Phe Ala Trp Ile Leu Ala Arg Asn Pro Asn Leu Pro Pro Glu Thr Val
145                 150                 155                 160

Asp Ser Leu Lys Asn Ile Leu Thr Ser Asn Asn Ile Asp Val Lys Lys
                165                 170                 175

Met Thr Val Thr Asp Gln Val Asn Cys Pro Lys Leu Ser
            180                 185
```

<210> SEQ ID NO 15
<211> LENGTH: 317
<212> TYPE: PRT
<213> ORGANISM: Homo sapiens

<400> SEQUENCE: 15

```
Met Lys Val Leu Trp Ala Ala Leu Leu Val Thr Phe Leu Ala Gly Cys
1               5                   10                  15

Gln Ala Lys Val Glu Gln Ala Val Glu Thr Glu Pro Glu Pro Glu Leu
            20                  25                  30

Arg Gln Gln Thr Glu Trp Gln Ser Gly Gln Arg Trp Glu Leu Ala Leu
        35                  40                  45

Gly Arg Phe Trp Asp Tyr Leu Arg Trp Val Gln Thr Leu Ser Glu Gln
50                  55                  60

Val Gln Glu Glu Leu Leu Ser Ser Gln Val Thr Gln Glu Leu Arg Ala
65                  70                  75                  80

Leu Met Asp Glu Thr Met Lys Glu Leu Lys Ala Tyr Lys Ser Glu Leu
                85                  90                  95
```

Glu Glu Gln Leu Thr Pro Val Ala Glu Thr Arg Ala Arg Leu Ser
            100                 105                 110

Lys Glu Leu Gln Ala Ala Gln Ala Arg Leu Gly Ala Asp Met Glu Asp
        115                 120                 125

Val Cys Gly Arg Leu Val Gln Tyr Arg Gly Val Gln Ala Met Leu
130                 135                 140

Gly Gln Ser Thr Glu Glu Leu Arg Val Arg Leu Ala Ser His Leu Arg
145                 150                 155                 160

Lys Leu Arg Lys Arg Leu Leu Arg Asp Ala Asp Asp Leu Gln Lys Arg
                165                 170                 175

Leu Ala Val Tyr Gln Ala Gly Ala Arg Glu Gly Ala Glu Arg Gly Leu
            180                 185                 190

Ser Ala Ile Arg Glu Arg Leu Gly Pro Leu Val Glu Gln Gly Arg Val
        195                 200                 205

Arg Ala Ala Thr Val Gly Ser Leu Ala Gly Gln Pro Leu Gln Glu Arg
210                 215                 220

Ala Gln Ala Trp Gly Glu Arg Leu Arg Ala Arg Met Glu Glu Met Gly
225                 230                 235                 240

Ser Arg Thr Arg Asp Arg Leu Asp Glu Val Lys Glu Gln Val Ala Glu
                245                 250                 255

Val Arg Ala Lys Leu Glu Glu Gln Ala Gln Gln Ile Arg Leu Gln Ala
            260                 265                 270

Glu Ala Phe Gln Ala Arg Leu Lys Ser Trp Phe Glu Pro Leu Val Glu
        275                 280                 285

Asp Met Gln Arg Gln Trp Ala Gly Leu Val Glu Lys Val Gln Ala Ala
290                 295                 300

Val Gly Thr Ser Ala Ala Pro Val Pro Ser Asp Asn His
305                 310                 315

<210> SEQ ID NO 16
<211> LENGTH: 308
<212> TYPE: PRT
<213> ORGANISM: Homo sapiens

<400> SEQUENCE: 16

Met Ile Pro Val Glu Leu Leu Leu Cys Tyr Leu Leu Leu His Pro Val
1               5                   10                  15

Asp Ala Thr Ser Tyr Gly Lys Gln Thr Asn Val Leu Met His Phe Pro
            20                  25                  30

Leu Ser Leu Glu Ser Gln Thr Pro Ser Ser Asp Pro Leu Ser Cys Gln
        35                  40                  45

Phe Leu His Pro Lys Ser Leu Pro Gly Phe Ser His Met Ala Pro Leu
    50                  55                  60

Pro Lys Phe Leu Val Ser Leu Ala Leu Arg Asn Ala Leu Glu Glu Ala
65                  70                  75                  80

Gly Cys Gln Ala Asp Val Trp Ala Leu Gln Leu Gln Leu Tyr Arg Gln
                85                  90                  95

Gly Gly Val Asn Ala Thr Gln Val Leu Ile Gln His Leu Arg Gly Leu
            100                 105                 110

Gln Lys Gly Arg Ser Thr Glu Arg Asn Val Ser Val Glu Ala Leu Ala
        115                 120                 125

Ser Ala Leu Gln Leu Leu Ala Arg Glu Gln Gln Ser Thr Gly Arg Val
    130                 135                 140

Gly Arg Ser Leu Pro Thr Glu Asp Cys Glu Asn Glu Lys Glu Gln Ala

-continued

```
            145                 150                 155                 160
        Val His Asn Val Val Gln Leu Leu Pro Gly Val Gly Thr Phe Tyr Asn
                            165                 170                 175

Leu Gly Thr Ala Leu Tyr Tyr Ala Thr Gln Asn Cys Leu Gly Lys Ala
                    180                 185                 190

Arg Glu Arg Gly Arg Asp Gly Ala Ile Asp Leu Gly Tyr Asp Leu Leu
                195                 200                 205

Met Thr Met Ala Gly Met Ser Gly Gly Pro Met Gly Leu Ala Ile Ser
            210                 215                 220

Ala Ala Leu Lys Pro Ala Leu Arg Ser Gly Val Gln Gln Leu Ile Gln
        225                 230                 235                 240

Tyr Tyr Gln Asp Gln Lys Asp Ala Asn Ile Ser Gln Pro Glu Thr Thr
                        245                 250                 255

Lys Glu Gly Leu Arg Ala Ile Ser Asp Val Ser Asp Leu Glu Glu Thr
                    260                 265                 270

Thr Thr Leu Ala Ser Phe Ile Ser Glu Val Val Ser Ser Ala Pro Tyr
                275                 280                 285

Trp Gly Trp Ala Ile Ile Lys Ser Tyr Asp Leu Asp Pro Gly Ala Gly
            290                 295                 300

Ser Leu Glu Ile
        305

<210> SEQ ID NO 17
<211> LENGTH: 345
<212> TYPE: PRT
<213> ORGANISM: Homo sapiens

<400> SEQUENCE: 17

Met Ile Ser Pro Val Leu Ile Leu Phe Ser Ser Phe Leu Cys His Val
        1               5                   10                  15

Ala Ile Ala Gly Arg Thr Cys Pro Lys Pro Asp Asp Leu Pro Phe Ser
                    20                  25                  30

Thr Val Val Pro Leu Lys Thr Phe Tyr Glu Pro Gly Glu Glu Ile Thr
                35                  40                  45

Tyr Ser Cys Lys Pro Gly Tyr Val Ser Arg Gly Gly Met Arg Lys Phe
            50                  55                  60

Ile Cys Pro Leu Thr Gly Leu Trp Pro Ile Asn Thr Leu Lys Cys Thr
        65                  70                  75                  80

Pro Arg Val Cys Pro Phe Ala Gly Ile Leu Glu Asn Gly Ala Val Arg
                        85                  90                  95

Tyr Thr Thr Phe Glu Tyr Pro Asn Thr Ile Ser Phe Ser Cys Asn Thr
                    100                 105                 110

Gly Phe Tyr Leu Asn Gly Ala Asp Ser Ala Lys Cys Thr Glu Glu Gly
                115                 120                 125

Lys Trp Ser Pro Glu Leu Pro Val Cys Ala Pro Ile Ile Cys Pro Pro
            130                 135                 140

Pro Ser Ile Pro Thr Phe Ala Thr Leu Arg Val Tyr Lys Pro Ser Ala
        145                 150                 155                 160

Gly Asn Asn Ser Leu Tyr Arg Asp Thr Ala Val Phe Glu Cys Leu Pro
                        165                 170                 175

Gln His Ala Met Phe Gly Asn Asp Thr Ile Thr Cys Thr Thr His Gly
                    180                 185                 190

Asn Trp Thr Lys Leu Pro Glu Cys Arg Glu Val Lys Cys Pro Phe Pro
                195                 200                 205
```

```
Ser Arg Pro Asp Asn Gly Phe Val Asn Tyr Pro Ala Lys Pro Thr Leu
    210                 215                 220
Tyr Tyr Lys Asp Lys Ala Thr Phe Gly Cys His Asp Gly Tyr Ser Leu
225                 230                 235                 240
Asp Gly Pro Glu Glu Ile Glu Cys Thr Lys Leu Gly Asn Trp Ser Ala
                245                 250                 255
Met Pro Ser Cys Lys Ala Ser Cys Lys Val Pro Val Lys Lys Ala Thr
                260                 265                 270
Val Val Tyr Gln Gly Glu Arg Val Lys Ile Gln Glu Lys Phe Lys Asn
                275                 280                 285
Gly Met Leu His Gly Asp Lys Val Ser Phe Phe Cys Lys Asn Lys Glu
            290                 295                 300
Lys Lys Cys Ser Tyr Thr Glu Asp Ala Gln Cys Ile Asp Gly Thr Ile
305                 310                 315                 320
Glu Val Pro Lys Cys Phe Lys Glu His Ser Ser Leu Ala Phe Trp Lys
                325                 330                 335
Thr Asp Ala Ser Asp Val Lys Pro Cys
            340                 345

<210> SEQ ID NO 18
<211> LENGTH: 398
<212> TYPE: PRT
<213> ORGANISM: Homo sapiens

<400> SEQUENCE: 18

Met Glu Gly Ala Ala Leu Leu Arg Val Ser Val Leu Cys Ile Trp Met
1               5                   10                  15
Ser Ala Leu Phe Leu Gly Val Gly Val Arg Ala Glu Glu Ala Gly Ala
                20                  25                  30
Arg Val Gln Gln Asn Val Pro Ser Gly Thr Asp Thr Gly Asp Pro Gln
            35                  40                  45
Ser Lys Pro Leu Gly Asp Trp Ala Ala Gly Thr Met Asp Pro Glu Ser
50                  55                  60
Ser Ile Phe Ile Glu Asp Ala Ile Lys Tyr Phe Lys Glu Lys Val Ser
65                  70                  75                  80
Thr Gln Asn Leu Leu Leu Leu Thr Asp Asn Glu Ala Trp Asn Gly
                85                  90                  95
Phe Val Ala Ala Ala Glu Leu Pro Arg Asn Glu Ala Asp Glu Leu Arg
                100                 105                 110
Lys Ala Leu Asp Asn Leu Ala Arg Gln Met Ile Met Lys Asp Lys Asn
            115                 120                 125
Trp His Asp Lys Gly Gln Gln Tyr Arg Asn Trp Phe Leu Lys Glu Phe
        130                 135                 140
Pro Arg Leu Lys Ser Glu Leu Glu Asp Asn Ile Arg Arg Leu Arg Ala
145                 150                 155                 160
Leu Ala Asp Gly Val Gln Lys Val His Lys Gly Thr Thr Ile Ala Asn
                165                 170                 175
Val Val Ser Gly Ser Leu Ser Ile Ser Ser Gly Ile Leu Thr Leu Val
                180                 185                 190
Gly Met Gly Leu Ala Pro Phe Thr Glu Gly Gly Ser Leu Val Leu Leu
            195                 200                 205
Glu Pro Gly Met Glu Leu Gly Ile Thr Ala Ala Leu Thr Gly Ile Thr
        210                 215                 220
Ser Ser Thr Met Asp Tyr Gly Lys Lys Trp Trp Thr Gln Ala Gln Ala
225                 230                 235                 240
```

```
His Asp Leu Val Ile Lys Ser Leu Asp Lys Leu Lys Glu Val Arg Glu
            245                 250                 255

Phe Leu Gly Glu Asn Ile Ser Asn Phe Leu Ser Leu Ala Gly Asn Thr
        260                 265                 270

Tyr Gln Leu Thr Arg Gly Ile Gly Lys Asp Ile Arg Ala Leu Arg Arg
            275                 280                 285

Ala Arg Ala Asn Leu Gln Ser Val Pro His Ala Ser Ala Ser Arg Pro
    290                 295                 300

Arg Val Thr Glu Pro Ile Ser Ala Glu Ser Gly Gln Val Glu Arg
305                 310                 315                 320

Val Asn Glu Pro Ser Ile Leu Glu Met Ser Arg Gly Val Lys Leu Thr
                325                 330                 335

Asp Val Ala Pro Val Ser Phe Phe Leu Val Leu Asp Val Tyr Leu
            340                 345                 350

Val Tyr Glu Ser Lys His Leu His Glu Gly Ala Lys Ser Glu Thr Ala
        355                 360                 365

Glu Glu Leu Lys Lys Val Ala Gln Glu Leu Glu Lys Leu Asn Ile
    370                 375                 380

Leu Asn Asn Asn Tyr Lys Ile Leu Gln Ala Asp Gln Glu Leu
385                 390                 395

<210> SEQ ID NO 19
<211> LENGTH: 337
<212> TYPE: PRT
<213> ORGANISM: Homo sapiens

<400> SEQUENCE: 19

Met Asn Pro Glu Ser Ser Ile Phe Ile Glu Asp Tyr Leu Lys Tyr Phe
1               5                   10                  15

Gln Asp Gln Val Ser Arg Glu Asn Leu Leu Gln Leu Leu Thr Asp Asp
                20                  25                  30

Glu Ala Trp Asn Gly Phe Val Ala Ala Ala Glu Leu Pro Arg Asp Glu
            35                  40                  45

Ala Asp Glu Leu Arg Lys Ala Leu Asn Lys Leu Ala Ser His Met Val
    50                  55                  60

Met Lys Asp Lys Asn Arg His Asp Lys Asp Gln Gln His Arg Gln Trp
65                  70                  75                  80

Phe Leu Lys Glu Phe Pro Arg Leu Lys Arg Glu Leu Glu Asp His Ile
                85                  90                  95

Arg Lys Leu Arg Ala Leu Ala Glu Glu Val Glu Gln Val His Arg Gly
            100                 105                 110

Thr Thr Ile Ala Asn Val Val Ser Asn Ser Val Gly Thr Thr Ser Gly
        115                 120                 125

Ile Leu Thr Leu Leu Gly Leu Gly Leu Ala Pro Phe Thr Glu Gly Ile
    130                 135                 140

Ser Phe Val Leu Leu Asp Thr Gly Met Gly Leu Gly Ala Ala Ala Ala
145                 150                 155                 160

Val Ala Gly Ile Thr Cys Ser Val Val Glu Leu Val Asn Lys Leu Arg
                165                 170                 175

Ala Arg Ala Gln Ala Arg Asn Leu Asp Gln Ser Gly Thr Asn Val Ala
            180                 185                 190

Lys Val Met Lys Glu Phe Val Gly Gly Asn Thr Pro Asn Val Leu Thr
        195                 200                 205

Leu Val Asp Asn Trp Tyr Gln Val Thr Gln Gly Ile Gly Arg Asn Ile
```

```
            210                 215                 220
Arg Ala Ile Arg Arg Ala Arg Ala Asn Pro Gln Leu Gly Ala Tyr Ala
225                 230                 235                 240

Pro Pro Pro His Ile Ile Gly Arg Ile Ser Ala Glu Gly Gly Glu Gln
                245                 250                 255

Val Glu Arg Val Val Glu Gly Pro Ala Gln Ala Met Ser Arg Gly Thr
                260                 265                 270

Met Ile Val Gly Ala Ala Thr Gly Gly Ile Leu Leu Leu Leu Asp Val
                275                 280                 285

Val Ser Leu Ala Tyr Glu Ser Lys His Leu Leu Glu Gly Ala Lys Ser
                290                 295                 300

Glu Ser Ala Glu Glu Leu Lys Lys Arg Ala Gln Glu Leu Glu Gly Lys
305                 310                 315                 320

Leu Asn Phe Leu Thr Lys Ile His Glu Met Leu Gln Pro Gly Gln Asp
                325                 330                 335

Gln

<210> SEQ ID NO 20
<211> LENGTH: 402
<212> TYPE: PRT
<213> ORGANISM: Homo sapiens

<400> SEQUENCE: 20

Met Gly Leu Gly Gln Gly Trp Gly Trp Glu Ala Ser Cys Phe Ala Cys
1               5                   10                  15

Leu Ile Arg Ser Cys Cys Gln Val Val Thr Phe Thr Phe Pro Phe Gly
                20                  25                  30

Phe Gln Gly Ile Ser Gln Ser Leu Glu Asn Val Ser Gly Tyr Tyr Ala
                35                  40                  45

Asp Ala Arg Leu Glu Val Gly Ser Thr Gln Leu Arg Thr Ala Gly Ser
                50                  55                  60

Cys Ser His Ser Phe Lys Arg Ser Phe Leu Glu Lys Lys Arg Phe Thr
65                  70                  75                  80

Glu Glu Ala Thr Lys Tyr Phe Arg Glu Arg Val Ser Pro Val His Leu
                85                  90                  95

Gln Ile Leu Leu Thr Asn Asn Glu Ala Trp Lys Arg Phe Val Thr Ala
                100                 105                 110

Ala Glu Leu Pro Arg Asp Glu Ala Asp Ala Leu Tyr Glu Ala Leu Lys
                115                 120                 125

Lys Leu Arg Thr Tyr Ala Ala Ile Glu Asp Glu Tyr Val Gln Gln Lys
                130                 135                 140

Asp Glu Gln Phe Arg Glu Trp Phe Leu Lys Glu Phe Pro Gln Val Lys
145                 150                 155                 160

Arg Lys Ile Gln Glu Ser Ile Glu Lys Leu Arg Ala Leu Ala Asn Gly
                165                 170                 175

Ile Glu Glu Val His Arg Gly Cys Thr Ile Ser Asn Val Val Ser Ser
                180                 185                 190

Ser Thr Gly Ala Ala Ser Gly Ile Met Ser Leu Ala Gly Leu Val Leu
                195                 200                 205

Ala Pro Phe Thr Ala Gly Thr Ser Leu Ala Leu Thr Ala Ala Gly Val
                210                 215                 220

Gly Leu Gly Ala Ala Ser Ala Val Thr Gly Ile Thr Thr Ser Ile Val
225                 230                 235                 240

Glu His Ser Tyr Thr Ser Ser Ala Glu Ala Glu Ala Ser Arg Leu Thr
```

```
                    245                 250                 255
Ala Thr Ser Ile Asp Arg Leu Lys Val Phe Lys Glu Val Met Arg Asp
            260                 265                 270

Ile Thr Pro Asn Leu Leu Ser Leu Leu Asn Asn Tyr Tyr Glu Ala Thr
        275                 280                 285

Gln Thr Ile Gly Ser Glu Ile Arg Ala Ile Arg Gln Ala Arg Ala Arg
    290                 295                 300

Ala Arg Leu Pro Val Thr Thr Trp Arg Ile Ser Ala Gly Ser Gly Gly
305                 310                 315                 320

Gln Ala Glu Arg Thr Ile Ala Gly Thr Thr Arg Ala Val Ser Arg Gly
                325                 330                 335

Ala Arg Ile Leu Ser Ala Thr Thr Ser Gly Ile Phe Leu Ala Leu Asp
            340                 345                 350

Val Val Asn Leu Val Tyr Glu Ser Lys His Leu His Glu Gly Ala Lys
        355                 360                 365

Ser Ala Ser Ala Glu Glu Leu Arg Arg Gln Ala Gln Glu Leu Glu Glu
    370                 375                 380

Asn Leu Met Glu Leu Thr Gln Ile Tyr Gln Arg Leu Asn Pro Cys His
385                 390                 395                 400

Thr His

<210> SEQ ID NO 21
<211> LENGTH: 351
<212> TYPE: PRT
<213> ORGANISM: Homo sapiens

<400> SEQUENCE: 21

Met Glu Gly Ala Ala Leu Leu Lys Ile Phe Val Val Cys Ile Trp Val
1               5                   10                  15

Gln Gln Asn His Pro Gly Trp Thr Val Ala Gly Gln Phe Gln Glu Lys
            20                  25                  30

Lys Arg Phe Thr Glu Glu Val Ile Glu Tyr Phe Gln Lys Lys Val Ser
        35                  40                  45

Pro Val His Leu Lys Ile Leu Leu Thr Ser Asp Glu Ala Trp Lys Arg
    50                  55                  60

Phe Val Arg Val Ala Glu Leu Pro Arg Glu Glu Ala Asp Ala Leu Tyr
65                  70                  75                  80

Glu Ala Leu Lys Asn Leu Thr Pro Tyr Val Ala Ile Glu Asp Lys Asp
                85                  90                  95

Met Gln Gln Lys Glu Gln Gln Phe Arg Glu Trp Phe Leu Lys Glu Phe
            100                 105                 110

Pro Gln Ile Arg Trp Lys Ile Gln Glu Ser Ile Glu Arg Leu Arg Val
        115                 120                 125

Ile Ala Asn Glu Ile Glu Lys Val His Arg Gly Cys Val Ile Ala Asn
    130                 135                 140

Val Val Ser Gly Ser Thr Gly Ile Leu Ser Val Ile Gly Val Met Leu
145                 150                 155                 160

Ala Pro Phe Thr Ala Gly Leu Ser Leu Ser Ile Thr Ala Ala Gly Val
                165                 170                 175

Gly Leu Gly Ile Ala Ser Ala Thr Ala Gly Ile Ala Ser Ser Ile Val
            180                 185                 190

Glu Asn Thr Tyr Thr Arg Ser Ala Glu Leu Thr Ala Ser Arg Leu Thr
        195                 200                 205

Ala Thr Ser Thr Asp Gln Leu Glu Ala Leu Arg Asp Ile Leu Arg Asp
```

```
                210                 215                 220
Ile Thr Pro Asn Val Leu Ser Phe Ala Leu Asp Phe Asp Glu Ala Thr
225                 230                 235                 240

Lys Met Ile Ala Asn Asp Val His Thr Leu Arg Arg Ser Lys Ala Thr
                245                 250                 255

Val Gly Arg Pro Leu Ile Ala Trp Arg Tyr Val Pro Ile Asn Val Val
                260                 265                 270

Glu Thr Leu Arg Thr Arg Gly Ala Pro Thr Arg Ile Val Arg Lys Val
                275                 280                 285

Ala Arg Asn Leu Gly Lys Ala Thr Ser Gly Val Leu Val Leu Asp
        290                 295                 300

Val Val Asn Leu Val Gln Asp Ser Leu Asp Leu His Lys Gly Ala Lys
305                 310                 315                 320

Ser Glu Ser Ala Glu Ser Leu Arg Gln Trp Ala Gln Glu Leu Glu Glu
                325                 330                 335

Asn Leu Asn Glu Leu Thr His Ile His Gln Ser Leu Lys Ala Gly
                340                 345                 350

<210> SEQ ID NO 22
<211> LENGTH: 433
<212> TYPE: PRT
<213> ORGANISM: Homo sapiens

<400> SEQUENCE: 22

Met Pro Cys Gly Lys Gln Gly Asn Leu Gln Val Pro Gly Ser Lys Val
1               5                   10                  15

Leu Pro Gly Leu Gly Glu Gly Cys Lys Glu Met Trp Leu Arg Lys Val
                20                  25                  30

Ile Tyr Gly Gly Glu Val Trp Gly Lys Ser Pro Glu Pro Glu Phe Pro
            35                  40                  45

Ser Leu Val Asn Leu Cys Gln Ser Trp Lys Ile Asn Asn Leu Met Ser
        50                  55                  60

Thr Val His Ser Asp Glu Ala Gly Met Leu Ser Tyr Phe Leu Phe Glu
65                  70                  75                  80

Glu Leu Met Arg Cys Asp Lys Asp Ser Met Pro Asp Gly Asn Leu Ser
                85                  90                  95

Glu Glu Glu Lys Leu Phe Leu Ser Tyr Phe Pro Leu His Lys Phe Glu
                100                 105                 110

Leu Glu Gln Asn Ile Lys Glu Leu Asn Thr Leu Ala Asp Gln Val Asp
            115                 120                 125

Thr Thr His Glu Leu Leu Thr Lys Thr Ser Leu Val Ala Ser Ser Ser
        130                 135                 140

Gly Ala Val Ser Gly Val Met Asn Ile Leu Gly Leu Ala Leu Ala Pro
145                 150                 155                 160

Val Thr Ala Gly Gly Ser Leu Met Leu Ser Ala Thr Gly Thr Gly Leu
                165                 170                 175

Gly Ala Ala Ala Ala Ile Thr Asn Ile Val Thr Asn Val Leu Glu Asn
                180                 185                 190

Arg Ser Asn Ser Ala Ala Arg Asp Lys Ala Ser Arg Leu Gly Pro Leu
            195                 200                 205

Thr Thr Ser His Glu Ala Phe Gly Gly Ile Asn Trp Ser Glu Ile Glu
        210                 215                 220

Ala Ala Gly Phe Cys Val Asn Lys Cys Val Lys Ala Ile Gln Gly Ile
225                 230                 235                 240
```

```
Lys Asp Leu His Ala Tyr Gln Met Ala Lys Ser Asn Ser Gly Phe Met
                245                 250                 255
Ala Met Val Lys Asn Phe Val Ala Lys Arg His Ile Pro Phe Trp Thr
            260                 265                 270
Ala Arg Gly Val Gln Arg Ala Phe Glu Gly Thr Thr Leu Ala Met Thr
        275                 280                 285
Asn Gly Ala Trp Val Met Gly Ala Ala Gly Ala Gly Phe Leu Leu Met
    290                 295                 300
Lys Asp Met Ser Ser Phe Leu Gln Ser Trp Lys His Leu Glu Asp Gly
305                 310                 315                 320
Ala Arg Thr Glu Thr Ala Glu Glu Leu Arg Ala Leu Ala Lys Lys Leu
                325                 330                 335
Glu Gln Glu Leu Asp Arg Leu Thr Gln His His Arg His Leu Pro Gln
            340                 345                 350
Lys Ala Ser Gln Thr Cys Ser Ser Ser Arg Gly Arg Ala Val Arg Gly
        355                 360                 365
Ser Arg Val Val Lys Pro Glu Gly Ser Arg Ser Pro Leu Pro Trp Pro
    370                 375                 380
Val Val Glu His Gln Pro Arg Leu Gly Pro Gly Val Ala Leu Arg Thr
385                 390                 395                 400
Pro Lys Arg Thr Val Ser Ala Pro Arg Met Leu Gly His Gln Pro Ala
                405                 410                 415
Pro Pro Ala Pro Ala Arg Lys Gly Arg Gln Ala Pro Gly Arg His Arg
            420                 425                 430
Gln

<210> SEQ ID NO 23
<211> LENGTH: 343
<212> TYPE: PRT
<213> ORGANISM: Homo sapiens

<400> SEQUENCE: 23

Met Asp Asn Gln Ala Glu Arg Glu Ser Glu Ala Gly Val Gly Leu Gln
1               5                   10                  15
Arg Asp Glu Asp Asp Ala Pro Leu Cys Glu Asp Val Glu Leu Gln Asp
            20                  25                  30
Gly Asp Leu Ser Pro Glu Glu Lys Ile Phe Leu Arg Glu Phe Pro Arg
        35                  40                  45
Leu Lys Glu Asp Leu Lys Gly Asn Ile Asp Lys Leu Arg Ala Leu Ala
    50                  55                  60
Asp Asp Ile Asp Lys Thr His Lys Lys Phe Thr Lys Ala Asn Met Val
65                  70                  75                  80
Ala Thr Ser Thr Ala Val Ile Ser Gly Val Met Ser Leu Leu Gly Leu
                85                  90                  95
Ala Leu Ala Pro Ala Thr Gly Gly Ser Leu Leu Leu Ser Thr Ala
            100                 105                 110
Gly Gln Gly Leu Ala Thr Ala Ala Gly Val Thr Ser Ile Val Ser Gly
        115                 120                 125
Thr Leu Glu Arg Ser Lys Asn Lys Glu Ala Gln Ala Arg Ala Glu Asp
    130                 135                 140
Ile Leu Pro Thr Tyr Asp Gln Glu Asp Arg Glu Asp Glu Glu Glu Lys
145                 150                 155                 160
Ala Asp Tyr Val Thr Ala Ala Gly Lys Ile Ile Tyr Asn Leu Arg Asn
                165                 170                 175
```

Thr Leu Lys Tyr Ala Lys Asn Val Arg Ala Phe Trp Lys Leu Arg
            180                 185                 190

Ala Asn Pro Arg Leu Ala Asn Ala Thr Lys Arg Leu Leu Thr Thr Gly
            195                 200                 205

Gln Val Ser Ser Arg Ser Arg Val Gln Val Gln Lys Ala Phe Ala Gly
210                 215                 220

Thr Thr Leu Ala Met Thr Lys Asn Ala Arg Val Leu Gly Gly Val Met
225                 230                 235                 240

Ser Ala Phe Ser Leu Gly Tyr Asp Leu Ala Thr Leu Ser Lys Glu Trp
                245                 250                 255

Lys His Leu Lys Glu Gly Ala Arg Thr Lys Phe Ala Glu Glu Leu Arg
            260                 265                 270

Ala Lys Ala Leu Glu Leu Glu Arg Lys Leu Thr Glu Leu Thr Gln Leu
        275                 280                 285

Tyr Lys Ser Leu Gln Gln Lys Val Arg Ser Arg Ala Arg Gly Val Gly
    290                 295                 300

Lys Asp Leu Thr Gly Thr Cys Glu Thr Glu Ala Tyr Trp Lys Glu Leu
305                 310                 315                 320

Arg Glu His Val Trp Met Trp Leu Trp Leu Cys Val Cys Leu Cys Val
                325                 330                 335

Cys Val Tyr Val Gln Phe Thr
                340

<210> SEQ ID NO 24
<211> LENGTH: 188
<212> TYPE: PRT
<213> ORGANISM: Homo sapiens

<400> SEQUENCE: 24

Met Phe His Gln Ile Trp Ala Ala Leu Leu Tyr Phe Tyr Gly Ile Ile
1               5                   10                  15

Leu Asn Ser Ile Tyr Gln Cys Pro Glu His Ser Gln Leu Thr Thr Leu
            20                  25                  30

Gly Val Asp Gly Lys Glu Phe Pro Glu Val His Leu Gly Gln Trp Tyr
        35                  40                  45

Phe Ile Ala Gly Ala Ala Pro Thr Lys Glu Glu Leu Ala Thr Phe Asp
    50                  55                  60

Pro Val Asp Asn Ile Val Phe Asn Met Ala Ala Gly Ser Ala Pro Met
65                  70                  75                  80

Gln Leu His Leu Arg Ala Thr Ile Arg Met Lys Asp Gly Leu Cys Val
                85                  90                  95

Pro Arg Lys Trp Ile Tyr His Leu Thr Glu Gly Ser Thr Asp Leu Arg
            100                 105                 110

Thr Glu Gly Arg Pro Asp Met Lys Thr Glu Leu Phe Ser Ser Ser Cys
        115                 120                 125

Pro Gly Gly Ile Met Leu Asn Glu Thr Gly Gln Gly Tyr Gln Arg Phe
    130                 135                 140

Leu Leu Tyr Asn Arg Ser Pro His Pro Glu Lys Cys Val Glu Glu
145                 150                 155                 160

Phe Lys Ser Leu Thr Ser Cys Leu Asp Ser Lys Ala Phe Leu Leu Thr
                165                 170                 175

Pro Arg Asn Gln Glu Ala Cys Glu Leu Ser Asn Asn
            180                 185

<210> SEQ ID NO 25

<211> LENGTH: 198
<212> TYPE: PRT
<213> ORGANISM: Homo sapiens

<400> SEQUENCE: 25

```
Met Phe Lys Val Ile Gln Arg Ser Val Gly Pro Ala Ser Leu Ser Leu
1               5                   10                  15

Leu Thr Phe Lys Val Tyr Ala Ala Pro Lys Lys Asp Ser Pro Pro Lys
            20                  25                  30

Asn Ser Val Lys Val Asp Glu Leu Ser Leu Tyr Ser Val Pro Glu Gly
        35                  40                  45

Gln Ser Lys Tyr Val Glu Glu Ala Arg Ser Gln Leu Glu Glu Ser Ile
    50                  55                  60

Ser Gln Leu Arg His Tyr Cys Glu Pro Tyr Thr Thr Trp Cys Gln Glu
65                  70                  75                  80

Thr Tyr Ser Gln Thr Lys Pro Lys Met Gln Ser Leu Val Gln Trp Gly
                85                  90                  95

Leu Asp Ser Tyr Asp Tyr Leu Gln Asn Ala Pro Pro Gly Phe Phe Pro
            100                 105                 110

Arg Leu Gly Val Ile Gly Phe Ala Gly Leu Ile Gly Leu Leu Leu Ala
        115                 120                 125

Arg Gly Ser Lys Ile Lys Lys Leu Val Tyr Pro Pro Gly Phe Met Gly
    130                 135                 140

Leu Ala Ala Ser Leu Tyr Tyr Pro Gln Gln Ala Ile Val Phe Ala Gln
145                 150                 155                 160

Val Ser Gly Glu Arg Leu Tyr Asp Trp Gly Leu Arg Gly Tyr Ile Val
                165                 170                 175

Ile Glu Asp Leu Trp Lys Glu Asn Phe Gln Lys Pro Gly Asn Val Lys
            180                 185                 190

Asn Ser Pro Gly Thr Lys
        195
```

<210> SEQ ID NO 26
<211> LENGTH: 268
<212> TYPE: PRT
<213> ORGANISM: Homo sapiens

<400> SEQUENCE: 26

```
Met Ala Ala Ile Arg Met Gly Lys Leu Thr Thr Met Pro Ala Gly Leu
1               5                   10                  15

Ile Tyr Ala Ser Val Ser Val His Ala Ala Lys Gln Glu Glu Ser Lys
            20                  25                  30

Lys Gln Leu Val Lys Pro Glu Gln Leu Pro Ile Tyr Thr Ala Pro Pro
        35                  40                  45

Leu Gln Ser Lys Tyr Val Glu Glu Pro Gly His Leu Gln Met Gly
    50                  55                  60

Phe Ala Ser Ile Arg Thr Ala Thr Gly Cys Tyr Ile Gly Trp Cys Lys
65                  70                  75                  80

Gly Val Tyr Val Phe Val Lys Asn Gly Ile Met Asp Thr Val Gln Phe
                85                  90                  95

Gly Lys Asp Ala Tyr Val Tyr Leu Lys Asn Pro Pro Arg Asp Phe Leu
            100                 105                 110

Pro Lys Met Gly Val Ile Thr Val Ser Gly Leu Ala Gly Leu Val Ser
        115                 120                 125

Ala Arg Lys Gly Ser Lys Phe Lys Ile Thr Tyr Pro Leu Gly Leu
    130                 135                 140
```

```
Ala Thr Leu Gly Ala Thr Val Cys Tyr Pro Val Gln Ser Val Ile Ile
145                 150                 155                 160

Ala Lys Val Thr Ala Lys Lys Val Tyr Ala Thr Ser Gln Gln Ile Phe
                165                 170                 175

Gly Ala Val Lys Ser Leu Trp Thr Lys Ser Ser Lys Glu Glu Ser Leu
            180                 185                 190

Pro Lys Pro Lys Glu Lys Thr Lys Leu Gly Ser Ser Glu Ile Glu
            195                 200                 205

Val Pro Ala Lys Thr Thr His Val Leu Lys His Ser Val Pro Leu Pro
210                 215                 220

Thr Glu Leu Ser Ser Glu Ala Lys Thr Lys Ser Glu Ser Thr Ser Gly
225                 230                 235                 240

Ala Thr Gln Phe Met Pro Asp Pro Lys Leu Met Asp His Gly Gln Ser
                245                 250                 255

His Pro Glu Asp Ile Asp Met Tyr Ser Thr Arg Ser
            260                 265
```

<210> SEQ ID NO 27
<211> LENGTH: 449
<212> TYPE: PRT
<213> ORGANISM: Homo sapiens

<400> SEQUENCE: 27

```
Met Met Lys Thr Leu Leu Leu Phe Val Gly Leu Leu Leu Thr Trp Glu
1               5                   10                  15

Ser Gly Gln Val Leu Gly Asp Gln Thr Val Ser Asp Asn Glu Leu Gln
            20                  25                  30

Glu Met Ser Asn Gln Gly Ser Lys Tyr Val Asn Lys Glu Ile Gln Asn
        35                  40                  45

Ala Val Asn Gly Val Lys Gln Ile Lys Thr Leu Ile Glu Lys Thr Asn
50                  55                  60

Glu Glu Arg Lys Thr Leu Leu Ser Asn Leu Glu Glu Ala Lys Lys Lys
65                  70                  75                  80

Lys Glu Asp Ala Leu Asn Glu Thr Arg Glu Ser Glu Thr Lys Leu Lys
                85                  90                  95

Glu Leu Pro Gly Val Cys Asn Glu Thr Met Met Ala Leu Trp Glu Glu
            100                 105                 110

Cys Lys Pro Cys Leu Lys Gln Thr Cys Met Lys Phe Tyr Ala Arg Val
        115                 120                 125

Cys Arg Ser Gly Ser Gly Leu Val Gly Arg Gln Leu Glu Glu Phe Leu
130                 135                 140

Asn Gln Ser Ser Pro Phe Tyr Phe Trp Met Asn Gly Asp Arg Ile Asp
145                 150                 155                 160

Ser Leu Leu Glu Asn Asp Arg Gln Gln Thr His Met Leu Asp Val Met
                165                 170                 175

Gln Asp His Phe Ser Arg Ala Ser Ser Ile Ile Asp Glu Leu Phe Gln
            180                 185                 190

Asp Arg Phe Phe Thr Arg Glu Pro Gln Asp Thr Tyr His Tyr Leu Pro
        195                 200                 205

Phe Ser Leu Pro His Arg Arg Pro His Phe Phe Pro Lys Ser Arg
210                 215                 220

Ile Val Arg Ser Leu Met Pro Phe Ser Pro Tyr Glu Pro Leu Asn Phe
225                 230                 235                 240

His Ala Met Phe Gln Pro Phe Leu Glu Met Ile His Glu Ala Gln Gln
```

```
                    245                 250                 255
Ala Met Asp Ile His Phe His Ser Pro Ala Phe Gln His Pro Pro Thr
            260                 265                 270

Glu Phe Ile Arg Glu Gly Asp Asp Arg Thr Val Cys Arg Glu Ile
            275                 280                 285

Arg His Asn Ser Thr Gly Cys Leu Arg Met Lys Asp Gln Cys Asp Lys
            290                 295                 300

Cys Arg Glu Ile Leu Ser Val Asp Cys Ser Thr Asn Asn Pro Ser Gln
305                 310                 315                 320

Ala Lys Leu Arg Arg Glu Leu Asp Glu Ser Leu Gln Val Ala Glu Arg
                325                 330                 335

Leu Thr Arg Lys Tyr Asn Glu Leu Leu Lys Ser Tyr Gln Trp Lys Met
                340                 345                 350

Leu Asn Thr Ser Ser Leu Leu Glu Gln Leu Asn Glu Gln Phe Asn Trp
            355                 360                 365

Val Ser Arg Leu Ala Asn Leu Thr Gln Gly Glu Asp Gln Tyr Tyr Leu
            370                 375                 380

Arg Val Thr Thr Val Ala Ser His Thr Ser Asp Ser Asp Val Pro Ser
385                 390                 395                 400

Gly Val Thr Glu Val Val Lys Leu Phe Asp Ser Asp Pro Ile Thr
                405                 410                 415

Val Thr Val Pro Val Glu Val Ser Arg Lys Asn Pro Lys Phe Met Glu
            420                 425                 430

Thr Val Ala Glu Lys Ala Leu Gln Glu Tyr Arg Lys Lys His Arg Glu
                435                 440                 445

Glu

<210> SEQ ID NO 28
<211> LENGTH: 267
<212> TYPE: PRT
<213> ORGANISM: Homo sapiens

<400> SEQUENCE: 28

Met Lys Ala Ala Val Leu Thr Leu Ala Val Leu Phe Leu Thr Gly Ser
1               5                   10                  15

Gln Ala Arg His Phe Trp Gln Gln Asp Glu Pro Pro Gln Ser Pro Trp
            20                  25                  30

Asp Arg Val Lys Asp Leu Ala Thr Val Tyr Val Asp Val Leu Lys Asp
        35                  40                  45

Ser Gly Arg Asp Tyr Val Ser Gln Phe Glu Gly Ser Ala Leu Gly Lys
    50                  55                  60

Gln Leu Asn Leu Lys Leu Leu Asp Asn Trp Asp Ser Val Thr Ser Thr
65                  70                  75                  80

Phe Ser Lys Leu Arg Glu Gln Leu Gly Pro Val Thr Gln Glu Phe Trp
                85                  90                  95

Asp Asn Leu Glu Lys Glu Thr Glu Gly Leu Arg Gln Glu Met Ser Lys
            100                 105                 110

Asp Leu Glu Glu Val Lys Ala Lys Val Gln Pro Tyr Leu Asp Asp Phe
        115                 120                 125

Gln Lys Lys Trp Gln Glu Glu Met Glu Leu Tyr Arg Gln Lys Val Glu
    130                 135                 140

Pro Leu Arg Ala Glu Leu Gln Glu Gly Ala Arg Gln Lys Leu His Glu
145                 150                 155                 160

Leu Gln Glu Lys Leu Ser Pro Leu Gly Glu Glu Met Arg Asp Arg Ala
```

```
                165                 170                 175
Arg Ala His Val Asp Ala Leu Arg Thr His Leu Ala Pro Tyr Ser Asp
            180                 185                 190

Glu Leu Arg Gln Arg Leu Ala Ala Arg Leu Glu Ala Leu Lys Glu Asn
        195                 200                 205

Gly Gly Ala Arg Leu Ala Glu Tyr His Ala Lys Ala Thr Glu His Leu
    210                 215                 220

Ser Thr Leu Ser Glu Lys Ala Lys Pro Ala Leu Glu Asp Leu Arg Gln
225                 230                 235                 240

Gly Leu Leu Pro Val Leu Glu Ser Phe Lys Val Ser Phe Leu Ser Ala
                245                 250                 255

Leu Glu Glu Tyr Thr Lys Lys Leu Asn Thr Gln
            260                 265

<210> SEQ ID NO 29
<211> LENGTH: 267
<212> TYPE: PRT
<213> ORGANISM: Homo sapiens

<400> SEQUENCE: 29

Met Lys Ala Ala Val Leu Thr Leu Ala Val Leu Phe Leu Thr Gly Ser
1               5                   10                  15

Gln Ala Arg His Phe Trp Gln Gln Asp Glu Pro Pro Gln Ser Pro Trp
            20                  25                  30

Asp Arg Val Lys Asp Leu Ala Thr Val Tyr Val Asp Val Leu Lys Asp
        35                  40                  45

Ser Gly Arg Asp Tyr Val Ser Gln Phe Glu Gly Ser Ala Leu Gly Lys
    50                  55                  60

Gln Leu Asn Leu Lys Leu Leu Asp Asn Trp Asp Ser Val Thr Ser Thr
65                  70                  75                  80

Phe Ser Lys Leu Arg Glu Gln Leu Gly Pro Val Thr Gln Glu Phe Trp
                85                  90                  95

Asp Asn Leu Glu Lys Glu Thr Glu Gly Leu Arg Gln Glu Met Ser Lys
            100                 105                 110

Asp Leu Glu Glu Val Lys Ala Lys Val Gln Pro Tyr Leu Asp Asp Phe
        115                 120                 125

Gln Lys Lys Trp Gln Glu Glu Met Glu Leu Tyr Arg Gln Lys Val Glu
    130                 135                 140

Pro Leu Arg Ala Glu Leu Gln Glu Gly Ala Arg Gln Lys Leu His Glu
145                 150                 155                 160

Leu Gln Glu Lys Leu Ser Pro Leu Gly Glu Glu Met Arg Asp Arg Ala
                165                 170                 175

Arg Ala His Val Asp Ala Leu Arg Thr His Leu Ala Pro Tyr Ser Asp
            180                 185                 190

Glu Leu Arg Gln Arg Leu Ala Ala Arg Leu Glu Ala Leu Lys Glu Asn
        195                 200                 205

Gly Gly Ala Arg Leu Ala Glu Tyr His Ala Lys Ala Thr Glu His Leu
    210                 215                 220

Ser Thr Leu Ser Glu Lys Ala Lys Pro Ala Leu Glu Asp Leu Arg Gln
225                 230                 235                 240

Gly Leu Leu Pro Val Leu Glu Ser Phe Lys Val Ser Phe Leu Ser Ala
                245                 250                 255

Leu Glu Glu Tyr Thr Lys Lys Leu Asn Thr Gln
            260                 265
```

```
<210> SEQ ID NO 30
<211> LENGTH: 267
<212> TYPE: PRT
<213> ORGANISM: Homo sapiens

<400> SEQUENCE: 30

Met Lys Ala Thr Val Leu Thr Leu Ala Val Leu Phe Leu Thr Gly Ser
1               5                   10                  15

Gln Ala Arg His Phe Trp Gln Gln Asp Glu Pro Pro Gln Thr Pro Trp
            20                  25                  30

Asp Arg Val Lys Asp Leu Val Thr Val Tyr Val Glu Ala Leu Lys Asp
        35                  40                  45

Ser Gly Lys Asp Tyr Val Ser Gln Phe Glu Gly Ser Ala Leu Gly Lys
    50                  55                  60

Gln Leu Asn Leu Lys Leu Leu Asp Asn Trp Asp Ser Val Thr Ser Thr
65                  70                  75                  80

Val Ser Lys Leu Arg Glu Gln Leu Gly Pro Val Thr Gln Glu Phe Trp
                85                  90                  95

Asp Asn Leu Glu Lys Glu Thr Glu Gly Leu Arg Gln Glu Met Ser Lys
            100                 105                 110

Asp Leu Glu Glu Val Lys Ala Lys Val Gln Pro Tyr Leu Asp Asp Phe
        115                 120                 125

Gln Lys Lys Trp Gln Glu Glu Met Glu Leu Tyr Arg Gln Lys Val Glu
    130                 135                 140

Pro Leu Arg Ala Glu Leu His Glu Gly Thr Arg Gln Lys Leu His Glu
145                 150                 155                 160

Leu His Glu Lys Leu Ser Pro Leu Gly Glu Glu Val Arg Asp Arg Ala
                165                 170                 175

Arg Ala His Val Asp Ala Leu Arg Thr His Leu Ala Pro Tyr Ser Asp
            180                 185                 190

Glu Leu Arg Gln Arg Leu Ala Ala Arg Leu Glu Ala Leu Lys Glu Asn
        195                 200                 205

Gly Gly Ala Arg Leu Ala Glu Tyr His Ala Lys Ala Ser Glu His Leu
    210                 215                 220

Ser Thr Leu Ser Glu Lys Ala Lys Pro Ala Leu Glu Asp Leu Arg Gln
225                 230                 235                 240

Gly Leu Leu Pro Val Leu Glu Ser Phe Lys Val Ser Phe Leu Ser Ala
                245                 250                 255

Leu Glu Glu Tyr Thr Lys Lys Leu Ser Thr Gln
            260                 265

<210> SEQ ID NO 31
<211> LENGTH: 265
<212> TYPE: PRT
<213> ORGANISM: Homo sapiens

<400> SEQUENCE: 31

Met Lys Ala Val Val Leu Thr Leu Ala Val Leu Phe Leu Thr Gly Ser
1               5                   10                  15

Gln Ala Arg His Phe Trp Gln Gln Asp Asp Pro Gln Ser Ser Trp Asp
            20                  25                  30

Arg Val Lys Asp Phe Ala Thr Val Tyr Val Glu Ala Ile Lys Asp Ser
        35                  40                  45

Gly Arg Asp Tyr Val Ala Gln Phe Glu Ala Ser Ala Leu Gly Lys Gln
    50                  55                  60
```

```
Leu Asn Leu Lys Leu Leu Asp Asn Trp Asp Thr Leu Ala Ser Thr Leu
 65                  70                  75                  80

Ser Lys Val Arg Glu Gln Leu Gly Pro Val Thr Gln Glu Phe Trp Asp
                 85                  90                  95

Asn Leu Glu Lys Glu Thr Ala Ser Leu Arg Gln Glu Met His Lys Asp
            100                 105                 110

Leu Glu Glu Val Lys Gln Lys Val Gln Pro Tyr Leu Asp Glu Phe Gln
        115                 120                 125

Lys Lys Trp His Glu Val Glu Ile Tyr Arg Gln Lys Val Ala Pro
    130                 135                 140

Leu Gly Glu Glu Phe Arg Glu Gly Ala Arg Gln Lys Val Gln Glu Leu
145                 150                 155                 160

Gln Asp Lys Leu Ser Pro Leu Ala Gln Glu Leu Arg Asp Arg Ala Arg
                165                 170                 175

Ala His Val Glu Thr Leu Arg Gln Gln Leu Ala Pro Tyr Ser Asp Asp
            180                 185                 190

Leu Arg Gln Arg Leu Thr Ala Arg Leu Glu Ala Leu Lys Glu Gly Gly
        195                 200                 205

Gly Ser Leu Ala Glu Tyr His Ala Lys Ala Ser Glu Gln Leu Lys Ala
    210                 215                 220

Leu Gly Glu Lys Ala Lys Pro Val Leu Glu Asp Leu Arg Gln Gly Leu
225                 230                 235                 240

Leu Pro Val Leu Glu Ser Leu Lys Val Ser Ile Leu Ala Ala Ile Asp
                245                 250                 255

Glu Ala Ser Lys Lys Leu Asn Ala Gln
                260                 265

<210> SEQ ID NO 32
<211> LENGTH: 264
<212> TYPE: PRT
<213> ORGANISM: Homo sapiens

<400> SEQUENCE: 32

Met Lys Ala Trp Leu Thr Leu Ala Val Leu Phe Leu Thr Gly Ser Gln
 1                5                  10                  15

Ala Arg His Phe Trp Gln Gln Asp Pro Gln Ser Pro Trp Asp Arg
                 20                  25                  30

Val Lys Asp Phe Ala Thr Val Tyr Val Asp Ala Ile Lys Asp Ser Gly
             35                  40                  45

Arg Asp Tyr Val Ala Gln Phe Glu Ala Ser Ala Leu Gly Lys His Leu
     50                  55                  60

Asn Leu Lys Leu Leu Asp Asn Trp Asp Ser Leu Gly Ser Thr Phe Thr
 65                  70                  75                  80

Lys Val Arg Glu Gln Leu Gly Pro Val Thr Gln Glu Phe Trp Asp Asn
                 85                  90                  95

Leu Glu Lys Glu Thr Glu Ala Leu Arg Gln Glu Met Ser Lys Asp Leu
            100                 105                 110

Glu Glu Val Lys Lys Val Gln Pro Tyr Leu Asp Asp Phe Gln Asn
        115                 120                 125

Lys Trp Gln Glu Glu Met Glu Thr Tyr Arg Gln Lys Met Ala Pro Leu
    130                 135                 140

Gly Ala Glu Phe Arg Glu Gly Ala Arg Gln Lys Val Gln Glu Leu Gln
145                 150                 155                 160

Glu Lys Leu Ser Pro Leu Ala Glu Glu Leu Arg Asp Arg Leu Arg Ala
                165                 170                 175
```

His Val Glu Ala Leu Arg Gln His Val Ala Pro Tyr Ser Asp Asp Leu
            180                 185                 190

Arg Gln Arg Met Ala Ala Arg Phe Glu Ala Leu Lys Glu Gly Gly Gly
        195                 200                 205

Ser Leu Ala Glu Tyr Gln Ala Lys Ala Gln Glu Gln Leu Lys Ala Leu
    210                 215                 220

Gly Glu Lys Ala Lys Pro Ala Leu Glu Asp Leu Arg Gln Gly Leu Leu
225                 230                 235                 240

Pro Val Leu Glu Asn Leu Lys Val Ser Ile Leu Ala Ala Ile Asp Glu
                245                 250                 255

Ala Ser Lys Lys Leu Asn Ala Gln
            260

<210> SEQ ID NO 33
<211> LENGTH: 266
<212> TYPE: PRT
<213> ORGANISM: Homo sapiens

<400> SEQUENCE: 33

Met Lys Ala Ala Leu Leu Thr Leu Ala Val Leu Phe Leu Thr Gly Ser
1               5                   10                  15

Gln Ala Arg His Phe Trp Gln Gln Asp Glu Pro Gln Ser Pro Trp Asp
            20                  25                  30

Arg Val Lys Asp Leu Ala Thr Val Tyr Val Asp Ala Val Lys Asp Ser
        35                  40                  45

Gly Arg Asp Tyr Val Ala Gln Phe Glu Ala Ser Ala Leu Gly Lys Gln
    50                  55                  60

Leu Asn Leu Lys Leu Leu Asp Asn Trp Asp Ser Leu Ser Ser Thr Val
65                  70                  75                  80

Thr Lys Leu Arg Glu Gln Ile Gly Pro Val Thr Gln Glu Phe Trp Asp
                85                  90                  95

Asn Leu Glu Lys Glu Thr Glu Val Leu Arg Gln Glu Met Ser Lys Asp
            100                 105                 110

Leu Glu Glu Val Lys Gln Lys Val Gln Pro Tyr Leu Asp Asp Phe Gln
        115                 120                 125

Lys Lys Trp Gln Glu Glu Val Glu Leu Tyr Arg Gln Lys Val Ala Pro
    130                 135                 140

Leu Gly Ser Glu Leu Arg Glu Gly Ala Arg Gln Lys Leu Gln Glu Leu
145                 150                 155                 160

Gln Glu Lys Leu Ser Pro Leu Ala Glu Glu Leu Arg Asp Arg Ala Arg
                165                 170                 175

Thr His Val Asp Ala Leu Arg Ala Gln Leu Ala Pro Tyr Ser Asp Asp
            180                 185                 190

Leu Arg Glu Arg Leu Ala Ala Arg Leu Glu Ala Leu Lys Glu Gly Gly
        195                 200                 205

Gly Ala Ser Leu Ala Glu Tyr His Ala Arg Ala Ser Glu Gln Leu Ser
    210                 215                 220

Ala Leu Gly Glu Lys Ala Arg Pro Ala Leu Glu Asp Leu Arg Gln Gly
225                 230                 235                 240

Leu Leu Pro Val Leu Glu Ser Phe Lys Val Ser Leu Leu Ala Ala Ile
                245                 250                 255

Asp Glu Ala Thr Lys Lys Leu Asn Ala Gln
            260                 265

```
<210> SEQ ID NO 34
<211> LENGTH: 206
<212> TYPE: PRT
<213> ORGANISM: Homo sapiens

<400> SEQUENCE: 34

Met Lys Ala Val Val Leu Thr Leu Ala Val Leu Phe Leu Thr Gly Ser
1               5                   10                  15

Gln Ala Arg His Phe Trp Gln Arg Asp Glu Pro Arg Ser Ser Trp Asp
            20                  25                  30

Lys Ile Lys Asp Phe Ala Thr Val Tyr Val Asp Thr Val Lys Asp Ser
        35                  40                  45

Gly Arg Glu Tyr Val Ala Gln Phe Glu Ala Ser Ala Phe Gly Lys Gln
    50                  55                  60

Leu Asn Leu Lys Leu Leu Asp Asn Trp Asp Ser Leu Ser Ser Thr Val
65                  70                  75                  80

Ser Lys Leu Gln Glu Gln Leu Gly Pro Val Thr Gln Glu Phe Trp Asp
                85                  90                  95

Asn Leu Glu Lys Glu Thr Glu Gly Leu Arg Glu Met Asn Lys Asp
            100                 105                 110

Leu Gln Glu Val Arg Gln Lys Val Gln Pro Tyr Leu Asp Glu Phe Gln
        115                 120                 125

Lys Lys Trp Gln Glu Glu Val Glu Arg Tyr Arg Gln Lys Val Glu Pro
    130                 135                 140

Leu Gly Ala Glu Leu Arg Glu Ser Ala Arg Gln Lys Leu Thr Glu Leu
145                 150                 155                 160

Gln Glu Lys Leu Ser Pro Leu Ala Glu Glu Leu Arg Asp Ser Ala Arg
                165                 170                 175

Thr His Val Gly Leu Leu Pro Val Leu Glu Ser Phe Lys Ala Ser Val
            180                 185                 190

Gln Asn Val Leu Asp Glu Ala Thr Lys Lys Leu Asn Thr Gln
        195                 200                 205

<210> SEQ ID NO 35
<211> LENGTH: 265
<212> TYPE: PRT
<213> ORGANISM: Homo sapiens

<400> SEQUENCE: 35

Met Lys Ala Val Val Leu Thr Leu Ala Val Leu Phe Leu Thr Gly Ser
1               5                   10                  15

Gln Ala Arg His Phe Trp Gln Gln Asp Glu Pro Gln Ser Ser Trp Asp
            20                  25                  30

Arg Val Arg Asp Leu Ala Asn Val Tyr Val Asp Ala Val Lys Glu Ser
        35                  40                  45

Gly Arg Glu Tyr Val Ser Gln Leu Glu Ala Ser Ala Leu Gly Lys Gln
    50                  55                  60

Leu Asn Leu Lys Leu Val Asp Asn Trp Asp Thr Leu Gly Ser Thr Phe
65                  70                  75                  80

Gln Lys Val His Glu His Leu Gly Pro Val Ala Gln Glu Phe Trp Glu
                85                  90                  95

Lys Leu Glu Lys Glu Thr Glu Glu Leu Arg Arg Glu Ile Asn Lys Asp
            100                 105                 110

Leu Glu Asp Val Arg Gln Lys Thr Gln Pro Phe Leu Asp Glu Ile Gln
        115                 120                 125

Lys Lys Trp Gln Glu Asp Leu Glu Arg Tyr Arg Gln Lys Val Glu Pro
```

```
                    130                 135                 140
Leu Ser Ala Gln Leu Arg Glu Gly Ala Arg Gln Lys Leu Met Glu Leu
145                 150                 155                 160

Gln Glu Gln Val Thr Pro Leu Gly Asp Leu Arg Asp Ser Val Arg
                165                 170                 175

Ala Tyr Ala Asp Thr Leu Arg Thr Gln Leu Ala Pro Tyr Ser Glu Gln
                180                 185                 190

Met Arg Lys Thr Leu Gly Ala Arg Leu Glu Ala Ile Lys Glu Gly Gly
                195                 200                 205

Ser Ala Ser Leu Ala Glu Tyr His Ala Lys Ala Ser Glu Gln Leu Ser
                210                 215                 220

Ala Leu Gly Glu Lys Ala Lys Pro Val Leu Glu Asp Ile His Gln Gly
225                 230                 235                 240

Leu Met Pro Met Trp Glu Ser Phe Lys Thr Gly Val Leu Asn Val Ile
                245                 250                 255

Asp Glu Ala Ala Lys Lys Leu Thr Ala
                260                 265

<210> SEQ ID NO 36
<211> LENGTH: 264
<212> TYPE: PRT
<213> ORGANISM: Homo sapiens

<400> SEQUENCE: 36

Met Lys Ala Val Val Leu Ala Val Ala Leu Val Phe Leu Thr Gly Ser
1               5                   10                  15

Gln Ala Trp His Val Trp Gln Gln Asp Glu Pro Gln Ser Gln Trp Asp
                20                  25                  30

Lys Val Lys Asp Phe Ala Asn Val Tyr Val Asp Ala Val Lys Asp Ser
                35                  40                  45

Gly Arg Asp Tyr Val Ser Gln Phe Glu Ser Ser Ser Leu Gly Gln Gln
                50                  55                  60

Leu Asn Leu Asn Leu Leu Glu Asn Trp Asp Thr Leu Gly Ser Thr Val
65                  70                  75                  80

Ser Gln Leu Gln Glu Arg Leu Gly Pro Leu Thr Arg Asp Phe Trp Asp
                85                  90                  95

Asn Leu Glu Lys Glu Thr Asp Trp Val Arg Gln Glu Met Asn Lys Asp
                100                 105                 110

Leu Glu Glu Val Lys Gln Lys Val Gln Pro Tyr Leu Asp Glu Phe Gln
                115                 120                 125

Lys Lys Trp Lys Glu Asp Val Glu Leu Tyr Arg Gln Lys Val Ala Pro
                130                 135                 140

Leu Gly Ala Glu Leu Gln Glu Ser Ala Arg Gln Lys Leu Gln Glu Leu
145                 150                 155                 160

Gln Gly Arg Leu Ser Pro Val Ala Glu Glu Phe Arg Asp Arg Met Arg
                165                 170                 175

Thr His Val Asp Ser Leu Arg Thr Gln Leu Ala Pro His Ser Glu Gln
                180                 185                 190

Met Arg Glu Ser Leu Ala Gln Arg Leu Ala Glu Leu Lys Ser Asn Pro
                195                 200                 205

Thr Leu Asn Glu Tyr His Thr Arg Ala Lys Thr His Leu Lys Thr Leu
                210                 215                 220

Gly Glu Lys Ala Arg Pro Ala Leu Glu Asp Leu Arg His Ser Leu Met
225                 230                 235                 240
```

```
Pro Met Leu Glu Thr Leu Lys Thr Lys Ala Gln Ser Val Ile Asp Lys
                245                 250                 255

Ala Ser Glu Thr Leu Thr Ala Gln
            260

<210> SEQ ID NO 37
<211> LENGTH: 259
<212> TYPE: PRT
<213> ORGANISM: Homo sapiens

<400> SEQUENCE: 37

Met Lys Ala Ala Val Leu Ala Val Ala Leu Val Phe Leu Thr Gly Cys
1               5                   10                  15

Gln Ala Trp Glu Phe Trp Gln Gln Asp Glu Pro Gln Ser Gln Trp Asp
            20                  25                  30

Arg Val Lys Asp Phe Ala Thr Val Tyr Val Asp Ala Val Lys Asp Ser
        35                  40                  45

Gly Arg Asp Tyr Val Ser Gln Phe Glu Ser Ser Thr Leu Gly Lys Gln
    50                  55                  60

Leu Asn Leu Asn Leu Leu Asp Asn Trp Asp Thr Leu Gly Ser Thr Val
65                  70                  75                  80

Gly Arg Leu Gln Glu Gln Leu Gly Pro Val Thr Gln Glu Phe Trp Ala
                85                  90                  95

Asn Leu Glu Lys Glu Thr Asp Trp Leu Arg Asn Glu Met Asn Lys Asp
            100                 105                 110

Leu Glu Asn Val Lys Gln Lys Met Gln Pro His Leu Asp Glu Phe Gln
        115                 120                 125

Glu Lys Trp Asn Glu Glu Val Glu Ala Tyr Arg Gln Lys Leu Glu Pro
    130                 135                 140

Leu Gly Thr Glu Leu His Lys Asn Ala Lys Glu Met Gln Arg His Leu
145                 150                 155                 160

Lys Val Val Ala Glu Glu Phe Arg Asp Arg Met Arg Val Asn Ala Asp
                165                 170                 175

Ala Leu Arg Ala Lys Phe Gly Leu Tyr Ser Asp Gln Met Arg Glu Asn
            180                 185                 190

Leu Ala Gln Arg Leu Thr Glu Ile Arg Asn His Pro Thr Leu Ile Glu
        195                 200                 205

Tyr His Thr Lys Ala Gly Asp His Leu Arg Thr Leu Gly Glu Lys Ala
    210                 215                 220

Lys Pro Ala Leu Asp Asp Leu Gly Gln Gly Leu Met Pro Val Leu Glu
225                 230                 235                 240

Ala Trp Lys Ala Lys Ile Met Ser Met Ile Asp Glu Ala Lys Lys Lys
                245                 250                 255

Leu Asn Ala

<210> SEQ ID NO 38
<211> LENGTH: 241
<212> TYPE: PRT
<213> ORGANISM: Homo sapiens

<400> SEQUENCE: 38

Asp Glu Ala Lys Ser Tyr Trp Asp Gln Ile Lys Asp Met Leu Thr Val
1               5                   10                  15

Tyr Val Asp Thr Ala Lys Asp Ser Gly Lys Asp Tyr Leu Thr Ser Leu
            20                  25                  30

Asp Thr Ser Ala Leu Gly Gln Gln Leu Asn Lys Lys Leu Ala Asp Asn
```

```
              35                  40                  45
Trp Asp Thr Val Ser Ser Ala Leu Leu Lys Ala Arg Glu Gln Met Lys
 50                  55                  60
Pro Ile Ala Met Glu Phe Trp Gly Asn Leu Glu Lys Asp Thr Glu Gly
 65                  70                  75                  80
Leu Arg Gln Thr Val Ser Lys Asp Leu Glu Leu Val Lys Glu Lys Val
                 85                  90                  95
Gln Pro Tyr Leu Asp Ser Phe Gln Lys Lys Val Glu Glu Leu Glu
                100                 105                 110
Leu Tyr Arg Gln Lys Val Ala Pro Leu Ser Ala Glu Trp Arg Glu Gln
                115                 120                 125
Ala Arg Gln Lys Ala Gln Glu Leu Gln Gln Lys Ala Gly Glu Leu Gly
        130                 135                 140
Gln Gln His Arg Asp Arg Val Arg Thr His Val Asp Ala Leu Arg Thr
145                 150                 155                 160
Asp Leu Ala Pro Tyr Gly Glu Glu Ala Arg Lys Leu Leu Gln Arg
                165                 170                 175
Leu Gln Asp Ile Lys Ala Lys Ser Gly Asp Leu Ala Glu Tyr Gln Thr
                180                 185                 190
Lys Leu Ser Glu His Leu Lys Ser Phe Gly Glu Lys Ala Gln Pro Thr
                195                 200                 205
Leu Gln Asp Leu Arg His Gly Leu Glu Pro Leu Trp Glu Gly Ile Lys
        210                 215                 220
Ala Gly Ala Met Ser Met Leu Glu Glu Leu Gly Lys Lys Leu Asn Ser
225                 230                 235                 240
Gln

<210> SEQ ID NO 39
<211> LENGTH: 264
<212> TYPE: PRT
<213> ORGANISM: Homo sapiens

<400> SEQUENCE: 39

Met Arg Gly Val Leu Val Thr Leu Ala Val Leu Phe Leu Thr Gly Thr
  1                5                  10                  15
Gln Ala Arg Ser Phe Trp Gln His Asp Glu Pro Gln Thr Pro Leu Asp
                 20                  25                  30
Arg Ile Arg Asp Met Val Asp Val Tyr Leu Glu Thr Val Lys Ala Ser
                 35                  40                  45
Gly Lys Asp Ala Ile Ala Gln Phe Glu Ser Ser Ala Val Gly Lys Gln
         50                  55                  60
Leu Asp Leu Lys Leu Ala Asp Asn Leu Asp Thr Leu Ser Ala Ala Ala
 65                  70                  75                  80
Ala Lys Leu Arg Glu Asp Met Ala Pro Tyr Tyr Lys Glu Val Arg Glu
                 85                  90                  95
Met Trp Leu Lys Asp Thr Glu Ala Leu Arg Ala Glu Leu Thr Lys Asp
                100                 105                 110
Leu Glu Glu Val Lys Glu Lys Ile Arg Pro Phe Leu Asp Gln Phe Ser
                115                 120                 125
Ala Lys Trp Thr Glu Glu Leu Glu Gln Tyr Arg Gln Arg Leu Thr Pro
         130                 135                 140
Val Ala Gln Glu Leu Lys Glu Leu Thr Lys Gln Lys Val Glu Leu Met
145                 150                 155                 160
Gln Ala Lys Leu Thr Pro Val Ala Glu Glu Ala Arg Asp Arg Leu Arg
```

```
                        165                 170                 175
Gly His Val Glu Glu Leu Arg Lys Asn Leu Ala Pro Tyr Ser Asp Glu
            180                 185                 190

Leu Arg Gln Lys Leu Ser Gln Lys Leu Glu Glu Ile Arg Glu Lys Gly
            195                 200                 205

Ile Pro Gln Ala Ser Glu Tyr Gln Ala Lys Val Met Glu Gln Leu Ser
    210                 215                 220

Asn Leu Arg Glu Lys Met Thr Pro Leu Val Gln Glu Phe Arg Glu Arg
225                 230                 235                 240

Leu Thr Pro Tyr Ala Glu Asn Leu Lys Asn Arg Leu Ile Ser Phe Leu
                245                 250                 255

Asp Glu Leu Gln Lys Ser Val Ala
            260

<210> SEQ ID NO 40
<211> LENGTH: 264
<212> TYPE: PRT
<213> ORGANISM: Homo sapiens

<400> SEQUENCE: 40

Met Arg Gly Val Leu Val Thr Leu Ala Val Leu Phe Leu Thr Gly Thr
1               5                   10                  15

Gln Ala Arg Ser Phe Trp Gln His Asp Asp Pro Gln Thr Pro Leu Asp
            20                  25                  30

Arg Ile Arg Asp Met Leu Asp Val Tyr Leu Glu Thr Val Lys Ala Ser
        35                  40                  45

Gly Lys Asp Ala Ile Ser Gln Phe Glu Ser Ser Ala Val Gly Lys Gln
    50                  55                  60

Leu Asp Leu Lys Leu Ala Asp Asn Leu Asp Thr Leu Ser Ala Ala Ala
65                  70                  75                  80

Ala Lys Leu Arg Glu Asp Met Thr Pro Tyr Tyr Arg Glu Val Arg Glu
                85                  90                  95

Met Trp Leu Lys Asp Thr Glu Ala Leu Arg Ala Glu Leu Thr Lys Asp
            100                 105                 110

Leu Glu Glu Val Lys Glu Lys Ile Arg Pro Phe Leu Asp Gln Phe Ser
        115                 120                 125

Ala Lys Trp Thr Glu Glu Val Glu Gln Tyr Arg Gln Arg Leu Ala Pro
    130                 135                 140

Val Ala Gln Glu Leu Lys Asp Leu Thr Lys Gln Lys Val Glu Leu Met
145                 150                 155                 160

Gln Ala Lys Leu Thr Pro Val Ala Glu Val Arg Asp Arg Leu Arg
                165                 170                 175

Glu Gln Val Glu Glu Leu Arg Lys Asn Leu Ala Pro Tyr Ser Ser Glu
            180                 185                 190

Leu Arg Gln Lys Leu Ser Gln Lys Leu Glu Glu Ile Arg Glu Arg Gly
        195                 200                 205

Ile Pro Gln Ala Ser Glu Tyr Gln Ala Lys Val Val Glu Gln Leu Ser
    210                 215                 220

Asn Leu Arg Glu Lys Met Thr Pro Leu Val Gln Glu Phe Lys Glu Arg
225                 230                 235                 240

Leu Thr Pro Tyr Ala Glu Asn Leu Lys Asn Arg Leu Ile Asp Leu Leu
                245                 250                 255

Asp Glu Val Gln Lys Thr Met Ala
            260
```

<210> SEQ ID NO 41
<211> LENGTH: 264
<212> TYPE: PRT
<213> ORGANISM: Homo sapiens

<400> SEQUENCE: 41

Met Arg Val Val Val Thr Leu Ala Leu Phe Leu Thr Gly Thr
1               5                   10                  15

Gln Ala Arg Tyr Phe Trp Gln His Asp Glu Pro Gln Ala Pro Leu Asp
            20                  25                  30

Arg Leu Arg Asp Leu Val Asp Val Tyr Leu Glu Thr Val Lys Ala Ser
        35                  40                  45

Gly Lys Asp Ala Ile Ala Gln Phe Glu Ala Ser Ala Val Gly Lys Gln
    50                  55                  60

Leu Asp Leu Lys Leu Ala Asp Asn Leu Asp Thr Leu Gly Ala Ala Ala
65                  70                  75                  80

Ala Lys Leu Arg Glu Asp Met Ala Pro Tyr Tyr Lys Glu Val Arg Glu
                85                  90                  95

Met Trp Leu Lys Asp Thr Glu Ser Leu Arg Ala Glu Leu Thr Lys Asp
            100                 105                 110

Leu Glu Glu Val Lys Glu Lys Ile Arg Pro Phe Leu Asp Gln Phe Ser
        115                 120                 125

Ala Lys Trp Thr Glu Glu Leu Glu Gln Tyr Arg Gln Arg Leu Ala Pro
    130                 135                 140

Val Ala Glu Glu Leu Lys Glu Leu Thr Lys Gln Lys Val Glu Leu Met
145                 150                 155                 160

Gln Gln Lys Leu Thr Pro Val Ala Glu Ala Arg Asp Arg Leu Arg
                165                 170                 175

Gly His Val Glu Glu Leu Arg Lys Asn Leu Ala Pro Tyr Ser Asp Glu
            180                 185                 190

Leu Arg Gln Lys Leu Ser Gln Lys Leu Glu Glu Ile Arg Glu Lys Gly
        195                 200                 205

Ile Pro Gln Ala Ala Glu Tyr Gln Ala Lys Val Val Glu Gln Leu Ser
    210                 215                 220

Asn Leu Arg Glu Lys Met Thr Pro Leu Val Gln Asp Phe Lys Glu Arg
225                 230                 235                 240

Leu Thr Pro Tyr Ala Glu Asn Leu Lys Thr Arg Phe Ile Ser Leu Leu
                245                 250                 255

Asp Glu Leu Gln Lys Thr Val Ala
            260

<210> SEQ ID NO 42
<211> LENGTH: 262
<212> TYPE: PRT
<213> ORGANISM: Homo sapiens

<400> SEQUENCE: 42

Met Lys Phe Leu Ala Leu Ala Leu Thr Ile Leu Leu Ala Ala Gly Thr
1               5                   10                  15

Gln Ala Phe Pro Met Gln Ala Asp Ala Pro Ser Gln Leu Glu His Val
            20                  25                  30

Lys Ala Ala Leu Ser Met Tyr Ile Ala Gln Val Lys Leu Thr Ala Gln
        35                  40                  45

Arg Ser Ile Asp Leu Leu Asp Asp Thr Glu Tyr Lys Glu Tyr Lys Met
    50                  55                  60

Gln Leu Thr Gln Ser Leu Asp Asn Leu Gln Gln Tyr Ala Asp Ala Thr
65                  70                  75                  80

Ser Gln Ser Leu Ala Pro Tyr Ser Glu Ala Phe Gly Thr Gln Leu Thr
            85                  90                  95

Asp Ala Thr Ala Ala Val Arg Ala Glu Val Met Lys Asp Val Glu Glu
        100                 105                 110

Leu Arg Ser Gln Leu Glu Pro Lys Arg Ala Glu Leu Lys Glu Val Leu
    115                 120                 125

Asp Lys His Ile Asp Glu Tyr Arg Lys Lys Leu Glu Pro Leu Ile Lys
130                 135                 140

Glu His Ile Glu Leu Arg Arg Thr Glu Met Glu Ala Phe Arg Ala Lys
145                 150                 155                 160

Met Glu Pro Ile Val Glu Glu Leu Arg Ala Lys Val Ala Ile Asn Val
            165                 170                 175

Glu Glu Thr Lys Thr Lys Leu Met Pro Ile Val Glu Ile Val Arg Ala
        180                 185                 190

Lys Leu Thr Glu Arg Leu Glu Glu Leu Arg Thr Leu Ala Ala Pro Tyr
    195                 200                 205

Ala Glu Glu Tyr Lys Gly Gln Met Ile Lys Ala Val Gly Glu Val Arg
210                 215                 220

Glu Lys Val Ser Pro Leu Ser Glu Asp Phe Lys Gly Gln Val Gly Pro
225                 230                 235                 240

Ala Ala Glu Gln Ala Lys Gln Lys Leu Leu Ala Phe Tyr Glu Thr Ile
            245                 250                 255

Ser Gln Ala Met Lys Ala
        260

<210> SEQ ID NO 43
<211> LENGTH: 262
<212> TYPE: PRT
<213> ORGANISM: Homo sapiens

<400> SEQUENCE: 43

Met Lys Phe Leu Ala Leu Ala Leu Thr Ile Leu Leu Ala Ala Ala Thr
1               5                   10                  15

Gln Ala Val Pro Met Gln Ala Asp Ala Pro Ser Gln Leu Glu His Val
            20                  25                  30

Lys Val Ala Met Met Glu Tyr Met Ala Gln Val Lys Glu Thr Gly Gln
        35                  40                  45

Arg Ser Ile Asp Leu Leu Asp Asp Thr Glu Phe Lys Glu Tyr Lys Val
    50                  55                  60

Gln Leu Ser Gln Ser Leu Asp Asn Leu Gln Gln Tyr Ala Gln Thr Thr
65                  70                  75                  80

Ser Gln Ser Leu Ala Pro Tyr Ser Glu Ala Phe Gly Ala Gln Leu Thr
            85                  90                  95

Asp Ala Ala Ala Ala Val Arg Ala Glu Val Met Lys Asp Val Glu Asp
        100                 105                 110

Val Arg Thr Gln Leu Glu Pro Lys Arg Ala Glu Leu Lys Glu Val Leu
    115                 120                 125

Asp Lys His Ile Asp Glu Tyr Arg Lys Lys Leu Glu Pro Leu Ile Lys
130                 135                 140

Glu Ile Val Glu Gln Arg Arg Thr Glu Leu Glu Ala Phe Arg Val Lys
145                 150                 155                 160

Met Glu Pro Val Val Glu Glu Met Arg Ala Lys Val Ser Thr Asn Val
            165                 170                 175

Glu Glu Thr Lys Ala Lys Leu Met Pro Ile Val Thr Val Arg Ala
            180                 185                 190

Lys Leu Thr Glu Arg Leu Glu Leu Arg Thr Leu Ala Ala Pro Tyr
            195                 200                 205

Ala Glu Glu Tyr Lys Glu Gln Met Phe Lys Ala Val Gly Val Arg
            210                 215                 220

Glu Lys Val Gly Pro Leu Thr Asn Asp Phe Lys Gly Gln Val Gly Pro
225                 230                 235                 240

Ala Ala Glu Gln Ala Lys Glu Lys Leu Met Asp Phe Tyr Glu Thr Ile
                245                 250                 255

Ser Gln Ala Met Lys Ala
            260

<210> SEQ ID NO 44
<211> LENGTH: 258
<212> TYPE: PRT
<213> ORGANISM: Homo sapiens

<400> SEQUENCE: 44

Met Lys Phe Leu Val Leu Ala Leu Thr Ile Leu Leu Ala Ala Gly Thr
1               5                   10                  15

Gln Ala Phe Pro Met Gln Ala Asp Ala Pro Ser Gln Leu Glu His Val
            20                  25                  30

Lys Ala Ala Leu Asn Met Tyr Ile Ala Gln Val Lys Leu Thr Ala Gln
            35                  40                  45

Arg Ser Ile Asp Leu Leu Asp Asp Thr Glu Tyr Lys Glu Tyr Lys Met
50                  55                  60

Gln Leu Ser Gln Ser Leu Asp Asn Leu Gln Gln Phe Ala Asp Ser Thr
65                  70                  75                  80

Ser Lys Ser Trp Pro Pro Thr Pro Arg Ser Ser Ala Pro Ser Cys Asp
                85                  90                  95

Ala Thr Ala Thr Val Arg Ala Glu Val Met Lys Asp Val Glu Asp Val
            100                 105                 110

Arg Thr Gln Leu Glu Pro Lys Arg Ala Glu Leu Thr Glu Val Leu Asn
            115                 120                 125

Lys His Ile Asp Glu Tyr Arg Lys Lys Leu Glu Pro Leu Ile Lys Gln
            130                 135                 140

His Ile Glu Leu Arg Arg Thr Glu Met Asp Ala Phe Arg Ala Lys Ile
145                 150                 155                 160

Asp Pro Val Val Glu Glu Met Arg Ala Lys Val Ala Val Asn Val Glu
                165                 170                 175

Glu Thr Lys Thr Lys Leu Met Pro Ile Val Glu Ile Val Arg Ala Lys
            180                 185                 190

Leu Thr Glu Arg Leu Glu Glu Leu Arg Thr Leu Ala Ala Pro Tyr Ala
            195                 200                 205

Glu Glu Tyr Lys Glu Gln Met Phe Lys Ala Val Gly Glu Val Arg Glu
            210                 215                 220

Lys Val Ala Pro Leu Ser Glu Asp Phe Lys Ala Arg Trp Ala Pro Pro
225                 230                 235                 240

Pro Arg Arg Pro Ser Lys Ser Ser Trp Leu Ser Thr Arg Pro Ser Ala
                245                 250                 255

Arg Pro

<210> SEQ ID NO 45

<211> LENGTH: 262
<212> TYPE: PRT
<213> ORGANISM: Homo sapiens

<400> SEQUENCE: 45

Met Lys Phe Val Ala Leu Ala Leu Leu Leu Ala Leu Gly Ser
1               5                   10                  15

Gln Ala Asn Leu Phe Gln Ala Asp Ala Pro Thr Gln Leu Glu His Tyr
            20                  25                  30

Lys Ala Ala Ala Leu Val Tyr Leu Asn Gln Val Lys Asp Gln Ala Glu
        35                  40                  45

Lys Ala Leu Asp Asn Leu Asp Gly Thr Asp Tyr Glu Gln Tyr Lys Leu
    50                  55                  60

Gln Leu Ser Glu Ser Leu Thr Lys Leu Gln Glu Tyr Ala Gln Thr Thr
65                  70                  75                  80

Ser Gln Ala Leu Thr Pro Tyr Ala Glu Thr Ile Ser Thr Gln Leu Met
                85                  90                  95

Glu Asn Thr Lys Gln Leu Arg Glu Arg Val Met Thr Asp Val Glu Asp
            100                 105                 110

Leu Arg Ser Lys Leu Glu Pro His Arg Ala Glu Leu Tyr Thr Ala Leu
        115                 120                 125

Gln Lys His Ile Asp Glu Tyr Arg Glu Lys Leu Glu Pro Val Phe Gln
    130                 135                 140

Glu Tyr Ser Ala Leu Asn Arg Gln Asn Ala Glu Gln Leu Arg Ala Lys
145                 150                 155                 160

Leu Glu Pro Leu Met Asp Asp Ile Arg Lys Ala Phe Glu Ser Asn Ile
                165                 170                 175

Glu Glu Thr Lys Ser Lys Val Val Pro Met Val Glu Ala Val Arg Thr
            180                 185                 190

Lys Leu Thr Glu Arg Leu Glu Asp Leu Arg Thr Met Ala Ala Pro Tyr
        195                 200                 205

Ala Glu Glu Tyr Lys Glu Gln Leu Val Lys Ala Val Glu Glu Ala Arg
    210                 215                 220

Glu Lys Ile Ala Pro His Thr Gln Asp Leu Gln Thr Arg Met Glu Pro
225                 230                 235                 240

Tyr Met Glu Asn Val Arg Thr Thr Phe Ala Gln Met Tyr Glu Thr Ile
                245                 250                 255

Ala Lys Ala Ile Gln Ala
            260

<210> SEQ ID NO 46
<211> LENGTH: 260
<212> TYPE: PRT
<213> ORGANISM: Homo sapiens

<400> SEQUENCE: 46

Met Lys Phe Ala Ala Leu Ala Leu Ala Leu Leu Leu Ala Val Gly Ser
1               5                   10                  15

His Ala Ala Ser Met Gln Ala Asp Ala Pro Ser Gln Leu Asp His Ala
            20                  25                  30

Arg Ala Val Leu Asp Val Tyr Leu Thr Gln Val Lys Asp Met Ser Leu
        35                  40                  45

Arg Ala Val Asn Gln Leu Asp Asp Pro Gln Tyr Ala Glu Phe Lys Thr
    50                  55                  60

Asn Leu Ala Gln Arg Ile Glu Glu Met Tyr Thr Gln Ile Lys Thr Leu
65                  70                  75                  80

```
Gln Gly Ser Val Ser Pro Met Thr Asp Ser Phe Tyr Asn Thr Val Met
                85                  90                  95

Glu Val Thr Lys Asp Thr Arg Glu Ser Leu Asn Val Asp Leu Glu Ala
            100                 105                 110

Leu Lys Ser Ser Leu Ala Pro Gln Asn Glu Gln Leu Lys Gln Val Ile
        115                 120                 125

Glu Lys His Leu Asn Asp Tyr Arg Thr Leu Leu Thr Pro Ile Tyr Asn
    130                 135                 140

Asp Tyr Lys Thr Lys His Asp Glu Glu Met Ala Ala Leu Lys Thr Arg
145                 150                 155                 160

Leu Glu Pro Val Met Glu Glu Leu Arg Thr Lys Ile Gln Ala Asn Val
                165                 170                 175

Glu Glu Thr Lys Ala Val Leu Met Pro Met Val Glu Thr Val Arg Thr
            180                 185                 190

Lys Val Thr Glu Arg Leu Glu Ser Leu Arg Glu Val Val Gln Pro Tyr
        195                 200                 205

Val Gln Glu Tyr Lys Glu Gln Met Lys Gln Met Tyr Asp Gln Ala Gln
    210                 215                 220

Thr Val Asp Thr Asp Ala Leu Arg Thr Lys Ile Thr Pro Leu Val Glu
225                 230                 235                 240

Glu Ile Lys Val Lys Met Asn Ala Ile Phe Glu Ile Ile Ala Ala Ser
                245                 250                 255

Val Thr Lys Ser
        260

<210> SEQ ID NO 47
<211> LENGTH: 396
<212> TYPE: PRT
<213> ORGANISM: Homo sapiens

<400> SEQUENCE: 47

Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
            20                  25                  30

Asp Tyr Phe Ser Gln Leu Ser Asn Asn Ala Lys Glu Ala Val Glu His
        35                  40                  45

Leu Gln Lys Ser Glu Leu Thr Gln Gln Leu Asn Ala Leu Phe Gln Asp
    50                  55                  60

Lys Leu Gly Glu Val Asn Thr Tyr Ala Gly Asp Leu Gln Lys Lys Leu
65                  70                  75                  80

Val Pro Phe Ala Thr Glu Leu His Glu Arg Leu Ala Lys Asp Ser Glu
                85                  90                  95

Lys Leu Lys Glu Glu Ile Gly Lys Glu Leu Glu Glu Leu Arg Ala Arg
            100                 105                 110

Leu Leu Pro His Ala Asn Glu Val Ser Gln Lys Ile Gly Asp Asn Leu
        115                 120                 125

Arg Glu Leu Gln Gln Arg Leu Glu Pro Tyr Ala Asp Gln Leu Arg Thr
    130                 135                 140

Gln Val Asn Thr Gln Ala Glu Gln Leu Arg Arg Gln Leu Thr Pro Tyr
145                 150                 155                 160

Ala Gln Arg Met Glu Arg Val Leu Arg Glu Asn Ala Asp Ser Leu Gln
                165                 170                 175

Ala Ser Leu Arg Pro His Ala Asp Glu Leu Lys Ala Lys Ile Asp Gln
```

-continued

```
                180                 185                 190
Asn Val Glu Glu Leu Lys Gly Arg Leu Thr Pro Tyr Ala Asp Glu Phe
            195                 200                 205
Lys Val Lys Ile Asp Gln Thr Val Glu Glu Leu Arg Arg Ser Leu Ala
        210                 215                 220
Pro Tyr Ala Gln Asp Thr Gln Glu Lys Leu Asn His Gln Leu Glu Gly
225                 230                 235                 240
Leu Thr Phe Gln Met Lys Lys Asn Ala Glu Glu Leu Lys Ala Arg Ile
                245                 250                 255
Ser Ala Ser Ala Glu Glu Leu Arg Gln Arg Leu Ala Pro Leu Ala Glu
            260                 265                 270
Asp Val Arg Gly Asn Leu Lys Gly Asn Thr Glu Gly Leu Gln Lys Ser
        275                 280                 285
Leu Ala Glu Leu Gly Gly His Leu Asp Gln Gln Val Glu Glu Phe Arg
        290                 295                 300
Arg Arg Val Glu Pro Tyr Gly Glu Asn Phe Asn Lys Ala Leu Val Gln
305                 310                 315                 320
Gln Met Glu Gln Leu Arg Gln Lys Leu Gly Pro His Ala Gly Asp Val
                325                 330                 335
Glu Gly His Leu Ser Phe Leu Glu Lys Asp Leu Arg Asp Lys Val Asn
            340                 345                 350
Ser Phe Phe Ser Thr Phe Lys Glu Lys Glu Ser Gln Asp Lys Thr Leu
        355                 360                 365
Ser Leu Pro Glu Leu Glu Gln Gln Gln Glu Gln Gln Gln Glu Gln Gln
370                 375                 380
Gln Glu Gln Val Gln Met Leu Ala Pro Leu Glu Ser
385                 390                 395

<210> SEQ ID NO 48
<211> LENGTH: 429
<212> TYPE: PRT
<213> ORGANISM: Homo sapiens

<400> SEQUENCE: 48

Met Phe Leu Lys Ala Val Val Leu Thr Leu Ala Leu Val Ala Val Thr
1               5                   10                  15
Gly Ala Arg Ala Glu Val Ser Ala Asp Gln Val Ala Thr Val Met Trp
            20                  25                  30
Asp Tyr Phe Ser Gln Leu Ser Ser Asn Ala Lys Glu Ala Val Glu His
        35                  40                  45
Leu Gln Lys Ser Glu Leu Thr Gln Gln Leu Asn Ala Leu Phe Gln Asp
    50                  55                  60
Lys Leu Gly Glu Val Asn Thr Tyr Ala Gly Asp Leu Gln Lys Lys Leu
65                  70                  75                  80
Val Pro Phe Ala Thr Glu Leu His Glu Arg Leu Ala Lys Asp Ser Glu
                85                  90                  95
Lys Leu Lys Glu Glu Ile Arg Lys Glu Leu Glu Glu Val Arg Ala Arg
            100                 105                 110
Leu Leu Pro His Ala Asn Glu Val Ser Gln Lys Ile Gly Glu Asn Val
        115                 120                 125
Arg Glu Leu Gln Gln Arg Leu Glu Pro Tyr Thr Asp Gln Leu Arg Thr
    130                 135                 140
Gln Val Asn Thr Gln Thr Glu Gln Leu Arg Arg Gln Leu Thr Pro Tyr
145                 150                 155                 160
```

```
Ala Gln Arg Met Glu Arg Val Leu Arg Glu Asn Ala Asp Ser Leu Gln
                165                 170                 175

Thr Ser Leu Arg Pro His Ala Asp Gln Leu Lys Ala Lys Ile Asp Gln
            180                 185                 190

Asn Val Glu Glu Leu Lys Glu Arg Leu Thr Pro Tyr Ala Asp Glu Phe
        195                 200                 205

Lys Val Lys Ile Asp Gln Thr Val Glu Glu Leu Arg Arg Ser Leu Ala
    210                 215                 220

Pro Tyr Ala Gln Asp Ala Gln Glu Lys Leu Asn His Gln Leu Glu Gly
225                 230                 235                 240

Leu Ala Phe Gln Met Lys Lys Asn Ala Glu Glu Leu Lys Ala Arg Ile
                245                 250                 255

Ser Ala Ser Ala Glu Glu Leu Arg Gln Arg Leu Ala Pro Leu Ala Glu
            260                 265                 270

Asp Met Arg Gly Asn Leu Arg Gly Asn Thr Glu Gly Leu Gln Lys Ser
        275                 280                 285

Leu Ala Glu Leu Gly Gly His Leu Asp Arg His Val Glu Glu Phe Arg
    290                 295                 300

Leu Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
                325                 330                 335

Glu Gly His Leu Ser Phe Leu Glu Lys Asp Leu Arg Asp Lys Val Asn
            340                 345                 350

Ser Phe Phe Ser Thr Phe Lys Glu Lys Glu Ser Gln Asp Asn Thr Leu
        355                 360                 365

Ser Leu Pro Glu Pro Glu Gln Gln Arg Glu Gln Gln Gln Glu Gln Gln
    370                 375                 380

Gln Glu Gln Glu Gln Glu Gln Gln Gln Gln Gln Gln Gln Gln Gln Gln
385                 390                 395                 400

Gln Glu Gln Gln Arg Gln Gln Gln Glu Gln Gln Gln Gln Gln Glu Gln
                405                 410                 415

Gln Gln Glu Gln Val Gln Met Leu Ala Pro Leu Glu Ser
            420                 425

<210> SEQ ID NO 49
<211> LENGTH: 395
<212> TYPE: PRT
<213> ORGANISM: Homo sapiens

<400> SEQUENCE: 49

Met Phe Leu Lys Ala Ala Val Leu Thr Leu Ala Leu Val Ala Ile Thr
1               5                   10                  15

Gly Thr Arg Ala Glu Val Thr Ser Asp Gln Val Ala Asn Val Val Trp
                20                  25                  30

Asp Tyr Phe Thr Gln Leu Ser Asn Asn Ala Lys Glu Ala Val Glu Gln
            35                  40                  45

Phe Gln Lys Thr Asp Val Thr Gln Gln Leu Ser Thr Leu Phe Gln Asp
        50                  55                  60

Lys Leu Gly Asp Ala Ser Thr Tyr Ala Asp Gly Val His Asn Lys Leu
65                  70                  75                  80

Val Pro Phe Val Val Gln Leu Ser Gly His Leu Ala Lys Glu Thr Glu
                85                  90                  95

Arg Val Lys Glu Glu Ile Lys Lys Glu Leu Glu Asp Leu Arg Asp Arg
            100                 105                 110
```

```
Met Met Pro His Ala Asn Lys Val Thr Gln Thr Phe Gly Glu Asn Met
        115                 120                 125

Gln Lys Leu Gln Glu His Leu Lys Pro Tyr Ala Val Asp Leu Gln Asp
    130                 135                 140

Gln Ile Asn Thr Gln Thr Gln Glu Met Lys Leu Gln Leu Thr Pro Tyr
145                 150                 155                 160

Ile Gln Arg Met Gln Thr Thr Ile Lys Glu Asn Val Asp Asn Leu His
                165                 170                 175

Thr Ser Met Met Pro Leu Ala Thr Asn Leu Lys Asp Lys Phe Asn Arg
            180                 185                 190

Asn Met Glu Glu Leu Lys Gly His Leu Thr Pro Arg Ala Asn Glu Leu
        195                 200                 205

Lys Ala Thr Ile Asp Gln Asn Leu Glu Asp Leu Arg Arg Ser Leu Ala
    210                 215                 220

Pro Leu Thr Val Gly Val Gln Glu Lys Leu Asn His Gln Met Glu Gly
225                 230                 235                 240

Leu Ala Phe Gln Met Lys Lys Asn Ala Glu Glu Leu Gln Thr Lys Val
                245                 250                 255

Ser Ala Lys Ile Asp Gln Leu Gln Lys Asn Leu Ala Pro Leu Val Glu
            260                 265                 270

Asp Val Gln Ser Lys Val Lys Gly Asn Thr Glu Gly Leu Gln Lys Ser
        275                 280                 285

Leu Glu Asp Leu Asn Arg Gln Leu Glu Gln Gln Val Glu Glu Phe Arg
    290                 295                 300

Arg Thr Val Glu Pro Met Gly Glu Met Phe Asn Lys Ala Leu Val Gln
305                 310                 315                 320

Gln Leu Glu Gln Phe Arg Gln Leu Gly Pro Asn Ser Gly Glu Val
                325                 330                 335

Glu Ser His Leu Ser Phe Leu Glu Lys Ser Leu Arg Glu Lys Val Asn
            340                 345                 350

Ser Phe Met Ser Thr Leu Glu Lys Lys Gly Ser Pro Asp Gln Pro Gln
        355                 360                 365

Ala Leu Pro Leu Pro Glu Gln Ala Gln Glu Gln Ala Gln Glu Gln Ala
    370                 375                 380

Gln Glu Gln Val Gln Pro Lys Pro Leu Glu Ser
385                 390                 395

<210> SEQ ID NO 50
<211> LENGTH: 401
<212> TYPE: PRT
<213> ORGANISM: Homo sapiens

<400> SEQUENCE: 50

Gly Ala Arg Ala Glu Val Ser Ala Asp Gln Val Ala Thr Val Met Trp
1               5                   10                  15

Asp Tyr Phe Ser Gln Leu Ser Ser Asn Ala Lys Glu Ala Val Glu His
                20                  25                  30

Leu Gln Lys Ser Glu Leu Thr Gln Gln Leu Asn Ala Leu Phe Gln Asp
            35                  40                  45

Lys Leu Gly Glu Val Asn Thr Tyr Ala Gly Asp Leu Gln Lys Lys Leu
        50                  55                  60

Val Pro Phe Ala Thr Glu Leu His Glu Arg Leu Ala Lys Asp Ser Lys
65                  70                  75                  80

Lys Leu Lys Glu Glu Ile Arg Lys Glu Leu Glu Glu Val Arg Ala Arg
```

```
                    85                  90                  95
Leu Leu Pro His Ala Asn Glu Val Ser Gln Lys Ile Gly Glu Asn Val
                100                 105                 110

Arg Glu Leu Gln Gln Arg Leu Glu Pro Tyr Thr Asp Gln Leu Arg Thr
            115                 120                 125

Gln Val Asn Thr Gln Thr Glu Gln Leu Arg Arg Gln Leu Thr Pro Tyr
        130                 135                 140

Ala Gln Arg Met Glu Arg Val Leu Arg Glu Asn Ala Asp Ser Leu Gln
145                 150                 155                 160

Thr Ser Leu Arg Pro His Ala Asp Gln Leu Lys Ala Lys Ile Asp Gln
                165                 170                 175

Asn Val Glu Glu Leu Lys Gly Arg Leu Thr Pro Tyr Ala Asp Glu Phe
                180                 185                 190

Lys Val Lys Ile Asp Gln Thr Val Glu Glu Leu Arg Arg Ser Leu Ala
                195                 200                 205

Pro Tyr Ala Gln Asp Ala Gln Glu Lys Leu Asn His Gln Leu Glu Gly
            210                 215                 220

Leu Ala Phe Gln Met Lys Lys Asn Ala Glu Glu Leu Lys Ala Arg Ile
225                 230                 235                 240

Ser Ala Ser Ala Glu Glu Leu Arg Gln Arg Leu Ala Pro Leu Ala Glu
                245                 250                 255

Asp Met Arg Gly Asn Leu Arg Gly Asn Thr Glu Gly Leu Gln Lys Ser
            260                 265                 270

Leu Ala Glu Leu Gly Gly His Leu Asp Arg His Val Glu Glu Phe Arg
        275                 280                 285

Leu Arg Val Glu Pro Tyr Gly Glu Asn Phe Asn Lys Ala Leu Val Gln
        290                 295                 300

Gln Met Glu Gln Leu Arg Gln Lys Leu Gly Pro His Ala Gly Asp Val
305                 310                 315                 320

Glu Gly His Leu Ser Phe Leu Glu Lys Asp Leu Arg Asp Lys Val Asn
                325                 330                 335

Ser Phe Phe Ser Thr Phe Lys Glu Lys Glu Ser Gln Asp Asn Thr Leu
                340                 345                 350

Ser Leu Pro Glu Pro Glu Gln Gln Gln Gln Gln Gln Gln Gln Gln Glu
            355                 360                 365

Gln Gln Gln Glu Gln Gln Glu Gln Gln Gln Glu Gln Gln Glu Gln Gln
        370                 375                 380

Glu Gln Glu Gln Gln Gln Glu Gln Val Gln Met Leu Ala Pro Leu Glu
385                 390                 395                 400

Ser

<210> SEQ ID NO 51
<211> LENGTH: 382
<212> TYPE: PRT
<213> ORGANISM: Homo sapiens

<400> SEQUENCE: 51

Met Phe Leu Lys Ala Val Val Leu Ser Leu Ala Leu Val Ala Val Thr
1               5                   10                  15

Gly Ala Arg Ala Glu Val Asn Ala Asp Gln Val Ala Thr Val Met Trp
            20                  25                  30

Asp Tyr Phe Ser Gln Leu Gly Ser Asn Ala Lys Lys Ala Val Glu His
        35                  40                  45

Leu Gln Lys Ser Glu Leu Thr Gln Gln Leu Asn Thr Leu Phe Gln Asp
```

```
            50                  55                  60
Lys Leu Gly Glu Val Asn Thr Tyr Thr Glu Asp Leu Gln Lys Leu
 65                  70                  75                  80

Val Pro Phe Ala Thr Glu Leu His Glu Arg Leu Thr Lys Asp Ser Glu
                     85                  90                  95

Lys Leu Lys Glu Glu Ile Arg Arg Glu Leu Glu Leu Arg Ala Arg
                100                 105                 110

Leu Leu Pro His Ala Thr Glu Val Ser Gln Lys Ile Gly Asp Asn Val
                115                 120                 125

Arg Glu Leu Gln Gln Arg Leu Gly Pro Phe Thr Gly Gly Leu Arg Thr
130                 135                 140

Gln Val Asn Thr Gln Val Gln Gln Leu Gln Arg Gln Leu Lys Pro Tyr
145                 150                 155                 160

Ala Glu Arg Met Glu Ser Val Leu Arg Gln Asn Ile Arg Asn Leu Glu
                165                 170                 175

Ala Ser Val Ala Pro Tyr Ala Asp Glu Phe Lys Ala Lys Ile Asp Gln
                180                 185                 190

Asn Val Glu Glu Leu Lys Gly Ser Leu Thr Pro Tyr Ala Glu Glu Leu
                195                 200                 205

Lys Ala Lys Ile Asp Gln Asn Val Glu Glu Leu Arg Arg Ser Leu Ala
210                 215                 220

Pro Tyr Ala Gln Asp Val Gln Glu Lys Leu Asn His Gln Leu Glu Gly
225                 230                 235                 240

Leu Ala Phe Gln Met Lys Lys Gln Ala Glu Glu Leu Lys Ala Lys Ile
                245                 250                 255

Ser Ala Asn Ala Asp Glu Leu Arg Gln Lys Leu Val Pro Val Ala Glu
                260                 265                 270

Asn Val His Gly His Leu Lys Gly Asn Thr Glu Gly Leu Gln Lys Ser
                275                 280                 285

Leu Leu Glu Leu Arg Ser His Leu Asp Gln Gln Val Glu Glu Phe Arg
290                 295                 300

Leu Lys Val Glu Pro Tyr Gly Glu Thr Phe Asn Lys Ala Leu Val Gln
305                 310                 315                 320

Gln Val Glu Asp Leu Arg Gln Lys Leu Gly Pro Leu Ala Gly Asp Val
                325                 330                 335

Glu Gly His Leu Ser Phe Leu Glu Lys Asp Leu Arg Asp Lys Val Asn
                340                 345                 350

Thr Phe Phe Ser Thr Leu Lys Glu Glu Ala Ser Gln Gly Gln Ser Gln
                355                 360                 365

Ala Leu Pro Ala Gln Glu Lys Ala Gln Ala Pro Leu Glu Gly
                370                 375                 380

<210> SEQ ID NO 52
<211> LENGTH: 391
<212> TYPE: PRT
<213> ORGANISM: Homo sapiens

<400> SEQUENCE: 52

Met Phe Leu Lys Ala Val Val Leu Thr Val Ala Leu Val Ala Ile Thr
  1               5                  10                  15

Gly Thr Gln Ala Glu Val Thr Ser Asp Gln Val Ala Asn Val Met Trp
                 20                  25                  30

Asp Tyr Phe Thr Gln Leu Ser Asn Asn Ala Lys Glu Ala Val Glu Gln
                 35                  40                  45
```

```
Leu Gln Lys Thr Asp Val Thr Gln Gln Leu Asn Thr Leu Phe Gln Asp
 50                  55                  60
Lys Leu Gly Asn Ile Asn Thr Tyr Ala Asp Asp Leu Gln Asn Lys Leu
 65                      70                  75                  80
Val Pro Phe Ala Val Gln Leu Ser Gly His Leu Thr Lys Glu Thr Glu
                 85                  90                  95
Arg Val Arg Glu Glu Ile Gln Lys Glu Leu Glu Asp Leu Arg Ala Asn
            100                 105                 110
Met Met Pro His Ala Asn Lys Val Ser Gln Met Phe Gly Asp Asn Val
                115                 120                 125
Gln Lys Leu Gln Glu His Leu Arg Pro Tyr Ala Thr Asp Leu Gln Ala
130                 135                 140
Gln Ile Asn Ala Gln Thr Gln Asp Met Lys Arg Gln Leu Thr Pro Tyr
145                 150                 155                 160
Ile Gln Arg Met Gln Thr Thr Ile Gln Asp Asn Val Glu Asn Leu Gln
                    165                 170                 175
Ser Ser Met Val Pro Phe Ala Asn Glu Leu Lys Glu Lys Phe Asn Gln
                180                 185                 190
Asn Met Glu Gly Leu Lys Gly Gln Leu Thr Pro Arg Ala Asn Glu Leu
            195                 200                 205
Lys Ala Thr Ile Asp Gln Asn Leu Glu Asp Leu Arg Ser Arg Leu Ala
210                 215                 220
Pro Leu Ala Glu Gly Val Gln Glu Lys Leu Asn His Gln Met Glu Gly
225                 230                 235                 240
Leu Ala Phe Gln Met Lys Lys Asn Ala Glu Glu Leu Gln Thr Lys Val
                    245                 250                 255
Ser Thr Asn Ile Asp Gln Leu Gln Lys Asn Leu Ala Pro Leu Val Glu
                260                 265                 270
Asp Val Gln Ser Lys Leu Lys Gly Asn Thr Glu Gly Leu Gln Lys Ser
            275                 280                 285
Leu Glu Asp Leu Asn Lys Gln Leu Asp Gln Gln Val Glu Val Phe Arg
290                 295                 300
Arg Ala Val Glu Pro Leu Gly Asp Lys Phe Asn Met Ala Leu Val Gln
305                 310                 315                 320
Gln Met Glu Lys Phe Arg Gln Gln Leu Gly Ser Asp Ser Gly Asp Val
                    325                 330                 335
Glu Ser His Leu Ser Phe Leu Glu Lys Asn Leu Arg Glu Lys Val Ser
                340                 345                 350
Ser Phe Met Ser Thr Leu Gln Lys Lys Gly Ser Pro Asp Gln Pro Leu
            355                 360                 365
Ala Leu Pro Leu Pro Glu Gln Val Gln Glu Gln Val Gln Glu Gln Val
370                 375                 380
Gln Pro Lys Pro Leu Glu Ser
385                 390

<210> SEQ ID NO 53
<211> LENGTH: 51
<212> TYPE: PRT
<213> ORGANISM: Homo sapiens

<400> SEQUENCE: 53

Glu Pro Pro Thr Gln Lys Pro Lys Lys Ile Val Asn Ala Lys Lys Asp
 1               5                  10                  15
Val Val Asn Thr Lys Met Phe Glu Glu Leu Lys Ser Arg Leu Asp Thr
                20                  25                  30
```

```
Leu Ala Gln Glu Val Ala Leu Leu Lys Glu Gln Gln Ala Leu Gln Thr
            35                  40                  45

Val Cys Leu
    50

<210> SEQ ID NO 54
<211> LENGTH: 40
<212> TYPE: PRT
<213> ORGANISM: Homo sapiens

<400> SEQUENCE: 54

Ile Val Asn Ala Lys Lys Asp Val Val Asn Thr Lys Met Phe Glu Glu
1               5                   10                  15

Leu Lys Ser Arg Leu Asp Thr Leu Ala Gln Glu Val Ala Leu Leu Lys
            20                  25                  30

Glu Gln Gln Ala Leu Gln Thr Val
            35                  40

<210> SEQ ID NO 55
<211> LENGTH: 9
<212> TYPE: PRT
<213> ORGANISM: Homo sapiens

<400> SEQUENCE: 55

Cys Asp Leu Pro Gln Thr His Ser Leu
1               5

<210> SEQ ID NO 56
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 56

His His His His His His
1               5

<210> SEQ ID NO 57
<211> LENGTH: 310
<212> TYPE: PRT
<213> ORGANISM: Artificial Sequence
<220> FEATURE:
<223> OTHER INFORMATION: Description of Artificial Sequence: Synthetic
      fusion polypeptide

<400> SEQUENCE: 57

Met Cys Asp Leu Pro Gln Thr His Ser Leu Gly Ser His His His His
1               5                   10                  15

His His Gly Ser Val Val Ala Pro Pro Ala Pro Ile Val Asn Ala Lys
            20                  25                  30

Lys Asp Val Val Asn Thr Lys Met Phe Glu Glu Leu Lys Ser Arg Leu
            35                  40                  45

Asp Thr Leu Ala Gln Glu Val Ala Leu Leu Lys Glu Gln Gln Ala Leu
        50                  55                  60

Gln Thr Val Asp Glu Pro Gln Ser Pro Trp Asp Arg Val Lys Asp
65                  70                  75                  80

Leu Ala Thr Val Tyr Val Asp Val Leu Lys Asp Ser Gly Arg Asp Tyr
                85                  90                  95

Val Ser Gln Phe Glu Gly Ser Ala Leu Gly Lys Gln Leu Asn Leu Lys
```

```
                100                 105                 110
Leu Leu Asp Asn Trp Asp Ser Val Thr Ser Thr Phe Ser Lys Leu Arg
        115                 120                 125

Glu Gln Leu Gly Pro Val Thr Gln Glu Phe Trp Asp Asn Leu Glu Lys
    130                 135                 140

Glu Thr Glu Gly Leu Arg Gln Glu Met Ser Lys Asp Leu Glu Glu Val
145                 150                 155                 160

Lys Ala Lys Val Gln Pro Tyr Leu Asp Asp Phe Gln Lys Lys Trp Gln
                165                 170                 175

Glu Glu Met Glu Leu Tyr Arg Gln Lys Val Glu Pro Leu Arg Ala Glu
            180                 185                 190

Leu Gln Glu Gly Ala Arg Gln Lys Leu His Glu Leu Gln Glu Lys Leu
        195                 200                 205

Ser Pro Leu Gly Glu Glu Met Arg Asp Arg Ala Arg Ala His Val Asp
    210                 215                 220

Ala Leu Arg Thr His Leu Ala Pro Tyr Ser Asp Glu Leu Arg Gln Arg
225                 230                 235                 240

Leu Ala Ala Arg Leu Glu Ala Leu Lys Glu Asn Gly Gly Ala Arg Leu
                245                 250                 255

Ala Glu Tyr His Ala Lys Ala Thr Glu His Leu Ser Thr Leu Ser Glu
            260                 265                 270

Lys Ala Lys Pro Ala Leu Glu Asp Leu Arg Gln Gly Leu Leu Pro Val
        275                 280                 285

Leu Glu Ser Phe Lys Val Ser Phe Leu Ser Ala Leu Glu Glu Tyr Thr
    290                 295                 300

Lys Lys Leu Asn Thr Gln
305                 310

<210> SEQ ID NO 58
<211> LENGTH: 35
<212> TYPE: DNA
<213> ORGANISM: Artificial Sequence
<220> FEATURE:
<223> OTHER INFORMATION: Description of Artificial Sequence: Synthetic
      primer N1

<400> SEQUENCE: 58
aaaaaagcgg ccgcgacaat tcgcgcgcga aggcg                          35

<210> SEQ ID NO 59
<211> LENGTH: 36
<212> TYPE: DNA
<213> ORGANISM: Artificial Sequence
<220> FEATURE:
<223> OTHER INFORMATION: Description of Artificial Sequence: Synthetic
      primer N2

<400> SEQUENCE: 59
aaaaaagcgg ccgctcactg cccgctttcc agtcgg                         36

<210> SEQ ID NO 60
<211> LENGTH: 7
<212> TYPE: PRT
<213> ORGANISM: Artificial Sequence
<220> FEATURE:
<223> OTHER INFORMATION: Description of Artificial Sequence: Synthetic
      IgA protease cleavage site peptide

<400> SEQUENCE: 60

Val Val Ala Pro Pro Ala Pro
```

<210> SEQ ID NO 61
<211> LENGTH: 5
<212> TYPE: PRT
<213> ORGANISM: Artificial Sequence
<220> FEATURE:
<223> OTHER INFORMATION: Description of Artificial Sequence: Synthetic
      IgA protease cleavage site peptide

<400> SEQUENCE: 61

Pro Ala Pro Ser Pro
1               5

<210> SEQ ID NO 62
<211> LENGTH: 4
<212> TYPE: PRT
<213> ORGANISM: Artificial Sequence
<220> FEATURE:
<223> OTHER INFORMATION: Description of Artificial Sequence: Synthetic
      IgA protease cleavage site peptide

<400> SEQUENCE: 62

Pro Pro Ser Pro
1

<210> SEQ ID NO 63
<211> LENGTH: 4
<212> TYPE: PRT
<213> ORGANISM: Artificial Sequence
<220> FEATURE:
<223> OTHER INFORMATION: Description of Artificial Sequence: Synthetic
      IgA protease cleavage site peptide

<400> SEQUENCE: 63

Pro Pro Ala Pro
1

<210> SEQ ID NO 64
<211> LENGTH: 4
<212> TYPE: PRT
<213> ORGANISM: Artificial Sequence
<220> FEATURE:
<223> OTHER INFORMATION: Description of Artificial Sequence: Synthetic
      IgA protease cleavage site peptide

<400> SEQUENCE: 64

Pro Pro Thr Pro
1

<210> SEQ ID NO 65
<211> LENGTH: 4
<212> TYPE: PRT
<213> ORGANISM: Artificial Sequence
<220> FEATURE:
<223> OTHER INFORMATION: Description of Artificial Sequence: Synthetic
      IgA protease cleavage site peptide

<400> SEQUENCE: 65

Pro Pro Gly Pro
1

<210> SEQ ID NO 66
<211> LENGTH: 285
<212> TYPE: PRT
<213> ORGANISM: Artificial Sequence
<220> FEATURE:
<223> OTHER INFORMATION: Description of Artificial Sequence: Synthetic Tetranectin-apolipoprotein A-I polypeptide
<220> FEATURE:
<221> NAME/KEY: MOD_RES
<222> LOCATION: (1)..(1)
<223> OTHER INFORMATION: Ala, Gly, Ser or Thr

<400> SEQUENCE: 66

Xaa Pro Ile Val Asn Ala Lys Lys Asp Val Val Asn Thr Lys Met Phe
1               5                   10                  15

Glu Glu Leu Lys Ser Arg Leu Asp Thr Leu Ala Gln Glu Val Ala Leu
            20                  25                  30

Leu Lys Glu Gln Gln Ala Leu Gln Thr Val Asp Glu Pro Pro Gln Ser
        35                  40                  45

Pro Trp Asp Arg Val Lys Asp Leu Ala Thr Val Tyr Val Asp Val Leu
    50                  55                  60

Lys Asp Ser Gly Arg Asp Tyr Val Ser Gln Phe Glu Gly Ser Ala Leu
65                  70                  75                  80

Gly Lys Gln Leu Asn Leu Lys Leu Leu Asp Asn Trp Asp Ser Val Thr
            85                  90                  95

Ser Thr Phe Ser Lys Leu Arg Glu Gln Leu Gly Pro Val Thr Gln Glu
        100                 105                 110

Phe Trp Asp Asn Leu Glu Lys Glu Thr Glu Gly Leu Arg Gln Glu Met
    115                 120                 125

Ser Lys Asp Leu Glu Glu Val Lys Ala Lys Val Gln Pro Tyr Leu Asp
130                 135                 140

Asp Phe Gln Lys Lys Trp Gln Glu Glu Met Glu Leu Tyr Arg Gln Lys
145                 150                 155                 160

Val Glu Pro Leu Arg Ala Glu Leu Gln Glu Gly Ala Arg Gln Lys Leu
            165                 170                 175

His Glu Leu Gln Glu Lys Leu Ser Pro Leu Gly Glu Glu Met Arg Asp
        180                 185                 190

Arg Ala Arg Ala His Val Asp Ala Leu Arg Thr His Leu Ala Pro Tyr
    195                 200                 205

Ser Asp Glu Leu Arg Gln Arg Leu Ala Ala Arg Leu Glu Ala Leu Lys
210                 215                 220

Glu Asn Gly Gly Ala Arg Leu Ala Glu Tyr His Ala Lys Ala Thr Glu
225                 230                 235                 240

His Leu Ser Thr Leu Ser Glu Lys Ala Lys Pro Ala Leu Glu Asp Leu
            245                 250                 255

Arg Gln Gly Leu Leu Pro Val Leu Glu Ser Phe Lys Val Ser Phe Leu
        260                 265                 270

Ser Ala Leu Glu Glu Tyr Thr Lys Lys Leu Asn Thr Gln
    275                 280                 285

<210> SEQ ID NO 67
<211> LENGTH: 307
<212> TYPE: PRT
<213> ORGANISM: Artificial Sequence
<220> FEATURE:
<223> OTHER INFORMATION: Description of Artificial Sequence: Synthetic
      Tetranectin-apolipoprotein A-I polypeptide with
      N-terminal His-tag
<220> FEATURE:
<221> NAME/KEY: MOD_RES
<222> LOCATION: (1)..(1)
<223> OTHER INFORMATION: May or may not be present
<220> FEATURE:
<221> NAME/KEY: MOD_RES
<222> LOCATION: (8)..(24)
<223> OTHER INFORMATION: This region may encompass 1 to 17 residues selected from Ala, Gly, Ser, Pro, "Ala Pro," "Gly Pro," "Ser Pro," "Pro Pro" or any of the sequences disclosed as SEQ ID NOS 68-105, wherein some residues in this region may be absent

<400> SEQUENCE: 67

```
Met His His His His His Xaa Xaa Xaa Xaa Xaa Xaa Xaa Xaa
1               5                  10                  15

Xaa Xaa Xaa Xaa Xaa Xaa Xaa Ile Val Asn Ala Lys Lys Asp Val
            20                  25                  30

Val Asn Thr Lys Met Phe Glu Glu Leu Lys Ser Arg Leu Asp Thr Leu
                35                  40                  45

Ala Gln Glu Val Ala Leu Leu Lys Glu Gln Gln Ala Leu Gln Thr Val
    50                  55                  60

Asp Glu Pro Pro Gln Ser Pro Trp Asp Arg Val Lys Asp Leu Ala Thr
65                  70                  75                  80

Val Tyr Val Asp Val Leu Lys Asp Ser Gly Arg Asp Tyr Val Ser Gln
                85                  90                  95

Phe Glu Gly Ser Ala Leu Gly Lys Gln Leu Asn Leu Lys Leu Leu Asp
            100                 105                 110

Asn Trp Asp Ser Val Thr Ser Thr Phe Ser Lys Leu Arg Glu Gln Leu
        115                 120                 125

Gly Pro Val Thr Gln Glu Phe Trp Asp Asn Leu Glu Lys Glu Thr Glu
130                 135                 140

Gly Leu Arg Gln Glu Met Ser Lys Asp Leu Glu Glu Val Lys Ala Lys
145                 150                 155                 160

Val Gln Pro Tyr Leu Asp Asp Phe Gln Lys Lys Trp Gln Glu Glu Met
                165                 170                 175

Glu Leu Tyr Arg Gln Lys Val Glu Pro Leu Arg Ala Glu Leu Gln Glu
            180                 185                 190

Gly Ala Arg Gln Lys Leu His Glu Leu Gln Glu Lys Leu Ser Pro Leu
        195                 200                 205

Gly Glu Glu Met Arg Asp Arg Ala Arg Ala His Val Asp Ala Leu Arg
210                 215                 220

Thr His Leu Ala Pro Tyr Ser Asp Glu Leu Arg Gln Arg Leu Ala Ala
225                 230                 235                 240

Arg Leu Glu Ala Leu Lys Glu Asn Gly Gly Ala Arg Leu Ala Glu Tyr
                245                 250                 255

His Ala Lys Ala Thr Glu His Leu Ser Thr Leu Ser Glu Lys Ala Lys
            260                 265                 270

Pro Ala Leu Glu Asp Leu Arg Gln Gly Leu Leu Pro Val Leu Glu Ser
        275                 280                 285

Phe Lys Val Ser Phe Leu Ser Ala Leu Glu Glu Tyr Thr Lys Lys Leu
290                 295                 300

Asn Thr Gln
305
```

<210> SEQ ID NO 68
<211> LENGTH: 4
<212> TYPE: PRT
<213> ORGANISM: Artificial Sequence
<220> FEATURE:
<223> OTHER INFORMATION: Description of Artificial Sequence: Synthetic linker peptide

<400> SEQUENCE: 68

```
Gly Ser Ala Pro
1
```

```
<210> SEQ ID NO 69
<211> LENGTH: 4
<212> TYPE: PRT
<213> ORGANISM: Artificial Sequence
<220> FEATURE:
<223> OTHER INFORMATION: Description of Artificial Sequence: Synthetic
      linker 2 peptide

<400> SEQUENCE: 69

Gly Ser Gly Pro
1

<210> SEQ ID NO 70
<211> LENGTH: 4
<212> TYPE: PRT
<213> ORGANISM: Artificial Sequence
<220> FEATURE:
<223> OTHER INFORMATION: Description of Artificial Sequence: Synthetic
      linker 3 peptide

<400> SEQUENCE: 70

Gly Ser Ser Pro
1

<210> SEQ ID NO 71
<211> LENGTH: 4
<212> TYPE: PRT
<213> ORGANISM: Artificial Sequence
<220> FEATURE:
<223> OTHER INFORMATION: Description of Artificial Sequence: Synthetic
      linker 4 peptide

<400> SEQUENCE: 71

Gly Ser Pro Pro
1

<210> SEQ ID NO 72
<211> LENGTH: 4
<212> TYPE: PRT
<213> ORGANISM: Artificial Sequence
<220> FEATURE:
<223> OTHER INFORMATION: Description of Artificial Sequence: Synthetic
      linker 5 peptide

<400> SEQUENCE: 72

Gly Gly Gly Ser
1

<210> SEQ ID NO 73
<211> LENGTH: 5
<212> TYPE: PRT
<213> ORGANISM: Artificial Sequence
<220> FEATURE:
<223> OTHER INFORMATION: Description of Artificial Sequence: Synthetic
      linker 6 peptide

<400> SEQUENCE: 73

Gly Gly Gly Gly Ser
1               5

<210> SEQ ID NO 74
<211> LENGTH: 8
<212> TYPE: PRT
<213> ORGANISM: Artificial Sequence
<220> FEATURE:
<223> OTHER INFORMATION: Description of Artificial Sequence: Synthetic
      linker 7 peptide
```

<400> SEQUENCE: 74

Gly Gly Gly Ser Gly Gly Gly Ser
1               5

<210> SEQ ID NO 75
<211> LENGTH: 10
<212> TYPE: PRT
<213> ORGANISM: Artificial Sequence
<220> FEATURE:
<223> OTHER INFORMATION: Description of Artificial Sequence: Synthetic
      linker 8 peptide

<400> SEQUENCE: 75

Gly Gly Gly Gly Ser Gly Gly Gly Gly Ser
1               5                   10

<210> SEQ ID NO 76
<211> LENGTH: 12
<212> TYPE: PRT
<213> ORGANISM: Artificial Sequence
<220> FEATURE:
<223> OTHER INFORMATION: Description of Artificial Sequence: Synthetic
      linker 9 peptide

<400> SEQUENCE: 76

Gly Gly Gly Ser Gly Gly Gly Ser Gly Gly Gly Ser
1               5                   10

<210> SEQ ID NO 77
<211> LENGTH: 15
<212> TYPE: PRT
<213> ORGANISM: Artificial Sequence
<220> FEATURE:
<223> OTHER INFORMATION: Description of Artificial Sequence: Synthetic
      linker 10 peptide

<400> SEQUENCE: 77

Gly Gly Gly Gly Ser Gly Gly Gly Gly Ser Gly Gly Gly Gly Ser
1               5                   10                  15

<210> SEQ ID NO 78
<211> LENGTH: 6
<212> TYPE: PRT
<213> ORGANISM: Artificial Sequence
<220> FEATURE:
<223> OTHER INFORMATION: Description of Artificial Sequence: Synthetic
      linker 11 peptide

<400> SEQUENCE: 78

Gly Gly Gly Ser Ala Pro
1               5

<210> SEQ ID NO 79
<211> LENGTH: 6
<212> TYPE: PRT
<213> ORGANISM: Artificial Sequence
<220> FEATURE:
<223> OTHER INFORMATION: Description of Artificial Sequence: Synthetic
      linker 12 peptide

<400> SEQUENCE: 79

Gly Gly Gly Ser Gly Pro
1               5

<210> SEQ ID NO 80
<211> LENGTH: 6

```
<212> TYPE: PRT
<213> ORGANISM: Artificial Sequence
<220> FEATURE:
<223> OTHER INFORMATION: Description of Artificial Sequence: Synthetic
      linker 13 peptide

<400> SEQUENCE: 80

Gly Gly Gly Ser Ser Pro
1               5

<210> SEQ ID NO 81
<211> LENGTH: 6
<212> TYPE: PRT
<213> ORGANISM: Artificial Sequence
<220> FEATURE:
<223> OTHER INFORMATION: Description of Artificial Sequence: Synthetic
      linker 14 peptide

<400> SEQUENCE: 81

Gly Gly Gly Ser Pro Pro
1               5

<210> SEQ ID NO 82
<211> LENGTH: 7
<212> TYPE: PRT
<213> ORGANISM: Artificial Sequence
<220> FEATURE:
<223> OTHER INFORMATION: Description of Artificial Sequence: Synthetic
      linker 15 peptide

<400> SEQUENCE: 82

Gly Gly Gly Gly Ser Ala Pro
1               5

<210> SEQ ID NO 83
<211> LENGTH: 7
<212> TYPE: PRT
<213> ORGANISM: Artificial Sequence
<220> FEATURE:
<223> OTHER INFORMATION: Description of Artificial Sequence: Synthetic
      linker 16 peptide

<400> SEQUENCE: 83

Gly Gly Gly Gly Ser Gly Pro
1               5

<210> SEQ ID NO 84
<211> LENGTH: 7
<212> TYPE: PRT
<213> ORGANISM: Artificial Sequence
<220> FEATURE:
<223> OTHER INFORMATION: Description of Artificial Sequence: Synthetic
      linker 17 peptide

<400> SEQUENCE: 84

Gly Gly Gly Gly Ser Ser Pro
1               5

<210> SEQ ID NO 85
<211> LENGTH: 7
<212> TYPE: PRT
<213> ORGANISM: Artificial Sequence
<220> FEATURE:
<223> OTHER INFORMATION: Description of Artificial Sequence: Synthetic
      linker 18 peptide

<400> SEQUENCE: 85

Gly Gly Gly Gly Ser Pro Pro
```

```
<210> SEQ ID NO 86
<211> LENGTH: 10
<212> TYPE: PRT
<213> ORGANISM: Artificial Sequence
<220> FEATURE:
<223> OTHER INFORMATION: Description of Artificial Sequence: Synthetic
      linker 19 peptide

<400> SEQUENCE: 86

Gly Gly Gly Ser Gly Gly Gly Ser Ala Pro
1               5                   10

<210> SEQ ID NO 87
<211> LENGTH: 10
<212> TYPE: PRT
<213> ORGANISM: Artificial Sequence
<220> FEATURE:
<223> OTHER INFORMATION: Description of Artificial Sequence: Synthetic
      linker 20 peptide

<400> SEQUENCE: 87

Gly Gly Gly Ser Gly Gly Gly Ser Gly Pro
1               5                   10

<210> SEQ ID NO 88
<211> LENGTH: 10
<212> TYPE: PRT
<213> ORGANISM: Artificial Sequence
<220> FEATURE:
<223> OTHER INFORMATION: Description of Artificial Sequence: Synthetic
      linker 21 peptide

<400> SEQUENCE: 88

Gly Gly Gly Ser Gly Gly Gly Ser Ser Pro
1               5                   10

<210> SEQ ID NO 89
<211> LENGTH: 10
<212> TYPE: PRT
<213> ORGANISM: Artificial Sequence
<220> FEATURE:
<223> OTHER INFORMATION: Description of Artificial Sequence: Synthetic
      linker 22 peptide

<400> SEQUENCE: 89

Gly Gly Gly Ser Gly Gly Gly Ser Pro Pro
1               5                   10

<210> SEQ ID NO 90
<211> LENGTH: 14
<212> TYPE: PRT
<213> ORGANISM: Artificial Sequence
<220> FEATURE:
<223> OTHER INFORMATION: Description of Artificial Sequence: Synthetic
      linker 23 peptide

<400> SEQUENCE: 90

Gly Gly Gly Ser Gly Gly Gly Ser Gly Gly Gly Ser Ala Pro
1               5                   10

<210> SEQ ID NO 91
<211> LENGTH: 14
<212> TYPE: PRT
<213> ORGANISM: Artificial Sequence
<220> FEATURE:
<223> OTHER INFORMATION: Description of Artificial Sequence: Synthetic
```

-continued

```
                  linker 24 peptide

<400> SEQUENCE: 91

Gly Gly Gly Ser Gly Gly Gly Ser Gly Gly Gly Ser Gly Pro
1               5                   10

<210> SEQ ID NO 92
<211> LENGTH: 14
<212> TYPE: PRT
<213> ORGANISM: Artificial Sequence
<220> FEATURE:
<223> OTHER INFORMATION: Description of Artificial Sequence: Synthetic
      linker 25 peptide

<400> SEQUENCE: 92

Gly Gly Gly Ser Gly Gly Gly Ser Gly Gly Gly Ser Ser Pro
1               5                   10

<210> SEQ ID NO 93
<211> LENGTH: 14
<212> TYPE: PRT
<213> ORGANISM: Artificial Sequence
<220> FEATURE:
<223> OTHER INFORMATION: Description of Artificial Sequence: Synthetic
      linker 26 peptide

<400> SEQUENCE: 93

Gly Gly Gly Ser Gly Gly Gly Ser Gly Gly Gly Ser Pro Pro
1               5                   10

<210> SEQ ID NO 94
<211> LENGTH: 7
<212> TYPE: PRT
<213> ORGANISM: Artificial Sequence
<220> FEATURE:
<223> OTHER INFORMATION: Description of Artificial Sequence: Synthetic
      linker 27 peptide

<400> SEQUENCE: 94

Gly Gly Gly Gly Ser Ala Pro
1               5

<210> SEQ ID NO 95
<211> LENGTH: 7
<212> TYPE: PRT
<213> ORGANISM: Artificial Sequence
<220> FEATURE:
<223> OTHER INFORMATION: Description of Artificial Sequence: Synthetic
      linker 28 peptide

<400> SEQUENCE: 95

Gly Gly Gly Gly Ser Gly Pro
1               5

<210> SEQ ID NO 96
<211> LENGTH: 7
<212> TYPE: PRT
<213> ORGANISM: Artificial Sequence
<220> FEATURE:
<223> OTHER INFORMATION: Description of Artificial Sequence: Synthetic
      linker 29 peptide

<400> SEQUENCE: 96

Gly Gly Gly Gly Ser Ser Pro
1               5

<210> SEQ ID NO 97
```

```
<211> LENGTH: 7
<212> TYPE: PRT
<213> ORGANISM: Artificial Sequence
<220> FEATURE:
<223> OTHER INFORMATION: Description of Artificial Sequence: Synthetic
      linker 30 peptide

<400> SEQUENCE: 97

Gly Gly Gly Gly Ser Pro Pro
1               5

<210> SEQ ID NO 98
<211> LENGTH: 12
<212> TYPE: PRT
<213> ORGANISM: Artificial Sequence
<220> FEATURE:
<223> OTHER INFORMATION: Description of Artificial Sequence: Synthetic
      linker 31 peptide

<400> SEQUENCE: 98

Gly Gly Gly Gly Ser Gly Gly Gly Gly Ser Ala Pro
1               5                   10

<210> SEQ ID NO 99
<211> LENGTH: 12
<212> TYPE: PRT
<213> ORGANISM: Artificial Sequence
<220> FEATURE:
<223> OTHER INFORMATION: Description of Artificial Sequence: Synthetic
      linker 32 peptide

<400> SEQUENCE: 99

Gly Gly Gly Gly Ser Gly Gly Gly Gly Ser Gly Pro
1               5                   10

<210> SEQ ID NO 100
<211> LENGTH: 12
<212> TYPE: PRT
<213> ORGANISM: Artificial Sequence
<220> FEATURE:
<223> OTHER INFORMATION: Description of Artificial Sequence: Synthetic
      linker 33 peptide

<400> SEQUENCE: 100

Gly Gly Gly Gly Ser Gly Gly Gly Gly Ser Ser Pro
1               5                   10

<210> SEQ ID NO 101
<211> LENGTH: 12
<212> TYPE: PRT
<213> ORGANISM: Artificial Sequence
<220> FEATURE:
<223> OTHER INFORMATION: Description of Artificial Sequence: Synthetic
      linker 34 peptide

<400> SEQUENCE: 101

Gly Gly Gly Gly Ser Gly Gly Gly Gly Ser Pro Pro
1               5                   10

<210> SEQ ID NO 102
<211> LENGTH: 17
<212> TYPE: PRT
<213> ORGANISM: Artificial Sequence
<220> FEATURE:
<223> OTHER INFORMATION: Description of Artificial Sequence: Synthetic
      linker 35 peptide

<400> SEQUENCE: 102
```

```
Gly Gly Gly Gly Ser Gly Gly Gly Gly Ser Gly Gly Gly Ser Ala
1               5                   10                  15
Pro

<210> SEQ ID NO 103
<211> LENGTH: 17
<212> TYPE: PRT
<213> ORGANISM: Artificial Sequence
<220> FEATURE:
<223> OTHER INFORMATION: Description of Artificial Sequence: Synthetic
      linker 36 peptide

<400> SEQUENCE: 103

Gly Gly Gly Gly Ser Gly Gly Gly Gly Ser Gly Gly Gly Ser Gly
1               5                   10                  15
Pro

<210> SEQ ID NO 104
<211> LENGTH: 17
<212> TYPE: PRT
<213> ORGANISM: Artificial Sequence
<220> FEATURE:
<223> OTHER INFORMATION: Description of Artificial Sequence: Synthetic
      linker 37 peptide

<400> SEQUENCE: 104

Gly Gly Gly Gly Ser Gly Gly Gly Gly Ser Gly Gly Gly Ser Ser
1               5                   10                  15
Pro

<210> SEQ ID NO 105
<211> LENGTH: 17
<212> TYPE: PRT
<213> ORGANISM: Artificial Sequence
<220> FEATURE:
<223> OTHER INFORMATION: Description of Artificial Sequence: Synthetic
      linker 38 peptide

<400> SEQUENCE: 105

Gly Gly Gly Gly Ser Gly Gly Gly Gly Ser Gly Gly Gly Ser Pro
1               5                   10                  15
Pro
```